(12) United States Patent
Ruben et al.

(10) Patent No.: US 6,448,230 B1
(45) Date of Patent: *Sep. 10, 2002

(54) TESTIS EXPRESSED POLYPEPTIDE

(75) Inventors: Steven M. Ruben, Olney, MD (US); Craig A. Rosen, Laytonsville, MD (US); Zhizhen Zeng, Gaithersburg, MD (US)

(73) Assignee: Human Genome Sciences, Inc., Rockville, MD (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 137 days.

(21) Appl. No.: 09/152,060

(22) Filed: Sep. 11, 1998

Related U.S. Application Data

(63) Continuation-in-part of application No. PCT/US98/04858, filed on Mar. 12, 1998.
(60) Provisional application No. 60/040,762, filed on Mar. 14, 1997, provisional application No. 60/040,710, filed on Mar. 14, 1997, provisional application No. 60/050,934, filed on May 30, 1997, provisional application No. 60/048,100, filed on May 30, 1997, provisional application No. 60/048,357, filed on May 30, 1997, provisional application No. 60/048,189, filed on May 30, 1997, provisional application No. 60/057,765, filed on Sep. 5, 1997, provisional application No. 60/048,970, filed on Jun. 6, 1997, and provisional application No. 60/068,368, filed on Dec. 19, 1997.

(51) Int. Cl.[7] .......................... A61K 38/00; C07K 1/00; C07K 5/00; C07K 7/00
(52) U.S. Cl. ............................. 514/21; 514/12; 514/2; 514/44; 530/300; 530/350; 530/305; 530/324; 424/185.1; 424/193.1; 424/194.1; 424/234.1

(58) Field of Search ................... 435/6, 69.1, 252.3, 435/320.1, 325; 514/12, 2, 44, 21; 530/300, 350, 305, 324, 333, 344, 345, 356, 358, 362, 391.5; 424/234.1, 184.1, 185.1, 193.1, 194.1

(56) References Cited

U.S. PATENT DOCUMENTS 5,536,637 A  7/1996  Jacobs

FOREIGN PATENT DOCUMENTS

| EP | 0679 716 A | 11/1995 |
|---|---|---|
| WO | WO97/07198 | 2/1997 |
| WO | WO 98/40483 | 9/1998 |
| WO | WO00/09709 | 2/2000 |

OTHER PUBLICATIONS

Barton et al., Protein Structure Prediction, A practical Approach, IRL Press at Oxford Unv. Press, UK, pp. 31–63 (1996).
George et al., Macromolecular Sequencing & Synthesis, D.H. Schlesinger (Ed.) Alan R. Liss, Inc. New York, pp. 127–149 (1988).
Suzuki et al., An Introduction to Genetic Analysis, 3$^{rd}$. Edition, W.H. Freeman and Company, New York pp. 421–423 (1986).

*Primary Examiner*—Avis M. Davenport
(74) *Attorney, Agent, or Firm*—Human Genome Sciences Inc.

(57) ABSTRACT

The present invention relates to novel human secreted proteins and isolated nucleic acids containing the coding regions of the genes encoding such proteins. Also provided are vectors, host cells, antibodies, and recombinant methods for producing human secreted proteins. The invention further relates to diagnostic and therapeutic methods useful for diagnosing and treating disorders related to these novel human secreted proteins.

40 Claims, 7 Drawing Sheets

FIG. 1A

| Gene No. | cDNA Clone ID | ATCC Deposit No:Z and Date | Vector | NT SEQ ID NO:X | Total NT Seq. | 5' NT of Clone Seq. | 3' NT of Clone Seq. | 5' NT of Start Codon | 5' NT of First AA of Signal Pep | AA SEQ ID NO:Y | First AA of Sig Pep | Last AA of Sig Pep | First AA of Secreted Portion | Last AA of ORF |
|---|---|---|---|---|---|---|---|---|---|---|---|---|---|---|
| 1 | HCEAB46 | 97921 03/07/97 | Uni-ZAP XR | 11 | 2084 | 695 | 2084 | 908 | 908 | 52 | 1 | 27 | 28 | 61 |
| 2 | HCEDH81 | 97921 03/07/97 | Uni-ZAP XR | 12 | 1586 | 1 | 1586 | 72 | 72 | 53 | 1 | 1 | 2 | 243 |
| 2 | HCEDH81 | 97921 03/07/97 | Uni-ZAP XR | 39 | 1907 | 1 | 1907 | 1211 | 1211 | 80 | 1 | 16 | 17 | 45 |
| 3 | HCEDO84 | 97921 03/07/97 | Uni-ZAP XR | 13 | 689 | 99 | 689 | 1 | 1 | 54 | 1 | 36 | 37 | 65 |
| 3 | HCEDO84 | 97921 03/07/97 | Uni-ZAP XR | 40 | 2350 | 1800 | 2328 | 1666 | 1666 | 81 | 1 | 37 | 38 | 39 |
| 4 | HCUHF89 | 97921 03/07/97 | ZAP Express | 14 | 1348 | 955 | 1348 | 976 | 976 | 55 | 1 | 33 | 34 | 37 |
| 5 | HELDY41 | 97921 03/07/97 | Uni-ZAP XR | 15 | 1123 | 1 | 1123 | 41 | 41 | 56 | 1 | 20 | 21 | 317 |
| 5 | HELDY41 | 97921 03/07/97 | Uni-ZAP XR | 41 | 1114 | 1 | 1114 | 19 | 19 | 82 | 1 | 21 | 22 | 36 |
| 6 | HETTM20 | 97921 03/07/97 | Uni-ZAP XR | 16 | 890 | 19 | 772 | 134 | 134 | 57 | 1 | 40 | 41 | 41 |

FIG. 1B

| Gene No. | cDNA Clone ID | ATCC Deposit No:Z and Date | Vector | NT SEQ ID NO: X | Total NT Seq. | 5' NT of Clone Seq. | 3' NT of Clone Seq. | 5' NT of Start Codon | 5' NT of First AA of Signal Pep | AA SEQ ID NO: Y | First AA of Sig Pep | Last AA of Sig Pep | First AA of Secreted Portion | Last AA of ORF |
|---|---|---|---|---|---|---|---|---|---|---|---|---|---|---|
| 7 | HFVGR41 | 97921 03/07/97 | pBluescript | 17 | 619 | 63 | 619 | 198 | 198 | 58 | 1 | 27 | 28 | 57 |
| 8 | HIBCO28 | 97921 03/07/97 | Other | 18 | 1768 | 15 | 1768 | | 1 | 59 | 1 | 17 | 18 | 32 |
| 9 | HJBCD89 | 97921 03/07/97 | pBluescript SK- | 19 | 1699 | 23 | 1679 | 30 | 30 | 60 | 1 | 48 | 49 | 296 |
| 9 | HJBCD89 | 97921 03/07/97 | pBluescript SK- | 42 | 1652 | 16 | 1652 | | 1 | 83 | 1 | 42 | 43 | 293 |
| 10 | HJTAA17 | 97921 03/07/97 | Lambda ZAP II | 20 | 736 | 85 | 685 | 123 | 123 | 61 | 1 | 32 | 33 | 100 |
| 11 | HLTBS22 | 97921 03/07/97 | Uni-ZAP XR | 21 | 1688 | 1 | 1682 | 186 | 186 | 62 | 1 | 21 | 22 | 47 |
| 12 | HTEBY84 | 97921 03/07/97 | Uni-ZAP XR | 22 | 2045 | 76 | 1980 | 221 | 221 | 63 | 1 | | | 13 |
| 13 | HNFCV70 | 97922 03/07/97 209070 05/22/97 | Uni-ZAP XR | 23 | 1101 | 77 | 1101 | 96 | 96 | 64 | 1 | 21 | 22 | 335 |

FIG. 1C

| Gene No. | cDNA Clone ID | ATCC Deposit No:Z and Date | Vector | NT SEQ ID NO: X | Total NT Seq. | 5' NT of Clone Seq. | 3' NT of Clone Seq. | 5' NT of Start Codon | 5' NT of First AA of Signal Pep | AA SEQ ID NO: Y | First AA of Sig Pep | Last AA of Sig Pep | First AA of Secreted Portion | Last AA of ORF |
|---|---|---|---|---|---|---|---|---|---|---|---|---|---|---|
| 13 | HNFCV70 | 97922 03/07/97 209070 05/22/97 | Uni-ZAP XR | 43 | 1473 | 1 | 1473 | 50 | 50 | 84 | 1 | 20 | 21 | 143 |
| 14 | HNFEY18 | 97922 03/07/97 209070 05/22/97 | Uni-ZAP XR | 24 | 1659 | 1 | 1659 | 1378 | 1378 | 65 | 1 | | | 18 |
| 15 | HNFGF45 | 97922 03/07/97 209070 05/22/97 | Uni-ZAP XR | 25 | 1329 | 4 | 1329 | 696 | 696 | 66 | 1 | 37 | 38 | 125 |
| 16 | HUSAQ32 | 97922 03/07/97 209070 05/22/97 | Lambda ZAP II | 26 | 700 | 47 | 609 | 280 | 280 | 67 | 1 | 18 | 19 | 77 |

FIG. 1D

| Gene No. | cDNA Clone ID | ATCC Deposit No:Z and Date | Vector | NT SEQ ID NO: X | Total NT Seq. | 5' NT of Clone Seq. | 3' NT of Clone Seq. | 5' NT of Start Codon | 5' NT of First AA of Signal Pep | AA SEQ ID NO: Y | First AA of Sig Pep | Last AA of Sig Pep | First AA of Secreted Portion | Last AA of ORF |
|---|---|---|---|---|---|---|---|---|---|---|---|---|---|---|
| 17 | HPMBQ91 | 97922 03/07/97 209070 05/22/97 | Uni-ZAP XR | 27 | 832 | 1 | 832 | 141 | 141 | 68 | 1 | 16 | 17 | 121 |
| 17 | HPMBQ91 | 97922 03/07/97 209070 05/22/97 | Uni-ZAP XR | 44 | 772 | 1 | 772 | 127 | 127 | 85 | 1 | 18 | 19 | 121 |
| 18 | HOEBI94 | 209007 04/28/97 | Uni-ZAP XR | 28 | 2361 | 411 | 2285 | 596 | 596 | 69 | 1 | 17 | 18 | 26 |
| 18 | HRSAJ18 | 97922 03/07/97 209070 05/22/97 | ZAP Express | 45 | 403 | 69 | 403 | 111 | 111 | 86 | 1 | 18 | 19 | 25 |
| 19 | HRSMC69 | 97922 03/07/97 209070 05/22/97 | ZAP Express | 29 | 879 | 565 | 879 | 13 | 13 | 70 | 1 | 21 | 22 | 235 |

FIG. 1E

| Gene No. | cDNA Clone ID | ATCC Deposit No:Z and Date | Vector | NT SEQ ID NO: X | Total NT Seq. | 5' NT of Clone Seq. | 3' NT of Clone Seq. | 5' NT of Start Codon | 5' NT of First AA of Signal Pep | AA SEQ ID NO: Y | First AA of Sig Pep | Last AA of Sig Pep | First AA of Secreted Portion | Last AA of ORF |
|---|---|---|---|---|---|---|---|---|---|---|---|---|---|---|
| 19 | HRSMC69 | 97922 03/07/97 209070 05/22/97 | ZAP Express | 46 | 928 | 204 | 418 | | 381 | 87 | 1 | | | 4 |
| 19 | HBMSH54 | 209551 12/12/97 | Uni-ZAP XR | 47 | 885 | 1 | 885 | 21 | 21 | 88 | 1 | 22 | 23 | 235 |
| 20 | HSDEG01 | 97922 03/07/97 209070 05/22/97 | Uni-ZAP XR | 30 | 1732 | 1 | 1732 | 267 | 267 | 71 | 1 | 30 | 31 | 217 |
| 20 | HSDEG01 | 97922 03/07/97 209070 05/22/97 | Uni-ZAP XR | 48 | 2315 | 1 | 2315 | 2055 | 2055 | 89 | 1 | 21 | 22 | 87 |
| 22 | HSVCB57 | 97922 03/07/97 209070 05/22/97 | Uni-ZAP XR | 32 | 454 | 1 | 454 | 61 | 61 | 73 | 1 | 18 | 19 | 36 |

FIG. 1F

| Gene No. | cDNA Clone ID | ATCC Deposit No:Z and Date | Vector | NT SEQ ID NO: X | Total NT Seq. | 5' NT of Clone Seq. | 3' NT of Clone Seq. | 5' NT of Start Codon | 5' NT of First AA of Signal Pep | AA SEQ ID NO: Y | First AA of Sig Pep | Last AA of Sig Pep | First AA of Secreted Portion | Last AA of ORF |
|---|---|---|---|---|---|---|---|---|---|---|---|---|---|---|
| 23 | HTFAE62 | 97922 03/07/97 209070 05/22/97 | Uni-ZAP XR | 33 | 230 | 27 | 162 | 7 | 7 | 74 | 1 | 21 | 22 | 74 |
| 24 | HTEBY11 | 97922 03/07/97 209070 05/22/97 | Uni-ZAP XR | 34 | 753 | 43 | 753 | 31 | 31 | 75 | 1 | 21 | 22 | 133 |
| 24 | HTEBY11 | 97922 03/07/97 209070 05/22/97 | Uni-ZAP XR | 50 | 783 | 30 | 783 | 254 | 254 | 91 | 1 | 29 | 30 | 59 |
| 25 | HTEEB42 | 97922 03/07/97 209070 05/22/97 | Uni-ZAP XR | 35 | 1022 | 20 | 1022 | 59 | 59 | 76 | 1 | 22 | 23 | 298 |

FIG. 1G

| Gene No. | cDNA Clone ID | ATCC Deposit No:Z and Date | Vector | NT SEQ ID NO: X | Total NT Seq. | 5' NT of Clone Seq. | 3' NT of Clone Seq. | 5' NT of Start Codon | 5' NT of First AA of Signal Pep | AA SEQ ID NO: Y | First AA of Sig Pep | Last AA of Sig Pep | First AA of Secreted Portion | Last AA of ORF |
|---|---|---|---|---|---|---|---|---|---|---|---|---|---|---|
| 26 | HTPBY11 | 97922 03/07/97 209070 05/22/97 | Uni-ZAP XR | 36 | 3044 | 1 | 3035 | 336 | 336 | 77 | 1 | 1 | 2 | 856 |
| 26 | HTPBY11 | 97922 03/07/97 209070 05/22/97 | Uni-ZAP XR | 51 | 3030 | 1 | 3030 | 1908 | 1908 | 92 | 1 | 31 | 32 | 32 |
| 27 | H2MBT68 | 97922 03/07/97 209070 05/22/97 | pBluescript SK- | 37 | 541 | 4 | 541 | 187 | 187 | 78 | 1 | 23 | 24 | 39 |
| 28 | HAGAI85 | 97922 03/07/97 209070 05/22/97 | Uni-ZAP XR | 38 | 1752 | 52 | 1752 | 166 | 166 | 79 | 1 | 23 | 24 | 30 |

SEQUENCE LISTING

<160> NUMBER OF SEQ ID NOS: 118

<210> SEQ ID NO 1
<211> LENGTH: 733
<212> TYPE: DNA
<213> ORGANISM: Homo sapiens

<400> SEQUENCE: 1

```
gggatccgga gcccaaatct tctgacaaaa ctcacacatg cccaccgtgc ccagcacctg      60
aattcgaggg tgcaccgtca gtcttcctct tcccccaaa acccaaggac accctcatga     120
tctcccggac tcctgaggtc acatgcgtgg tggtggacgt aagccacgaa gaccctgagg     180
tcaagttcaa ctggtacgtg gacggcgtgg aggtgcataa tgccaagaca aagccgcggg     240
```

```
aggagcagta caacagcacg taccgtgtgg tcagcgtcct caccgtcctg caccaggact    300
ggctgaatgg caaggagtac aagtgcaagg tctccaacaa agccctccca accccatcg    360 agaaaaccat ctccaaagcc aaagggcagc ccgagaacc acaggtgtac accctgcccc    420
catcccggga tgagctgacc aagaaccagg tcagcctgac ctgcctggtc aaaggcttct    480
atccaagcga catcgccgtg gagtgggaga gcaatgggca gccggagaac aactacaaga    540
ccacgcctcc cgtgctggac tccgacggct ccttcttcct ctacagcaag ctcaccgtgg    600
acaagagcag gtggcagcag gggaacgtct tctcatgctc cgtgatgcat gaggctctgc    660
acaaccacta cacgcagaag agcctctccc tgtctccggg taaatgagtg cgacggccgc    720
gactctagag gat                                                       733

<210> SEQ ID NO 2
<211> LENGTH: 5
<212> TYPE: PRT
<213> ORGANISM: Homo sapiens
<220> FEATURE:
<221> NAME/KEY: Site
<222> LOCATION: (3)
<223> OTHER INFORMATION: Xaa equals any of the twenty naturally ocurring
      L-amino acids

<400> SEQUENCE: 2

Trp Ser Xaa Trp Ser
 1               5

<210> SEQ ID NO 3
<211> LENGTH: 86
<212> TYPE: DNA
<213> ORGANISM: Homo sapiens

<400> SEQUENCE: 3
gcgcctcgag atttccccga aatctagatt tccccgaaat gatttccccg aaatgatttc    60
cccgaaatat ctgccatctc aattag                                         86

<210> SEQ ID NO 4
<211> LENGTH: 27
<212> TYPE: DNA
<213> ORGANISM: Homo sapiens

<400> SEQUENCE: 4
gcggcaagct ttttgcaaag cctaggc                                        27

<210> SEQ ID NO 5
<211> LENGTH: 271
<212> TYPE: DNA
<213> ORGANISM: Homo sapiens

<400> SEQUENCE: 5
ctcgagattt ccccgaaatc tagatttccc cgaaatgatt tccccgaaat gatttccccg    60
aaatatctgc catctcaatt agtcagcaac catagtcccg cccctaactc cgcccatccc   120
gcccctaact ccgcccagtt ccgcccattc tccgcccat ggctgactaa ttttttttat    180
ttatgcagag gccgaggccg cctcggcctc tgagctattc cagaagtagt gaggaggctt    240
ttttggaggc ctaggctttt gcaaaaagct t                                   271

<210> SEQ ID NO 6
<211> LENGTH: 32
<212> TYPE: DNA
```

```
<213> ORGANISM: Homo sapiens

<400> SEQUENCE: 6
gcgctcgagg gatgacagcg atagaaccccc gg                                32

<210> SEQ ID NO 7
<211> LENGTH: 31
<212> TYPE: DNA
<213> ORGANISM: Homo sapiens

<400> SEQUENCE: 7
gcgaagcttc gcgactcccc ggatccgcct c                                  31

<210> SEQ ID NO 8
<211> LENGTH: 12
<212> TYPE: DNA
<213> ORGANISM: Homo sapiens

<400> SEQUENCE: 8
ggggactttc cc                                                       12

<210> SEQ ID NO 9
<211> LENGTH: 73
<212> TYPE: DNA
<213> ORGANISM: Homo sapiens

<400> SEQUENCE: 9
gcggcctcga ggggactttc ccggggactt tccggggact ttccatcctg              60
ccatctcaat tag                                                      73

<210> SEQ ID NO 10
<211> LENGTH: 256
<212> TYPE: DNA
<213> ORGANISM: Homo sapiens

<400> SEQUENCE: 10
ctcgagggga ctttcccggg gactttccgg ggactttccg ggactttcca tctgccatct   60
caattagtca gcaaccatag tcccgcccct aactccgccc atcccgcccc taactccgcc  120
cagttccgcc cattctccgc cccatggctg actaattttt tttatttatg cagaggccga  180
ggccgcctcg gcctctgagc tattccagaa gtagtgagga ggcttttttg gaggcctagg  240
cttttgcaaa aagctt                                                  256

<210> SEQ ID NO 11
<211> LENGTH: 2084
<212> TYPE: DNA
<213> ORGANISM: Homo sapiens
<220> FEATURE:
<221> NAME/KEY: SITE
<222> LOCATION: (839)
<223> OTHER INFORMATION: n equals a,t,g, or c

<400> SEQUENCE: 11
ctatcagatg ctgggcctcc tcagccatag ccccctgctc ctaccccctg actggctctt   60
gtgtcctcac ctctcaccct ctccttcctg ggaggccctg ggaggtgatc attgacaccc  120
agccaagcag acagctgcgg gtgcccaagc ccttgctggg cctgcgcgtg aggagtccca  180
ctgcttctaa aggaagtcct gggcaggagg tggctttggt ggttggttcc aaagttgaaa  240
atgcttgcag tttgacctta aagaagtgg gaagaagaag gagctctaca gggtcagctt  300
tgtttgattt gtccagtcta agaagtccca ttgccaaagc tttctgcagg agggtgaatg  360
```

```
ccgcagcttg gcagcccctg ggtttctctt ggaaatggtc agtttcccct caaagtaccc      420
aaagtagcct tggcttgagt ttttgtcctt gcctccttt tagagaagag ggcatttaga      480
ctgcattttc ctggttaaag aaggttaaag caaatgttta ttgccttttc tagtgaacta      540
actcgtagag atgttctcag caggaagaca gtcttagcac tgtcacttag cagattgcac      600
ttaagtccct tgtgctggcc agatggcgtg gctggttgcc ttaatatgtc ccaggacccc      660
tgacagggct gcctggcctc tccctcgtgc tcctcaagag cccagtccat acactgtgga      720
tgtcattgct gtcgggttag gaagtcttgt cctagaacgc cctggctggt atgaccacag      780
ttcatggcgg ctcttctcgc ttgggtcatg gtcatcttcc agcacctgct gtgctgggna      840
aggccgagga tgggggccca gcactgtcca ggcctgctgg ggcctggctg ggagtcctgt      900
gggcagcatg gaacatgcag ctgggcttcc tgtgaccagg caccctctgg cactgttgct      960
tgccctgtgc cctggacctt ttcctgccct tctccttcct ctgctccctt ggggctaccc     1020
cttggcccct cctggtctgt gcaaactccc tcagggagcc ccctgccct gtagctctcr     1080 cttaacttcc taggggctgc tgagcccacc cagaggttgt tggagttcag cggggcagct     1140 tgtctcccctt gtcagcaggg gcgtaagggc tgggtttggc catacaaggt tggctacgcc     1200
ctcaatccct gaccgttcca ggcactgagc tgggcaccca cggaaggaca tgctgtccag     1260
actgtgatga ctgccagcac agggcatctc gggcttggct ggtctgcgag gccttgcccc     1320
tgtggaactc tggggttcctg ttttctcagt ctttttttgcg gctttgctgt ggttggcagc     1380
tgccgtactc caggcttgtg tcggccactc agatgagggc tgtggtgcga gccagtgcag     1440
gagagctgcg cttgggattg tgccctctcc tgtgtctgtc ctccggacct acccaggtct     1500
ccaccatcag gaccctgtct ttgggtttag aagaccaagt atggggaaaa ccaggcacca     1560
gcctctgcag caatgggtcc ctctagcctg tggacaccag ctggggatc cagggtcagg     1620 cccctcctc tccccagttt ccctctgctg tgggttctgg gctgtcatgt ctccaccact     1680
taaggatgtc tttacactga cttcaggata gatgctggga tgcctgggca tggccacatg     1740
ttacatgtac agaactttgt ctacagcaca aattaagtta tataaacaca gtgactggta     1800
tttaatgctg atctactata aggtattcta tatttatatg acttcagaga cgcgtatgta     1860
ataaaggacg ccctccctcc agtgtccaca tccagttcac cccagagggt cgggcaggtt     1920
gacatattta ttttttgtcta ttctgtaggc ttccatgtcc agaatcctgc ttaaggtttt     1980
agggtacctt cagtacttt tgcaataaaa gtatttccta tccaaaaaaa aaaaaaaaa      2040 actcgagggg ggcccggta cccaattcgc cctataaag agtc                       2084
```

<210> SEQ ID NO 12
<211> LENGTH: 1586
<212> TYPE: DNA
<213> ORGANISM: Homo sapiens

<400> SEQUENCE: 12

```
aattcggcac caggagaagt ggagtttgga agttcagggg cacagggca caggcccacg       60 actgcagcgg gatggaccag tactgcatcc tgggccgcat cggggagggc gcccamggca      120
tcgtcttcaa ggccaagcac gtggagactg gcgagatagt tgccctcaag aaggtggccc      180
taaggcggtt ggaagacggc ttccctaacc aggccctgcg ggagattaag gctctgcagg      240
aratggagga caatcagtat gtggtacaac tgaaggctgt gttcccacac ggtggaggct      300
ttgtgctggc ctttgagttc atgctgtcgg atctggccga ggtggtgcgc catgcccaga      360
```

```
ggccactagc ccaggcacag gtcaagagct acctgcagat gctgctcaag ggtgtcgcct      420
tctgccatgc caacaacatt gtacatcggg acctgaaacc tgccaacctg ctcatcagcg      480
cctcaggcca gctcaagata gcggactttg gcctggctcg agtcttttcc ccagacggca      540
gccgcctcta cacacaccag gtggccacca ggagctcact gagctgccgg actacaacaa      600
gatctccttt aaggagcagg tgcccatgcc cctggaggak gtgctgcctg acgtctctcc      660
ccaggcattg gatctgctgg gtcaattcct tctctaccct cctcaccagc gcatcgcagc      720
ttccaaggct ctcctccatc agtacttctt cacagctccc ctgcctgccc atccatctga      780
gctgccgatt cctcagcgtc tagggggacc tgcccccaag gcccatccag gccccccca       840 catccatgac ttccacgtgg accggcctct tgaggartcg ctgttgaacc cararctgat      900
tcggcccttc atcctggarg ggtgagaagt tggccctggt cccgtctgcc tgctcctcag      960
gaccactcag tccacctgtt cctctgccac ctgcctggct tcaccctcca aggcctcccc     1020
atggccacag tgggcccaca ccacaccctg cccttagcc cttgcgaagg ttggtctcga      1080
rgcagargtc atgttcccag ccaagagtat gagaacatcc agtcgagcag aggagattca     1140
tggcctgtsc tcggtgagcc ttaccttctg tgtgcttcac atcactgagc actcatttag     1200
aagtgaggga gacagaagtc tagscccagg gatggctcca gttggggatc cagcaggaga     1260
ccctctgcac atgaggctgg tttmccaaca tctactccct caggatgagc gtgagccaga     1320
agcagctgtg tatttaagga acaagcgtt cctggaatta atttataaat ttaataaatc      1380
ccaatataat cccagctagt gcttttttcct tattataatt tgataaggtg attataaaag     1440
atacatggaa ggaagtggaa ccagatgcag aagaggaaat gatggaagga cttatggtat     1500
cagataccaa tatttaaaag tttgtataat aataaagagt atgattgtgg ttcaaggata     1560
aaaaaaaaaa aaaaaaaaaa actcga                                          1586

<210> SEQ ID NO 13
<211> LENGTH: 689
<212> TYPE: DNA
<213> ORGANISM: Homo sapiens

<400> SEQUENCE: 13
atggaagcta agtttggcct gctttgcttt ttagtctcca caccatgggc agaactgctg       60
tctttactac ttcatctcac ccaagtcccg ttcccaggca gccagggcct gggtttgaat      120
aattgcaggg cagcctgcca tgatcttttct cacttactcc tctcccattc agcaatcaac      180
cagactaagg agttttgatc cctagtgatt acagccctga agaaaattaa atctgaatta      240
attttacatg gccttcgtga tctttctgct gttcttactt tttcgaatgt agttgggggg      300
tgggagggac aggttatggt atttaaagag aataaacatt ttgcacatac atgtattgta      360
caacagtaag atcctctgtt aaaccagct gtcctgttct ccatctccat ttcttcccat       420
gctgtaaccc caggctccac cagctgttcc ccagtgatgt tacctagctt ccctctaccg      480
ttgtctactg accatttcca ctacatgcct ttcctacctt cccttcacaa ccaatcaagt      540
gaatacttga ttattatctc ttccttactg tgctttatct ttttgtttg gattggttct      600 aattaatgaa aataaaagtt tctaaattta cattttttata gggtattgta aataaaaaca     660
aatgtatact taaaaaaaaa aaaaaaaaa                                        689

<210> SEQ ID NO 14
<211> LENGTH: 1348
<212> TYPE: DNA
<213> ORGANISM: Homo sapiens
```

<220> FEATURE:
<221> NAME/KEY: SITE
<222> LOCATION: (45)
<223> OTHER INFORMATION: n equals a,t,g, or c

<400> SEQUENCE: 14

| | | | | | |
|---|---|---|---|---|---|
| acgaagacac | cagaccctgt | ggagcctgtg | gtgaccaccg | aaggncagtt | cgggtgcagc | 60 |
| agggctcgag | cccagaaaac | tatcctctaa | gaccagacgt | gacaaggaga | agcagagctg | 120 |
| taagagctgt | ggtgagacct | tcaactccat | caccaagagg | aggcatcact | gcaagctgtg | 180 |
| tggggcggtc | atctgtggga | agtgctccga | gttcaaggcc | gagaacagcc | ggcagagcct | 240 |
| gtctgcagag | attgtttcct | gacacagcca | gtggcccctg | agagcacaga | gaagacaccc | 300 |
| actgcagacc | cccagcccag | cctgctctgc | ggcccctgc | ggctgtyaga | gagcggtgag | 360 |
| acctggagcg | aggtgtgggc | cgccatcccc | atgtcagatc | cccaggtgct | gcacctgcag | 420 |
| gkaggcagcc | aggacggccg | gctgcccgc | accatccctc | tccccagctg | caaactgagt | 480 |
| gtgccggacc | ctgaggagag | gctggactcg | gggcatgtgt | ggaagctgca | gtgggccaag | 540 |
| cagtcctggt | acctgagcgc | ctcctccgca | gagctgcagc | agcagtggct | ggaaacccta | 600 |
| agcactgctg | cccatgggga | cacggcccag | gacagcccgg | gggccctgca | gcttcaggtc | 660 |
| cctatgggcg | cagtgctccg | tgagctgagt | ctcccactgc | cctgcacacc | accacattgg | 720 |
| acctgtgctg | tcctgggagg | tggtgttgga | ggccccatga | agagcgccct | ggacttgctt | 780 |
| gagggtgggc | aacagccca | gagytcagga | catttggctt | tgggggaag | gaaaytgagg | 840 |
| cccagagagg | ggcaaccayt | ggccaagggt | cacccagcaa | gttttggyta | agagcctggc | 900 |
| ctccagcccc | agcagtktgg | cccagagcag | gggccgaytg | ccaaagtaac | catcatccat | 960 |
| atgggccgtg | tggtgatgct | ggcccggaag | gcagaaagag | gcagcatggg | cactgccagg | 1020 |
| gacagccaca | tcctgctggt | ctgcagcgtg | gtccaccccg | cctctgccca | gcctgtctac | 1080 |
| accgtgtgag | ctgaatcgtg | acttgcttcc | cacctccttt | ctctgtcctc | tcctgaggtt | 1140 |
| ctgcctgcag | cccccaggag | gtgggcctgc | cccatcctag | ctggactcat | ggttcctaaa | 1200 |
| taaccacgct | cagaagctct | gctaggactt | accccagcca | ctgagtggca | ggcgcatgag | 1260 |
| atttgtggct | gttcctgatg | ctagtggcac | acagtgctta | tctgcataaa | taaacactgg | 1320 |
| scaccaaaaa | aaaaaaaaa | aaaaaaac | | | | 1348 |

<210> SEQ ID NO 15
<211> LENGTH: 1123
<212> TYPE: DNA
<213> ORGANISM: Homo sapiens

<400> SEQUENCE: 15

| | | | | | |
|---|---|---|---|---|---|
| cgcgcccagc | ccctgctgct | ctgggcagac | gatgctgaag | atgctctcct | ttaagctgct | 60 |
| gctgctggcc | gtggctctgg | gcttctttga | aggagatgct | aagtttgggg | aaagaaacga | 120 |
| agggagcgga | gcaaggagga | gaaggtgcct | gaatgggaac | cccccgaagc | gcctgaaaag | 180 |
| gagagacagg | aggatgatgt | cccagctgga | gctgctgagt | gggggagaga | tgctgtgcgg | 240 |
| tggcttctac | cctcggctgt | cctgctgcct | gcggagtgac | agcccggggc | tagggcgcct | 300 |
| ggagaataag | atattttctg | ttaccaacaa | cacagaatgt | gggaagttac | tggaggaaat | 360 |
| caaatgtgca | ctttgctctc | cacattctca | agcctgttc | cactcacctg | agagagaagt | 420 |
| cttggaaaga | gacctagtac | ttcctctgct | ctgcaaagac | tattgcaaag | aattcttta | 480 |
| cacttgccga | ggccatattc | caggtttcct | tcaaacaact | gcggatgagt | tttgcttta | 540 |

-continued

```
ctatgcaaga aaagatggtg ggttgtgctt tccagatttt ccaagaaaac aagtcagagg      600
accagcatct aactacttgg accagatgga agaatatgac aaagtggaag agatcagcag      660
aaagcacaaa cacaactgct tctgtattca ggaggttgtg agtgggctgc ggcagcccgt      720
tggtgccctg catagtgggg atggctcgca acgtctcttc attctggaaa agaaggtta      780 tgtgaagata cttaccectg aaggagaaat tttcaaggag ccttatttgg acattcacaa      840
acttgttcaa agtggaataa aggttggctt tttaaatttt atttattttt gtgctggcta      900
cgttaatttt attttagtgt taccttcctc actgaaggta tttctttgta ataaagaaa       960 gaatcttgca ggagaaaata aggggcaac ataagaaaca ataattatgg cacctgaatt      1020
aggacagtga cattaaattt ctgttatttg ttaaaaaaaa aaaaaaaaaa aaaaaaaaa      1080 aaaaaaaaaa aaaaaaaaa aaaaaaaaa aaaaaaaaa aaa                          1123
```

<210> SEQ ID NO 16
<211> LENGTH: 890
<212> TYPE: DNA
<213> ORGANISM: Homo sapiens

<400> SEQUENCE: 16

```
ttttaattga tctgtgaraa aacttaagaa aatcacaatt tcagctaaca gcaattgtgt       60
cccaaagatg aagatactat aacctcaaat ggtgcagatc cagaactggg ctggatgaca      120
tccctactgt gccatgtcct ggggcatttg gaagggactg gacctctttc ccctcatcaa      180
aggaaacagc agtctttgcc tctttctgtt ggttgtgccc aagggctaca gtagctctga      240
aataacaaga gctctgtaat aacagtaata aatagctctg aaataacagt cctaagaact      300
cctaaagtcc tgagaacttt tcttgtaatg cagcttttc tcttcctgag aaacagtgtg      360
ttctaatggg attcccaggc agttcctaca cctacggtgt gtgttccagc agggaggagt      420
tatgggctgg gctgcctttt cccatgggtc ttcattccca atggaaagtt cactctgctt      480
agtttggaat tattttctt tcagttgttc tggaaccttt gctttttatt gatttataca      540
atacaattgg tgggagggtg gacttgggat gggagtggga aaagcatgta agagctcctt      600
ttgtgatggt ccatctaccc aaaagagatc tgctttagtg aacgatactc tttcatttt       660 ctaaattaga tcaagttgtt attgatttta gatgacttgt atgcaaattt gaaaactt        720 ttttttttaaa gctgattggg aactacaaac aatgaatgga atctactgac acagctaatt     780
ggaaaacaga tgtcttcttc tgtcctattg atgctggtgt ttaaaaaaca tcacttaaaa     840
aaaaagaata aatagttcta aaagcaaaaa aaaaaaaaaa aaaaaaattc                 890
```

<210> SEQ ID NO 17
<211> LENGTH: 619
<212> TYPE: DNA
<213> ORGANISM: Homo sapiens

<400> SEQUENCE: 17

```
tcaggccccg ctgactccgc cccgcaacac tctcactcgc ccttcgtgtc ccatcaggtc       60
ccgctgactc cgccccgcaa tactctcact cgcccttygt gtcccatcag gtcccgctga      120
ctccgccccg caacactctc acttgccctt cgtgtcccat caggtcctgc tgactccatc      180
tcctcagcgt ctccaacatg tcccttcctt gccacctctt gcctggatta ctacagcagc      240
ttctaacgag tctccctgcc tttcagttct ccgcaccgct tcaagtgttc agtctggatg      300
gtctgtcact cccagcgcca aaactgctga cggcttccct ttgccttcag gacgaagtcc      360
gtgctgtctg acataactta taggacctt tagccagcct gggcaacata gcaagaccct      420
```

```
gtctctacca gaaaatacaa aaatgagcca ggcatagtgg tgtgcacctg tagtcccagc    480
tacttgggag gctgaggtgg gaggatcacc tgagcccagg aagtcaaggc tgccagtgag    540
ccatgatcac accactgcac tccagcctgg gccacagagt gagaccctgt ctcaaaaaaa    600
aaaaaaaaaa aaaactcga                                                 619
```

<210> SEQ ID NO 18
<211> LENGTH: 1768
<212> TYPE: DNA
<213> ORGANISM: Homo sapiens
<220> FEATURE:
<221> NAME/KEY: SITE
<222> LOCATION: (483)
<223> OTHER INFORMATION: n equals a,t,g, or c

<400> SEQUENCE: 18

```
gaagccagac agtgacctca aatgttgcct tggagtcccc tacagcccct cagcagaggg     60
cagcacttga atgcttagct ccatcccata gttctctaca ttaacatgct gtctctaagg    120
gtggcccctc ctctcaggcg ttcagatggt gcgaacagca gagcaggcaa gggaaactgg    180
ggagatgggg atggaggagg aaggctgata tcctctgggg agcacatcac ctgaaggtgc    240
caaggaggaa ggctgagagg ggggmcaccc atttytggta cccaatttgg ttcttcagcc    300
caacttgcaa ggggttcctt ctggtcctcc catccactgc caccttccat tttgtccatc    360
tcatgctggc cttggtggat gggatggctg tatctagaca aaattttttct aaaactccat    420 caaggctctt attcaatacc acgttccgag ttggcctttc atcttctttg agactggccc    480
tgnctaacct ctaccatcaa tgagctcttg gcccttctgc ccttccctgt gtttctcact    540
ttccaaccta atccctggct cagggttatt gccagtggag actggtgagc tgggcctact    600
ctcagctgcc tatcttctgc ctttcacttg catccaactc ctggggctgg daccgtagta    660
gctgcggggg ggaagaaaca cagggtcggt gagcccagca tgtgcgttgg tttgagggg     720 cgggcggtgt gtgtgtgttc tggtgggagg gatctgagca agtgcaagcc tggctgacac    780
aggtgtgaag aggccatcct ggaacccagk tgagggcaag atgaaggctt ccaggcagaa    840
cagctgcaga gagtttggct atatgcatct gcagccccaa gagctcccac tgcaagacaa    900
gtgttgggga agatgggagg ttgtgggtga ggcctctaaa ggtcctctcc caaactgacc    960
aggctgatgt caacctaacc ccctcagggg cagggaacag gggagggctc cacaagcgtg   1020
tctggcattc ccacccacca tggaagactg gatacgcacc tggaaacaaa aggactatgg   1080
aagctgttca agatacattt gatcttcaga aaagcagaat ttggttcaac tgttgacaga   1140
ggacacaaat acgttgttcc agagctcagc cttctcactc taaaagaaag atatttttct   1200
atttattttc tacatctggc cagtggctct ggtgctagat gccactgtag ccagatctcc   1260
aacagtgcct tggaccatgg actcatactc aactgagtaa aaggggctg gtgccagtcg    1320 gggtggctga gctggtcctt aataggttgt ttcttggtct tgctttcttc atgccctccc   1380 cactgctcc gccacctttta gataagtttc tctagctaat tttgtggcca atgtaaaatt   1440
cgtcatcaac ctaacaaaca caaccttctc agcagcattt ctcccctgtg atggaaataa   1500
agtgtttagg gcagtgggag gagaaaattc yyccaggtga atgggaagg gtctgttcca    1560 gcctctccct actcccatcc catttccacc aactggggaa ctgtgactat ctatctcccc   1620
cgacttctac cagggatgcc ttcagccaag gctgttctca ccagctgcct cagatgacaa   1680
atgaggctaa tggacataat ctacagtgtc ctttttcact tgcacctttt ttataagaat   1740
```

-continued

| | |
|---|---|
| atattgtaat actaaaaaat attaaatt | 1768 |

<210> SEQ ID NO 19
<211> LENGTH: 1699
<212> TYPE: DNA
<213> ORGANISM: Homo sapiens
<220> FEATURE:
<221> NAME/KEY: SITE
<222> LOCATION: (871)
<223> OTHER INFORMATION: n equals a,t,g, or c

<400> SEQUENCE: 19

| | |
|---|---|
| ctcgtgccga attcggcacg agcgaaaaga tggcggtctt ggcacctcta attgctctcg | 60 |
| tgtattcggt gccgcgactt tcacgatggc tcgcccaacc ttactacctt ctgtcggccc | 120 |
| tgctctctgc tgccttccta ctcgtgagga aactgccgcc gctctgccac ggtctgccca | 180 |
| cccaacgcga agacggtaac ccgtgtgact ttgactggag agaagtggag atcctgatgt | 240 |
| ttctcagtgc cattgtgatg atgaagaacc gcagatccat cactgtggag caacatatag | 300 |
| gcaacatttt catgtttagt aaagtggcca acacaattct tttcttccgc ttggatattc | 360 |
| gcatgggcct actttacatc acactctgca tagtgttcct gatgacgtgc aaaccccccc | 420 |
| tatatatggg ccctgagtat atcaagtact tcaatgataa aaccattgat gaggaactag | 480 |
| aacgggacaa gagggtcact tggattgtgg agttctttgc caattggtct aatgactgcc | 540 |
| aatcatttgc ccctatctat gctgacctct cccttaaata caactgtaca gggctaaatt | 600 |
| ttgggaaggt ggatgttgga cgctatactg atgttagtac gcggtacaaa gtgagcacat | 660 |
| caccccctcac caagcaactc cctacccctga tcctgttcca aggtggcaag gaggcaatgc | 720 |
| ggcggccaca gattgacaag aaaggacggg ctgtctcatg gaccttctct gaggagaatg | 780 |
| tgatccgaga atttaactta aatgagctat accagcgggc caagaaacta tcaaaggctg | 840 |
| gagacaatat ccctgaggag cagcctgtgg nttcaacccc caccacagtg tcagatgggg | 900 |
| aaaacaagaa ggataaataa gatcctcact ttggcagtgc ttcctctcct gtcaattcca | 960 |
| ggctcttttcc ataaccacaa gcctgaggct gcagcctttt atttatgttt tcccttttggc | 1020 |
| tgtgactggg tggggcagca tgcagcttct gattttaaag aggcatctag ggaattgtca | 1080 |
| ggcaccctac aggaaggcct gccatgctgt ggccaactgt tcactggag caagaaagag | 1140 |
| atctcatagg acggaggggg aaatggtttc cctccaagct tgggtyagtg tgttaactgc | 1200 |
| ttatcagcta ttcagacatc tccatggttt ctccatgaaa ctctgtggtt tcatcattcc | 1260 |
| ttcttagttg acctgcacag cttggttaga cctagattta accctaaggt aagatgctgg | 1320 |
| ggtatagaac gctaagaatt ttcccccaag gactcttgct tccttaagcc cttctggctt | 1380 |
| cgtttatggt cttcattaaa agtataagcc taactttgtc gctagtccta aggagaaacc | 1440 |
| tttaaccaca aagttttttat cattgaagac aatattgaac aacccctat tttgtgggga | 1500 |
| ttgagaaggg gtgaatagag gcttgagact ttcctttgtg tggtaggact tggaggagaa | 1560 |
| atcccctgga cttttcactaa ccctctgaca tactccccac acccagttga tggctttccg | 1620 |
| taataaaaag attgggattt ccttttgaaa aaaaaaaaa aaaaaaaa aaaaaaaaa | 1680 |
| aaaaaaaaaa aaaaaaaag | 1699 |

<210> SEQ ID NO 20
<211> LENGTH: 736
<212> TYPE: DNA
<213> ORGANISM: Homo sapiens
<220> FEATURE:
<221> NAME/KEY: SITE

```
<222> LOCATION: (701)
<223> OTHER INFORMATION: n equals a,t,g, or c
<220> FEATURE:
<221> NAME/KEY: SITE
<222> LOCATION: (728)
<223> OTHER INFORMATION: n equals a,t,g, or c
<220> FEATURE:
<221> NAME/KEY: SITE
<222> LOCATION: (733)
<223> OTHER INFORMATION: n equals a,t,g, or c

<400> SEQUENCE: 20
aagtgagtta aggacgtact cgtcttggtg agagcgtgac tgctgagatt tgggagtctg      60
cgctaggccc gcttggagtt ctgagccgat ggaagagttc actcatgttt gcacccgcgg     120
tgatgcgtgc ttttcgcaag aacaagactc tcggctatgg agtccccatg ttgttgctga     180
ttgttggagg ttcttttggt cttcgtgagt tttctcaaat ccgatatgat gctgtgaaga     240
gtaaaatgga tcctgagctt gaaaaaaaac tgaaagagaa taaatatctt ttagagtcgg     300
aatatgagaa aatcaaagac tccaagtttg atgactggaa gaatattcga ggacccaggc     360
cttgggaaga tcctgacctc ctccaaggaa gaaatccaga aagccttaag actaagacaa     420
cttgactctg ctgattcttt tttccttttt tttttttta aataaaaata ctattaactg      480
gacttcctaa tatatacttc tatcaagtgg aaaggaaatt ccaggcccat ggaaacttgg     540
atatgggtaa tttgatgaca ataatcttc actaaaggtc atgtacaggt ttttatactt      600
cccagctatt ccatctgtgg atgaaagtaa caatgttggc cacgtatatt ttacacctcg     660
aaataaaaaa tgtgaatact gctccaaaaa aaaaaaagt nggcgagctt tccctagggg      720
ggtaattngc tgntgc                                                     736

<210> SEQ ID NO 21
<211> LENGTH: 1688
<212> TYPE: DNA
<213> ORGANISM: Homo sapiens

<400> SEQUENCE: 21
caaagaaggg attcatcttg cattggtgga gctgctgaaa aatttaacca agtaccctac      60
tgatagggac tccatatgga agtgcttgaa gtttctggga agtcggcatc caaccctggt    120
gcttcccttg gtgccagagc ttctgagcac ccacccattt tttgacacag ctgaaccaga    180
catggatgat ccagcttata ttgcagtttt ggtacttatt ttcaatgctg ctaaaacctg    240
tccaacaatg ccagcattgt tctcagatca caccttcagg cactatgcct acctccgaga    300
cagtctttct catcttgttc ctgccttgag gttaccaggt agaaaactgg tgtcatcagc    360
tgtttctccc agcatcatac ctcaagagga tccttcccag cagttcctgc agcagagcct    420
tgaaagagtg tatagtcttc agcacttgga ccctcaggga gcccaggagc tgctggaatt    480
caccatcagg gatctgcaaa gacttggaga acttcaatct gaattggcag gagtagctga    540
tttctctgcc acctatcttc gctgtcaact acttctcatc aaggccttgc aggaaaagtt    600
gtggaatgta gctgcccctt tgtatttgaa gcagagtgat ttggcctcag cagcagcgaa    660
acagattatg gaagagacct acaaaatgga attcatgtac agtggtgtgg agaataagca    720
ggtggtgatt atacatcaca tgaggctgca ggccaaagct ttgcaactta tagtaacagc    780
acgaactaca cgaggacttg accccttatt tgggatgtgt gaaaaatttt tacaggaagt    840
agactttttt cagaggtatt tcatcgctga tttgccccac ttgcaggaca gctttgtgga    900
caaactcctt gaccttatgc cccgactcat gacatccaaa cctgcagaag tggtcaaaat    960
```

-continued

```
tctacagacc atgctgcgac agagtgcctt tctgcatctc ccgcttccag agcagatcca    1020
caaagcctca gccaccatca tcgagccagc gggcgagttc agacaaccct ttgcggttta    1080
cctctgggtt ggtggttgcc ctgggatgtt gatgcaaccc tggagcatgt gcaggatcct    1140
cagaacactg ttaaggtcca gggtcttata tccagatggc caggsttcag atgattcacc    1200
ccaagcctgc agacttccgg aatcctggcc cagggcggca ccggctcatc actcaggttt    1260
atctctccca caccgcttgg acagaggcat gccaggtgga agtgaggctg ctgctggcct    1320
acaactccag tgctcgcatt ccaaaatgcc cctggatgga gggtggtgag atgtcaccac    1380
aggtggaaac cagcatcgag ggcaccattc ccttcagcaa gcctgtaaaa gtttatataa    1440
tgcccaaacc tgcacggcgc taaggcaaaa acagtcttcc caaccgtgcc tagagggccc    1500
ttcttaggtg tcagaatgag ccaagcctga agcacttcac ctggaattga tgtgtaggct    1560
taaggagtat gtgaccctta cagtctcatc tggtatcaaa cacaggataa attgtttctt    1620
cattaaaaaa taaaaaacct tcaagtctac ttacccttct cctgtccaca ataaagttga    1680
gaaaacac                                                            1688
```

```
<210> SEQ ID NO 22
<211> LENGTH: 2045
<212> TYPE: DNA
<213> ORGANISM: Homo sapiens
<220> FEATURE:
<221> NAME/KEY: SITE
<222> LOCATION: (2040)
<223> OTHER INFORMATION: n equals a,t,g, or c
<220> FEATURE:
<221> NAME/KEY: SITE
<222> LOCATION: (2041)
<223> OTHER INFORMATION: n equals a,t,g, or c

<400> SEQUENCE: 22
```

```
gagctctcgg ggtatcgagg aggcaggccc gcgggcgcac gggcgagcgg gccgggagcc     60
ggagcggcgg aggagccggc agcagcggcg cggcgrgctc caggcgaggc ggtcgacgct    120
cctgaaaact tgcgcgcgcg ctcgcccact gcgcccggag cgatgaagat ggtcgcgccc    180
tggacgcggt tctactccaa cagctgctgc ttgtgctgcc atgtccgcac cggcaccatc    240
ctgctcggcg tctggtatct gatcatcaat gctgtggtac tgttgatttt attgagtgcc    300
ctggctgatc cggatcagta taacttttca agttctgaac tgggaggtga ctttgagttc    360
atggatgatg ccaacatgtg cattgccatt gcgatttctc ttctcatgat cctgatatgt    420
gctatggcta cttacggagc gtacaagcaa cgcgcagctg ggatcatccc attcttctgt    480
taccagatct ttgactttgc cctgaacatg ttggttgcaa tcactgtgct tatttatcca    540
aactccattc aggaatacat acggcaactg cctcctaatt ttccctacag agatgatgtc    600
atgtgcagtg aatcctacct gtttggtcct tattattctt ctgtttatta gcattatctt    660 gactttttaag ggttacttga ttagctgtgt ttggaactgc taccgataca tcaatggtag    720
gaactcctct gatgtcctgg tttatgttac cagcaatgac actacggtgc tgctaccccc    780
gtatgatgat gccactgtga atggtgctgc caaggagcca ccgccacctt acgtgtctgc    840
ctaagccttc aagtgggcgg actgagggca gcagcttgac tttgcagaca tctgagcaat    900
agttctgtta tttcactttt gccatgagcc tctctgagct tgtttgttgc tgaaatgcta    960
ctttttaaaa tttagatgtt agattgaaaa ctgtagtttt caacatatgc tttgctrgaa   1020
cactgtgata gattaactgt agaattcttc ctgtacgatt ggggatataa yggcttcac   1080 taaccttccc taggcattga aacttccccc aaatctgatg gacctagaag tctgcttttg   1140
```

```
tacctgctgg gccccaaagt tgggcatttt tctctctgtt ccctctcttt tgaaaatgta      1200
aaataaaacc aaaaatagac aactttttct tcagccattc cagcatagag aacaaaacct      1260
tatggaaaca ggaatgtcaa ttgtgtaatc attgttctaa ttaggtaaat agaagtcctt      1320
atgtatgtgt tacaagaatt tcccccacaa catcctttat gactgaagtt caatgacagt      1380
ttgtgtttgg tggtaaagga ttttctccat ggcctgaatt aagaccatta gaaagcacca      1440
ggccgtggga gcagtgacca tctgctgact gttcttgtgg atcttgtgtc cagggacatg      1500
gggtgacatg cctcgtatgt gttagagggt ggaatggatg tgtttggcgc tgcatgggat      1560
ctggtgcccc tcttctcctg gattcacatc cccacccagg gccgcttttt actaagtgtt      1620
ctgccctaga ttggttcaag gaggtcatcc aactgacttt atcaagtgga attgggatat      1680
atttgatata cttctgccta acaacatgga aagggttttt cttttccctg caagctacat      1740
cctactgctt tgaacttcca agtatgtcta gtcacctttt aaaatgtaaa cattttcaga      1800
aaaatgagga ttgccttcct tgtatgcgct ttttaccttg actacctgaa ttgcaaggga      1860 ttttttatata ttcatatgtt acaaagtcag caactctcct gttggttcat tattgaatgt      1920
gctgtaaatt aagtygtttg caattaaaac aaggtttgcc cacatccaaa aaaaaaaaa       1980 aaaaaaaaaa aaaaaaaaaa aaaaaaaaaa aaaaaaaaaa aaaaaaaaaa aaaaaaaan      2040 naaaa                                                                   2045

<210> SEQ ID NO 23
<211> LENGTH: 1101
<212> TYPE: DNA
<213> ORGANISM: Homo sapiens

<400> SEQUENCE: 23
ttgtttgccg accgtcaata ttcccgcgcc tggacggtta aatagctaaa gctggcgcgg        60
ggctgtcacc tccgcctctg ctccccgacc cggccatgcg cggcctcggg ctctggctgc       120
tgggcgcgat gatgctgcct gcgattgccc ccagccggcc ctgggccctc atggagcagt       180
atgaggtcgt gttgccgygg cgtctgccag gcccccgagt ccgccgagct ctgccctccc       240
acttgggcct gcacccagag agggtgagct acgtccttgg ggccacaggg cacaacttca       300
ccctccacct gcggaagaac agggacctgc tgggytccgg ctacacagag acctatacgg       360
ctgccaatgg ctccgaggtg acggagcagc ctcgcgggca ggaccactgc ttytaccagg       420
gccacgtaga ggggtacccg gactcagccg ccagcctcag cacctgtgcc ggcctcaggg       480
gtttcttcca ggtggggtca gacctgcacc tgatcgagcc cctggatgaa ggtggcgagg       540
gcggacggca cgccgtgtac caggctgagc acctgctgca gacggccggg acctgcgggg       600
tcagcgacga cagcctgggc agcctcctgg accccggac ggcagccgtc ttcaggcctc       660
ggcccgggga ctctctgcca tcccgagaga cccgctacgt ggagctgtat gtggtcgtgg       720
acaatgcaga gttccagatg ctggggagcg aagcagccgt gcgtcatcgg gtgctggagg       780
tggtgaatca cgtggacaag ctatatcaga aactcaactt ccgtgtggtc ctggtgggcc       840
tggagatttg gaatagtcag gacaggttcc acgtcagccc cgaccccagt gtcacactgg       900
agaacctcct gacctggcar gcacggcaac ggacacggcg gcacctgcat gacaacgtac       960
agctcatcac gggtgtcgac ttcamcggga ctactgtggg gtttgccagg gtgtccacca      1020
tgtgctccca cagctcaggg gctgtgaacc aggaccacag caagaacccc gtgggcgtgg      1080
cctgcaccat ggcccatgag a                                                1101
```

<210> SEQ ID NO 24
<211> LENGTH: 1659
<212> TYPE: DNA
<213> ORGANISM: Homo sapiens

<400> SEQUENCE: 24

| | | | | | |
|---|---|---|---|---|---|
| ccgggctgca | ggattcggca | cgaggtggga | gccaagaaga | aaggtttgct | cccgggtgga | 60 |
| acagggatta | tcctcctcct | cccttaaga | gtcatgctca | agagagacac | tctggcaact | 120 |
| ttcctggcag | agattcactt | cccttttgatt | tccaggggca | ttcggggcct | ccttttgcaa | 180 |
| atgtagagga | gcattctttc | agctatggag | ctagagacgg | accgcatggt | gactatcgag | 240 |
| gaggggaggg | acctggacat | gatttcaggg | ggggagattt | tcgtcttct | gatttccaga | 300 |
| gcagagattc | atcacagttg | gacttcaggg | gtagggacat | acattctggg | gattttcggg | 360 |
| atagagaagg | accacctatg | gactataggg | gtggagatgg | tacttctatg | gattatagag | 420 |
| gtagggaggc | acctcatatg | aactacagag | acagggatgc | tcacgctgtt | gacttcagag | 480 |
| gtagggatgc | tcctccatct | gacttcaggg | gccggggcac | ttatgattta | gattttagag | 540 |
| gccgggatgg | atcccatgca | gattttaggg | gaagggattt | atcagatttg | gattttaggg | 600 |
| ccagagaaca | gtcccgttct | gattttagga | atagagatgt | atctgatttg | gactttagag | 660 |
| acaaagacgg | aacacaagta | gactttagag | gccgaggttc | aggtactact | gatctagact | 720 |
| ttagggacag | ggatacgcca | cattcagatt | tcagaggtag | acaccgatct | aggactgatc | 780 |
| aggattttag | gggcagagag | atgggatctt | gtatggaatt | taaagatagg | gagatgcccc | 840 |
| ctgtggatcc | aaatattttg | gattacattc | agccctctac | acaagataga | gaacattctg | 900 |
| gtatgaatgt | gaacaggaga | gaagaatcca | cacatgacca | tacgatagaa | aggcctgctt | 960 |
| ttggcattca | gaagggagaa | tttgagcatt | cagaaacaag | agaaggagaa | acacaaggtg | 1020 |
| tagcctttga | acatgagtct | ccagcagact | ttcagaacag | ccaaagtcca | gttcaagacc | 1080 |
| aagataagtc | acagctttct | ggacgtgaag | agcagagttc | agatgctggt | ctgtttaaag | 1140 |
| aagaaggcgc | tctggacttt | cttgggcggc | aagacaccga | ttacagaagc | atggagtacc | 1200 |
| gtgatgtgga | tcataggctg | ccaggaagcc | agatgtttgg | ctatggccag | agcaagtctt | 1260 |
| ttccagaggg | caaaactgcc | cgagatgccc | aacgggacct | tcaggatcaa | gattatagga | 1320 |
| ccggcccaag | tgaggagaaa | cccagcaggc | ttattcgatt | aagtggggta | cctgaagatg | 1380 |
| ccacaaaaga | agagattctt | aatgcttttc | ggactcctga | tggcatgcct | gtaaagaatt | 1440 |
| gcagttgaag | gagtataaca | caggttacga | ctatggctat | gtctgcgtgg | agttttcact | 1500 |
| cttggaagat | gccatcggat | gcatggaggc | caaccaggct | ggtgattagt | aactaaagca | 1560 |
| tatgctgtgg | aacatccagc | actgatgcca | gattacctgt | ccctaatact | gagcagaagc | 1620 |
| tggtgaatga | aacaggagat | ccctcagtca | aaacaaaaa | | | 1659 |

<210> SEQ ID NO 25
<211> LENGTH: 1329
<212> TYPE: DNA
<213> ORGANISM: Homo sapiens
<220> FEATURE:
<221> NAME/KEY: SITE
<222> LOCATION: (520)
<223> OTHER INFORMATION: n equals a,t,g, or c
<220> FEATURE:
<221> NAME/KEY: SITE
<222> LOCATION: (1140)
<223> OTHER INFORMATION: n equals a,t,g, or c

<400> SEQUENCE: 25

-continued

```
tctgttcctc tctcctggaa gcttgcagac ctcccttcag aaccaatccc aagaagccac      60
ctatccggaa caacacaagg atgctgccgg actggaagag stccttgatc ctcatggctt     120
acatcatcat cttcctcact ggcctccctg ccaacctcct ggccctgcgg gcctttgtgg     180
ggcggatccg ccagccccag cctgcacctg tgcacatcct cctgctgagc ctgacgctgg     240
ccgacctcct cctgctgctg ctgctgccct tcaagatcat cgaggctgcg tcgaacttcc     300
gctggtacct gcccaaggtc gtctgcgccc tcacgagttt tggsttctac agcagcatct     360
actgcagcac gtggctcctg gcgggcatca gcatcgagcg ctacctggga gtggctttcc     420
ccgtgcagta caagctctcc cgccggcctc tgtatggagt gattgcagct ctggtggcct     480
gggttatgtc ctttggtcac tgcaccatcg tgatcatcgn tcaatacttg aacacgactg     540
agcaggtcag aagtggcaat gaaattacct gctacgagaa cttcaccgat aaccagttgg     600
acgtggtgct gcccgtgmgg stggagctgt gcctggtgct cttcttcats cccatggcag     660
tcaccatctt ctgctactgg cgttttgtgt ggatcatgct ctcccagccc cttgtggggg     720
cccagaggcg gcgccgagcc gtggggctgg ctgtggtgac gctgctcaat ttcctggtgt     780
gcttcggacc ttacaacgtg tcccacctgg tggggtatca ccagagaaaa gcccctggt     840
ggcggtcaat agccgtgktg ttcagttcac tcaacgccag tctggacccc ctgctcttct     900
atttctcttc ttcagtggtg cgcagggcat ttgggagagg gctgcaggtg ctgcggaatc     960
agggctcctc cctgttggga cgcagaggca agacacagc agaggggaca aatgaggaca    1020
ggggtgtggg tcaaggagaa gggatgccaa gttcggactt cactacagag tagcagtttc    1080
cctggacctt cagaggtcgc ctgggttaca caggagctgg gaagcctggg agaggcggan    1140
caggaaggct cccatccaga ttcagaaatc cttagaccca gcccaggact gcgactttga    1200
aaaaaatgcc tttcaccagc ttggtatccc ttcctgactg aattgtccta ctcaaaggag    1260
cataagtcag agatgcacga agaagtagtt aggtatagaa gcacctgccg ggtgtggtgg    1320
ctcatgcct                                                           1329
```

<210> SEQ ID NO 26
<211> LENGTH: 700
<212> TYPE: DNA
<213> ORGANISM: Homo sapiens
<220> FEATURE:
<221> NAME/KEY: SITE
<222> LOCATION: (81)
<223> OTHER INFORMATION: n equals a,t,g, or c
<220> FEATURE:
<221> NAME/KEY: SITE
<222> LOCATION: (659)
<223> OTHER INFORMATION: n equals a,t,g, or c
<220> FEATURE:
<221> NAME/KEY: SITE
<222> LOCATION: (692)
<223> OTHER INFORMATION: n equals a,t,g, or c
<220> FEATURE:
<221> NAME/KEY: SITE
<222> LOCATION: (700)
<223> OTHER INFORMATION: n equals a,t,g, or c

<400> SEQUENCE: 26

```
ggcagagagc accatctgtc atggcggctg ggctgtttgg tttgagcgct cgccgtcttt      60
tggcggcagc ggcgacgcga ngggctcccg gccgccgcg tccgctggga atctagcttc     120
tccaggactg tggtcgcccc gtccgctgtg gcggraaagc ggcccccaga accgaccaca     180
ccgtggcaag aggacccaga acccgaggac gaaaacttgt atgagaagaa cccagactcc     240
```

```
catggttatg acaaggaccc cgttttggac gtctggaaca tgcgacttgt cttcttcttt      300
ggcgtctcca tcatcctggt ccttggcagc acctttgtgg cctatctgcc tgactacagg      360
tgcacagggt gtccaagagc gtgggatggg atgaaagagt ggtcccgccg cgaagctgag      420
aggcttgtga ataccgaga ggccaatggc cttcccatca tggaatccaa ctgcttcgac       480
cccagcaaga tccagctgcc agaggatgag tgaccagttg ctaagtgggg ctcaagaagc      540
accgccttcc ccaccccctg cctgccattc tgacctcttc tcagagcacc taattaaagg      600
ggctgaaagt ctgaaaaaaa aaaaaaaaaa aaaaaaaaaa aaaaaaaaaa aaaaaaaana      660
aaaaaaaaaa aaaaaaaaaa aaaaaaaaa anggggggn                             700
```

```
<210> SEQ ID NO 27
<211> LENGTH: 832
<212> TYPE: DNA
<213> ORGANISM: Homo sapiens
<220> FEATURE:
<221> NAME/KEY: SITE
<222> LOCATION: (821)
<223> OTHER INFORMATION: n equals a,t,g, or c
<220> FEATURE:
<221> NAME/KEY: SITE
<222> LOCATION: (825)
<223> OTHER INFORMATION: n equals a,t,g, or c

<400> SEQUENCE: 27
```

```
ggcacgagct ccactcggtt tctctctttg caggagcacc ggcagcacca gtgtgtgagg      60
ggagcaggca gcggtcctag ccagttcctt gatcctgcca gaccacccag cccctggcac     120
agagctgctc cacaggcacc atgaggatca tgctgctatt cacagccatc ctggccttca     180
gcctagctca gagctttggg gctgtctgta aggagccaca ggaggaggtg gttcctggcg     240
ggggccgcag caagagggat ccagatctct accagctgct ccagagactc ttcaaaagcc     300
actcatctct ggagggattg ctcaaagccc tgagccaggc tagcacagat cctaaggaat     360
caacatctcc cgagaaacgt gacatgcatg acttctttgt gggacttatg ggcaagagga     420
gcgtccagcc agactctcct acggatgtga atcaagagaa cgtccccagc tttggcatcc     480
tcaagtatcc cccgagagca gaataggtac tccacttccg gactcctgga ctgcattagg     540
aagacctctt tccctgtccc aatccccagg tgcgcacgct cctgttaccc tttctcttcc     600
ctgttcttgt aacattcttg tgctttgact ccttctccat cttttctacc tgaccctggt     660
gtggaaactg catagtgaat atccccaacc ccaatgggca ttgactgtag aatacctag      720 agttcctgta gtgtcctaca ttaaaaatat aatgtctctc tctattcctc aacaataaag     780 gattttttgca tatgaaaaaa aaaaaaaaaa aaaaaaaaaa naaanaaaaa aa            832
```

```
<210> SEQ ID NO 28
<211> LENGTH: 2361
<212> TYPE: DNA
<213> ORGANISM: Homo sapiens
<220> FEATURE:
<221> NAME/KEY: SITE
<222> LOCATION: (2361)
<223> OTHER INFORMATION: n equals a,t,g, or c

<400> SEQUENCE: 28
```

```
ggcacgaggc tccctaagcg gttgtcaccg ctggagacgg ttgggagaac cgttgtggcg      60
agcgctacac gaggcaaacg acttctccct tctttgaact ggaccccgcg agcaccagag     120
tcggcgtaac tatcgcctga caggcattta aatcaaacg tattgagatg gattgggtta      180
tgaaacataa tggtccaaat gacgctatga tgggacagta cgacttcgtg gactaccatt     240
```

```
tggttgcagc aaagaggaaa tagttcagtt ctttcaaggg ttggaaatcg tgccaatggg      300
ataacattga cgatggacta ccaggggaga agcacagggg aggccttcgt gcagtttgct      360
tcaaaggaga tagcagaaaa tgctctgggg aaacacaagg aaagaatagg gcacaggtat      420
attgagatct tcagaagtag caggagtgaa atcaaaggat tttatgatcc accaagaaga      480
ttgctgggac agcgaccggg accatatgat agaccaatag gaggaagagg gggttattat      540
ggagctgggc gtggaagtat gtatgacaga atgcgacgag gaggtgatgg atatgatggt      600
ggttatggag gttttgatga ctatggtggc tataataatt acggctatgg gaatgatggc      660
tttgatgaca gaatgagaga tggaagaggt atgggaggac atggctatgg tggagctggt      720
gatgcaagtt caggttttca tggtggtcat ttcgtacata tgagagggtt gccttttcgt      780
gcaactgaaa atgacattgc taatttcttc tcaccactaa atccaatacg agttcatatt      840
gatattggag ctgatggcag agcacaggag aagcagatgt agagtttgtg acacatgaag      900
atgcagtagc tgccatgtct aaagataaaa ataacatgca acatcgatat attgaactct      960
tcttgaattc tactcctgga ggcggctctg gcatgggagg ttctggaatg ggaggctacg     1020
gaagagatgg aatggataat cagggaggct atggatcagt tggaagaatg ggaatgggga     1080
acaattacag tggaggatat ggtactcctg atggtttggg tggttatggc cgtggtggtg     1140
gaggcagtgg aggttactat gggcaaggcg gcatgagtgg aggtggatgg cgtgggatgt     1200
actgaaagca aaaacaccaa catacaagtc ttgacaacag catctggtct actagacttt     1260
cttacagatt taatttcttt tgtatttaa gaactttata atgactgaag gaatgtgttt      1320
tcaaaatatt atttggtaaa gcaacagatt gtgatgggaa aatgttttct gtaggtttat     1380
ttgttgcata ctttgactta aaaataaatt tttatattca aaccactgat gttgatactt     1440
tttatatact agttactcct aaagatgtgc tgccttcata agatttgggt tgatgtatt      1500
tactattagt tctacaagaa gtagtgtggt gtaatttag aggataatgg ttcacctctg     1560
cgtaaactgc aagtcttaag cagacatctg aatagagct tgacaaataa ttagtgtaac      1620
tttttttcttt agttcctcct ggacaacact gtaaatataa agcctaaaga tgaagtggct     1680
tcaggagtat aaattcagct aattatttct atattattat ttttcaaatg tcatttatca     1740
ggcatagctc tgaaacattg atgatctaag aggtattgat ttctgaatat tcataattgt     1800
gttacctggg tatgagagtg ttggaagctg aattctagcc ctagattttg gagtaaaacc     1860
ccttcagcac ttgaccgaaa taccaaaaat gtctccaaaa aattgatagt tgcaggttat     1920
cgcaagatgt cttagagtag ggttaaggtt ctcagtgaca caagaattca gtattaagta     1980
cataggtatt tactatggag tataattctc acaattgtat tttcagtttt ctgcccaata     2040
gagtttaaat aactgtataa atgatgactt taaaaaaatg taagcaacaa gtccatgtca     2100
tagtcaataa aaacaatcct gcagttgggt tttgtatctg atccctgctt ggagttttag     2160
tttaaagaat ctatatgtag caaggaaaag gtgctttta attttaatcc ctttgatcaa      2220
tatggctttt ttccaaattg gctaatggat caaaatgaaa cctgttgatg tgaattcagt     2280
tattgaactt gttacttgtt tttgccagaa atgttattaa taaatgtcaa tgtgggagat     2340
aataaaaaaa aaaaaaaaa n                                                2361
```

<210> SEQ ID NO 29
<211> LENGTH: 879
<212> TYPE: DNA
<213> ORGANISM: Homo sapiens

<400> SEQUENCE: 29

```
ggaatctgca ccatgccctg ggttctgctc ctcctgaccc tcctcactca ctctgcagtg      60
tcagtggtcc aggcagggct gactcagccc ccctcggtgt ccaaggactt gagacagacc     120
gccacactca cctgcaccgg gaacaacaac aatgttggcg accaaggagc agcttggctg     180
cagcagcacc agggccaccc tcccaaactc ctgtcctaca ggaataataa ccggccctca     240
gggatctcag agagattatc tgcatccagg tcaggagcca catcctccct gaccattact     300
ggactccagc ctgaggacga ggctgactat tactgcgcag catatgacag cagcctcgca     360
gtttggatgt tcggcggagg gaccaagctg accgtcctag gtcagcccaa ggctgccccc     420
tcggtcactc tgttcccacc ctcctctgag gagcttcaag ccaacaaggc cacactggtg     480
tgtctcataa gtgacttcta cccgggagcc gtgacagtgg cctggaaggc agatagcagc     540
cccgtcaagg cgggagtgga gaccaccaca ccctccaaac agagcaacaa caagtacgcg     600
gccagcagct acctgagcct gacgcctgag cagtggaagt cccacagaag ctacagctgc     660
caggtcacgc atgaagggag caccgtggag aagacggtgg cccctacaga atgttcatag     720
gttcccaact ctaaccccac ccacgggagc ctggagctgc aggatcccag ggagggggtc     780
tctctcccca tcccaagtca tccagcccct ctccctgcac tcatgaaacc ccaataaata     840
ttctcattgt caatcagaaa aaaaaaaaaa aaaaaaaa                              879
```

<210> SEQ ID NO 30
<211> LENGTH: 1732
<212> TYPE: DNA
<213> ORGANISM: Homo sapiens

<400> SEQUENCE: 30

```
gttcggaggg aaacgtgtat tgtggtctca agmmttgccc cawattaacc tgtgccttcc      60
cagtctctgt tccagattcc tgctgccggg tatgcagagg agatggagaa ctgtcatggg     120
aacattctga tggtgatatc ttccggcaac ctgccaacag agaagcaaga cattcttacc     180
accgctctca ctatgatcct ccaccaagcc gacaggctgg aggtctgtcc cgctttcctg     240
gggccagaag tcaccgggga gctcttatgg attcccagca agcatcagga accattgtgc     300
aaattgtcat caataacaaa cacaagcatg acaagtgtgt gtttccaat ggaaagacct     360
attctcatgg cgagtcctgg cacccaaacc tccgggcatt tggcattgtg gagtgtgtgc     420
tatgtacttg taatgtcacc aagcaagagt gtaagaaaat ccactgcccc aatcgatacc     480
cctgcaagta tcctcaaaaa atagacggaa aatgctgcaa ggtgtgtcca agaacttc      540
caggccaaag ctttgacaat aaaggctact ctgcgggga agaaacgatg cctgtgtatg     600
agtctgtatt catggaggat ggggagacaa ccagaaaaat agcactggag actgagagac     660
cacctcaggt agaggtccac gtttggacta ttcgaaaggg cattctccag cacttccata     720
ttgagaagat ctccaagagg atgtttgagg agcttcctca cttcaagctg gtgaccagaa     780
caaccctgag ccagtggaag atcttcaccg aaggagaagc tcagatcagc cagatgtgtt     840
caagtcgtgt atgcagaaca gagcttgaag atttagtcaa ggttttgtac ctggagagat     900
ctgaaaaggg ccactgttag gcaagacaga cagtattgga tagggtaaag caagaaaact     960
caagctgcag ctggactgca ggcttatttt gcttaagtca acagtgccct aaaactccaa    1020
actcaaatgc agtcaattat tcacgccatg cacagcataa tttgctcctt tgtgtgtgtg    1080
tgtgtgtgtg tgtgtgtgtg tgtggtaaag gggggaaggt gttatgcggc tgctccctcc    1140
gtcccagagg tggcagtgat tccataatgt ggagactagt aactagatcc taaggcaaag    1200
```

```
aggtgtttct ccttctggat gattcatccc aaagccttcc cacccaggtg ttctctgaaa    1260
gcttagcctt aagagaacac gcagagagtt tccctagata tactcctgcc tccaggtgct    1320
gggacacacc tttgcaaaat gctgtgggaa gcaggagctg gggagctgtg ttaagtcaaa    1380
gtagaaaccc tccagtgttt ggtgttgtgt agagaatagg catagggta aagaggccaa     1440 gctgcctgta gttagtagag aagaatggat gtggttcttc ttgtgtattt atttgtatca    1500
taaacacttg gaacaacaaa gaccataagc atcatttagc agttgtagcc attttctagt    1560
taactcatgt aaacaagtaa gagtaacata acagtattac cctttcactg ttctcacagg    1620
acatgtacct aattatggta cttatttatg tagtcactgt atttctggat ttttaaatta    1680 ataaaaagt taattttgaa aaatcaaaaa aaaaaaaaa aaaaaactc ga               1732

<210> SEQ ID NO 31
<211> LENGTH: 3259
<212> TYPE: DNA
<213> ORGANISM: Homo sapiens

<400> SEQUENCE: 31
tttgcagtac gggccggatt tcccgggtcg acccacgcgt ccgcggaggc tacgtgaaga     60
gaggcgcggc gtgactgagc tacggttctg gctgcgtcct agaggcatcc ggggcagtaa    120
aaccgctgcg atcgcggagg cggcggccag gccgagaggc aggccgggca ggggtgtcgg    180 acgcagggc ctgggccggg tttcggcttc ggccacagct ttttttctca aggtgcaatg     240
aaagccttcc acactttctg tgttgtcctt ctggtgtttg ggagtgtctc tgaagccaag    300
tttgatgatt ttgaggatga ggaggacata gtagagtatg atgataatga cttcgctgaa    360
tttgaggatg tcatggaaga ctctgttact gaatctcctc aacgggtcat aatcactgaa    420
gatgatgaag atgagaccac tgtggagttg aagggcagg atgaaaacca agaaggagat     480
tttgaagatg cagataccca ggagggagat actgagagtg aaccatatga tgatgaagaa    540
tttgaaggtt atgaagacaa accagatact tcttctagca aaaataaaga cccaataacg    600
attgttgatg ttcctgcaca cctccagaac agctgggaga gttattatct agaaattttg    660
atggtgactg tctgcttgc ttatatcatg aattacatca ttgggaagaa taaaaacagt     720
cgccttgcac aggcctggtt taacactcat agggagcttt tggagagcaa ctttactttta   780 gtggggatg atggaactaa caaagaagcc acaagcacag gaaagttgaa ccaggagaat     840
gagcacatct ataacctgtg gtgttctggt cgagtgtgct gtgagggcat gcttatccag    900
ctgaggttcc tcaagagaca agacttactg aatgtcctgg cccggatgat gaggccagtg    960
agtgatcaag tgcaaataaa agtaaccatg aatgatgaag acatggatac ctacgtatt    1020 gctgttggca cacggaaagc cttggtgcga ctacagaaag agatgcagga tttgagtgag    1080
ttttgtagtg ataaacctaa gtctggagca aagtatggac tgccggactc tttggccatc    1140
ctgtcagaga tgggagaagt cacagacgga atgatggata caaagatggt tcactttctt    1200
acacactatg ctgacaagat tgaatctgtt catttttcag accagttctc tggtccaaaa    1260
attatgcaag aggaaggtca gcctttaaag ctacctgaca ctaagaggac actgttgttt    1320
acatttaatg tgcctggctc aggtaacact tacccaaagg atatggaggc actgctaccc    1380
ctgatgaaca tggtgattta ttctattgat aaagccaaaa agttccgact caacagagaa    1440
ggcaaacaaa aagcagataa gaaccgtgcc cgagtagaag agaacttctt gaaactgaca   1500
catgtgcaaa gacaggaagc agcacagtct cggcgggagg agaaaaaaag agcagagaag   1560
```

-continued

```
gagcgaatca tgaatgagga agatcctgag aaacagcgca ggctggagga ggctgcattg    1620
aggcgtgagc aaaagaagtt ggaaaagaag caaatgaaaa tgaaacaaat caaagtgaaa    1680
gcccatgtaa agccatccca gagatttgag ttctgatgcc acctgtaagc tctgaattca    1740
caggaaacat gaaaaacgcc agtccatttc tcaaccttaa atttcagaca gtcttgggca    1800
actgagaaat ccttatttca tcatctactc tgtttgggt ttgggtttta cagagattga    1860
agatacctgg aaagggctct gtttccaaga attttttttt ccagataatc aaattatttt    1920
gattatttta taaaggaat gatctatgaa atctgtgtag gttttaaata ttttaaaaat    1980
tataatacaa atcatcagtg cttttagtac ttcagtgttt aaagaaatac cgtgaaattt    2040
ataggtagat aaccagattg ttgcttttg tttaaaccaa gcagttgaaa tggctataaa    2100
gactgactct aaaccaagat tctgcaaata atgattggaa ttgcacaata aacattgctt    2160
gatgttttct atttcaggga cccagaacat aatgtagtgt atgtttttag gtgggagatg    2220
ctgataacaa aattaatagg aagtctgtag gcattaggat actgacatgt acatggaaaa    2280
ttctagggac aggagcatca ttttttcctt acctgatacc acgaaccagt gacaacgtga    2340
atgctgtatt ttaagtggtt gtatgtttat tttctggagt aacaaatgca tgaaaaatta    2400
atgcttcacc taggtaagat cattggtctg tgtgaaatca caaatgtttt ttccttcttg    2460
gttgctgcag cctggtggat gttcatggag aagctctgtt ctctatatta tggctgtgtg    2520
ccgttgcttc tccctctgct tttatctttt ccacagttga ggctgggtat gttctttcaa    2580
agaaatggcc atgaatatgt gtaagtatac ttttgaaaat gagcttcct aaactattga     2640 gagttctttc cacctcttgc ggaaccaact cttggaggag aggcccatgt atctgcacga    2700
gcacttagct tgttcagatc tctgcatttt ataaatgctt cttaccaaga aagcatttt    2760 aggtcattgc ttgtaccagg tatttttgc cggggatggg taagggttgg gttttctggt    2820
gggagtgggg tggtgggtat ttttgttga tgctttagtg caggcctgtt ctgaggcaat    2880
aacaagttgc tgtgaaaacg catgtgctgc tgccttgta actgccatgg aaactttca     2940 catgggtttt tctccaagtt aatacagaaa tatgtaaact gagagatgca aatgtaatat    3000
ttttaacagt tcatgaagtt gttattaaaa taactaacat aaaacttaat tactttaata    3060
ttatataatt atagtagtgg ccttgtttta caaacctta aattcattt tagaaatcaa      3120 agttgatagt cttagttatc ttttgagtaa gaaaagcttt cctaaagtcc catacatttg    3180
gaccatggca gctaattttg taacttaagc attcatatga actacctatg gacatctatt    3240
aaagtgattg acaaaaaaa                                                 3259
```

<210> SEQ ID NO 32
<211> LENGTH: 454
<212> TYPE: DNA
<213> ORGANISM: Homo sapiens

<400> SEQUENCE: 32

```
ggcacgaggt cttgtctgcg aagagtttac gaggtttcac ccactccttc attcttgaac      60 atgcttttc tctgcttatt accctccctg tttcctcctg ggctgccaac aacacattat     120
attacctcca tctgcaacca gagctgctac caccactgtg cccgagcctg aattttcata    180
gttatattaa aaaaaatcaa ggtgctggga ttacaggcgt gagccaccgc gcccggctgt    240
agcccctgtc tttattcctc ccctgtctaa cccgtcctca gcatgaatgc cagagttacc    300
tcttaaawta tgtcagggtg ctaggcacag tggctcatgc ctgtaatccc agctcttggg    360
aaggcagagg caggaggaca amttgagccc aggagtttga gacctgcttg gggaatgtag    420
```

```
tgagaccttg ttctccacaa aaaggaaaaa aaaa                                454
```

<210> SEQ ID NO 33
<211> LENGTH: 230
<212> TYPE: DNA
<213> ORGANISM: Homo sapiens
<220> FEATURE:
<221> NAME/KEY: SITE
<222> LOCATION: (26)
<223> OTHER INFORMATION: n equals a,t,g, or c
<220> FEATURE:
<221> NAME/KEY: SITE
<222> LOCATION: (219)
<223> OTHER INFORMATION: n equals a,t,g, or c

<400> SEQUENCE: 33

```
gctgctatgg ctgaactttt attgancgtg ttgtctgtgc agagcgctgt gcacgaggtg     60
gaagcaaacg agggaggaaa acaaagccac acccctgccc acagaggatg aacagaagg    120
gccgctgagg tcaggaaggc aaggttgcca ctaggtgtta ctgtggggcc cagatgccgc   180
catgctgttc acccttcaaa gggtggcatc tcagcccang cagtcctcct             230
```

<210> SEQ ID NO 34
<211> LENGTH: 753
<212> TYPE: DNA
<213> ORGANISM: Homo sapiens

<400> SEQUENCE: 34

```
ggcacgagga aaggctggcc tctcttcaac atgggatctt ctggactttt gagcctcctg    60
gtgctattcg tcctcttagc gaatgtccag ggacctggtc tgactgattg gttatttccc   120
aggagatgtc ccaaaatcag agaagaatgt gaattccaag aaagggatgt gtgtacaaag   180
gacagacaat gccaggacaa caagaagtgt tgtgtcttca gctgcggaaa aaaatgttta   240
gatctcaaac aagatgtatg cgaaatgcca aaagaaactg gcccctgcct ggcttatttt   300
cttcattggt ggtatgacaa gaaagataat acttgctcca tgtttgtcta tggtggctgc   360
cagggaaaca ataacaactt ccaatccaaa gccaactgcc tgaacacctg caagaataaa   420
cgctttccct gattggataa ggatgcactg gaagaactgc cagaatgtgg ctcatgctct   480
gagtactgtt cctgtacctg actgatgctc cagactggct tccagtttca ctctcagcat   540
tccaagatct tagcccttcc cagaacagaa cgcttgcatc tacctcctct tcctccatct   600
ttggctcttt tgatgcacaa tatccatccg ttttgatttc atctttatgt cccctttatc   660
tccaacttct agaactccca gtttatacct gtgtcactct caattttttc cagtaaagta   720
cttgatgtag taaaaaaaaa aaaaaaaaaa aaa                                753
```

<210> SEQ ID NO 35
<211> LENGTH: 1022
<212> TYPE: DNA
<213> ORGANISM: Homo sapiens

<400> SEQUENCE: 35

```
cgctcctgcc gccgggaccc tcgacctcct cagagcagcc ggctgccgcc ccgggaagat    60
ggcgaggagg agccgccacc gcctcctcct gctgctgctg cgctacctgg tggtcgccct   120
gggctatcat aaggcctatg gttttctgc cccaaaagac caacaagtag tcacagcagt   180
agwgtaccaa gaggctattt tagcctgcaa accccaaag aagactgttt sctccagatt    240
agagtggaag aaactgggtc ggagtgtctc ctttgtctac tatcaacaga ctcttcaagg   300
```

```
tgattttaaa aatcgagctg agatgataga tttcaatatc cggatcaaaa atgtgacaag    360
aagtgatgcg gggaaatatc gttgtgaagt tagtgcccca tctgagcaag gccaaaacct   420
ggaagaggat acagtcactc tggaagtatt agtggctcca gcagttccat catgtgaagt   480
accctcttct gctctgagtg gaactgtggt agagctacga tgtcaagaca aagaagggaa   540
tccagctcct gaatacacat ggtttaagga tggcatccgt ttgctagaaa atcccagact   600
tggctcccaa agcaccaaca gctcatacac aatgaataca aaaactggaa ctctgcaatt   660
taatactgtt tccaaactgg acactggaga atattcctgt gaagcccgca attctgttgg   720
atatcgcagg tgtcctggga aacgaatgca agtagatgat ctcaacataa gtggcatcat   780
agcagccgta gtagttgtgg ccttagtgat tccgttttgt ggccttggtg tatgctatgc   840
tcagaggaaa ggctactttt caaaagaaac ctccttccag aagagtaatt cttcatctaa   900
agccacgaca atgagtgaaa atgatttcaa gcacacaaaa tcctttataa tttaaagact   960
ccactttaga gatacaccaa agccaccgtt gttacacaag ttattaaact attataaaac  1020
tc                                                                 1022

<210> SEQ ID NO 36
<211> LENGTH: 3044
<212> TYPE: DNA
<213> ORGANISM: Homo sapiens
<220> FEATURE:
<221> NAME/KEY: SITE
<222> LOCATION: (2383)
<223> OTHER INFORMATION: n equals a,t,g, or c

<400> SEQUENCE: 36
ctctaagaac ctagtggatc cccccggcct gcaggaattc gggcacgagg ggagactgct    60
gtggctaagg agggcgggaa gggccctctg tggggctgcc attttggctg ggacctaaat   120
gcagtaaagg agcagctacg ggaatataga gagtgggggct tccaggcaga gaagcctgca   180
gtgcaaaggt ctgcagacaa cgacctgggc gtcttcaagg gacacaagga atcatattgc   240
cagaacacat tgtacaggta gccaggtgtc ggtctccagc ctgagaactc tggctgttgt   300
tccttgtgtc gtcccatatt cctgcctggc ctgcgatgga catcagcaag ggcctcccag   360
gcatgcaggg aggcctccac atatggatct ctgagaaccg gaagatggtg ccggtacccg   420
aggggggctta cgggaacttt ttcgaggaac actgctatgt catcctccac gtcccccaga   480
gcccgaaggy cacgcagggg gcgtccagcg acctgcacta ctgggtcggg aagcaggcgg   540
gtgcggaagc gcagggcgct gcggaggcct ccagcagcg cctacaggac gagctggggg   600
gccagaccgt gctgcaccgc gaggcgcagg gccacgagtc cgactgcttc tgcagctact   660
tccgcccggg aatcatctac aggaagggag gcctagcatc tgacctcaag catgtggaga   720
ccaacttgtt caacatccag cgactgctgc acatcaaagg gaggaagcac gtgtctgcca   780
ctgaggtgga gctctcctgg aacagcttta taagggtga catcttcctg ctggacctag   840
gcaagatgat gattcagtgg aatgggccca agaccagcat ttctgagaag gctcgggggc   900
tggycttgac ctacagcctc cgggacaggg aacgtggtgg tggtcgtgca cagattggtg   960
tggtggatga tgaggccaaa gccccggacc tcatgcagat catggaggct gtgctgggcc  1020
gcagggtggg cagmctgcgt gccgccacgc ccagcaagga tatcaaccag ctgcagaagg  1080
ccaatgttcg cctgtaccat gtctatgaga agggcaaaga cctggtggtc ctggagttgg  1140
cgacccccc actgacccag gacctgctgc aggaggagga cttctacatc ctggaccagg  1200
gtggcttcaa gatctatgtg tggcagggac gcatgtctag cctccaggag agaaaggctg  1260
```

```
ccttcagccg ggctgtgggc ttcatccagg ccaagggcta cccgacctac accaacgtgg    1320
aggtggtgaa cgacggcgcc gagtcggccg cgttcaagca gctcttccgg acttggtctg    1380
agaagcggcg caggaaccag aagctcggcg ggagggataa atcgattcat gtaaagctgg    1440
acgtgggcaa gctgcacacc cagcctaagt tagcggccca gctcaggatg gtggacgacg    1500
gctctgggaa ggtggaggtg tggtgcatcc aggacttaca caggcagccc gtggacccca    1560
agcgtcatgg acagctgtgt gcaggcaact gctaccttgt gctctacaca taccagaggc    1620
tgggccgtgt ccagtacatc ctgtacctat ggcagggcca ccaggccact gcggatgaga    1680
ttgaggccct gaacagcaac gctgaggaac tagatgtcat gtatggtggc gtcctagtac    1740
aggagcatgt gaccatgggc agcgagcccc cccacttcct cgccatcttc cagggccagc    1800
tggtgatctt ccaggagaga gctgggcacc acggaaaggg gcagtcagca tccaccacaa    1860
ggcttttcca agtgcaaggc actgacagcc acaacaccag gaccatggag gtgccagccc    1920
gtgcctcatc cctcaactcc agtgacatct tcttgctggt cacagccagc gtctgctacc    1980
tctggtttgg gaagggctgt aatggtgatc agcgtgagat ggcacgggtg gtggtcactg    2040
tcatttccag gaagaatgag gaaacggtgc tggagggtca ggagcctccc cacttctggg    2100
aggccctggg aggccgggsc ccctacccca gcaacaagag gctccctgag gaggtcccca    2160
gcttccagcc acgactgttt gagtgctcca gccacatggg ctgcctggtc ctcgcagaag    2220
tggggttctt cagccaggag gacctggaca agtatgacat catgttactg gacacctggc    2280
aggagatctt cctgtggctt ggggaagctg caagtgagtg gaaggaggcg gtggcctggg    2340
gccaggagta cctgaagact cacccagcag ggaggagccc ggncacaccc atcgtgctgg    2400
tcaagcaggg ccatgagcct cccaccttca ttggatggtt cttcacttgg gaccctaca    2460 agtggactag ccacccatcc acaaggaag tggtggatgg cagcccggca gcagcatcaa    2520
ccatctctga gataacagca gaagtcaaca acttccggct atccagatgg ccgggcaatg    2580
gcagggcagg tgccgtggcc ctgcaggccc tcaagggctc ccaggacagc tcagagaatg    2640
atctggtgcg aagccccaag tcggctggca gcagaaccag cagctccgtc agcagcacca    2700
gcgccacgat caacggggc ctgcgccggg aacaactgat gcaccaggct gttgaggacc    2760
tgccagaggg cgtggaccct gcccgcaggg agttctatct ctcagactct gacttccaag    2820
atatctttgg gaaatccaag gaggaattct acagcatggc cacgtggagg cagcggcagg    2880
agaaaaagca gctgggcttc ttctgaaccc aagccctctc gactgcccct atccctgga    2940 ccccaacata cctacaatgc tggggaggcc ctgcttccac tcccctcaga ggcttttggt    3000
catcctctgc gtgtcagtaa aagcaggcag cccataaaaa aaaa               3044
```

<210> SEQ ID NO 37
<211> LENGTH: 541
<212> TYPE: DNA
<213> ORGANISM: Homo sapiens
<220> FEATURE:
<221> NAME/KEY: SITE
<222> LOCATION: (420)
<223> OTHER INFORMATION: n equals a,t,g, or c
<220> FEATURE:
<221> NAME/KEY: SITE
<222> LOCATION: (486)
<223> OTHER INFORMATION: n equals a,t,g, or c
<220> FEATURE:
<221> NAME/KEY: SITE
<222> LOCATION: (530)
<223> OTHER INFORMATION: n equals a,t,g, or c

```
<400> SEQUENCE: 37
ttcaaggatt ataatatgct gagtaaactt ttggcactaa ggaagccagc tacaggccac      60
gtaatgaaaa ctattcagaa aacagttcag caaatactac tatttgaata cagttcaaat    120
cgtatttata taaatactct gcctacatta tttaacccaa actggattat tcaccattct    180
ttgaagatgc cttgtgtttt ctgttatcta cttctgctcg tgcagtttac ttacaccttc    240
acccttcaa atcctaactc ttcttcaagg cctgattcag attttaactt tttaaaggct     300
atctgaatca ttcaagggag aagataccct ttctctcata aaaacactta gagcaaacta    360
ccactattaa atcacttatt gcatactgaa aaaaaaaaa aaaaaactc gaagggggn       420
ccggtaccca attcgcccta tagtgagtcg tattacaatt cactgggccg tcgttttaca    480
acgtcntgac tgggaaaacc ctggcgttac ccaacttaat cgccttgcan cacatcccc     540
t                                                                     541

<210> SEQ ID NO 38
<211> LENGTH: 1752
<212> TYPE: DNA
<213> ORGANISM: Homo sapiens
<220> FEATURE:
<221> NAME/KEY: SITE
<222> LOCATION: (356)
<223> OTHER INFORMATION: n equals a,t,g, or c

<400> SEQUENCE: 38
gtcggcggcg gcggcggcgg ttgaactgac tcggagcgag gagacccgag cgagcagacg      60
cggccctggc gcccgccctg cgcactcacc atggcgatgc atttcatctt ctcagataca    120
gcggtgcttc tgtttgattt ctggagtgtc cacagtcctg ctggcatggc cctttcggtg    180
ttggtgctcc tgcttctggc tgtactgtat gaaggcatca aggttggcaa agcaagctgc    240
tcaaccaggt actggtgaac ctgccaacct ccatcagcca gcagaccatc gcagagacag    300
acggggactc tgcaggctca gattcattcc ctgttggcag aacccaccac aggtgntatt    360
tgtgtcactt tggccagtct ctaatccatg tcatccaggt ggtcatcggc tacttcatca    420
tgctggccgt aatgtcctac aacacctgga ttttccttgg tgtggtcttg ggctctgctg    480
tgggctacta cctagcttac ccacttctca gcacagctta gctggtgagg aacgtgcagg    540
cactgaggct ggagggacat ggagcccct cttccagaca ctatacttcc aactgccctt    600
tcttctgatg ctattcctc caccttattc ccagcccctg gaaactttga gctgaagcca    660
gcacttgctc cctggagttc ggaagccatt gcagcaacct tccttctcag ccagcctaca    720
tagggcccag gcatggtctt gtgtcttaag acagctgctg tgaccaaagg gagaatggag    780
ataacagggg tggcagggtt actgagccca tgacaatgct tctctgtgac tcaaaccagg    840
aatttccaaa gatttcaagc cagggagaag ggttcttggt gatgcagggc atggaacctg    900
gacaccctca gctctcctgc tttgtgcctt atctacagga gcatcgccca ttggacttcc    960
tgacctcttc tgtctttgag ggacagagac caagctagat cctttttctc acctttctgc   1020
ctttggaaca catgaagatc atctcgtcta tggatcatgt tgacaaacta agtttttttt   1080
attttcccca ttgaactcct agttggcaat tttgcacatt catacaaaaa aatttttaat   1140
gaaatgattt cattgattca tgatggatgg cagaaactgc tgagacctat ttccctttct   1200
tggggagaga ataagtgaca gctgattaaa ggcagagaca caggactgct ttcaggctcc   1260
tggtttattc tctgatagac tgagctcctt ccaccagaag gcactgcctg caggaagaag   1320
awgatctgat ggccgtgggt gtctgggaag ctcttcgtgg cctcaatgcc ctcctttatc   1380
```

-continued

| | |
|---|---|
| ctcatctttc ttctatgcag aacaaaaagc tgcatctaat aatgttcaat acttaatatt | 1440 |
| ctctatttat tacttactgc ttactcgtaa tgatctagtg gggaaacatg attcattcac | 1500 |
| ttaaaatact gattaagcca tggcaggtac tgactgaaga tgcaatccaa ccaaagccat | 1560 |
| tacattttt gagttagatg ggactstctg gatagttgaa cctcttcact ttataaaaaa | 1620 |
| ggaaagagag aaaatcactg ctgtatacta aatacctcac agattagatg aaaagatggt | 1680 |
| tgtaagcttt gggaattaaa aacaaacaaa tacattttag taaatatata tttttaaata | 1740 |
| aaaaaaagaa aa | 1752 |

<210> SEQ ID NO 39
<211> LENGTH: 1907
<212> TYPE: DNA
<213> ORGANISM: Homo sapiens

<400> SEQUENCE: 39

| | |
|---|---|
| agttcagggg cacaggggca caggcccacg actgcagcgg gatggaccag tactgcatcc | 60 |
| tgggccgcat cggggagggc gcccamggca tcgtcttcaa ggccaagcac gtggagactg | 120 |
| gcgagatagt tgccctcaag aaggtggccc taaggcggtt ggaagacggc ttccctaacc | 180 |
| aggccctgcg ggagattaag gctctgcagg aratggagga caatcagtat gtggtacaac | 240 |
| tgaaggctgt gttcccacac ggtggaggct ttgtgctggc ctttgagttc atgctgtcgg | 300 |
| atctggccga ggtggtgcgc catgcccaga ggccactagc ccaggcacag gtcaagagct | 360 |
| acctgcagat gctgctcaag ggtgtcgcct tctgccatgc caacaacatt gtacatcggg | 420 |
| acctgaaacc tgccaacctg ctcatcagcg cctcaggcca gctcaagata gcggactttg | 480 |
| gcctggctcg agtcttttcc ccagacggca gccgcctcta cacacaccag gtggccacca | 540 |
| ggagctcact gagctgccgg actacaacaa gatctccttt aaggagcagg tgcccatgcc | 600 |
| cctggaggag gtgctgcctg acgtctctcc ccaggcattg gatctgctgg gtcaattcct | 660 |
| tctctaccct cctcaccagc gcatcgcagc ttccaaggct ctcctccatc agtacttctt | 720 |
| cacagctccc ctgcctgccc atccatctga gctgccgatt cctcagcgtc taggggggacc | 780 |
| tgccccaag gcccatccag ggccccccca catccatgac ttccacgtgg accggcctct | 840 |
| tgaggagtcg ctgttgaacc cagagctgat tcggcccttc atcctggagg ggtgagaagt | 900 |
| tggccctggt cccgtctgcc tgctcctcag gaccactcag tccacctgtt cctctgccac | 960 |
| ctgcctggct tcaccctcca aggcctcccc atggccacag tgggcccaca ccacaccctg | 1020 |
| ccccttagcc cttgcgargg ttggtctcga ggcagaggtc atgttcccag ccaagagtat | 1080 |
| gagaacatcc agtcgagcag aggagattca tggcctgtgc tcggtgagcc ttaccttctg | 1140 |
| tgtgctactg acgtacccat caggacagtg agytctgctg ccagtcaagg cctgcatatg | 1200 |
| cagaatgacg atgcctgcct tggtgctgct tccccgagtg ctgcctcctg gtcaaggaga | 1260 |
| agtgcagaga gtaaggtgtc cttatgttgg aaactcaagt ggaaggaaga tttggtttgg | 1320 |
| ttttattctc agagccatta aacactagtt cagtatgtga gatatagatt ctaaaaacct | 1380 |
| caggtggctc tgccttatgt ctgttcctcc ttcatttctc tcaagggaaa tggctaaggt | 1440 |
| ggcattgtct catggctctc gttttttggg tcatggggag ggtagcacca ggcatagcca | 1500 |
| cttttgccct gagggactcc tgtgtgcttc acatcactga gcactcattt agaagtgagg | 1560 |
| gagacagaag tctaggccca gggatggctc cagttgggga tccagcagga gaccctctgc | 1620 |
| acatgaggct ggtttaccaa catctactcc ctcaggatga gcgtgagcca gaagcagctg | 1680 |

| | |
|---|---:|
| tgtatttaag gaaacaagcg ttcctggaat taatttataa atttaataaa tcccaatata | 1740 |
| atcccagcta gtgcttttc cttattataa tttgataagg tgattataaa agatacatgg | 1800 |
| aaggaagtgg aaccagatgc agaagaggaa atgatggaag gacttatggt atcagatacc | 1860 |
| aatatttaaa agtttgtata ataataaaga gtatgattgt ggttcaa | 1907 |

<210> SEQ ID NO 40
<211> LENGTH: 2350
<212> TYPE: DNA
<213> ORGANISM: Homo sapiens

<400> SEQUENCE: 40

| | |
|---|---:|
| gaagaagagc gacctgccct aatggatgac agaaagcaca aaatttgtag catgtatgac | 60 |
| aacttaaggg ggaaattgcc tggacaagag aggcctagtg atgaccactt tgtacagatc | 120 |
| atgtgtatcc gaaaagggaa gagaatggtt gcccgtattc ttcctttcct ctccacagag | 180 |
| caagcagctg acattctcat gacaacagcc aggaacctcc ctttccttat caagaaggat | 240 |
| gcacaagatg aggtgctgcc atgcttactg agtcccttct ctctccttct ctatcatctt | 300 |
| ccatcagtga gtatcaccag cctttttgcga cataatgaac ctacctcaaa gtgcagctac | 360 |
| accagcactc tccaatcctc acctcactgc tgtgctccag aacaagtttg gcctgtcact | 420 |
| gstcctcatc ctcctgagcc gtggtgaaga cctacagagt tcagaccctg ctacagaatc | 480 |
| aacacaaaat aatcagtgga cggaggtgat gttcatggca acacgagaac ttctgcggat | 540 |
| tccccaagca gccctggcca agccaatctc tatacctaca aacctagtgt ccctcttttc | 600 |
| tcgctatgtt gaccggcaga aactgaactt gctggagasa aaactgcagc tagttcaggg | 660 |
| gatacgataa aagatctcca aatgtgtcct gtacctcctt ttggctgcca cctgcactgc | 720 |
| tgccatcacc aatggrgtgt ttaatgag ggaaggaagg tagctttttc cccaaagcaa | 780 |
| agkmttgtgg gatcgattcc tgtttacagg ggttgtctct ctaaatgtca gatatttccc | 840 |
| cactgctcta tgaaatttgg ctgggtgata cttctgctgg tttctttacc ttctgtgtta | 900 |
| cagttctgca tgtcctactt ttactcagtt ctgttttgca tttwctttgc cctagagaca | 960 |
| caagtgtaat ctctcccttt atccctccac tactccacct cagagtagat tgtagcctgc | 1020 |
| caaaggattc cttccctcat cctattgaag ttgttttttc attgccccat attaatatga | 1080 |
| ctatagaaga gccaattaag tagaaatcaa gatatacaca cacacataga tacacacaca | 1140 |
| cacaccccat acatgtattt atgtggtctt cagagggtcc ttaaagaatg aatttttagat | 1200 |
| tgaaaaatat ttagttgtct cattacctct tctaaacaca aaccagctga tgtattttaa | 1260 |
| tctgtttctg ttctatcttg taattaattt ggtgggttct acttgttta acataaataa | 1320 |
| agagtatgca gcacgtttaa taaaatcaga actcttaatt ggcttatgcc caggtctagg | 1380 |
| ctgagaagtc cttttcttc ttcccacctt tatttcctta gtttctgtcc accttaatcg | 1440 |
| aaacaacaca tggttatgtc ttttttcctgc tacaactaca gggtacttga gcctttcccc | 1500 |
| tcaagtgcat tcgaagtcac ccaggatgat cctcactagt agcctgcttt ggcagtgtgg | 1560 |
| cttttttgcac acttgccctg tcttcctgag actacttcag taagccatgc ttccttcttc | 1620 |
| cccactttta tttggtgtca tgaatagaaa cttccaaatg taaccatgga agctaagttt | 1680 |
| ggcctgcttt gctttttagt ctccacacca tgggcagaac tgctgtctt actacttcat | 1740 |
| ctcacccaag tccgttccc aggcagccar gggcctgggt tttgaataat tgcaagggcc | 1800 |
| agcctgccat gatctttctc acttactcct ctcccattca gcaatcaacc agactaagga | 1860 |
| gttttgatcc ctagtgatta cagccctgaa gaaaattaaa tctgaattaa ttttacatgg | 1920 |

```
ccttcgtgat ctttctgctg ttcttacttt ttcgaatgta gttgggggt gggagggaca     1980 ggttatggta tttaaagaga ataaacattt tgcacataca tgtattgtac aacagtaaga     2040
tcctctgtta aaaccagctg tcctgttctc catctccatt tcttcccatg ctgtaacccc     2100
aggctccacc agctgttccc cagtgatgtt acctagcttc cctctaccgt tgtctactga     2160
ccatttccac tacatgcctt tcctaccttc ccttcacaac caatcaagtg aatacttgat     2220
tattatctct tccttactgt gctttatctt ttttgtttgg attggttcta attaatgaaa     2280
ataaaagttt ctaaatttac atttttatag ggtattgtaa ataaaaacaa attgtatact    2340
taaaaaaaaa                                                            2350
```

<210> SEQ ID NO 41
<211> LENGTH: 1114
<212> TYPE: DNA
<213> ORGANISM: Homo sapiens

<400> SEQUENCE: 41

```
gggcagacga tgctgaagat gctctccttt aagctgctgc tgctggccgt ggctctgggc       60
ttctttgaag gagatgctaa gtttggggaa agaaacgaag ggagcggaca aggaggagaa      120
ggtgcctgaa tgggaacccc ccgaagcgcc tgaaaaggag agacaggagg atgatgtccc      180
agctggagct gctgagtggg ggagagatgc tgtgcggtgg cttctaccct cggctgtcct      240
gctgcctgcg gagtgacagc ccggggctag ggcgcctgga gaataagata ttttctgtta      300
ccaacaacac agaatgtggg aagttactgg aggaaatcaa atgtgcactt tgctctccac      360
attctcaaag cctgttccac tcacctgaga gagaagtctt ggaaagagac ctagtacttc      420
ctctgctctg caaagactat tgcaaagaat tcttttacac ttgccgaggc catattccag      480
gtttccttca aacaactgcg gatgagtttt gcttttacta tgcaagaaaa gatggtgggt      540
tgtgctttcc agattttcca agaaaacaag tcagaggacc agcatctaac tacttggacc      600
agatggaaga atatgacaaa gtggaagaga tcagcagaaa gcacaaacac aactgcttct      660
gtattcagga ggttgtgagt gggctgcggc agcccgttgg tgccctgcat agtggggatg      720
gctcgcaacg tctcttcatt ctggaaaaag aaggttatgt gaagatactt accccctgaag     780 gagaaatttt caaggagcct tatttggaca ttcacaaact tgttcaaagt ggaataaagg      840
ttggcttttt aaattttatt tattttttgtg ctggctacgt taattttatt ttagtgttac     900
cttcctcact gaaggtattt ctttgtaata aagaaagaa tcttgcagga gaaaataagg       960
gggcaacata agaaacaata attatggcac ctgaattagg acagtgacat taaakgttgg     1020
ctktttawat tttaaaaaaa aaaaaaaaaa aaaaaaaaaa aaaaaaaaaa aaaaaaaaaa     1080
aaaaaaaaaa aaaaaaaaaa aaaaaaaaaa aaaa                                 1114
```

<210> SEQ ID NO 42
<211> LENGTH: 1652
<212> TYPE: DNA
<213> ORGANISM: Homo sapiens
<220> FEATURE:
<221> NAME/KEY: SITE
<222> LOCATION: (1640)
<223> OTHER INFORMATION: n equals a,t,g, or c
<220> FEATURE:
<221> NAME/KEY: SITE
<222> LOCATION: (1644)
<223> OTHER INFORMATION: n equals a,t,g, or c
<220> FEATURE:
<221> NAME/KEY: SITE
<222> LOCATION: (1648)

<223> OTHER INFORMATION: n equals a,t,g, or c

<400> SEQUENCE: 42

```
ttggcacctc taattgctct cgtgtattcg gtgccgcgac tttcacgatg gctcgcccaa      60
ccttactacc ttctgtcggc cctgctctct gctgccttcc tactcgtgag gaaactgccg     120
ccgctctgcc acggtctgcc cacccaacgc gaagacggta acccgtgtga ctttgactgg     180
agagaagtgg agatcctgat gtttctcagt gccattgtga tgatgaagaa ccgcagatcc     240
atcactgtgg agcaacatat aggcaacatt ttcatgttta gtaaagtggc caacacaatt     300
cttttcttcc gcttggatat tcgcatgggc ctactttaca tcacactctg catagtgttc     360
ctgatgacgt gcaaaccccc cctatatatg ggscctgagt atatcaagta cttcaatgat     420
aaaaccattg atgaggaact agaacgggac aagagggtca cttggattgt ggagttcttt     480
gccaattggt ctaatgactg ccaatcattt gcccctatct atgctgacct ctcccttaaa     540
tacaactgta cagggctaaa ttttgggaag gtggatgttg gacgctatac tgatgttagt     600
acgcggtaca aagtgagcac atcacccctc accaagcaac tccctaccct gatcctgttc     660
caaggtggca aggaggcaat gcggcggcca cagattgaca agaaaggacg ggctgtctca     720
tggaccttct ctgaggagaa tgtgatccga gaatttaact taaatgagct ataccagcgg     780
gccaagaaac tatcaaaggc tggagacaat atccctgagg agcagcctgt ggcttcaacc     840
cccaccacag tgtcagatgg ggaaaacaag aaggataaat aagatcctca ctttggcagt     900
gcttcctctc ctgtcaattc caggctcttt ccataaccac aagcctgagg ctgcagcytt     960
ttatttatgt tttcccttg gctgtgactg ggtggggcag catgcagctt ctgattttaa    1020
agaggcatct agggaattgt caggcaccct acaggaaggc ctgccatgct gtggccaact    1080
gtttcactgg agcaagaaag agatctcata ggacggaggg ggaaatggtt tccctccaag    1140
cttgggtyag tgtgttaact gcttatcagc tattcagaca tctccatggt ttctccatga    1200
aactctgtgg tttcatcatt ccttcttagt tgacctgcac agcttggtta gacctagatt    1260
taaccctaag gtaagatgct ggggtataga acgctaagaa ttttcccca aggactcttg    1320
cttccttaag cccttctggc ttcgtttatg gtcttcatta aagtataag cctaactttg    1380
tcgctagtcc taaggagaaa cctttaacca caaagtttttt atcattgaag acaatattga    1440
acaaccccct attttgtggg gattgagaag gggtgaatag aggcttgaga cttttccttg    1500
tgtggtagga cttggaggag aaatcccctg gactttcact aaccctctga catactcccc    1560
acacccagtt gatggctttc cgtaataaaa agattgggat ttcctttga aaaaaaaaa    1620
aaaaaggggg ccgctctagn ggtnccangc tt                                1652
```

<210> SEQ ID NO 43
<211> LENGTH: 1473
<212> TYPE: DNA
<213> ORGANISM: Homo sapiens

<400> SEQUENCE: 43

```
ggcacgagcc gcggggctgt cacctccgcc tctgctcccc gacccggcca tgcgcggcct      60
cgggctctgg ctgctgggcg cgatgatgct gcctgcgatt gccccagcc ggccctgggc     120
cctcatggag cagtatgagg tcgtgttgcc gtggcgtctg ccaggccccc gagtccgccg     180
agctctgccc tcccacttgg gcctgcaccc agagagggtg agctacgtcc ttggggccac     240
agggcacaac ttcaccctcc acctgcggaa gaacaggac ctgctgggct ccggctacac     300
agagacctat acggctgcca atggctccga ggtgacggag cagcctcgcg ggcaggacca     360
```

```
ctgcttctac cagggccact tagagggtac cggactcagc cgccagcctc agcacctgtg    420
ccggcctcag gggtttcttc caggtggggt cagacctgca cctgatcgag ccctggatg    480 aaggtggcga gggcggacgg cacgccgtgt accaggctga gcacctgctg cagacggccg    540
ggacctgcgg ggtcagcgac gacagcctgg gcagcctcct gggacccggg acggcagccg    600
tcttcaggcc tcggcccggg gactctctgc catcccgaga gacccgctac gtggagctgt    660
atgtggtcgt ggacaatgca gagttccaga tgctggggag cgaagcagcc gtgcgtcatc    720
gggtgctgga ggtggtgaat cacgtggaca agctatatca gaaactcaac ttccgtgtgg    780
tcctggtggg cctggagatt tggaatagtc aggacaggtt ccacgtcagc cccgacccca    840
gtgtcacact ggagaacctc ctgacctggc aggcacggca acggacacgg cggcacctgc    900
atgacaacgt acagctcatc acgggtgtcg acttcaccgg gactactgtg gggtttgcca    960
gggtgtccgc catgtgctcc cacagctcag ggctgtgaa ccaggaccac agcaagaacc    1020
ccgtgggcgt ggcctgcacc atggcccatg agatgggcca caacctgggc atggaccatg    1080
atgagaacgt ccagggctgc cgctgccagg aaacgcttcg aggccggccg ctgcatcatg    1140
gcaaggccag cattggctcc cagtttcccc aggatgttca gtgactgcag ccaggcctac    1200
ctggagagct ttttgagcg gccgcagtcg gtgtgcctcg ccaacgcccc tgacctcagc    1260
cacctggtgg gcggccccgt gtgtgggaac ctgtttgtgg agcgtgggga gcagtgcgac    1320 tgcggcccc cgaggactg ccggaaccgc tgctgcaact ctaccacctg ccagctggct    1380
gagggggccc agtgtgcgca cggtacctgc tgccaggagt gcaaggtgaa gccggctggt    1440
gagctgtgcc gtcccaagaa ggacatgtgt gac    1473
```

<210> SEQ ID NO 44
<211> LENGTH: 772
<212> TYPE: DNA
<213> ORGANISM: Homo sapiens

<400> SEQUENCE: 44

```
tcggtttctc tctttgcagg agcaccggca gcaccagtgt gtgagggag caggcagcgg    60 tcctagccag ttccttgatc ctgccagacc acccagcccc tggcacagag ctgctccaca    120
ggcaccatga ggatcatgct gctattcaca gccatcctgg ccttcagcct agctcagagc    180
tttggggctg tctgtaagga gccacaggag gaggtggttc ctggcggggg ccgcagcaag    240
agggatccag atctctacca gctgctccag agactcttca aaagccactc atctctggag    300
ggattgctca aagccctgag ccaggytagc acagatccta aggaatcaac atctcccgag    360
aaacgtgaca tgcatgactt cttttgtggga yttatgggca agaggagcgt ccagccagac    420
tctcctacgg atgtgaatca agagaacgtc cccagctttg gcatcctcaa gtatccccg    480 agagcagaat aggtactcca cttccggact cctggactgc attaggaaga cctctttccc    540
tgtcccaatc cccaggtgcg cacgctcctg ttacccttc tcttccctgt tcttgtaaca    600
ttcttgtgct tgactccttt ctccatcttt tctacctgac cctggtgtgg aaactgcata    660
gtgaatatcc ccaaccccaa tgggcattga ctgtagaata ccctagagtt cctgtagtgt    720
cctacattaa aaatataatg tctctctcta ttcctcaaca aataaaggat tt    772
```

<210> SEQ ID NO 45
<211> LENGTH: 403
<212> TYPE: DNA
<213> ORGANISM: Homo sapiens
<220> FEATURE:

```
<221> NAME/KEY: SITE
<222> LOCATION: (15)
<223> OTHER INFORMATION: n equals a,t,g, or c

<400> SEQUENCE: 45
aattcggcac gagcntggaa tgggaggcta cggaagagat ggaatggata atcagggagg      60
ctatggwtca kttggaagaw tgggaatggg gaacaattac agtggaggat atggtactcc    120
tgatggtttg ggtggttatg gccgtggtgg tggaggcagt ggaggttact atgggcaagg    180
cggcatgagt ggaggtggat ggcgtgggat gtactgaaag caaaaacacc aacatacaag    240
tcttgacaac agcatctggt ctactagact ttcttacaga tttaatttct tttgtatttt    300 aagaactta taatgactga aggaatgtgt tttcaaaata ttatttggta aagcaacaga    360
ttgtgatggg gaaaaaaaaa aaaaaagaa ttcaaaaagc ttc                         403

<210> SEQ ID NO 46
<211> LENGTH: 928
<212> TYPE: DNA
<213> ORGANISM: Homo sapiens
<220> FEATURE:
<221> NAME/KEY: SITE
<222> LOCATION: (49)
<223> OTHER INFORMATION: n equals a,t,g, or c
<220> FEATURE:
<221> NAME/KEY: SITE
<222> LOCATION: (78)
<223> OTHER INFORMATION: n equals a,t,g, or c
<220> FEATURE:
<221> NAME/KEY: SITE
<222> LOCATION: (148)
<223> OTHER INFORMATION: n equals a,t,g, or c
<220> FEATURE:
<221> NAME/KEY: SITE
<222> LOCATION: (163)
<223> OTHER INFORMATION: n equals a,t,g, or c
<220> FEATURE:
<221> NAME/KEY: SITE
<222> LOCATION: (532)
<223> OTHER INFORMATION: n equals a,t,g, or c

<400> SEQUENCE: 46
cctctcgcta attacccaa ttggccaaaa gggggatgtt gcctgcaang ccaattaaat      60
ttgggtaaac cccaggntt ttccccaagt ccacgacgtt gtaaaaaacg acggcccaat    120
tgaaattgtw aaaaacsaac ycactaanag ggccaawtgg gtnacsgggc cccccccga    180 rtttttttttt ttttttttt ctgrttgwca atgagratat ttattgaggg tttattgagt    240
gcagggagaa gggctkgatg mcttgggrtg ggaggagaga cccctcccct gggatcctgc    300
agctcyagkc tcccgtgggt gggggtkagr gttgrgaacc tatgaacatt ctgtaggggc    360
cactgtcttc tccacggtgc tcccttcatg cgtgacctgg cagctgtagc ttctgtggga    420
cttccactgc tcrggcgtca ggctcaggta gctgctggcc gcgtacttgt tgttgctytg    480
tttggagggt ktggtggtct ccactcccgc cttgacgggg ctgcyatctg cnttccaggc    540
cactgtcacr gctcccgggt agaagtcact katsagacac acyagtgtgg ccttgttggc    600
ttgragctcc tcagaggagg gcgggaacag agtgacmgwg gggkyrgcct tgggctgacc    660
taggacggtg accttggtcc cagttccgaa gacmccatga ttaccactgc tgtctgttga    720
gtaacagtag tagtcagccg catcctccac ctgggcccca ctgatagtca aggtggccac    780
tgtccctgar ctggagccar agaatctcts agggatccgg agggtcgttt gttgtcctca    840
tagatgacca ggcacagggg cctggcctga cttctgktgg taccaatawa catatttctt    900
cggcaatgca tctccaggag caggtgat                                       928
```

<210> SEQ ID NO 47
<211> LENGTH: 885
<212> TYPE: DNA
<213> ORGANISM: Homo sapiens

<400> SEQUENCE: 47

| | | | | | |
|---|---|---|---|---|---|
| ggcacgaggg | aatctgcacc | atgccctggg | ttctgctcct | cctgaccctc | ctcactcact | 60 |
| ctgcagtgtc | agtggtccag | gcagggctga | ctcagccccc | ctcggtgtcc | aaggacttga | 120 |
| gacagaccgc | cacactcacc | tgcaccggga | acaacaacaa | tgttggcgac | caaggagcag | 180 |
| cttggctgca | gcagcaccag | ggccacccctc | ccaaactcct | gtcctacagg | aataataacc | 240 |
| ggccctcagg | gatctcagag | agattatctg | catccaggtc | aggagccaca | tcctccctga | 300 |
| ccattactgg | actccagcct | gaggacgagg | ctgactatta | ctgcgcagca | tatgacagca | 360 |
| gcctcgcagt | ttggatgttc | ggcggaggga | ccaagctgac | cgtcctaggt | cagcccaagg | 420 |
| ctgcccctc | ggtcactctg | ttcccaccct | cctctgagga | gcttcaagcc | aacaaggcca | 480 |
| cactggtgtg | tctcataagt | gacttctacc | cgggagccgt | gacagtggcc | tggaaggcag | 540 |
| atagcagccc | cgtcaaggcg | ggagtggaga | ccaccacacc | ctccaaacaa | agcaacaaca | 600 |
| agtacgcggc | cagcagctac | ctgagcctga | cgcctgagca | gtggaagtcc | cacaaaagct | 660 |
| acagctgcca | ggtcacgcat | gaagggagca | ccgtggagaa | gacagtggcc | cctacagaat | 720 |
| gttcataggt | tctcatccct | cacccccac | cacgggagac | tagagctgca | ggatcccagg | 780 |
| ggagggtct | ctcctcccac | cccaaggcat | caagcccttc | tccctgcact | caataaaccc | 840 |
| tcaataaata | ttctcattgt | caatcagaaa | aaaaaaaaa | aaaaa | | 885 |

<210> SEQ ID NO 48
<211> LENGTH: 2315
<212> TYPE: DNA
<213> ORGANISM: Homo sapiens
<220> FEATURE:
<221> NAME/KEY: SITE
<222> LOCATION: (2264)
<223> OTHER INFORMATION: n equals a,t,g, or c
<220> FEATURE:
<221> NAME/KEY: SITE
<222> LOCATION: (2312)
<223> OTHER INFORMATION: n equals a,t,g, or c
<220> FEATURE:
<221> NAME/KEY: SITE
<222> LOCATION: (2315)
<223> OTHER INFORMATION: n equals a,t,g, or c

<400> SEQUENCE: 48

| | | | | | |
|---|---|---|---|---|---|
| tttttttttt | tttgatttt | caaaattaac | ttttttatta | atttaaaaat | ccagaaatac | 60 |
| agtgactaca | taaataagta | ccataattag | gtacatgtcc | tgtgagaaca | gtgaagggt | 120 |
| aatactgtta | tgttactctt | acttgtttac | atgagttaac | tagaaaatgg | ctacaactgc | 180 |
| taaatgatgc | ttatggtctt | tgttgttcca | agtgtttatg | atacaaataa | atacacaaga | 240 |
| agaaccacat | ccattcttct | ctactaacta | caggcagctt | ggcctctta | ccctatgtcc | 300 |
| tattctctac | acaacaccaa | acactggagg | gttctactt | tgacttaaca | cagctcccca | 360 |
| gctcctgctt | cccacagcat | tttgcaaagg | tgtgtcccag | cacctggagg | caggagtata | 420 |
| tctagggaaa | ctctctgcgt | gttctcttaa | ggctaagctt | tcagagaaca | cctgggtggg | 480 |
| aaggctttgg | gatgaatcat | ccagaaggag | aaacacctct | ttgccttagg | atctagttac | 540 |
| tagtctccac | attatggaat | cactgccacc | tctgggacgg | agggagcagc | cgcataacac | 600 |

-continued

```
cttcccccct ttaccacaca cacacacaca cacacacaca cacacacaaa ggagcaaatt      660
atgctgtgca tggcgtgaat aattgactgc atttgagttt ggagttttag ggcactgttg      720
acttaagcaa aataagcctg cagtccagct gcagcttgag ttttcttgct ttaccctatc      780
caatactgtc tgtcttgcct aacagtggcc cttttcagat ctctccaggt acaaaacctt      840
gactaaatct tcaagctctg ttctgcatac acgacttgaa cacatctggc tgatctgagc      900
ttctccttcg gtgaagatct tccactggct cagggttgtt ctggtcacca gcttgaagtg      960
aggaagctcc tcaaacatcc tcttggagat cttctcaata tggaagtgct ggagaatgcc     1020
ctttcgaata gtccaaacgt ggacctctac ctgaggtggt ctctcagtct ccagtgctat     1080
ttttctggtt gtctccccat cctccatgaa tacagactca tacacaggca tcgtttcttc     1140
cccgcagaag tagcctttat tgtcaaagct ttggcctgga agttcttctg gacacacctt     1200
gcagcatttt ccgtctattt tttgaggata cttgcagggg tatcgattgg ggcagtggat     1260
tttcttacac tcttgcttgg tgacattaca agtacatagc acacactcca caatgccaaa     1320
tgcccggagg tttgggtgcc aggactcgcc atgagaatag gtctttccat tggaaacaca     1380
cacttgtcca tgcttgtgtt tgttattgat gacaatttgc acaatggttc ctgatgcttg     1440
ctgggaatcc ataagagctc cccggtgact tctggcccca ggaaagcggg acagacctcc     1500
agcctgtcgg cttggtggag gatcatagtg agagcggtgg taagaatgtc ttgcttctct     1560
gttggcaggt tgccggaaga tatcaccatc agaatgttcc catgacagtt ctccatctcc     1620
tctgcatacc cggcagcagg aatctggaac agagactggg aaggcacagg ttaatttggg     1680
gcaagtcttg agaccacaat acacgtttcc ctccgaacag ctgcactggg tgcattgatt     1740
gggttgccga ttctgaaaga gcccttcagc tacgaacagc tctccatgtt ggtaagttgt     1800
cccattgtac tcgcaagact tgctggtcac cttattgttc actgggggta aggagtcttc     1860
tgggcagcga gggcagcaca gatgaggaat atgcacagga gaaaggcaat gaacatttgg     1920
acatctgact cggctgcaaa gcacattccc attctctgag cagatgcagt tcacgcagta     1980
aaccaaccca taaggttcca ggtaaggatg ccatctctca cccactctgt acttcttgtc     2040
ttgaaacatg caatatgtct ctgaatgttt tacttgctct gtttkgcctc cttctagcaa     2100
aagaaagctc gtgccgaatt cctgcagccc gggggatcc actagttcta gagcggccgc      2160
caccgcggtg ggagctccag cttttggttc cctttagtga ggggttaatt tcgagcttgg     2220
cggtaatcat gggtcatagc ttgtttcctg gtgttgaaat tggntatccc gctcacaaat     2280
tccacaacaa caatacgagc cggaagcata angtn                                2315
```

<210> SEQ ID NO 49
<211> LENGTH: 3175
<212> TYPE: DNA
<213> ORGANISM: Homo sapiens

<400> SEQUENCE: 49

```
tttttttgt caatcacttt aatagatgtc cataggtagt tcatatgaat gcttaagtta       60
caaaattagc tgccatggtc caaatgtatg ggactttagg aaagcttttc ttactcaaaa      120
gataactaag actatcaact ttgatttcta aaatgtaatt taaggtttg taaacaagg       180 ccactactat aattatataa tattaaagta attaagtttt atgttagtta ttttaataac      240
aacttcatga actgttaaaa atattacatt tgcatctctc agtttacata tttctgtatt      300
aacttggaga aaaacccatg tgaaaagttt ccatgcagtt acaaaggcag cagcacatgc      360
tgttttcaca gcaacttgtt attgcctcag aacaggcctg cactaaagca tcaacaaaaa     420
```

```
atacccacca ccccactccc accagaaaac ccaaccctta cccatcccg gcaaaaatta      480 cctggtacaa gcaatgacct aaaaatgctt tcttggtaag aagcatttat aaaatgcaga     540
gatctgaaca agctaagtgc tcgtgcagat acatgggcct ctcctccaag agttggttcc    600
gcaagaggtg gaaagaactc tcaatagttt aggaaagctc attttcaaaa gtatacttac    660
acatattcat ggccatttct ttgaaagaac atacccagcc tcaactgtgg aaaagataaa    720
agcagaggga gaagcaacgg cacacagcca taatatagag aacagagctt ctccatgaac    780
atccaccagg ctgcagcaac caagaaggaa aaaacatttg tgatttcaca cagaccaatg    840
atcttaccta ggtgaagcat taattttca tgcatttgtt actcaagaaa ataaacatac     900
aaccacttaa aatacagcat tcacgttgtc actggttcgt ggtatcaggt aaggaaaaaa    960
tgatgctcct gtccctagaa ttttccatgt acatgtcagt atcctaatgc ctacagactt   1020
cctattaatt ttgttatcag catctcccac ctaaaaacat acactacatt atgttctggg   1080
tccctgaaat agaaacatc aagcaatgtt tattgtgcaa ttccaatcat tatttgcaga    1140
atcttggttt agagtcagtc tttatagcca tttcaactgc ttggtttaaa caaaaagcaa    1200
caatctggtt atctacctat aaatttcayg gtatttcttt aaacactgaa gtactaaaag    1260
cactgatgat ttgtattata attttttaaaa tatttaaaac ctacacagat ttcatagatc    1320
attcctttta taaaataatc aaaataattt gattatctgg aaaaaaaaat tcttgaaaca    1380 gagcccttc caggtatctt caatctctgt aaaaccccaa accccaaaca gagtagatga     1440
tgaaataagg atttctcagt tgcccaagac tgtctgaaat ttaaggttga gaaatggact    1500 ggcgttttc atgtttcctg tgaattcaga gcttacaggt ggcatcagaa ctcaaatctc     1560
tgggatggct ttacatggct ttcactttga tttgtttcat tttcatttgc ttctttcca    1620 acttcttttk ctcacgcctc aatgcagcct cctccagcct cgcgtgtttc tcaggatctt    1680
cctcattcat gattcgctcc ttctctgctc ttttttttctc ctcccgccga gactgtgctg   1740
cttcctgtct ttgcacatgt gtcagtttca agaagttctc ttctactcgg gcacggttct   1800
tatctgcttt ttgtttgcct tctctgttga gtcggaactt tttggcttta tcaatagaat    1860
aaatcaccat gttcatcagg ggtagcagtg cctccatatc ctttgggtaa gtgttacctg    1920
agccaggcac attaaatgta aacaacagtg tcctcttagt gtcaggtagc tttaaaggct    1980
gaccttcctc ttgcataatt tttgaccag agaactggtc tgaaaatga acagattcaa      2040 tcttgtcagc atagtgtgta agaaagtgaa ccatctttgt atccatcatt ccgtctgtga    2100
cttctcccat ctctgacagg atggccaaag agtccggcag tccatacttt gctccagact    2160
taggtttatc actacaaaac tcactcaaat cctgcatctc tttctgtagt cgcaccaagg    2220
ctttccgtgt gccaacagca aatacgtagg tatccatgtc ttcatcattc atggttactt    2280
ttatttgcac ttgatcactc actggcctca tcatccgggc caggacattc agtaagtctt    2340
gtctcttgag gaacctcagc tggataagca tgccctcaca gcacactcga ccagaacacc    2400
acaggttata gatgtgctca ttctcctggt tcaacttttcc tgtgcttgtg gcttctttgt   2460
tagttccatc atcccccact aaagtaaagt tgctctccaa aagctcccta tgagtgttaa    2520
accaggcctg tgcaaggcga ctgtttttat tcttcccaat gatgtaattc atgatataag    2580
caagcagacc agtcaccatc aaaatttcta gataataact ctcccagctg ttctggaggt    2640
gtgcaggaac atcaacaatc gttattgggt ctttattttt gctagaagaa gtatctggtt    2700
tgtcttcata accttcaaat tcttcatcat catatggttc actctcagta tctccctcct    2760
```

-continued

| | |
|---|---|
| gggtatctgc atcttcaaaa tctccttctt ggttttcatc ctgcccttcc aactccacag | 2820 |
| tggtctcatc ttcatcatct tcagtgatta tgacccgttg aggagattca gtaacagagt | 2880 |
| cttccatgac atcctcaaat tcagcgaagt cattatcatc atactctact atgtcctcct | 2940 |
| catcctcaaa atcatcaaac ttggcttcag agacactccc aaacaccaga aggacaacac | 3000 |
| agaaagtgtg gaaggctttc attgcacctt gagaaaaaaa gctgtggccg aagccgaaac | 3060 |
| ccggcccagc gccctgcgtc cgacacccct gcccggcctg ctctcggcct ggccgccgcc | 3120 |
| tccgcgatcg cagcggtttt actgccccgg atgcctctag gacgcagcca gaacc | 3175 |

<210> SEQ ID NO 50
<211> LENGTH: 783
<212> TYPE: DNA
<213> ORGANISM: Homo sapiens

<400> SEQUENCE: 50

| | |
|---|---|
| ggcacgcgga aaggctggcc tctcttcamc atgggmtctt ctggactttt gagcctcctg | 60 |
| gtgctattcg tcctcttagc gaatgtccag ggacctggtc tgactgattg gttatttccc | 120 |
| aggagatgtc ccaaaatcag agaagaatgt gaattccaag aaagggatgt gtgtacaaag | 180 |
| gacagacaat gccaggacaa caagaagtgt tgtgtcttca gctgcggaaa aaaatgttta | 240 |
| gatctcaaac aagatgtatg cgaaatgcca aaagaaactg gccctgcct ggcttatttt | 300 |
| cttcattggt ggtatgacaa gaaagataat acttgctcca tgtttgtcta tggtggctgc | 360 |
| caggggaaac aataacaact tccaatccaa agccaactgc ctgaacacct gcaagaataa | 420 |
| acgctttccc tgattggata aggatgcact ggaagaactg ccagaatgtg gctcatgctc | 480 |
| tgagtactgt tcctgtacct gactgatgct ccagactggc ttccagtttc actctcagca | 540 |
| ttccaagatc ttagcccttc ccagaacaga acgcttgcat ctacctcctc ttcctccatc | 600 |
| tttggctctt tgatgcaca atatccatcc gttttgattt catctttatg tccccttat | 660 |
| ctccaacttc tagaactccc agtttatacc tgtgtcactc tcaatttttt ccagtaaagt | 720 |
| acttgatgtw gaaaaaaaaa aaaaaaaaa aaaaccggca cgaggggggg cccggtaccc | 780 |
| aat | 783 |

<210> SEQ ID NO 51
<211> LENGTH: 3030
<212> TYPE: DNA
<213> ORGANISM: Homo sapiens
<220> FEATURE:
<221> NAME/KEY: SITE
<222> LOCATION: (60)
<223> OTHER INFORMATION: n equals a,t,g, or c
<220> FEATURE:
<221> NAME/KEY: SITE
<222> LOCATION: (2388)
<223> OTHER INFORMATION: n equals a,t,g, or c

<400> SEQUENCE: 51

| | |
|---|---|
| ctctaagaac ctagtggatc cccccggcct gcaggaattc gggcacggag gggagacttn | 60 |
| ctgtggctaa gggagggcgg gaagggccct ctgtggggct gccattttgg ctgggaccta | 120 |
| aatgcagtaa aggagcagct acggaatat agagagtggg gcttccaggc agagaagcct | 180 |
| gcagtgcaaa ggtctgcaga caacgacctg ggcgtcttca aggacacaa ggaatcatat | 240 |
| tgccagaaca cattgtacag gtagccaggt gtcggtctcc agcctgagaa ctctggctgt | 300 |
| tgttccttgt gtcgtcccat attcctgcct ggcctgcgat ggacatcagc aagggcctcc | 360 |
| caggcatgca gggaggcctc cacatatgga tctctgagaa ccggaagatg gtgccggtac | 420 |

```
ccgaggggc ttacgggaac tttttcgagg aacactgcta tgtcatcctc cacgtccccc    480
agagcccgaa ggycacgcag ggggcgtcca gcgacctgca ctactgggtc gggaagcagg   540
cgggtgcgga agcgcagggc gctgcggagg ccttccagca gcgcctacag gacgagctgg   600
ggggccagac cgtgctgcac cgcgaggcgc agggccacga gtccgactgc ttctgcagct   660
acttccgccc gggaatcatc tacaggaagg gaggcctagc atctgacctc aagcatgtgg   720
agaccaactt gttcaacatc cagcgactgc tgcacatcaa agggaggaag cacgtgtctg   780
ccactgaggt ggagctctcc tggaacagct ttaataaggg tgacatcttc ctgctggacc   840
taggcaagat gatgattcag tggaatgggc ccaagaccag catttctgag aaggctcggg   900 ggctggycytt gacctacagc ctccgggaca gggaacgtgg tggtggtcgt gcacagattg   960
gtgtggtgga tgatgaggcc aaagcccgg acctcatgca gatcatggag gctgtgctgg    1020
gccgcagggt gggcagmctg cgtgycgcca cgcccagcaa ggatatcaac cagctgcaga   1080
aggccaatgt tcgcctgtac catgtctatg agaagggcaa agacctggtg gtcctggagt   1140
tggcgacccc cccactgacc caggacctgc tgcaggagga ggacttctac atcctggacc   1200
agggtggctt caagatctat gtgtggcagg gacgcatgtc tagcctccag gagagaaagg   1260
ctgccttcag ccgggctgtg ggcttcatcc aggccaaggg ctacccgacc tacaccaacg   1320
tggaggtggt gaacgacggc gccgagtcgg ccgcgttcaa gcagctcttc cggacttggt   1380
ctgagaagcg gcgcaggaac cagaagmtcg gcgggaggga taaatcgatt catgtaaagc   1440
tggacgtggg caagctgcac acccagccta agttagcggc ccagctcagg atggtggacg   1500
acggctctgg gaaggtggag gtgtggtgca tccaggactt acacaggcag cccgtggacc   1560
ccaagcgtca tggacagctg tgtgcaggca actgctacct tgtgctctac acataccaga   1620
ggctgggccg tgtccagtac atcctgtacc tatgcaggg ccaccaggcc actgcggatg   1680
agattgaggc cctgaacagc aacgctgagg aactagatgt catgtatggt ggcgtcctag   1740
tacaggagca tgtgaccatg ggcagcgagc cccccacctt cctcgccatc ttccagggcc   1800
agctggtgat cttccaggag agagctgggc accacggaaa ggggcagtca gcatccacca   1860
caaggctttt ccaagtgcaa ggcactgaca gccacaacac caggaccatg gaggtgccag   1920
cccgtgcctc atccctcaac tccagtgaca tcttcttgct ggtcacagcc agcgtctgct   1980
acctctggtt tgggaaaggg ctgtaatggt gatcagcgtg agatggcacg ggtggtggtc   2040
actgtcattt ccaggaagaa tgaggaaacg gtgctggagg gtcaggagcc tccccacttc   2100
tgggaggccc tgggaggccg gggccccta ccccagcaac aagaggctcc ctgaggaggt   2160
ccccagcttc cagccacgac tgtttgagtg ctccagccaa atgggctgcc tggtcctcgc   2220
agaagtgggg ttcttcagcc aggaggacct ggacaagtat gacatcatgt tactggacac   2280
ctggcaggag atcttcctgt ggcttgggga agctgcaagt gagtggaagg aggcggtggc   2340
ctggggccag gagtacctga agactcaccc agcaggagg agcccggnca cacccatcgt    2400
gctggtcaag cagggscatg agcctcccac cttcattgga tggttcttca cttgggaccc   2460
ctacaagtgg actagccacc catcccacaa ggaagtggtg gatggcagcc ggcagcagc    2520 atcaaccatc tctgagataa cagcagaagt caacaacttc cggctatcca gatggccggg   2580
caatggcagg gcaggtgccg tggccctgca ggccctcaag ggctcccagg acagctcaga   2640
gaatgatytg gtgcgaagcc caagtcggc tggcagcaga accagcagct ccgtcagcag    2700
caccagcgcc acgatcaacg ggggcctgcg ccgggaacaa ctgatgcacc aggctgttga   2760
```

```
ggacctgcca gagggcgtgg accctgcccg cagggagttc tatctctcag actctgactt    2820
ccaagatatc tttgggaaat ccaaggagga attctacagc atggccacgt ggaggcagcg    2880
gcaggagaaa aagcagctgg gcttcttctg aacccaagcc ctctcgactg ccctatccc    2940 ctggacccca acatacctac aatgctgggg aggccctgct tccactcccc tcagaggctt    3000
ttggtcatcc tctgcgtgtc agtaaaagca                                     3030
```

<210> SEQ ID NO 52
<211> LENGTH: 61
<212> TYPE: PRT
<213> ORGANISM: Homo sapiens
<220> FEATURE:
<221> NAME/KEY: SITE
<222> LOCATION: (58)
<223> OTHER INFORMATION: Xaa equals any of the naturally occurring
      L-amino acids

<400> SEQUENCE: 52

```
Met Glu His Ala Ala Gly Leu Pro Val Thr Arg His Pro Leu Ala Leu
 1               5                  10                  15

Leu Leu Ala Leu Cys Pro Gly Pro Phe Pro Ala Leu Leu Leu Pro Leu
            20                  25                  30

Leu Pro Trp Gly Tyr Pro Leu Ala Pro Pro Gly Leu Cys Lys Leu Pro
        35                  40                  45

Gln Gly Ala Pro Leu Pro Cys Ser Ser Xaa Leu Thr Ser
    50                  55                  60
```

<210> SEQ ID NO 53
<211> LENGTH: 243
<212> TYPE: PRT
<213> ORGANISM: Homo sapiens
<220> FEATURE:
<221> NAME/KEY: SITE
<222> LOCATION: (15)
<223> OTHER INFORMATION: Xaa equals any of the naturally occurring
      L-amino acids
<220> FEATURE:
<221> NAME/KEY: SITE
<222> LOCATION: (190)
<223> OTHER INFORMATION: Xaa equals any of the naturally occurring
      L-amino acids

<400> SEQUENCE: 53

```
Met Asp Gln Tyr Cys Ile Leu Gly Arg Ile Gly Glu Gly Ala Xaa Gly
 1               5                  10                  15

Ile Val Phe Lys Ala Lys His Val Glu Thr Gly Glu Ile Val Ala Leu
            20                  25                  30

Lys Lys Val Ala Leu Arg Arg Leu Glu Asp Gly Phe Pro Asn Gln Ala
        35                  40                  45

Leu Arg Glu Ile Lys Ala Leu Gln Glu Met Glu Asp Asn Gln Tyr Val
    50                  55                  60

Val Gln Leu Lys Ala Val Phe Pro His Gly Gly Phe Val Leu Ala
65                  70                  75                  80

Phe Glu Phe Met Leu Ser Asp Leu Ala Glu Val Val Arg His Ala Gln
                85                  90                  95

Arg Pro Leu Ala Gln Ala Gln Val Lys Ser Tyr Leu Gln Met Leu Leu
            100                 105                 110

Lys Gly Val Ala Phe Cys His Ala Asn Asn Ile Val His Arg Asp Leu
        115                 120                 125

Lys Pro Ala Asn Leu Leu Ile Ser Ala Ser Gly Gln Leu Lys Ile Ala
    130                 135                 140
```

```
Asp Phe Gly Leu Ala Arg Val Phe Ser Pro Asp Gly Ser Arg Leu Tyr
145                 150                 155                 160

Thr His Gln Val Ala Thr Arg Ser Ser Leu Ser Cys Arg Thr Thr Thr
                165                 170                 175

Arg Ser Pro Leu Arg Ser Arg Cys Pro Cys Pro Trp Arg Xaa Cys Cys
            180                 185                 190

Leu Thr Ser Leu Pro Arg His Trp Ile Cys Trp Val Asn Ser Phe Ser
        195                 200                 205

Thr Leu Leu Thr Ser Ala Ser Gln Leu Pro Arg Leu Ser Ser Ile Ser
    210                 215                 220

Thr Ser Ser Gln Leu Pro Cys Leu Pro Ile His Leu Ser Cys Arg Phe
225                 230                 235                 240

Leu Ser Val
```

<210> SEQ ID NO 54
<211> LENGTH: 65
<212> TYPE: PRT
<213> ORGANISM: Homo sapiens

<400> SEQUENCE: 54

```
Met Glu Ala Lys Phe Gly Leu Leu Cys Phe Leu Val Ser Thr Pro Trp
1               5                   10                  15

Ala Glu Leu Leu Ser Leu Leu Leu His Leu Thr Gln Val Pro Phe Pro
                20                  25                  30

Gly Ser Gln Gly Leu Gly Leu Asn Asn Cys Arg Ala Ala Cys His Asp
            35                  40                  45

Leu Ser His Leu Leu Ser His Ser Ala Ile Asn Gln Thr Lys Glu
        50                  55                  60

Phe
 65
```

<210> SEQ ID NO 55
<211> LENGTH: 37
<212> TYPE: PRT
<213> ORGANISM: Homo sapiens

<400> SEQUENCE: 55

```
Met Leu Ala Arg Lys Ala Glu Arg Gly Ser Met Gly Thr Ala Arg Asp
1               5                   10                  15

Ser His Ile Leu Leu Val Cys Ser Val Val His Pro Ala Ser Ala Gln
                20                  25                  30

Pro Val Tyr Thr Val
            35
```

<210> SEQ ID NO 56
<211> LENGTH: 317
<212> TYPE: PRT
<213> ORGANISM: Homo sapiens

<400> SEQUENCE: 56

```
Met Leu Ser Phe Lys Leu Leu Leu Ala Val Ala Leu Gly Phe Phe
1               5                   10                  15

Glu Gly Asp Ala Lys Phe Gly Glu Arg Asn Gly Ser Gly Ala Arg
                20                  25                  30

Arg Arg Arg Cys Leu Asn Gly Asn Pro Pro Lys Arg Leu Lys Arg Arg
            35                  40                  45

Asp Arg Arg Met Met Ser Gln Leu Glu Leu Leu Ser Gly Gly Glu Met
```

```
              50                  55                  60
Leu Cys Gly Gly Phe Tyr Pro Arg Leu Ser Cys Cys Leu Arg Ser Asp
 65                  70                  75                  80

Ser Pro Gly Leu Gly Arg Leu Glu Asn Lys Ile Phe Ser Val Thr Asn
                 85                  90                  95

Asn Thr Glu Cys Gly Lys Leu Leu Glu Glu Ile Lys Cys Ala Leu Cys
            100                 105                 110

Ser Pro His Ser Gln Ser Leu Phe His Ser Pro Glu Arg Glu Val Leu
        115                 120                 125

Glu Arg Asp Leu Val Leu Pro Leu Leu Cys Lys Asp Tyr Cys Lys Glu
    130                 135                 140

Phe Phe Tyr Thr Cys Arg Gly His Ile Pro Gly Phe Leu Gln Thr Thr
145                 150                 155                 160

Ala Asp Glu Phe Cys Phe Tyr Tyr Ala Arg Lys Asp Gly Gly Leu Cys
                165                 170                 175

Phe Pro Asp Phe Pro Arg Lys Gln Val Arg Gly Pro Ala Ser Asn Tyr
            180                 185                 190

Leu Asp Gln Met Glu Glu Tyr Asp Lys Val Glu Ile Ser Arg Lys
        195                 200                 205

His Lys His Asn Cys Phe Cys Ile Gln Glu Val Val Ser Gly Leu Arg
    210                 215                 220

Gln Pro Val Gly Ala Leu His Ser Gly Asp Gly Ser Gln Arg Leu Phe
225                 230                 235                 240

Ile Leu Glu Lys Glu Gly Tyr Val Lys Ile Leu Thr Pro Glu Gly Glu
                245                 250                 255

Ile Phe Lys Glu Pro Tyr Leu Asp Ile His Lys Leu Val Gln Ser Gly
            260                 265                 270

Ile Lys Val Gly Phe Leu Asn Phe Ile Tyr Phe Cys Ala Gly Tyr Val
        275                 280                 285

Asn Phe Ile Leu Val Leu Pro Ser Ser Leu Lys Val Phe Leu Cys Asn
    290                 295                 300

Lys Arg Lys Asn Leu Ala Gly Glu Asn Lys Gly Ala Thr
305                 310                 315

<210> SEQ ID NO 57
<211> LENGTH: 41
<212> TYPE: PRT
<213> ORGANISM: Homo sapiens

<400> SEQUENCE: 57

Met Ser Trp Gly Ile Trp Lys Gly Leu Asp Leu Phe Pro Leu Ile Lys
 1               5                  10                  15

Gly Asn Ser Ser Leu Cys Leu Phe Leu Val Val Pro Lys Gly Tyr
                20                  25                  30

Ser Ser Ser Glu Ile Thr Arg Ala Leu
        35                  40

<210> SEQ ID NO 58
<211> LENGTH: 57
<212> TYPE: PRT
<213> ORGANISM: Homo sapiens

<400> SEQUENCE: 58

Met Ser Leu Pro Cys His Leu Leu Pro Gly Leu Leu Gln Gln Leu Leu
 1               5                  10                  15

Thr Ser Leu Pro Ala Phe Gln Phe Ser Ala Pro Leu Gln Val Phe Ser
```

-continued

```
                    20                  25                  30
Leu Asp Gly Leu Ser Leu Pro Ala Pro Lys Leu Leu Thr Ala Ser Leu
            35                  40                  45

Cys Leu Gln Asp Glu Val Arg Ala Val
        50                  55

<210> SEQ ID NO 59
<211> LENGTH: 52
<212> TYPE: PRT
<213> ORGANISM: Homo sapiens

<400> SEQUENCE: 59

Met Ser Ser Trp Pro Phe Cys Pro Ser Leu Cys Phe Ser Leu Ser Asn
  1               5                  10                  15

Leu Ile Pro Gly Ser Gly Leu Leu Pro Val Glu Thr Gly Glu Leu Gly
            20                  25                  30

Leu Leu Ser Ala Ala Tyr Leu Leu Pro Phe Thr Cys Ile Gln Leu Leu
            35                  40                  45

Gly Leu Gly Pro
        50

<210> SEQ ID NO 60
<211> LENGTH: 296
<212> TYPE: PRT
<213> ORGANISM: Homo sapiens
<220> FEATURE:
<221> NAME/KEY: SITE
<222> LOCATION: (281)
<223> OTHER INFORMATION: Xaa equals any of the naturally occurring
      L-amino acids

<400> SEQUENCE: 60

Met Ala Val Leu Ala Pro Leu Ile Ala Leu Val Tyr Ser Val Pro Arg
  1               5                  10                  15

Leu Ser Arg Trp Leu Ala Gln Pro Tyr Tyr Leu Leu Ser Ala Leu Leu
            20                  25                  30

Ser Ala Ala Phe Leu Leu Val Arg Lys Leu Pro Pro Leu Cys His Gly
            35                  40                  45

Leu Pro Thr Gln Arg Glu Asp Gly Asn Pro Cys Asp Phe Asp Trp Arg
        50                  55                  60

Glu Val Glu Ile Leu Met Phe Leu Ser Ala Ile Val Met Met Lys Asn
 65                  70                  75                  80

Arg Arg Ser Ile Thr Val Glu Gln His Ile Gly Asn Ile Phe Met Phe
                85                  90                  95

Ser Lys Val Ala Asn Thr Ile Leu Phe Phe Arg Leu Asp Ile Arg Met
            100                 105                 110

Gly Leu Leu Tyr Ile Thr Leu Cys Ile Val Phe Leu Met Thr Cys Lys
            115                 120                 125

Pro Pro Leu Tyr Met Gly Pro Glu Tyr Ile Lys Tyr Phe Asn Asp Lys
        130                 135                 140

Thr Ile Asp Glu Glu Leu Glu Arg Asp Lys Arg Val Thr Trp Ile Val
145                 150                 155                 160

Glu Phe Phe Ala Asn Trp Ser Asn Asp Cys Gln Ser Phe Ala Pro Ile
                165                 170                 175

Tyr Ala Asp Leu Ser Leu Lys Tyr Asn Cys Thr Gly Leu Asn Phe Gly
            180                 185                 190

Lys Val Asp Val Gly Arg Tyr Thr Asp Val Ser Thr Arg Tyr Lys Val
            195                 200                 205
```

```
Ser Thr Ser Pro Leu Thr Lys Gln Leu Pro Thr Leu Ile Leu Phe Gln
    210                 215                 220

Gly Gly Lys Glu Ala Met Arg Arg Pro Gln Ile Asp Lys Lys Gly Arg
225                 230                 235                 240

Ala Val Ser Trp Thr Phe Ser Glu Glu Asn Val Ile Arg Glu Phe Asn
                245                 250                 255

Leu Asn Glu Leu Tyr Gln Arg Ala Lys Lys Leu Ser Lys Ala Gly Asp
                260                 265                 270

Asn Ile Pro Glu Glu Gln Pro Val Xaa Ser Thr Pro Thr Thr Val Ser
            275                 280                 285

Asp Gly Glu Asn Lys Lys Asp Lys
    290                 295

<210> SEQ ID NO 61
<211> LENGTH: 100
<212> TYPE: PRT
<213> ORGANISM: Homo sapiens

<400> SEQUENCE: 61

Met Arg Ala Phe Arg Lys Asn Lys Thr Leu Gly Tyr Gly Val Pro Met
1               5                   10                  15

Leu Leu Leu Ile Val Gly Gly Ser Phe Gly Leu Arg Glu Phe Ser Gln
            20                  25                  30

Ile Arg Tyr Asp Ala Val Lys Ser Lys Met Asp Pro Glu Leu Glu Lys
        35                  40                  45

Lys Leu Lys Glu Asn Lys Ile Ser Leu Glu Ser Glu Tyr Glu Lys Ile
    50                  55                  60

Lys Asp Ser Lys Phe Asp Asp Trp Lys Asn Ile Arg Gly Pro Arg Pro
65                  70                  75                  80

Trp Glu Asp Pro Asp Leu Leu Gln Gly Arg Asn Pro Glu Ser Leu Lys
                85                  90                  95

Thr Lys Thr Thr
            100

<210> SEQ ID NO 62
<211> LENGTH: 47
<212> TYPE: PRT
<213> ORGANISM: Homo sapiens

<400> SEQUENCE: 62

Met Ile Gln Leu Ile Leu Gln Phe Trp Tyr Leu Phe Ser Met Leu Leu
1               5                   10                  15

Lys Pro Val Gln Gln Cys Gln His Cys Ser Gln Ile Thr Pro Ser Gly
            20                  25                  30

Thr Met Pro Thr Ser Glu Thr Val Phe Leu Ile Leu Phe Leu Pro
        35                  40                  45

<210> SEQ ID NO 63
<211> LENGTH: 162
<212> TYPE: PRT
<213> ORGANISM: Homo sapiens

<400> SEQUENCE: 63

Met Lys Met Val Ala Pro Trp Thr Arg Phe Tyr Ser Asn Ser Cys Cys
1               5                   10                  15

Leu Cys Cys His Val Arg Thr Gly Thr Ile Leu Leu Gly Val Trp Tyr
            20                  25                  30
```

-continued

```
Leu Ile Ile Asn Ala Val Val Leu Ile Leu Leu Ser Ala Leu Ala
             35                  40                  45

Asp Pro Asp Gln Tyr Asn Phe Ser Ser Glu Leu Gly Gly Asp Phe
         50                  55                  60

Glu Phe Met Asp Asp Ala Asn Met Cys Ile Ala Ile Ala Ile Ser Leu
 65                  70                  75                  80

Leu Met Ile Leu Ile Cys Ala Met Ala Thr Tyr Gly Ala Tyr Lys Gln
                     85                  90                  95

Arg Ala Ala Gly Ile Ile Pro Phe Phe Cys Tyr Gln Ile Phe Asp Phe
                100                 105                 110

Ala Leu Asn Met Leu Val Ala Ile Thr Val Leu Ile Tyr Pro Asn Ser
            115                 120                 125

Ile Gln Glu Tyr Ile Arg Gln Leu Pro Pro Asn Phe Pro Tyr Arg Asp
        130                 135                 140

Asp Val Met Cys Ser Glu Ser Tyr Leu Phe Gly Pro Tyr Tyr Ser Ser
145                 150                 155                 160

Val Tyr
```

<210> SEQ ID NO 64
<211> LENGTH: 335
<212> TYPE: PRT
<213> ORGANISM: Homo sapiens
<220> FEATURE:
<221> NAME/KEY: SITE
<222> LOCATION: (35)
<223> OTHER INFORMATION: Xaa equals any of the naturally occurring
      L-amino acids
<220> FEATURE:
<221> NAME/KEY: SITE
<222> LOCATION: (297)
<223> OTHER INFORMATION: Xaa equals any of the naturally occurring
      L-amino acids

<400> SEQUENCE: 64

```
Met Arg Gly Leu Gly Leu Trp Leu Leu Gly Ala Met Met Leu Pro Ala
 1               5                  10                  15

Ile Ala Pro Ser Arg Pro Trp Ala Leu Met Glu Gln Tyr Glu Val Val
                20                  25                  30

Leu Pro Xaa Arg Leu Pro Gly Pro Arg Val Arg Arg Ala Leu Pro Ser
            35                  40                  45

His Leu Gly Leu His Pro Glu Arg Val Ser Tyr Val Leu Gly Ala Thr
         50                  55                  60

Gly His Asn Phe Thr Leu His Leu Arg Lys Asn Arg Asp Leu Leu Gly
 65                  70                  75                  80

Ser Gly Tyr Thr Glu Thr Tyr Thr Ala Ala Asn Gly Ser Glu Val Thr
                 85                  90                  95

Glu Gln Pro Arg Gly Gln Asp His Cys Phe Tyr Gln Gly His Val Glu
                100                 105                 110

Gly Tyr Pro Asp Ser Ala Ala Ser Leu Ser Thr Cys Ala Gly Leu Arg
            115                 120                 125

Gly Phe Phe Gln Val Gly Ser Asp Leu His Leu Ile Glu Pro Leu Asp
        130                 135                 140

Glu Gly Gly Glu Gly Gly Arg His Ala Val Tyr Gln Ala Glu His Leu
145                 150                 155                 160

Leu Gln Thr Ala Gly Thr Cys Gly Val Ser Asp Asp Ser Leu Gly Ser
                165                 170                 175

Leu Leu Gly Pro Arg Thr Ala Ala Val Phe Arg Pro Arg Pro Gly Asp
                180                 185                 190
```

```
Ser Leu Pro Ser Arg Glu Thr Arg Tyr Val Glu Leu Tyr Val Val Val
            195                 200                 205

Asp Asn Ala Glu Phe Gln Met Leu Gly Ser Glu Ala Ala Val Arg His
210                 215                 220

Arg Val Leu Glu Val Val Asn His Val Asp Lys Leu Tyr Gln Lys Leu
225                 230                 235                 240

Asn Phe Arg Val Val Leu Val Gly Leu Glu Ile Trp Asn Ser Gln Asp
            245                 250                 255

Arg Phe His Val Ser Pro Asp Pro Ser Val Thr Leu Glu Asn Leu Leu
            260                 265                 270

Thr Trp Gln Ala Arg Gln Arg Thr Arg Arg His Leu His Asp Asn Val
            275                 280                 285

Gln Leu Ile Thr Gly Val Asp Phe Xaa Gly Thr Thr Val Gly Phe Ala
290                 295                 300

Arg Val Ser Thr Met Cys Ser His Ser Ser Gly Ala Val Asn Gln Asp
305                 310                 315                 320

His Ser Lys Asn Pro Val Gly Val Ala Cys Thr Met Ala His Glu
            325                 330                 335

<210> SEQ ID NO 65
<211> LENGTH: 356
<212> TYPE: PRT
<213> ORGANISM: Homo sapiens

<400> SEQUENCE: 65

Met Asp Tyr Arg Gly Gly Asp Gly Thr Ser Met Asp Tyr Arg Gly Arg
  1               5                  10                  15

Glu Ala Pro His Met Asn Tyr Arg Asp Arg Asp Ala His Ala Val Asp
                20                  25                  30

Phe Arg Gly Arg Asp Ala Pro Pro Ser Asp Phe Arg Gly Arg Gly Thr
            35                  40                  45

Tyr Asp Leu Asp Phe Arg Gly Arg Asp Gly Ser His Ala Asp Phe Arg
        50                  55                  60

Gly Arg Asp Leu Ser Asp Leu Asp Phe Arg Ala Arg Glu Gln Ser Arg
 65                 70                  75                  80

Ser Asp Phe Arg Asn Arg Asp Val Ser Asp Leu Asp Phe Arg Asp Lys
                85                  90                  95

Asp Gly Thr Gln Val Asp Phe Arg Gly Arg Gly Ser Gly Thr Thr Asp
            100                 105                 110

Leu Asp Phe Arg Asp Arg Asp Thr Pro His Ser Asp Phe Arg Gly Arg
        115                 120                 125

His Arg Ser Arg Thr Asp Gln Asp Phe Arg Gly Arg Glu Met Gly Ser
    130                 135                 140

Cys Met Glu Phe Lys Asp Arg Glu Met Pro Pro Val Asp Pro Asn Ile
145                 150                 155                 160

Leu Asp Tyr Ile Gln Pro Ser Thr Gln Asp Arg Glu His Ser Gly Met
                165                 170                 175

Asn Val Asn Arg Arg Glu Glu Ser Thr His Asp His Thr Ile Glu Arg
            180                 185                 190

Pro Ala Phe Gly Ile Gln Lys Gly Glu Phe Glu His Ser Glu Thr Arg
        195                 200                 205

Glu Gly Glu Thr Gln Gly Val Ala Phe Glu His Glu Ser Pro Ala Asp
    210                 215                 220

Phe Gln Asn Ser Gln Ser Pro Val Gln Asp Gln Asp Lys Ser Gln Leu
```

-continued

```
              225                 230                 235                 240
Ser Gly Arg Glu Glu Gln Ser Ser Asp Ala Gly Leu Phe Lys Glu Glu
                     245                 250                 255

Gly Gly Leu Asp Phe Leu Gly Arg Gln Asp Thr Asp Tyr Arg Ser Met
            260                 265                 270

Glu Tyr Arg Asp Val Asp His Arg Leu Pro Gly Ser Gln Met Phe Gly
        275                 280                 285

Tyr Gly Gln Ser Lys Ser Phe Pro Glu Gly Lys Thr Ala Arg Asp Ala
    290                 295                 300

Gln Arg Asp Leu Gln Asp Gln Asp Tyr Arg Thr Gly Pro Ser Glu Glu
305                 310                 315                 320

Lys Pro Ser Arg Leu Ile Arg Leu Ser Gly Val Pro Glu Asp Ala Thr
                325                 330                 335

Lys Glu Glu Ile Leu Asn Ala Phe Arg Thr Pro Asp Gly Met Pro Val
            340                 345                 350

Lys Asn Cys Ser
            355
```

```
<210> SEQ ID NO 66
<211> LENGTH: 125
<212> TYPE: PRT
<213> ORGANISM: Homo sapiens
<220> FEATURE:
<221> NAME/KEY: SITE
<222> LOCATION: (55)
<223> OTHER INFORMATION: Xaa equals any of the naturally occurring
      L-amino acids

<400> SEQUENCE: 66
```

```
Met Leu Ser Gln Pro Leu Val Gly Ala Gln Arg Arg Arg Ala Val
  1                 5                  10                 15

Gly Leu Ala Val Val Thr Leu Leu Asn Phe Leu Val Cys Phe Gly Pro
            20                  25                  30

Tyr Asn Val Ser His Leu Val Gly Tyr His Gln Arg Lys Ser Pro Trp
        35                  40                  45

Trp Arg Ser Ile Ala Val Xaa Phe Ser Ser Leu Asn Ala Ser Leu Asp
    50                  55                  60

Pro Leu Leu Phe Tyr Phe Ser Ser Val Val Arg Arg Ala Phe Gly
 65                  70                  75                  80

Arg Gly Leu Gln Val Leu Arg Asn Gln Gly Ser Ser Leu Leu Gly Arg
                85                  90                  95

Arg Gly Lys Asp Thr Ala Glu Gly Thr Asn Glu Asp Arg Gly Val Gly
            100                 105                 110

Gln Gly Glu Gly Met Pro Ser Ser Asp Phe Thr Thr Glu
        115                 120                 125
```

```
<210> SEQ ID NO 67
<211> LENGTH: 77
<212> TYPE: PRT
<213> ORGANISM: Homo sapiens

<400> SEQUENCE: 67
```

```
Met Arg Leu Val Phe Phe Phe Gly Val Ser Ile Ile Leu Val Leu Gly
  1                 5                  10                 15

Ser Thr Phe Val Ala Tyr Leu Pro Asp Tyr Arg Cys Thr Gly Cys Pro
            20                  25                  30

Arg Ala Trp Asp Gly Met Lys Glu Trp Ser Arg Arg Glu Ala Glu Arg
        35                  40                  45
```

```
Leu Val Lys Tyr Arg Glu Ala Asn Gly Leu Pro Ile Met Glu Ser Asn
     50                  55                  60

Cys Phe Asp Pro Ser Lys Ile Gln Leu Pro Glu Asp Glu
 65                  70                  75
```

<210> SEQ ID NO 68
<211> LENGTH: 121
<212> TYPE: PRT
<213> ORGANISM: Homo sapiens

<400> SEQUENCE: 68

```
Met Arg Ile Met Leu Leu Phe Thr Ala Ile Leu Ala Phe Ser Leu Ala
 1               5                  10                  15

Gln Ser Phe Gly Ala Val Cys Lys Glu Pro Gln Glu Glu Val Val Pro
                 20                  25                  30

Gly Gly Gly Arg Ser Lys Arg Asp Pro Asp Leu Tyr Gln Leu Leu Gln
             35                  40                  45

Arg Leu Phe Lys Ser His Ser Ser Leu Glu Gly Leu Leu Lys Ala Leu
 50                  55                  60

Ser Gln Ala Ser Thr Asp Pro Lys Glu Ser Thr Ser Pro Glu Lys Arg
 65                  70                  75                  80

Asp Met His Asp Phe Phe Val Gly Leu Met Gly Lys Arg Ser Val Gln
                 85                  90                  95

Pro Asp Ser Pro Thr Asp Val Asn Gln Glu Asn Val Pro Ser Phe Gly
                100                 105                 110

Ile Leu Lys Tyr Pro Pro Arg Ala Glu
             115                 120
```

<210> SEQ ID NO 69
<211> LENGTH: 26
<212> TYPE: PRT
<213> ORGANISM: Homo sapiens

<400> SEQUENCE: 69

```
Met Val Val Met Glu Val Leu Met Thr Met Val Ala Ile Ile Ile Thr
 1               5                  10                  15

Ala Met Gly Met Met Ala Leu Met Thr Glu
                 20                  25
```

<210> SEQ ID NO 70
<211> LENGTH: 235
<212> TYPE: PRT
<213> ORGANISM: Homo sapiens

<400> SEQUENCE: 70

```
Met Pro Trp Val Leu Leu Leu Thr Leu Thr His Ser Ala Val
 1               5                  10                  15

Ser Val Val Gln Ala Gly Leu Thr Gln Pro Pro Ser Val Ser Lys Asp
                 20                  25                  30

Leu Arg Gln Thr Ala Thr Leu Thr Cys Thr Gly Asn Asn Asn Asn Val
             35                  40                  45

Gly Asp Gln Gly Ala Ala Trp Leu Gln Gln His Gln Gly His Pro Pro
 50                  55                  60

Lys Leu Leu Ser Tyr Arg Asn Asn Asn Arg Pro Ser Gly Ile Ser Glu
 65                  70                  75                  80

Arg Leu Ser Ala Ser Arg Ser Gly Ala Thr Ser Ser Leu Thr Ile Thr
                 85                  90                  95
```

-continued

Gly Leu Gln Pro Glu Asp Glu Ala Asp Tyr Tyr Cys Ala Ala Tyr Asp
            100                 105                 110

Ser Ser Leu Ala Val Trp Met Phe Gly Gly Thr Lys Leu Thr Val
        115                 120                 125

Leu Gly Gln Pro Lys Ala Ala Pro Ser Val Thr Leu Phe Pro Pro Ser
    130                 135                 140

Ser Glu Glu Leu Gln Ala Asn Lys Ala Thr Leu Val Cys Leu Ile Ser
145                 150                 155                 160

Asp Phe Tyr Pro Gly Ala Val Thr Val Ala Trp Lys Ala Asp Ser Ser
                165                 170                 175

Pro Val Lys Ala Gly Val Glu Thr Thr Thr Pro Ser Lys Gln Ser Asn
            180                 185                 190

Asn Lys Tyr Ala Ala Ser Ser Tyr Leu Ser Leu Thr Pro Glu Gln Trp
        195                 200                 205

Lys Ser His Arg Ser Tyr Ser Cys Gln Val Thr His Glu Gly Ser Thr
    210                 215                 220

Val Glu Lys Thr Val Ala Pro Thr Glu Cys Ser
225                 230                 235

<210> SEQ ID NO 71
<211> LENGTH: 217
<212> TYPE: PRT
<213> ORGANISM: Homo sapiens

<400> SEQUENCE: 71

Met Asp Ser Gln Gln Ala Ser Gly Thr Ile Val Gln Ile Val Ile Asn
1               5                   10                  15

Asn Lys His Lys His Gly Gln Val Cys Val Ser Asn Gly Lys Thr Tyr
            20                  25                  30

Ser His Gly Glu Ser Trp His Pro Asn Leu Arg Ala Phe Gly Ile Val
        35                  40                  45

Glu Cys Val Leu Cys Thr Cys Asn Val Thr Lys Gln Glu Cys Lys Lys
    50                  55                  60

Ile His Cys Pro Asn Arg Tyr Pro Cys Lys Tyr Pro Gln Lys Ile Asp
65                  70                  75                  80

Gly Lys Cys Cys Lys Val Cys Pro Glu Glu Leu Pro Gly Gln Ser Phe
                85                  90                  95

Asp Asn Lys Gly Tyr Phe Cys Gly Glu Glu Thr Met Pro Val Tyr Glu
            100                 105                 110

Ser Val Phe Met Glu Asp Gly Glu Thr Thr Arg Lys Ile Ala Leu Glu
        115                 120                 125

Thr Glu Arg Pro Pro Gln Val Glu Val His Val Trp Thr Ile Arg Lys
    130                 135                 140

Gly Ile Leu Gln His Phe His Ile Glu Lys Ile Ser Lys Arg Met Phe
145                 150                 155                 160

Glu Glu Leu Pro His Phe Lys Leu Val Thr Arg Thr Thr Leu Ser Gln
                165                 170                 175

Trp Lys Ile Phe Thr Glu Gly Glu Ala Gln Ile Ser Gln Met Cys Ser
            180                 185                 190

Ser Arg Val Cys Arg Thr Glu Leu Glu Asp Leu Val Lys Val Leu Tyr
        195                 200                 205

Leu Glu Arg Ser Glu Lys Gly His Cys
    210                 215

<210> SEQ ID NO 72

-continued

```
<211> LENGTH: 492
<212> TYPE: PRT
<213> ORGANISM: Homo sapiens

<400> SEQUENCE: 72

Met Lys Ala Phe His Thr Phe Cys Val Val Leu Leu Val Phe Gly Ser
 1               5                  10                  15

Val Ser Glu Ala Lys Phe Asp Asp Phe Glu Asp Glu Glu Asp Ile Val
            20                  25                  30

Glu Tyr Asp Asp Asn Asp Phe Ala Glu Phe Glu Asp Val Met Glu Asp
        35                  40                  45

Ser Val Thr Glu Ser Pro Gln Arg Val Ile Ile Thr Glu Asp Asp Glu
    50                  55                  60

Asp Glu Thr Thr Val Glu Leu Glu Gly Gln Asp Glu Asn Gln Glu Gly
65                  70                  75                  80

Asp Phe Glu Asp Ala Asp Thr Gln Glu Gly Asp Thr Glu Ser Glu Pro
                85                  90                  95

Tyr Asp Asp Glu Glu Phe Glu Gly Tyr Glu Asp Lys Pro Asp Thr Ser
            100                 105                 110

Ser Ser Lys Asn Lys Asp Pro Ile Thr Ile Val Asp Val Pro Ala His
        115                 120                 125

Leu Gln Asn Ser Trp Glu Ser Tyr Tyr Leu Glu Ile Leu Met Val Thr
    130                 135                 140

Gly Leu Leu Ala Tyr Ile Met Asn Tyr Ile Ile Gly Lys Asn Lys Asn
145                 150                 155                 160

Ser Arg Leu Ala Gln Ala Trp Phe Asn Thr His Arg Glu Leu Leu Glu
                165                 170                 175

Ser Asn Phe Thr Leu Val Gly Asp Asp Gly Thr Asn Lys Glu Ala Thr
            180                 185                 190

Ser Thr Gly Lys Leu Asn Gln Glu Asn Glu His Ile Tyr Asn Leu Trp
        195                 200                 205

Cys Ser Gly Arg Val Cys Cys Glu Gly Met Leu Ile Gln Leu Arg Phe
    210                 215                 220

Leu Lys Arg Gln Asp Leu Leu Asn Val Leu Ala Arg Met Met Arg Pro
225                 230                 235                 240

Val Ser Asp Gln Val Gln Ile Lys Val Thr Met Asn Asp Glu Asp Met
                245                 250                 255

Asp Thr Tyr Val Phe Ala Val Gly Thr Arg Lys Ala Leu Val Arg Leu
            260                 265                 270

Gln Lys Glu Met Gln Asp Leu Ser Glu Phe Cys Ser Asp Lys Pro Lys
        275                 280                 285

Ser Gly Ala Lys Tyr Gly Leu Pro Asp Ser Leu Ala Ile Leu Ser Glu
    290                 295                 300

Met Gly Val Thr Asp Gly Met Met Asp Thr Lys Met Val His Phe
305                 310                 315                 320

Leu Thr His Tyr Ala Asp Lys Ile Glu Ser Val His Phe Ser Asp Gln
                325                 330                 335

Phe Ser Gly Pro Lys Ile Met Gln Glu Gly Gln Pro Leu Lys Leu
            340                 345                 350

Pro Asp Thr Lys Arg Thr Leu Leu Phe Thr Phe Asn Val Pro Gly Ser
        355                 360                 365

Gly Asn Thr Tyr Pro Lys Asp Met Glu Ala Leu Leu Pro Leu Met Asn
    370                 375                 380

Met Val Ile Tyr Ser Ile Asp Lys Ala Lys Lys Phe Arg Leu Asn Arg
```

```
                385                 390                 395                 400
Glu Gly Lys Gln Lys Ala Asp Lys Asn Arg Ala Arg Val Glu Glu Asn
                    405                 410                 415

Phe Leu Lys Leu Thr His Val Gln Arg Gln Glu Ala Ala Gln Ser Arg
                420                 425                 430

Arg Glu Glu Lys Lys Arg Ala Glu Lys Glu Arg Ile Met Asn Glu Glu
            435                 440                 445

Asp Pro Glu Lys Gln Arg Arg Leu Glu Glu Ala Ala Leu Arg Arg Glu
        450                 455                 460

Gln Lys Lys Leu Glu Lys Gln Met Lys Met Lys Gln Ile Lys Val
465                 470                 475                 480

Lys Ala His Val Lys Pro Ser Gln Arg Phe Glu Phe
                    485                 490

<210> SEQ ID NO 73
<211> LENGTH: 36
<212> TYPE: PRT
<213> ORGANISM: Homo sapiens

<400> SEQUENCE: 73

Met Leu Phe Leu Cys Leu Leu Pro Ser Leu Phe Pro Pro Gly Leu Pro
1               5                   10                  15

Thr Thr His Tyr Ile Thr Ser Ile Cys Asn Gln Ser Cys Tyr His His
                20                  25                  30

Cys Ala Arg Ala
            35

<210> SEQ ID NO 74
<211> LENGTH: 74
<212> TYPE: PRT
<213> ORGANISM: Homo sapiens
<220> FEATURE:
<221> NAME/KEY: SITE
<222> LOCATION: (7)
<223> OTHER INFORMATION: Xaa equals any of the naturally occurring
      L-amino acids
<220> FEATURE:
<221> NAME/KEY: SITE
<222> LOCATION: (71)
<223> OTHER INFORMATION: Xaa equals any of the naturally occurring
      L-amino acids

<400> SEQUENCE: 74

Met Ala Glu Leu Leu Leu Xaa Val Leu Ser Val Gln Ser Ala Val His
1               5                   10                  15

Glu Val Glu Ala Asn Glu Gly Gly Lys Gln Ser His Thr Pro Ala His
                20                  25                  30

Arg Gly Trp Asn Arg Arg Ala Ala Glu Val Arg Lys Ala Arg Leu Pro
            35                  40                  45

Leu Gly Val Thr Val Gly Pro Arg Cys Arg His Ala Val His Pro Ser
        50                  55                  60

Lys Gly Gly Ile Ser Ala Xaa Ala Val Leu
65                  70

<210> SEQ ID NO 75
<211> LENGTH: 133
<212> TYPE: PRT
<213> ORGANISM: Homo sapiens

<400> SEQUENCE: 75

Met Gly Ser Ser Gly Leu Leu Ser Leu Leu Val Leu Phe Val Leu Leu
```

-continued

```
                1               5                  10                   15
Ala Asn Val Gln Gly Pro Gly Leu Thr Asp Trp Leu Phe Pro Arg Arg
                        20                  25                  30

Cys Pro Lys Ile Arg Glu Glu Cys Glu Phe Gln Glu Arg Asp Val Cys
                35                  40                  45

Thr Lys Asp Arg Gln Cys Gln Asp Asn Lys Lys Cys Cys Val Phe Ser
         50                  55                  60

Cys Gly Lys Lys Cys Leu Asp Leu Lys Gln Asp Val Cys Glu Met Pro
 65                  70                  75                  80

Lys Glu Thr Gly Pro Cys Leu Ala Tyr Phe Leu His Trp Trp Tyr Asp
                        85                  90                  95

Lys Lys Asp Asn Thr Cys Ser Met Phe Val Tyr Gly Gly Cys Gln Gly
                100                 105                 110

Asn Asn Asn Asn Phe Gln Ser Lys Ala Asn Cys Leu Asn Thr Cys Lys
                115                 120                 125

Asn Lys Arg Phe Pro
         130
```

<210> SEQ ID NO 76
<211> LENGTH: 298
<212> TYPE: PRT
<213> ORGANISM: Homo sapiens
<220> FEATURE:
<221> NAME/KEY: SITE
<222> LOCATION: (42)
<223> OTHER INFORMATION: Xaa equals any of the naturally occurring
      L-amino acids
<220> FEATURE:
<221> NAME/KEY: SITE
<222> LOCATION: (58)
<223> OTHER INFORMATION: Xaa equals any of the naturally occurring
      L-amino acids

<400> SEQUENCE: 76

```
Met Ala Arg Arg Ser Arg His Arg Leu Leu Leu Leu Leu Leu Arg Tyr
 1               5                  10                  15

Leu Val Val Ala Leu Gly Tyr His Lys Ala Tyr Gly Phe Ser Ala Pro
                20                  25                  30

Lys Asp Gln Gln Val Val Thr Ala Val Xaa Tyr Gln Glu Ala Ile Leu
         35                  40                  45

Ala Cys Lys Thr Pro Lys Lys Thr Val Xaa Ser Arg Leu Glu Trp Lys
 50                  55                  60

Lys Leu Gly Arg Ser Val Ser Phe Val Tyr Tyr Gln Gln Thr Leu Gln
 65                  70                  75                  80

Gly Asp Phe Lys Asn Arg Ala Glu Met Ile Asp Phe Asn Ile Arg Ile
                85                  90                  95

Lys Asn Val Thr Arg Ser Asp Ala Gly Lys Tyr Arg Cys Glu Val Ser
                100                 105                 110

Ala Pro Ser Glu Gln Gly Gln Asn Leu Glu Glu Asp Thr Val Thr Leu
         115                 120                 125

Glu Val Leu Val Ala Pro Ala Val Pro Ser Cys Glu Val Pro Ser Ser
 130                 135                 140

Ala Leu Ser Gly Thr Val Val Glu Leu Arg Cys Gln Asp Lys Glu Gly
 145                 150                 155                 160

Asn Pro Ala Pro Glu Tyr Thr Trp Phe Lys Asp Gly Ile Arg Leu Leu
                165                 170                 175

Glu Asn Pro Arg Leu Gly Ser Gln Ser Thr Asn Ser Ser Tyr Thr Met
                180                 185                 190
```

```
Asn Thr Lys Thr Gly Thr Leu Gln Phe Asn Thr Val Ser Lys Leu Asp
        195                 200                 205

Thr Gly Glu Tyr Ser Cys Glu Ala Arg Asn Ser Val Gly Tyr Arg Arg
        210                 215                 220

Cys Pro Gly Lys Arg Met Gln Val Asp Asp Leu Asn Ile Ser Gly Ile
225                 230                 235                 240

Ile Ala Ala Val Val Val Ala Leu Val Ile Ser Val Cys Gly Leu
                245                 250                 255

Gly Val Cys Tyr Ala Gln Arg Lys Gly Tyr Phe Ser Lys Glu Thr Ser
                260                 265                 270

Phe Gln Lys Ser Asn Ser Ser Ser Lys Ala Thr Thr Met Ser Glu Asn
        275                 280                 285

Asp Phe Lys His Thr Lys Ser Phe Ile Ile
        290                 295

<210> SEQ ID NO 77
<211> LENGTH: 856
<212> TYPE: PRT
<213> ORGANISM: Homo sapiens
<220> FEATURE:
<221> NAME/KEY: SITE
<222> LOCATION: (52)
<223> OTHER INFORMATION: Xaa equals any of the naturally occurring
      L-amino acids
<220> FEATURE:
<221> NAME/KEY: SITE
<222> LOCATION: (190)
<223> OTHER INFORMATION: Xaa equals any of the naturally occurring
      L-amino acids
<220> FEATURE:
<221> NAME/KEY: SITE
<222> LOCATION: (233)
<223> OTHER INFORMATION: Xaa equals any of the naturally occurring
      L-amino acids
<220> FEATURE:
<221> NAME/KEY: SITE
<222> LOCATION: (595)
<223> OTHER INFORMATION: Xaa equals any of the naturally occurring
      L-amino acids
<220> FEATURE:
<221> NAME/KEY: SITE
<222> LOCATION: (683)
<223> OTHER INFORMATION: Xaa equals any of the naturally occurring
      L-amino acids

<400> SEQUENCE: 77

Met Asp Ile Ser Lys Gly Leu Pro Gly Met Gln Gly Gly Leu His Ile
  1                 5                  10                  15

Trp Ile Ser Glu Asn Arg Lys Met Val Pro Val Pro Glu Gly Ala Tyr
                 20                  25                  30

Gly Asn Phe Phe Glu Glu His Cys Tyr Val Ile Leu His Val Pro Gln
             35                  40                  45

Ser Pro Lys Xaa Thr Gln Gly Ala Ser Ser Asp Leu His Tyr Trp Val
         50                  55                  60

Gly Lys Gln Ala Gly Ala Glu Ala Gln Gly Ala Ala Glu Ala Phe Gln
 65                  70                  75                  80

Gln Arg Leu Gln Asp Glu Leu Gly Gly Gln Thr Val Leu His Arg Glu
                 85                  90                  95

Ala Gln Gly His Glu Ser Asp Cys Phe Cys Ser Tyr Phe Arg Pro Gly
            100                 105                 110

Ile Ile Tyr Arg Lys Gly Gly Leu Ala Ser Asp Leu Lys His Val Glu
        115                 120                 125
```

-continued

```
Thr Asn Leu Phe Asn Ile Gln Arg Leu Leu His Ile Lys Gly Arg Lys
    130                 135                 140

His Val Ser Ala Thr Glu Val Glu Leu Ser Trp Asn Ser Phe Asn Lys
145                 150                 155                 160

Gly Asp Ile Phe Leu Leu Asp Leu Gly Lys Met Met Ile Gln Trp Asn
                165                 170                 175

Gly Pro Lys Thr Ser Ile Ser Glu Lys Ala Arg Gly Leu Xaa Leu Thr
            180                 185                 190

Tyr Ser Leu Arg Asp Arg Glu Arg Gly Gly Arg Ala Gln Ile Gly
        195                 200                 205

Val Val Asp Asp Glu Ala Lys Ala Pro Asp Leu Met Gln Ile Met Glu
    210                 215                 220

Ala Val Leu Gly Arg Arg Val Gly Xaa Leu Arg Ala Ala Thr Pro Ser
225                 230                 235                 240

Lys Asp Ile Asn Gln Leu Gln Lys Ala Asn Val Arg Leu Tyr His Val
                245                 250                 255

Tyr Glu Lys Gly Lys Asp Leu Val Val Leu Glu Leu Ala Thr Pro Pro
            260                 265                 270

Leu Thr Gln Asp Leu Leu Gln Glu Glu Asp Phe Tyr Ile Leu Asp Gln
        275                 280                 285

Gly Gly Phe Lys Ile Tyr Val Trp Gln Gly Arg Met Ser Ser Leu Gln
    290                 295                 300

Glu Arg Lys Ala Ala Phe Ser Arg Ala Val Gly Phe Ile Gln Ala Lys
305                 310                 315                 320

Gly Tyr Pro Thr Tyr Thr Asn Val Glu Val Val Asn Asp Gly Ala Glu
                325                 330                 335

Ser Ala Ala Phe Lys Gln Leu Phe Arg Thr Trp Ser Glu Lys Arg Arg
            340                 345                 350

Arg Asn Gln Lys Leu Gly Gly Arg Asp Lys Ser Ile His Val Lys Leu
        355                 360                 365

Asp Val Gly Lys Leu His Thr Gln Pro Lys Leu Ala Ala Gln Leu Arg
    370                 375                 380

Met Val Asp Asp Gly Ser Gly Lys Val Glu Val Trp Cys Ile Gln Asp
385                 390                 395                 400

Leu His Arg Gln Pro Val Asp Pro Lys Arg His Gly Gln Leu Cys Ala
                405                 410                 415

Gly Asn Cys Tyr Leu Val Leu Tyr Thr Tyr Gln Arg Leu Gly Arg Val
            420                 425                 430

Gln Tyr Ile Leu Tyr Leu Trp Gln Gly His Gln Ala Thr Ala Asp Glu
        435                 440                 445

Ile Glu Ala Leu Asn Ser Asn Ala Glu Glu Leu Asp Val Met Tyr Gly
    450                 455                 460

Gly Val Leu Val Gln His Val Thr Met Gly Ser Glu Pro Pro His
465                 470                 475                 480

Phe Leu Ala Ile Phe Gln Gly Gln Leu Val Ile Phe Gln Glu Arg Ala
                485                 490                 495

Gly His His Gly Lys Gly Gln Ser Ala Ser Thr Thr Arg Leu Phe Gln
            500                 505                 510

Val Gln Gly Thr Asp Ser His Asn Thr Arg Thr Met Glu Val Pro Ala
        515                 520                 525

Arg Ala Ser Ser Leu Asn Ser Ser Asp Ile Phe Leu Leu Val Thr Ala
530                 535                 540

Ser Val Cys Tyr Leu Trp Phe Gly Lys Gly Cys Asn Gly Asp Gln Arg
```

```
545                 550                 555                 560

Glu Met Ala Arg Val Val Thr Val Ile Ser Arg Lys Asn Glu Glu
                565                 570                 575

Thr Val Leu Glu Gly Gln Glu Pro Pro His Phe Trp Glu Ala Leu Gly
            580                 585                 590

Gly Arg Xaa Pro Tyr Pro Ser Asn Lys Arg Leu Pro Glu Val Pro
        595                 600                 605

Ser Phe Gln Pro Arg Leu Phe Glu Cys Ser Ser His Met Gly Cys Leu
    610                 615                 620

Val Leu Ala Glu Val Gly Phe Phe Ser Gln Glu Asp Leu Asp Lys Tyr
625                 630                 635                 640

Asp Ile Met Leu Leu Asp Thr Trp Gln Glu Ile Phe Leu Trp Leu Gly
                645                 650                 655

Glu Ala Ala Ser Glu Trp Lys Glu Ala Val Ala Trp Gly Gln Glu Tyr
                660                 665                 670

Leu Lys Thr His Pro Ala Gly Arg Ser Pro Xaa Thr Pro Ile Val Leu
            675                 680                 685

Val Lys Gln Gly His Glu Pro Pro Thr Phe Ile Gly Trp Phe Phe Thr
690                 695                 700

Trp Asp Pro Tyr Lys Trp Thr Ser His Pro Ser His Lys Glu Val Val
705                 710                 715                 720

Asp Gly Ser Pro Ala Ala Ser Thr Ile Ser Glu Ile Thr Ala Glu
                725                 730                 735

Val Asn Asn Phe Arg Leu Ser Arg Trp Pro Gly Asn Gly Arg Ala Gly
                740                 745                 750

Ala Val Ala Leu Gln Ala Leu Lys Gly Ser Gln Asp Ser Ser Glu Asn
                755                 760                 765

Asp Leu Val Arg Ser Pro Lys Ser Ala Gly Ser Arg Thr Ser Ser Ser
            770                 775                 780

Val Ser Ser Thr Ser Ala Thr Ile Asn Gly Gly Leu Arg Arg Glu Gln
785                 790                 795                 800

Leu Met His Gln Ala Val Glu Asp Leu Pro Gly Val Asp Pro Ala
                805                 810                 815

Arg Arg Glu Phe Tyr Leu Ser Asp Ser Asp Phe Gln Asp Ile Phe Gly
            820                 825                 830

Lys Ser Lys Glu Glu Phe Tyr Ser Met Ala Thr Trp Arg Gln Arg Gln
            835                 840                 845

Glu Lys Lys Gln Leu Gly Phe Phe
    850                 855

<210> SEQ ID NO 78
<211> LENGTH: 39
<212> TYPE: PRT
<213> ORGANISM: Homo sapiens

<400> SEQUENCE: 78

Met Pro Cys Val Phe Cys Tyr Leu Leu Leu Val Gln Phe Thr Tyr
 1               5                  10                  15

Thr Phe Thr Leu Ser Asn Pro Asn Ser Ser Arg Pro Asp Ser Asp
                20                  25                  30

Phe Asn Phe Leu Lys Ala Ile
                35

<210> SEQ ID NO 79
<211> LENGTH: 30
```

```
<212> TYPE: PRT
<213> ORGANISM: Homo sapiens

<400> SEQUENCE: 79

Met Ala Leu Ser Val Leu Val Leu Leu Leu Ala Val Leu Tyr Glu
 1               5                  10                  15

Gly Ile Lys Val Gly Lys Ala Ser Cys Ser Thr Arg Tyr Trp
                20                  25                  30

<210> SEQ ID NO 80
<211> LENGTH: 45
<212> TYPE: PRT
<213> ORGANISM: Homo sapiens

<400> SEQUENCE: 80

Met Pro Ala Leu Val Leu Leu Pro Arg Val Leu Pro Gly Gln Gly
 1               5                  10                  15

Glu Val Gln Arg Val Arg Cys Pro Tyr Val Gly Asn Ser Ser Gly Arg
                20                  25                  30

Lys Ile Trp Phe Gly Phe Ile Leu Arg Ala Ile Lys His
            35                  40                  45

<210> SEQ ID NO 81
<211> LENGTH: 39
<212> TYPE: PRT
<213> ORGANISM: Homo sapiens

<400> SEQUENCE: 81

Met Glu Ala Lys Phe Gly Leu Leu Cys Phe Leu Val Ser Thr Pro Trp
 1               5                  10                  15

Ala Glu Leu Leu Ser Leu Leu Leu His Leu Thr Gln Val Pro Phe Pro
                20                  25                  30

Gly Ser Gln Gly Pro Gly Phe
            35

<210> SEQ ID NO 82
<211> LENGTH: 36
<212> TYPE: PRT
<213> ORGANISM: Homo sapiens

<400> SEQUENCE: 82

Met Leu Ser Phe Lys Leu Leu Leu Ala Val Ala Leu Gly Phe Phe
 1               5                  10                  15

Glu Gly Asp Ala Lys Phe Gly Glu Arg Asn Glu Gly Ser Gly Gln Gly
                20                  25                  30

Gly Glu Gly Ala
            35

<210> SEQ ID NO 83
<211> LENGTH: 293
<212> TYPE: PRT
<213> ORGANISM: Homo sapiens

<400> SEQUENCE: 83

Leu Ala Pro Leu Ile Ala Leu Val Tyr Ser Val Pro Arg Leu Ser Arg
 1               5                  10                  15

Trp Leu Ala Gln Pro Tyr Tyr Leu Leu Ser Ala Leu Leu Ser Ala Ala
                20                  25                  30

Phe Leu Leu Val Arg Lys Leu Pro Pro Leu Cys His Gly Leu Pro Thr
            35                  40                  45
```

```
Gln Arg Glu Asp Gly Asn Pro Cys Asp Phe Asp Trp Arg Glu Val Glu
 50                  55                  60
Ile Leu Met Phe Leu Ser Ala Ile Val Met Met Lys Asn Arg Arg Ser
 65                  70                  75                  80
Ile Thr Val Glu Gln His Ile Gly Asn Ile Phe Met Phe Ser Lys Val
                 85                  90                  95
Ala Asn Thr Ile Leu Phe Phe Arg Leu Asp Ile Arg Met Gly Leu Leu
            100                 105                 110
Tyr Ile Thr Leu Cys Ile Val Phe Leu Met Thr Cys Lys Pro Pro Leu
            115                 120                 125
Tyr Met Gly Pro Glu Tyr Ile Lys Tyr Phe Asn Asp Lys Thr Ile Asp
        130                 135                 140
Glu Leu Glu Arg Asp Lys Arg Val Thr Trp Ile Val Glu Phe Phe
145                 150                 155                 160
Ala Asn Trp Ser Asn Asp Cys Gln Ser Phe Ala Pro Ile Tyr Ala Asp
                165                 170                 175
Leu Ser Leu Lys Tyr Asn Cys Thr Gly Leu Asn Phe Gly Lys Val Asp
            180                 185                 190
Val Gly Arg Tyr Thr Asp Val Ser Thr Arg Tyr Lys Val Ser Thr Ser
        195                 200                 205
Pro Leu Thr Lys Gln Leu Pro Thr Leu Ile Leu Phe Gln Gly Gly Lys
    210                 215                 220
Glu Ala Met Arg Arg Pro Gln Ile Asp Lys Lys Gly Arg Ala Val Ser
225                 230                 235                 240
Trp Thr Phe Ser Glu Glu Asn Val Ile Arg Glu Phe Asn Leu Asn Glu
                245                 250                 255
Leu Tyr Gln Arg Ala Lys Lys Leu Ser Lys Ala Gly Asp Asn Ile Pro
            260                 265                 270
Glu Glu Gln Pro Val Ala Ser Thr Pro Thr Thr Val Ser Asp Gly Glu
        275                 280                 285
Asn Lys Lys Asp Lys
    290

<210> SEQ ID NO 84
<211> LENGTH: 143
<212> TYPE: PRT
<213> ORGANISM: Homo sapiens

<400> SEQUENCE: 84

Met Arg Gly Leu Gly Leu Trp Leu Leu Gly Ala Met Met Leu Pro Ala
  1               5                  10                  15
Ile Ala Pro Ser Arg Pro Trp Ala Leu Met Glu Gln Tyr Glu Val Val
             20                  25                  30
Leu Pro Trp Arg Leu Pro Gly Pro Arg Val Arg Arg Ala Leu Pro Ser
         35                  40                  45
His Leu Gly Leu His Pro Glu Arg Val Ser Tyr Val Leu Gly Ala Thr
     50                  55                  60
Gly His Asn Phe Thr Leu His Leu Arg Lys Asn Arg Asp Leu Leu Gly
 65                  70                  75                  80
Ser Gly Tyr Thr Glu Thr Tyr Thr Ala Ala Asn Gly Ser Glu Val Thr
                 85                  90                  95
Glu Gln Pro Arg Gly Gln Asp His Cys Phe Tyr Gln Gly His Leu Glu
            100                 105                 110
Gly Thr Gly Leu Ser Arg Gln Pro Gln His Leu Cys Arg Pro Gln Gly
            115                 120                 125
```

```
Phe Leu Pro Gly Gly Val Arg Pro Ala Pro Asp Arg Ala Pro Gly
        130                 135                 140
```

<210> SEQ ID NO 85
<211> LENGTH: 121
<212> TYPE: PRT
<213> ORGANISM: Homo sapiens
<220> FEATURE:
<221> NAME/KEY: SITE
<222> LOCATION: (67)
<223> OTHER INFORMATION: Xaa equals any of the naturally occurring
      L-amino acids
<220> FEATURE:
<221> NAME/KEY: SITE
<222> LOCATION: (89)
<223> OTHER INFORMATION: Xaa equals any of the naturally occurring
      L-amino acids

<400> SEQUENCE: 85

```
Met Arg Ile Met Leu Leu Phe Thr Ala Ile Leu Ala Phe Ser Leu Ala
 1               5                  10                  15

Gln Ser Phe Gly Ala Val Cys Lys Glu Pro Gln Glu Glu Val Val Pro
            20                  25                  30

Gly Gly Gly Arg Ser Lys Arg Asp Pro Asp Leu Tyr Gln Leu Leu Gln
        35                  40                  45

Arg Leu Phe Lys Ser His Ser Ser Leu Glu Gly Leu Leu Lys Ala Leu
    50                  55                  60

Ser Gln Xaa Ser Thr Asp Pro Lys Glu Ser Thr Ser Pro Glu Lys Arg
 65                  70                  75                  80

Asp Met His Asp Phe Phe Val Gly Xaa Met Gly Lys Arg Ser Val Gln
                85                  90                  95

Pro Asp Ser Pro Thr Asp Val Asn Gln Glu Asn Val Pro Ser Phe Gly
            100                 105                 110

Ile Leu Lys Tyr Pro Pro Arg Ala Glu
        115                 120
```

<210> SEQ ID NO 86
<211> LENGTH: 25
<212> TYPE: PRT
<213> ORGANISM: Homo sapiens

<400> SEQUENCE: 86

```
Met Val Leu Leu Met Val Trp Val Val Met Ala Val Val Val Glu Ala
 1               5                  10                  15

Val Glu Val Thr Met Gly Lys Ala Ala
            20                  25
```

<210> SEQ ID NO 87
<211> LENGTH: 4
<212> TYPE: PRT
<213> ORGANISM: Homo sapiens

<400> SEQUENCE: 87

```
Ser Leu His Ala
 1
```

<210> SEQ ID NO 88
<211> LENGTH: 235
<212> TYPE: PRT
<213> ORGANISM: Homo sapiens

<400> SEQUENCE: 88

```
Met Pro Trp Val Leu Leu Leu Thr Leu Thr His Ser Ala Val
  1               5                  10                 15

Ser Val Val Gln Ala Gly Leu Thr Gln Pro Ser Val Ser Lys Asp
             20                  25                  30

Leu Arg Gln Thr Ala Thr Leu Thr Cys Thr Gly Asn Asn Asn Val
         35                  40                  45

Gly Asp Gln Gly Ala Ala Trp Leu Gln Gln His Gln Gly His Pro Pro
     50                  55                  60

Lys Leu Leu Ser Tyr Arg Asn Asn Asn Arg Pro Ser Gly Ile Ser Glu
 65                  70                  75                  80

Arg Leu Ser Ala Ser Arg Ser Gly Ala Thr Ser Ser Leu Thr Ile Thr
                 85                  90                  95

Gly Leu Gln Pro Glu Asp Glu Ala Asp Tyr Tyr Cys Ala Ala Tyr Asp
             100                 105                 110

Ser Ser Leu Ala Val Trp Met Phe Gly Gly Thr Lys Leu Thr Val
             115                 120                 125

Leu Gly Gln Pro Lys Ala Ala Pro Ser Val Thr Leu Phe Pro Pro Ser
    130                 135                 140

Ser Glu Glu Leu Gln Ala Asn Lys Ala Thr Leu Val Cys Leu Ile Ser
145                 150                 155                 160

Asp Phe Tyr Pro Gly Ala Val Thr Val Ala Trp Lys Ala Asp Ser Ser
                165                 170                 175

Pro Val Lys Ala Gly Val Glu Thr Thr Thr Pro Ser Lys Gln Ser Asn
            180                 185                 190

Asn Lys Tyr Ala Ala Ser Ser Tyr Leu Ser Leu Thr Pro Glu Gln Trp
            195                 200                 205

Lys Ser His Lys Ser Tyr Ser Cys Gln Val Thr His Glu Gly Ser Thr
    210                 215                 220

Val Glu Lys Thr Val Ala Pro Thr Glu Cys Ser
225                 230                 235

<210> SEQ ID NO 89
<211> LENGTH: 87
<212> TYPE: PRT
<213> ORGANISM: Homo sapiens
<220> FEATURE:
<221> NAME/KEY: SITE
<222> LOCATION: (11)
<223> OTHER INFORMATION: Xaa equals any of the naturally occurring
      L-amino acids
<220> FEATURE:
<221> NAME/KEY: SITE
<222> LOCATION: (86)
<223> OTHER INFORMATION: Xaa equals any of the naturally occurring
      L-amino acids

<400> SEQUENCE: 89

Met Ser Leu Asn Val Leu Leu Ala Leu Phe Xaa Leu Leu Ala Lys
  1               5                  10                 15

Glu Ser Ser Cys Arg Ile Pro Ala Ala Arg Gly Asp Pro Leu Val Leu
                 20                  25                  30

Glu Arg Pro Pro Pro Arg Trp Glu Leu Gln Leu Val Pro Phe Ser
         35                  40                  45

Glu Gly Leu Ile Ser Ser Leu Ala Val Ile Met Gly His Ser Leu Phe
     50                  55                  60

Pro Gly Val Glu Ile Gly Tyr Pro Ala His Lys Phe His Asn Asn Asn
 65                  70                  75                  80

Thr Ser Arg Lys His Xaa Val
```

-continued

```
<210> SEQ ID NO 90
<211> LENGTH: 106
<212> TYPE: PRT
<213> ORGANISM: Homo sapiens
<220> FEATURE:
<221> NAME/KEY: SITE
<222> LOCATION: (22)
<223> OTHER INFORMATION: Xaa equals any of the naturally occurring
      L-amino acids

<400> SEQUENCE: 90

Met Ala Leu His Gly Phe His Phe Asp Leu Phe His Phe His Leu Leu
 1               5                  10                  15

Leu Phe Gln Leu Leu Xaa Leu Thr Pro Gln Cys Ser Leu Leu Gln Pro
             20                  25                  30

Ala Leu Phe Leu Arg Ile Phe Leu Ile His Asp Ser Leu Leu Leu Cys
         35                  40                  45

Ser Phe Phe Leu Leu Pro Pro Arg Leu Cys Cys Phe Leu Ser Leu His
     50                  55                  60

Met Cys Gln Phe Gln Glu Val Leu Phe Tyr Ser Gly Thr Val Leu Ile
 65                  70                  75                  80

Cys Phe Leu Phe Ala Phe Ser Val Glu Ser Glu Leu Phe Gly Phe Ile
                 85                  90                  95

Asn Arg Ile Asn His His Val His Gln Gly
            100                 105

<210> SEQ ID NO 91
<211> LENGTH: 59
<212> TYPE: PRT
<213> ORGANISM: Homo sapiens

<400> SEQUENCE: 91

Met Tyr Ala Lys Cys Gln Lys Lys Leu Ala Pro Ala Trp Leu Ile Phe
 1               5                  10                  15

Phe Ile Gly Gly Met Thr Arg Lys Ile Ile Leu Ala Pro Cys Leu Ser
             20                  25                  30

Met Val Ala Ala Arg Gly Asn Asn Asn Phe Gln Ser Lys Ala Asn
         35                  40                  45

Cys Leu Asn Thr Cys Lys Asn Lys Arg Phe Pro
     50                  55

<210> SEQ ID NO 92
<211> LENGTH: 32
<212> TYPE: PRT
<213> ORGANISM: Homo sapiens

<400> SEQUENCE: 92

Met Glu Val Pro Ala Arg Ala Ser Ser Leu Asn Ser Ser Asp Ile Phe
 1               5                  10                  15

Leu Leu Val Thr Ala Ser Val Cys Tyr Leu Trp Phe Gly Lys Gly Leu
             20                  25                  30

<210> SEQ ID NO 93
<211> LENGTH: 178
<212> TYPE: PRT
<213> ORGANISM: Homo sapiens

<400> SEQUENCE: 93

Phe Ser Val Thr Asn Asn Thr Glu Cys Gly Lys Leu Leu Glu Glu Ile
```

```
                1               5                       10                      15
            Lys Cys Ala Leu Cys Ser Pro His Ser Gln Ser Leu Phe His Ser Pro
                            20                      25                  30

Glu Arg Glu Val Leu Glu Arg Asp Leu Val Leu Pro Leu Leu Cys Lys
                        35                      40                  45

Asp Tyr Cys Lys Glu Phe Phe Tyr Thr Cys Arg Gly His Ile Pro Gly
                    50                      55                  60

Phe Leu Gln Thr Thr Ala Asp Glu Phe Cys Tyr Tyr Ala Arg Lys
             65                     70                  75                  80

Asp Gly Gly Leu Cys Phe Pro Asp Pro Arg Lys Gln Val Arg Gly
                                85                      90                  95

Pro Ala Ser Asn Tyr Leu Asp Gln Met Glu Glu Tyr Asp Lys Val Glu
                            100                     105                 110

Glu Ile Ser Arg Lys His Lys His Asn Cys Phe Cys Ile Gln Glu Val
                            115                     120                 125

Val Ser Gly Leu Arg Gln Pro Val Gly Ala Leu His Ser Gly Asp Gly
                    130                     135                 140

Ser Gln Arg Leu Phe Ile Leu Glu Lys Glu Gly Tyr Val Lys Ile Leu
             145                    150                     155                 160

Thr Pro Glu Gly Glu Ile Phe Lys Glu Pro Tyr Leu Asp Ile His Lys
                                165                     170                 175

Leu Val

<210> SEQ ID NO 94
            <211> LENGTH: 216
            <212> TYPE: PRT
            <213> ORGANISM: Homo sapiens

<400> SEQUENCE: 94

Asp Gly Asn Pro Cys Asp Phe Asp Trp Arg Glu Val Glu Ile Leu Met
             1               5                       10                      15

Phe Leu Ser Ala Ile Val Met Met Lys Asn Arg Arg Ser Ile Thr Val
                            20                      25                  30

Glu Gln His Ile Gly Asn Ile Phe Met Phe Ser Lys Val Ala Asn Thr
                        35                      40                  45

Ile Leu Phe Phe Arg Leu Asp Ile Arg Met Gly Leu Leu Tyr Ile Thr
                    50                      55                  60

Leu Cys Ile Val Phe Leu Met Thr Cys Lys Pro Pro Leu Tyr Met Gly
             65                     70                  75                  80

Pro Glu Tyr Ile Lys Tyr Phe Asn Asp Lys Thr Ile Asp Glu Glu Leu
                            85                      90                  95

Glu Arg Asp Lys Arg Val Thr Trp Ile Val Glu Phe Phe Ala Asn Trp
                            100                     105                 110

Ser Asn Asp Cys Gln Ser Phe Ala Pro Ile Tyr Ala Asp Leu Ser Leu
                            115                     120                 125

Lys Tyr Asn Cys Thr Gly Leu Asn Phe Gly Lys Val Asp Val Gly Arg
                    130                     135                 140

Tyr Thr Asp Val Ser Thr Arg Tyr Lys Val Ser Thr Ser Pro Leu Thr
             145                    150                     155                 160

Lys Gln Leu Pro Thr Leu Ile Leu Phe Gln Gly Gly Lys Glu Ala Met
                                165                     170                 175

Arg Arg Pro Gln Ile Asp Lys Lys Gly Arg Ala Val Ser Trp Thr Phe
                            180                     185                 190

Ser Glu Glu Asn Val Ile Arg Glu Phe Asn Leu Asn Glu Leu Tyr Gln
```

```
            195                 200                 205
Arg Ala Lys Lys Leu Ser Lys Ala
    210                 215
```

<210> SEQ ID NO 95
<211> LENGTH: 196
<212> TYPE: PRT
<213> ORGANISM: Homo sapiens
<220> FEATURE:
<221> NAME/KEY: SITE
<222> LOCATION: (141)
<223> OTHER INFORMATION: Xaa equals any of the naturally occurring
      L-amino acids

<400> SEQUENCE: 95

```
Gln Leu Ile Val Thr Ala Arg Thr Thr Arg Gly Leu Asp Pro Leu Phe
  1               5                  10                  15

Gly Met Cys Glu Lys Phe Leu Gln Glu Val Asp Phe Phe Gln Arg Tyr
             20                  25                  30

Phe Ile Ala Asp Leu Pro His Leu Gln Asp Ser Phe Val Asp Lys Leu
         35                  40                  45

Leu Asp Leu Met Pro Arg Leu Met Thr Ser Lys Pro Ala Glu Val Val
     50                  55                  60

Lys Ile Leu Gln Thr Met Leu Arg Gln Ser Ala Phe Leu His Leu Pro
 65                  70                  75                  80

Leu Pro Glu Gln Ile His Lys Ala Ser Ala Thr Ile Ile Glu Pro Ala
                 85                  90                  95

Gly Glu Phe Arg Gln Pro Phe Ala Val Tyr Leu Trp Val Gly Gly Cys
            100                 105                 110

Pro Gly Met Leu Met Gln Pro Trp Ser Met Cys Arg Ile Leu Arg Thr
            115                 120                 125

Leu Leu Arg Ser Arg Val Leu Tyr Pro Asp Gly Gln Xaa Ser Asp Asp
        130                 135                 140

Ser Pro Gln Ala Cys Arg Leu Pro Glu Ser Trp Pro Arg Ala Ala Pro
145                 150                 155                 160

Ala His His Ser Gly Leu Ser Leu Pro His Arg Leu Asp Arg Gly Met
                165                 170                 175

Pro Gly Gly Ser Glu Ala Ala Ala Gly Leu Gln Leu Gln Cys Ser His
            180                 185                 190

Ser Lys Met Pro
        195
```

<210> SEQ ID NO 96
<211> LENGTH: 255
<212> TYPE: PRT
<213> ORGANISM: Homo sapiens

<400> SEQUENCE: 96

```
Ile His Leu Ala Leu Val Glu Leu Leu Lys Asn Leu Thr Lys Tyr Pro
  1               5                  10                  15

Thr Asp Arg Asp Ser Ile Trp Lys Cys Leu Lys Phe Leu Gly Ser Arg
             20                  25                  30

His Pro Thr Leu Val Leu Pro Leu Val Pro Glu Leu Leu Ser Thr His
         35                  40                  45

Pro Phe Phe Asp Thr Ala Glu Pro Asp Met Asp Asp Pro Ala Tyr Ile
     50                  55                  60

Ala Val Leu Val Leu Ile Phe Asn Ala Ala Lys Thr Cys Pro Thr Met
 65                  70                  75                  80
```

-continued

```
Pro Ala Leu Phe Ser Asp His Thr Phe Arg His Tyr Ala Tyr Leu Arg
                85                  90                  95

Asp Ser Leu Ser His Leu Val Pro Ala Leu Arg Leu Pro Gly Arg Lys
            100                 105                 110

Leu Val Ser Ser Ala Val Ser Pro Ser Ile Ile Pro Gln Glu Asp Pro
            115                 120                 125

Ser Gln Gln Phe Leu Gln Gln Ser Leu Glu Arg Val Tyr Ser Leu Gln
    130                 135                 140

His Leu Asp Pro Gln Gly Ala Gln Glu Leu Leu Glu Phe Thr Ile Arg
145                 150                 155                 160

Asp Leu Gln Arg Leu Gly Glu Leu Gln Ser Glu Leu Ala Gly Val Ala
                165                 170                 175

Asp Phe Ser Ala Thr Tyr Leu Arg Cys Gln Leu Leu Leu Ile Lys Ala
                180                 185                 190

Leu Gln Glu Lys Leu Trp Asn Val Ala Ala Pro Leu Tyr Leu Lys Gln
            195                 200                 205

Ser Asp Leu Ala Ser Ala Ala Lys Gln Ile Met Glu Glu Thr Tyr
    210                 215                 220

Lys Met Glu Phe Met Tyr Ser Gly Val Glu Asn Lys Gln Val Val Ile
225                 230                 235                 240

Ile His His Met Arg Leu Gln Ala Lys Ala Leu Gln Leu Ile Val
                245                 250                 255

<210> SEQ ID NO 97
<211> LENGTH: 137
<212> TYPE: PRT
<213> ORGANISM: Homo sapiens

<400> SEQUENCE: 97

Arg Phe Tyr Ser Asn Ser Cys Cys Leu Cys Cys His Val Arg Thr Gly
  1               5                  10                  15

Thr Ile Leu Leu Gly Val Trp Tyr Leu Ile Ile Asn Ala Val Val Leu
                20                  25                  30

Leu Ile Leu Leu Ser Ala Leu Ala Asp Pro Asp Gln Tyr Asn Phe Ser
            35                  40                  45

Ser Ser Glu Leu Gly Gly Asp Phe Glu Phe Met Asp Asp Ala Asn Met
    50                  55                  60

Cys Ile Ala Ile Ala Ile Ser Leu Leu Met Ile Leu Ile Cys Ala Met
65                  70                  75                  80

Ala Thr Tyr Gly Ala Tyr Lys Gln Arg Ala Ala Gly Ile Ile Pro Phe
                85                  90                  95

Phe Cys Tyr Gln Ile Phe Asp Phe Ala Leu Asn Met Leu Val Ala Ile
            100                 105                 110

Thr Val Leu Ile Tyr Pro Asn Ser Ile Gln Glu Tyr Ile Arg Gln Leu
        115                     120                 125

Pro Pro Asn Phe Pro Tyr Arg Asp Asp
    130                 135

<210> SEQ ID NO 98
<211> LENGTH: 87
<212> TYPE: PRT
<213> ORGANISM: Homo sapiens

<400> SEQUENCE: 98

Phe Pro Thr Glu Met Met Ser Cys Ala Val Asn Pro Thr Cys Leu Val
  1               5                  10                  15
```

```
Leu Ile Ile Leu Leu Phe Ile Ser Ile Ile Leu Thr Phe Lys Gly Tyr
             20                  25                  30

Leu Ile Ser Cys Val Trp Asn Cys Tyr Arg Tyr Ile Asn Gly Arg Asn
         35                  40                  45

Ser Ser Asp Val Leu Val Tyr Val Thr Ser Asn Asp Thr Thr Val Leu
     50                  55                  60

Leu Pro Pro Tyr Asp Asp Ala Thr Val Asn Gly Ala Ala Lys Glu Pro
 65                  70                  75                  80

Pro Pro Pro Tyr Val Ser Ala
                 85

<210> SEQ ID NO 99
<211> LENGTH: 97
<212> TYPE: PRT
<213> ORGANISM: Homo sapiens

<400> SEQUENCE: 99

Ile Ala Pro Ser Arg Pro Trp Ala Leu Met Glu Gln Tyr Glu Val Val
 1               5                  10                  15

Leu Pro Trp Arg Leu Pro Gly Pro Arg Val Arg Arg Ala Leu Pro Ser
             20                  25                  30

His Leu Gly Leu His Pro Glu Arg Val Ser Tyr Val Leu Gly Ala Thr
         35                  40                  45

Gly His Asn Phe Thr Leu His Leu Arg Lys Asn Arg Asp Leu Leu Gly
     50                  55                  60

Ser Gly Tyr Thr Glu Thr Tyr Thr Ala Ala Asn Gly Ser Glu Val Thr
 65                  70                  75                  80

Glu Gln Pro Arg Gly Gln Asp His Cys Phe Tyr Gln Gly His Leu Glu
                 85                  90                  95

Gly

<210> SEQ ID NO 100
<211> LENGTH: 240
<212> TYPE: PRT
<213> ORGANISM: Homo sapiens

<400> SEQUENCE: 100

Pro Asp Ser Ala Ala Ser Leu Ser Thr Cys Ala Gly Leu Arg Gly Phe
 1               5                  10                  15

Phe Gln Val Gly Ser Asp Leu His Leu Ile Glu Pro Leu Asp Glu Gly
             20                  25                  30

Gly Glu Gly Gly Arg His Ala Val Tyr Gln Ala Glu His Leu Leu Gln
         35                  40                  45

Thr Ala Gly Thr Cys Gly Val Ser Asp Asp Ser Leu Gly Ser Leu Leu
     50                  55                  60

Gly Pro Arg Thr Ala Ala Val Phe Arg Pro Arg Pro Gly Asp Ser Leu
 65                  70                  75                  80

Pro Ser Arg Glu Thr Arg Tyr Val Glu Leu Tyr Val Val Val Asp Asn
                 85                  90                  95

Ala Glu Phe Gln Met Leu Gly Ser Glu Ala Ala Val Arg His Arg Val
                100                 105                 110

Leu Glu Val Val Asn His Val Asp Lys Leu Tyr Gln Lys Leu Asn Phe
             115                 120                 125

Arg Val Val Leu Val Gly Leu Glu Ile Trp Asn Ser Gln Asp Arg Phe
         130                 135                 140
```

```
His Val Ser Pro Asp Pro Ser Val Thr Leu Glu Asn Leu Leu Thr Trp
145                 150                 155                 160

Gln Ala Arg Gln Arg Thr Arg Arg His Leu His Asp Asn Val Gln Leu
                165                 170                 175

Ile Thr Gly Val Asp Phe Thr Gly Thr Thr Val Gly Phe Ala Arg Val
            180                 185                 190

Ser Ala Met Cys Ser His Ser Ser Gly Ala Val Asn Gln Asp His Ser
        195                 200                 205

Lys Asn Pro Val Gly Val Ala Cys Thr Met Ala His Glu Met Gly His
    210                 215                 220

Asn Leu Gly Met Asp His Asp Glu Asn Val Gln Gly Cys Arg Cys Gln
225                 230                 235                 240

<210> SEQ ID NO 101
<211> LENGTH: 118
<212> TYPE: PRT
<213> ORGANISM: Homo sapiens

<400> SEQUENCE: 101

Phe Glu Ala Gly Arg Cys Ile Met Ala Arg Pro Ala Leu Ala Pro Ser
1               5                   10                  15

Phe Pro Arg Met Phe Ser Asp Cys Ser Gln Ala Tyr Leu Glu Ser Phe
            20                  25                  30

Leu Glu Arg Pro Gln Ser Val Cys Leu Ala Asn Ala Pro Asp Leu Ser
        35                  40                  45

His Leu Val Gly Gly Pro Val Cys Gly Asn Leu Phe Val Glu Arg Gly
    50                  55                  60

Glu Gln Cys Asp Cys Gly Pro Pro Glu Asp Cys Arg Asn Arg Cys Cys
65                  70                  75                  80

Asn Ser Thr Thr Cys Gln Leu Ala Glu Gly Ala Gln Cys Ala His Gly
                85                  90                  95

Thr Cys Cys Gln Glu Cys Lys Val Lys Pro Ala Gly Glu Leu Cys Arg
            100                 105                 110

Pro Lys Lys Asp Met Cys
            115

<210> SEQ ID NO 102
<211> LENGTH: 471
<212> TYPE: PRT
<213> ORGANISM: Homo sapiens

<400> SEQUENCE: 102

Gly Ser Gln Glu Glu Arg Phe Ala Pro Gly Trp Asn Arg Asp Tyr Pro
1               5                   10                  15

Pro Pro Pro Leu Lys Ser His Ala Gln Glu Arg His Ser Gly Asn Phe
            20                  25                  30

Pro Gly Arg Asp Ser Leu Pro Phe Asp Phe Gln Gly His Ser Gly Pro
        35                  40                  45

Pro Phe Ala Asn Val Glu Glu His Ser Phe Ser Tyr Gly Ala Arg Asp
    50                  55                  60

Gly Pro His Gly Asp Tyr Arg Gly Glu Gly Pro Gly His Asp Phe
65                  70                  75                  80

Arg Gly Gly Asp Phe Ser Ser Asp Phe Gln Ser Arg Asp Ser Ser
                85                  90                  95

Gln Leu Asp Phe Arg Gly Arg Asp Ile His Ser Gly Asp Phe Arg Asp
            100                 105                 110
```

-continued

```
Arg Glu Gly Pro Pro Met Asp Tyr Arg Gly Asp Gly Thr Ser Met
            115                 120                 125

Asp Tyr Arg Gly Arg Glu Ala Pro His Met Asn Tyr Arg Asp Arg Asp
    130                 135                 140

Ala His Ala Val Asp Phe Arg Gly Arg Asp Ala Pro Pro Ser Asp Phe
145                 150                 155                 160

Arg Gly Arg Gly Thr Tyr Asp Leu Asp Phe Arg Gly Arg Asp Gly Ser
                165                 170                 175

His Ala Asp Phe Arg Gly Arg Asp Leu Ser Asp Leu Asp Phe Arg Ala
                180                 185                 190

Arg Glu Gln Ser Arg Ser Asp Phe Arg Asn Arg Asp Val Ser Asp Leu
            195                 200                 205

Asp Phe Arg Asp Lys Asp Gly Thr Gln Val Asp Phe Arg Gly Arg Gly
    210                 215                 220

Ser Gly Thr Thr Asp Leu Asp Phe Arg Asp Arg Asp Thr Pro His Ser
225                 230                 235                 240

Asp Phe Arg Gly Arg His Arg Ser Arg Thr Asp Gln Asp Phe Arg Gly
                245                 250                 255

Arg Glu Met Gly Ser Cys Met Glu Phe Lys Asp Arg Glu Met Pro Pro
            260                 265                 270

Val Asp Pro Asn Ile Leu Asp Tyr Ile Gln Pro Ser Thr Gln Asp Arg
    275                 280                 285

Glu His Ser Gly Met Asn Val Asn Arg Arg Glu Glu Ser Thr His Asp
            290                 295                 300

His Thr Ile Glu Arg Pro Ala Phe Gly Ile Gln Lys Gly Glu Phe Glu
305                 310                 315                 320

His Ser Glu Thr Arg Glu Gly Glu Thr Gln Gly Val Ala Phe Glu His
                325                 330                 335

Glu Ser Pro Ala Asp Phe Gln Asn Ser Gln Ser Pro Val Gln Asp Gln
                340                 345                 350

Asp Lys Ser Gln Leu Ser Gly Arg Glu Glu Gln Ser Ser Asp Ala Gly
            355                 360                 365

Leu Phe Lys Glu Glu Gly Gly Leu Asp Phe Leu Gly Arg Gln Asp Thr
    370                 375                 380

Asp Tyr Arg Ser Met Glu Tyr Arg Asp Val Asp His Arg Leu Pro Gly
385                 390                 395                 400

Ser Gln Met Phe Gly Tyr Gly Gln Ser Lys Ser Phe Pro Glu Gly Lys
                405                 410                 415

Thr Ala Arg Asp Ala Gln Arg Asp Leu Gln Asp Gln Asp Tyr Arg Thr
                420                 425                 430

Gly Pro Ser Glu Glu Lys Pro Ser Arg Leu Ile Arg Leu Ser Gly Val
            435                 440                 445

Pro Glu Asp Ala Thr Lys Glu Glu Ile Leu Asn Ala Phe Arg Thr Pro
    450                 455                 460

Asp Gly Met Pro Val Lys Asn
465                 470

<210> SEQ ID NO 103
<211> LENGTH: 125
<212> TYPE: PRT
<213> ORGANISM: Homo sapiens

<400> SEQUENCE: 103

Gly Leu Gln Asp Ser Ala Arg Gly Gly Ser Gln Glu Glu Arg Phe Ala
  1               5                  10                  15
```

```
Pro Gly Trp Asn Arg Asp Tyr Pro Pro Pro Leu Lys Ser His Ala
             20                  25                  30

Gln Glu Arg His Ser Gly Asn Phe Pro Gly Arg Asp Ser Leu Pro Phe
         35                  40                  45

Asp Phe Gln Gly His Ser Gly Pro Pro Phe Ala Asn Val Glu Glu His
     50                  55                  60

Ser Phe Ser Tyr Gly Ala Arg Asp Gly Pro His Gly Asp Tyr Arg Gly
 65                  70                  75                  80

Gly Glu Gly Pro Gly His Asp Phe Arg Gly Gly Asp Phe Ser Ser Ser
                 85                  90                  95

Asp Phe Gln Ser Arg Asp Ser Ser Gln Leu Asp Phe Arg Gly Arg Asp
             100                 105                 110

Ile His Ser Gly Asp Phe Arg Asp Arg Glu Gly Pro Pro
             115                 120                 125

<210> SEQ ID NO 104
<211> LENGTH: 330
<212> TYPE: PRT
<213> ORGANISM: Homo sapiens
<220> FEATURE:
<221> NAME/KEY: SITE
<222> LOCATION: (7)
<223> OTHER INFORMATION: Xaa equals any of the naturally occurring
      L-amino acids
<220> FEATURE:
<221> NAME/KEY: SITE
<222> LOCATION: (147)
<223> OTHER INFORMATION: Xaa equals any of the naturally occurring
      L-amino acids
<220> FEATURE:
<221> NAME/KEY: SITE
<222> LOCATION: (181)
<223> OTHER INFORMATION: Xaa equals any of the naturally occurring
      L-amino acids
<220> FEATURE:
<221> NAME/KEY: SITE
<222> LOCATION: (190)
<223> OTHER INFORMATION: Xaa equals any of the naturally occurring
      L-amino acids
<220> FEATURE:
<221> NAME/KEY: SITE
<222> LOCATION: (260)
<223> OTHER INFORMATION: Xaa equals any of the naturally occurring
      L-amino acids

<400> SEQUENCE: 104

Met Leu Pro Asp Trp Lys Xaa Ser Leu Ile Leu Met Ala Tyr Ile Ile
 1               5                  10                  15

Ile Phe Leu Thr Gly Leu Pro Ala Asn Leu Leu Ala Leu Arg Ala Phe
             20                  25                  30

Val Gly Arg Ile Arg Gln Pro Gln Pro Ala Pro Val His Ile Leu Leu
         35                  40                  45

Leu Ser Leu Thr Leu Ala Asp Leu Leu Leu Leu Leu Leu Leu Pro Phe
     50                  55                  60

Lys Ile Ile Glu Ala Ala Ser Asn Phe Arg Trp Tyr Leu Pro Lys Val
 65                  70                  75                  80

Val Cys Ala Leu Thr Ser Phe Gly Phe Tyr Ser Ser Ile Tyr Cys Ser
                 85                  90                  95

Thr Trp Leu Leu Ala Gly Ile Ser Ile Glu Arg Tyr Leu Gly Val Ala
             100                 105                 110

Phe Pro Val Gln Tyr Lys Leu Ser Arg Arg Pro Leu Tyr Gly Val Ile
             115                 120                 125
```

```
Ala Ala Leu Val Ala Trp Val Met Ser Phe Gly His Cys Thr Ile Val
        130                 135                 140

Ile Ile Xaa Gln Tyr Leu Asn Thr Thr Glu Gln Val Arg Ser Gly Asn
145                 150                 155                 160

Glu Ile Thr Cys Tyr Glu Asn Phe Thr Asp Asn Gln Leu Asp Val Val
                165                 170                 175

Leu Pro Val Arg Xaa Glu Leu Cys Leu Val Leu Phe Phe Xaa Pro Met
            180                 185                 190

Ala Val Thr Ile Phe Cys Tyr Trp Arg Phe Val Trp Ile Met Leu Ser
            195                 200                 205

Gln Pro Leu Val Gly Ala Gln Arg Arg Arg Ala Val Gly Leu Ala
        210                 215                 220

Val Val Thr Leu Leu Asn Phe Leu Val Cys Phe Gly Pro Tyr Asn Val
225                 230                 235                 240

Ser His Leu Val Gly Tyr His Gln Arg Lys Ser Pro Trp Trp Arg Ser
                245                 250                 255

Ile Ala Val Xaa Phe Ser Ser Leu Asn Ala Ser Leu Asp Pro Leu Leu
            260                 265                 270

Phe Tyr Phe Ser Ser Ser Val Val Arg Arg Ala Phe Gly Arg Gly Leu
        275                 280                 285

Gln Val Leu Arg Asn Gln Gly Ser Ser Leu Leu Gly Arg Arg Gly Lys
        290                 295                 300

Asp Thr Ala Glu Gly Thr Asn Glu Asp Arg Gly Val Gly Gln Gly Glu
305                 310                 315                 320

Gly Met Pro Ser Ser Asp Phe Thr Thr Glu
                325                 330

<210> SEQ ID NO 105
<211> LENGTH: 17
<212> TYPE: PRT
<213> ORGANISM: Homo sapiens

<400> SEQUENCE: 105

Cys Ser Thr Trp Leu Leu Ala Gly Ile Ser Ile Glu Arg Tyr Leu Gly
  1               5                  10                  15

Val

<210> SEQ ID NO 106
<211> LENGTH: 94
<212> TYPE: PRT
<213> ORGANISM: Homo sapiens
<220> FEATURE:
<221> NAME/KEY: SITE
<222> LOCATION: (7)
<223> OTHER INFORMATION: Xaa equals any of the naturally occurring
      L-amino acids
<220> FEATURE:
<221> NAME/KEY: SITE
<222> LOCATION: (41)
<223> OTHER INFORMATION: Xaa equals any of the naturally occurring
      L-amino acids
<220> FEATURE:
<221> NAME/KEY: SITE
<222> LOCATION: (50)
<223> OTHER INFORMATION: Xaa equals any of the naturally occurring
      L-amino acids

<400> SEQUENCE: 106

Cys Thr Ile Val Ile Ile Xaa Gln Tyr Leu Asn Thr Thr Glu Gln Val
  1               5                  10                  15

Arg Ser Gly Asn Glu Ile Thr Cys Tyr Glu Asn Phe Thr Asp Asn Gln
```

-continued

```
                  20                  25                  30
Leu Asp Val Val Leu Pro Val Arg Xaa Glu Leu Cys Leu Val Leu Phe
             35                  40                  45

Phe Xaa Pro Met Ala Val Thr Ile Phe Cys Tyr Trp Arg Phe Val Trp
         50                  55                  60

Ile Met Leu Ser Gln Pro Leu Val Gly Ala Gln Arg Arg Arg Arg Ala
 65                  70                  75                  80

Val Gly Leu Ala Val Val Thr Leu Leu Asn Phe Leu Val Cys
                 85                  90
```

<210> SEQ ID NO 107
<211> LENGTH: 143
<212> TYPE: PRT
<213> ORGANISM: Homo sapiens
<220> FEATURE:
<221> NAME/KEY: SITE
<222> LOCATION: (25)
<223> OTHER INFORMATION: Xaa equals any of the naturally occurring
      L-amino acids

<400> SEQUENCE: 107

```
Gly Leu Pro Ala Ala Arg Val Arg Trp Glu Ser Ser Phe Ser Arg Thr
  1               5                  10                  15

Val Val Ala Pro Ser Ala Val Ala Xaa Lys Arg Pro Pro Glu Pro Thr
             20                  25                  30

Thr Pro Trp Gln Glu Asp Pro Glu Pro Glu Asp Glu Asn Leu Tyr Glu
         35                  40                  45

Lys Asn Pro Asp Ser His Gly Tyr Asp Lys Asp Pro Val Leu Asp Val
 50                  55                  60

Trp Asn Met Arg Leu Val Phe Phe Gly Val Ser Ile Ile Leu Val
 65                  70                  75                  80

Leu Gly Ser Thr Phe Val Ala Tyr Leu Pro Asp Tyr Arg Cys Thr Gly
                 85                  90                  95

Cys Pro Arg Ala Trp Asp Gly Met Lys Glu Trp Ser Arg Glu Ala
            100                 105                 110

Glu Arg Leu Val Lys Tyr Arg Glu Ala Asn Gly Leu Pro Ile Met Glu
            115                 120                 125

Ser Asn Cys Phe Asp Pro Ser Lys Ile Gln Leu Pro Glu Asp Glu
            130                 135                 140
```

<210> SEQ ID NO 108
<211> LENGTH: 36
<212> TYPE: PRT
<213> ORGANISM: Homo sapiens

<400> SEQUENCE: 108

```
Pro Glu Lys Arg Asp Met His Asp Phe Val Gly Leu Met Gly Lys
  1               5                  10                  15

Arg Ser Val Gln Pro Asp Ser Pro Thr Asp Val Asn Gln Glu Asn Val
             20                  25                  30

Pro Ser Phe Gly
         35
```

<210> SEQ ID NO 109
<211> LENGTH: 15
<212> TYPE: PRT
<213> ORGANISM: Homo sapiens

<400> SEQUENCE: 109

Lys Arg Asp Met His Asp Phe Phe Val Gly Leu Met Gly Lys Arg
1               5                   10                  15

<210> SEQ ID NO 110
<211> LENGTH: 10
<212> TYPE: PRT
<213> ORGANISM: Homo sapiens

<400> SEQUENCE: 110

Asp Met His Asp Phe Phe Val Gly Leu Met
1               5                   10

<210> SEQ ID NO 111
<211> LENGTH: 16
<212> TYPE: PRT
<213> ORGANISM: Homo sapiens

<400> SEQUENCE: 111

Glu Trp Glu Ala Thr Glu Glu Met Glu Trp Ile Ile Arg Glu Ala Met
1               5                   10                  15

<210> SEQ ID NO 112
<211> LENGTH: 35
<212> TYPE: PRT
<213> ORGANISM: Homo sapiens

<400> SEQUENCE: 112

Trp Glu Trp Gly Thr Ile Thr Val Glu Asp Met Val Leu Leu Met Val
1               5                   10                  15
Trp Val Val Met Ala Val Val Val Glu Ala Val Glu Val Thr Met Gly
                20                  25                  30
Lys Ala Ala
        35

<210> SEQ ID NO 113
<211> LENGTH: 18
<212> TYPE: PRT
<213> ORGANISM: Homo sapiens

<400> SEQUENCE: 113

Gly Met Gly Gly Tyr Gly Arg Asp Gly Met Asp Asn Gln Gly Gly Tyr
1               5                   10                  15
Gly Ser

<210> SEQ ID NO 114
<211> LENGTH: 43
<212> TYPE: PRT
<213> ORGANISM: Homo sapiens

<400> SEQUENCE: 114

Gly Met Gly Asn Asn Tyr Ser Gly Gly Tyr Gly Thr Pro Asp Gly Leu
1               5                   10                  15
Gly Gly Tyr Gly Arg Gly Gly Gly Ser Gly Gly Tyr Tyr Gly Gln
                20                  25                  30
Gly Gly Met Ser Gly Gly Trp Arg Gly Met
        35                  40

<210> SEQ ID NO 115
<211> LENGTH: 43
<212> TYPE: PRT
<213> ORGANISM: Homo sapiens

<400> SEQUENCE: 115

Gly Met Gly Asn Asn Tyr Ser Gly Gly Tyr Gly Thr Pro Asp Gly Leu

```
            1               5              10              15
Gly Gly Tyr Gly Arg Gly Gly Gly Ser Gly Gly Tyr Tyr Gly Gln
                    20              25              30

Gly Gly Met Ser Gly Gly Trp Arg Gly Met
            35              40

<210> SEQ ID NO 116
<211> LENGTH: 223
<212> TYPE: PRT
<213> ORGANISM: Homo sapiens

<400> SEQUENCE: 116

Trp Asp Ser Thr Thr Ser Trp Thr Thr Ile Trp Leu Gln Gln Arg Gly
 1               5                  10                  15

Asn Ser Ser Val Leu Ser Arg Val Gly Asn Arg Ala Asn Gly Ile Thr
                20                  25                  30

Leu Thr Met Asp Tyr Gln Gly Arg Ser Thr Gly Glu Ala Phe Val Gln
            35                  40                  45

Phe Ala Ser Lys Glu Ile Ala Glu Asn Ala Leu Gly Lys His Lys Glu
        50                  55                  60

Arg Ile Gly His Arg Tyr Ile Glu Ile Phe Arg Ser Ser Arg Ser Glu
 65                  70                  75                  80

Ile Lys Gly Phe Tyr Asp Pro Pro Arg Arg Leu Leu Gly Gln Arg Pro
                85                  90                  95

Gly Pro Tyr Asp Arg Pro Ile Gly Arg Gly Tyr Tyr Gly Ala
                100                 105                 110

Gly Arg Gly Ser Met Tyr Asp Arg Met Arg Gly Gly Asp Gly Tyr
            115                 120                 125

Asp Gly Tyr Gly Gly Phe Asp Asp Tyr Gly Gly Tyr Asn Asn Tyr
        130                 135                 140

Gly Tyr Gly Asn Asp Gly Phe Asp Asp Arg Met Arg Asp Gly Arg Gly
145                 150                 155                 160

Met Gly Gly His Gly Tyr Gly Gly Ala Gly Asp Ala Ser Ser Gly Phe
                165                 170                 175

His Gly Gly His Phe Val His Met Arg Gly Leu Pro Phe Arg Ala Thr
            180                 185                 190

Glu Asn Asp Ile Ala Asn Phe Phe Ser Pro Leu Asn Pro Ile Arg Val
        195                 200                 205

His Ile Asp Ile Gly Ala Asp Gly Arg Ala Gln Glu Lys Gln Met
    210                 215                 220

<210> SEQ ID NO 117
<211> LENGTH: 26
<212> TYPE: PRT
<213> ORGANISM: Homo sapiens

<400> SEQUENCE: 117

Phe Thr His Ser Phe Ile Leu Glu His Ala Phe Ser Leu Leu Ile Thr
 1               5                  10                  15

Leu Pro Val Ser Ser Trp Ala Ala Asn Asn
                20                  25

<210> SEQ ID NO 118
<211> LENGTH: 384
<212> TYPE: PRT
<213> ORGANISM: Homo sapiens
<220> FEATURE:
<221> NAME/KEY: SITE
```

```
<222> LOCATION: (20)
<223> OTHER INFORMATION: Xaa equals any of the naturally occurring
      L-amino acids
<220> FEATURE:
<221> NAME/KEY: SITE
<222> LOCATION: (63)
<223> OTHER INFORMATION: Xaa equals any of the naturally occurring
      L-amino acids
<220> FEATURE:
<221> NAME/KEY: SITE
<222> LOCATION: (66)
<223> OTHER INFORMATION: Xaa equals any of the naturally occurring
      L-amino acids
<220> FEATURE:
<221> NAME/KEY: SITE
<222> LOCATION: (187)
<223> OTHER INFORMATION: Xaa equals any of the naturally occurring
      L-amino acids

<400> SEQUENCE: 118
```

| Met | Met | Ile | Gln | Trp | Asn | Gly | Pro | Lys | Thr | Ser | Ile | Ser | Glu | Lys | Ala |
|---|---|---|---|---|---|---|---|---|---|---|---|---|---|---|---|
| 1 | | | | 5 | | | | | 10 | | | | | 15 | |

| Arg | Gly | Leu | Xaa | Leu | Thr | Tyr | Ser | Leu | Arg | Asp | Arg | Glu | Arg | Gly | Gly |
|---|---|---|---|---|---|---|---|---|---|---|---|---|---|---|---|
| | | | 20 | | | | | 25 | | | | | 30 | | |

| Gly | Arg | Ala | Gln | Ile | Gly | Val | Val | Asp | Asp | Glu | Ala | Lys | Ala | Pro | Asp |
|---|---|---|---|---|---|---|---|---|---|---|---|---|---|---|---|
| | | | 35 | | | | | 40 | | | | | 45 | | |

| Leu | Met | Gln | Ile | Met | Glu | Ala | Val | Leu | Gly | Arg | Arg | Val | Gly | Xaa | Leu |
|---|---|---|---|---|---|---|---|---|---|---|---|---|---|---|---|
| 50 | | | | | 55 | | | | | 60 | | | | | |

| Arg | Xaa | Ala | Thr | Pro | Ser | Lys | Asp | Ile | Asn | Gln | Leu | Gln | Lys | Ala | Asn |
|---|---|---|---|---|---|---|---|---|---|---|---|---|---|---|---|
| 65 | | | | | 70 | | | | | 75 | | | | | 80 |

| Val | Arg | Leu | Tyr | His | Val | Tyr | Glu | Lys | Gly | Lys | Asp | Leu | Val | Val | Leu |
|---|---|---|---|---|---|---|---|---|---|---|---|---|---|---|---|
| | | | | 85 | | | | | 90 | | | | | 95 | |

| Glu | Leu | Ala | Thr | Pro | Pro | Leu | Thr | Gln | Asp | Leu | Leu | Gln | Glu | Glu | Asp |
|---|---|---|---|---|---|---|---|---|---|---|---|---|---|---|---|
| | | | 100 | | | | | 105 | | | | | 110 | | |

| Phe | Tyr | Ile | Leu | Asp | Gln | Gly | Gly | Phe | Lys | Ile | Tyr | Val | Trp | Gln | Gly |
|---|---|---|---|---|---|---|---|---|---|---|---|---|---|---|---|
| | | | 115 | | | | | 120 | | | | | 125 | | |

| Arg | Met | Ser | Ser | Leu | Gln | Glu | Arg | Lys | Ala | Ala | Phe | Ser | Arg | Ala | Val |
|---|---|---|---|---|---|---|---|---|---|---|---|---|---|---|---|
| | 130 | | | | | 135 | | | | | 140 | | | | |

| Gly | Phe | Ile | Gln | Ala | Lys | Gly | Tyr | Pro | Thr | Tyr | Thr | Asn | Val | Glu | Val |
|---|---|---|---|---|---|---|---|---|---|---|---|---|---|---|---|
| 145 | | | | | 150 | | | | | 155 | | | | | 160 |

| Val | Asn | Asp | Gly | Ala | Glu | Ser | Ala | Ala | Phe | Lys | Gln | Leu | Phe | Arg | Thr |
|---|---|---|---|---|---|---|---|---|---|---|---|---|---|---|---|
| | | | | 165 | | | | | 170 | | | | | 175 | |

| Trp | Ser | Glu | Lys | Arg | Arg | Arg | Asn | Gln | Lys | Xaa | Gly | Gly | Arg | Asp | Lys |
|---|---|---|---|---|---|---|---|---|---|---|---|---|---|---|---|
| | | | 180 | | | | | 185 | | | | | 190 | | |

| Ser | Ile | His | Val | Lys | Leu | Asp | Val | Gly | Lys | Leu | His | Thr | Gln | Pro | Lys |
|---|---|---|---|---|---|---|---|---|---|---|---|---|---|---|---|
| | | | 195 | | | | | 200 | | | | | 205 | | |

| Leu | Ala | Ala | Gln | Leu | Arg | Met | Val | Asp | Asp | Gly | Ser | Gly | Lys | Val | Glu |
|---|---|---|---|---|---|---|---|---|---|---|---|---|---|---|---|
| | 210 | | | | | 215 | | | | | 220 | | | | |

| Val | Trp | Cys | Ile | Gln | Asp | Leu | His | Arg | Gln | Pro | Val | Asp | Pro | Lys | Arg |
|---|---|---|---|---|---|---|---|---|---|---|---|---|---|---|---|
| 225 | | | | | 230 | | | | | 235 | | | | | 240 |

| His | Gly | Gln | Leu | Cys | Ala | Gly | Asn | Cys | Tyr | Leu | Val | Leu | Tyr | Thr | Tyr |
|---|---|---|---|---|---|---|---|---|---|---|---|---|---|---|---|
| | | | | 245 | | | | | 250 | | | | | 255 | |

| Gln | Arg | Leu | Gly | Arg | Val | Gln | Tyr | Ile | Leu | Tyr | Leu | Trp | Gln | Gly | His |
|---|---|---|---|---|---|---|---|---|---|---|---|---|---|---|---|
| | | | 260 | | | | | 265 | | | | | 270 | | |

| Gln | Ala | Thr | Ala | Asp | Glu | Ile | Glu | Ala | Leu | Asn | Ser | Asn | Ala | Glu | Glu |
|---|---|---|---|---|---|---|---|---|---|---|---|---|---|---|---|
| | | | 275 | | | | | 280 | | | | | 285 | | |

| Leu | Asp | Val | Met | Tyr | Gly | Gly | Val | Leu | Gln | Glu | His | Val | Thr | Met | |
|---|---|---|---|---|---|---|---|---|---|---|---|---|---|---|---|
| | 290 | | | | | 295 | | | | | 300 | | | | |

| Gly | Ser | Glu | Pro | Pro | His | Phe | Leu | Ala | Ile | Phe | Gln | Gly | Gln | Leu | Val |
|---|---|---|---|---|---|---|---|---|---|---|---|---|---|---|---|

```
305                 310                 315                 320
Ile Phe Gln Glu Arg Ala Gly His His Gly Lys Gly Gln Ser Ala Ser
                325                 330                 335

Thr Thr Arg Leu Phe Gln Val Gln Gly Thr Asp Ser His Asn Thr Arg
                340                 345                 350

Thr Met Glu Val Pro Ala Arg Ala Ser Ser Leu Asn Ser Ser Asp Ile
                355                 360                 365

Phe Leu Leu Val Thr Ala Ser Val Cys Tyr Leu Trp Phe Gly Lys Gly
            370                 375                 380
```

TESTIS EXPRESSED POLYPEPTIDE

This application is a continuation-in-part of, and claims benefit under 35 U.S.C. §120 of copending U.S. patent application Ser. No. PCT/US98/04858, filed Mar. 12, 1998 (published in English), which is hereby incorporated by reference, which claims benefit under 35 U.S.C. §119(e) based on U.S. Provision Applications.

|    | Filing Date  | U.S. patent application Ser. No. |
|----|--------------|----------------------------------|
| 1. | 14-Mar-1997  | 60/040,762                       |
| 2. | 14-Mar-1997  | 60/040,710                       |
| 3. | 30-May-1997  | 60/050,934                       |
| 4. | 30-May-1997  | 60/048,100                       |
| 5. | 30-May-1997  | 60/048,357                       |
| 6. | 30-May-1997  | 60/048,189                       |
| 7. | 05-Sep-1997  | 60/057,765                       |
| 8. | 06-Jun-1997  | 60/048,970                       |
| 9. | 19-Dec-1997  | 60/068,368                       |

FIELD OF THE INVENTION

This invention relates to newly identified polynucleotides and the polypeptides encoded by these polynucleotides, uses of such polynucleotides and polypeptides, and their production.

BACKGROUND OF THE INVENTION

Unlike bacterium, which exist as a single compartment surrounded by a membrane, human cells and other eucaryotes are subdivided by membranes into many functionally distinct compartments. Each membrane-bounded compartment, or organelle, contains different proteins essential for the function of the organelle. The cell uses "sorting signals," which are amino acid motifs located within the protein, to target proteins to particular cellular organelles.

One type of sorting signal, called a signal sequence, a signal peptide, or a leader sequence, directs a class of proteins to an organelle called the endoplasmic reticulum (ER). The ER separates the membrane-bounded proteins from all other types of proteins. Once localized to the ER, both groups of proteins can be further directed to another organelle called the Golgi apparatus. Here, the Golgi distributes the proteins to vesicles, including secretory vesicles, the cell membrane, lysosomes, and the other organelles.

Proteins targeted to the ER by a signal sequence can be released into the extracellular space as a secreted protein. For example, vesicles containing secreted proteins can fuse with the cell membrane and release their contents into the extracellular space—a process called exocytosis. Exocytosis can occur constitutively or after receipt of a triggering signal. In the latter case, the proteins are stored in secretory vesicles (or secretory granules) until exocytosis is triggered. Similarly, proteins residing on the cell membrane can also be secreted into the extracellular space by proteolytic cleavage of a "linker" holding the protein to the membrane.

Despite the great progress made in recent years, only a small number of genes encoding human secreted proteins have been identified. These secreted proteins include the commercially valuable human insulin, interferon, Factor VIII, human growth hormone, tissue plasminogen activator, and erythropoeitin. Thus, in light of the pervasive role of secreted proteins in human physiology, a need exists for identifying and characterizing novel human secreted proteins and the genes that encode them. This knowledge will allow one to detect, to treat, and to prevent medical disorders by using secreted proteins or the genes that encode them.

SUMMARY OF THE INVENTION

The present invention relates to novel polynucleotides and the encoded polypeptides. Moreover, the present invention relates to vectors, host cells, antibodies, and recombinant methods for producing the polypeptides and polynucleotides. Also provided are diagnostic methods for detecting disorders related to the polypeptides, and therapeutic methods for treating such disorders. The invention further relates to screening methods for identifying binding partners of the polypeptides.

DETAILED DESCRIPTION

Definitions

The following definitions are provided to facilitate understanding of certain terms used throughout this specification.

In the present invention, "isolated" refers to material removed from its original environment (e.g., the natural environment if it is naturally occurring), and thus is altered "by the hand of man" from its natural state. For example, an isolated polynucleotide could be part of a vector or a composition of matter, or could be contained within a cell, and still be "isolated" because that vector, composition of matter, or particular cell is not the original environment of the polynucleotide.

In the present invention, a "secreted" protein refers to those proteins capable of being directed to the ER, secretory vesicles, or the extracellular space as a result of a signal sequence, as well as those proteins released into the extracellular space without necessarily containing a signal sequence. If the secreted protein is released into the extracellular space, the secreted protein can undergo extracellular processing to produce a "mature" protein. Release into the extracellular space can occur by many mechanisms, including exocytosis and proteolytic cleavage.

As used herein, a "polynucleotide" refers to a molecule having a nucleic acid sequence contained in SEQ ID NO:X or the cDNA contained within the clone deposited with the ATCC. For example, the polynucleotide can contain the nucleotide sequence of the full length cDNA sequence, including the 5' and 3' untranslated sequences, the coding region, with or without the signal sequence, the secreted protein coding region, as well as fragments, epitopes, domains, and variants of the nucleic acid sequence. Moreover, as used herein, a "polypeptide" refers to a molecule having the translated amino acid sequence generated from the polynucleotide as broadly defined.

In the present invention, the full length sequence identified as SEQ ID NO:X was often generated by overlapping sequences contained in multiple clones (contig analysis). A representative clone containing all or most of the sequence for SEQ ID NO:X was deposited with the American Type Culture Collection ("ATCC"). As shown in FIGS. A–G, each clone is identified by a cDNA Clone ID (Identifier) and the ATCC Deposit Number. The ATCC is located at 10801 University Boulevard, Manassas, Va. 20110-2209, USA. The ATCC deposit was made pursuant to the terms of the Budapest Treaty on the international recognition of the deposit of microorganisms for purposes of patent procedure.

A "polynucleotide" of the present invention also includes those polynucleotides capable of hybridizing, under stringent hybridization conditions, to sequences contained in SEQ ID NO:X, the complement thereof, or the cDNA within the clone deposited with the ATCC. "Stringent hybridization conditions" refers to an overnight incubation at 42° C. in a solution comprising 50% formamide, 5×SSC (750 mM NaCl, 75 mM sodium citrate), 50 mM sodium phosphate (pH 7.6), 5×Denhardt's solution, 10% dextran sulfate, and 20 μg/ml denatured, sheared salmon sperm DNA, followed by washing the filters in 0.1×SSC at about 65° C.

Also contemplated are nucleic acid molecules that hybridize to the polynucleotides of the present invention at lower stringency hybridization conditions. Changes in the stringency of hybridization and signal detection are primarily accomplished through the manipulation of formamide concentration (lower percentages of formamide result in lowered stringency); salt conditions, or temperature. For example, lower stringency conditions include an overnight incubation at 37° C. in a solution comprising 6×SSPE (20×SSPE=3M NaCl; 0.2M $NaH_2PO_4$; 0.02M EDTA, pH 7.4), 0.5% SDS, 30% formamide, 100 ug/ml salmon sperm blocking DNA; followed by washes at 50° C. with 1×SSPE, 0.1% SDS. In addition, to achieve even lower stringency, washes performed following stringent hybridization can be done at higher salt concentrations (e.g. 5×SSC).

Note that variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility.

Of course, a polynucleotide which hybridizes only to polyA+ sequences (such as any 3' terminal polyA+ tract of a cDNA shown in the sequence listing), or to a complementary stretch of T (or U) residues, would not be included in the definition of "polynucleotide," since such a polynucleotide would hybridize to any nucleic acid molecule containing a poly (A) stretch or the complement thereof (e.g., practically any double-stranded cDNA clone).

The polynucleotide of the present invention can be composed of any polyribonucleotide or polydeoxribonucleotide, which may be unmodified RNA or DNA or modified RNA or DNA. For example, polynucleotides can be composed of single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, the polynucleotide can be composed of triple-stranded regions comprising RNA or DNA or both RNA and DNA. A polynucleotide may also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

The polypeptide of the present invention can be composed of amino acids joined to each other by peptide bonds or modified peptide bonds, i.e., peptide isosteres, and may contain amino acids other than the 20 gene-encoded amino acids. The polypeptides may be modified by either natural processes, such as posttranslational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched, for example, as a result of ubiquitination, and they may be cyclic, with or without branching. Cyclic, branched, and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, PROTEINS—STRUCTURE AND MOLECULAR PROPERTIES, 2nd Ed., T. E. Creighton, W. H. Freeman and Company, New York (1993); POSTTRANSLATIONAL COVALENT MODIFICATION OF PROTEINS, B. C. Johnson, Ed., Academic Press, New York, pgs. 1–12 (1983); Seifter et al., Meth Enzymol 182:626–646 (1990); Rattan et al., Ann NY Acad Sci 663:48–62 (1992).)

"SEQ ID NO:X" refers to a polynucleotide sequence while "SEQ ID NO:Y" refers to a polypeptide sequence, both sequences identified by an integer specified in FIGS. 1A–G.

"A polypeptide having biological activity" refers to polypeptides exhibiting activity similar, but not necessarily identical to, an activity of a polypeptide of the present invention, including mature forms, as measured in a particular biological assay, with or without dose dependency. In the case where dose dependency does exist, it need not be identical to that of the polypeptide, but rather substantially similar to the dose-dependence in a given activity as compared to the polypeptide of the present invention (i.e., the candidate polypeptide will exhibit greater activity or not more than about 25-fold less and, preferably, not more than about tenfold less activity, and most preferably, not more than about three-fold less activity relative to the polypeptide of the present invention.)

Polynucleotides and Polypeptides of the Invention
Features of Protein Enclded by Gene No: 1

The gene encoding the disclosed cDNA is thought to reside on chromosome 1. Accordingly, polynucleotides related to this invention are useful as a marker in linkage analysis for chromosome 1.

It has been discovered that this gene is expressed primarily in pituitary and to a lesser extent in T cells and endometrial stromal cells.

Therefore, polynucleotides and polypeptides of the invention are useful as reagents for differential identification of the tissue(s) or cell type(s) present in a biological sample and for diagnosis of diseases and conditions which include, but are not limited to, endocrine disorders and inflammation particularly in CNS injury. Similarly, polypeptides and antibodies directed to these polypeptides are useful in providing immunological probes for differential identification of the tissue(s) or cell type(s). For a number of disorders of the above tissues or cells, particularly of the immune system and central nervous system, expression of this gene at significantly higher or lower levels may be routinely detected in certain tissues and cell types (e.g. immune, pituitary, T-cells, and endometrium, and cancerous and wounded tissues) or bodily fluids (e.g.lymph, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The tissue distribution indicates that the protein product of this clone is useful for treating diseases of the endocrine system or disease that result in inflammation in the CNS. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:11 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 2070 of SEQ ID NO:11, b is an integer of 15 to 2084, where both a and b correspond to the positions of nucleotide residues shown in SEQ ID NO:11, and where the b is greater than or equal to a+14.

Features of Protein Encoded by Gene No: 2

The translation product of this gene shares sequence homology with CDC2 serine threonine kinase which is thought to be important in regulating progression through the cell cycle, and is required in higher cells for entry into S-phase and mitosis. CDC2 is a component of the kinase complex that phosphorylates the repetitive carboxyl-terminus of RNA polymerase II. The gene encoding the disclosed cDNA is thought to reside on chromosome 9. Accordingly, polynucleotides related to this invention are useful as a marker for linkage analysis for chromosome 9.

This gene is expressed primarily in adrenal gland tumors and to a lesser extent in brain, pineal gland and gall bladder.

Therefore, polynucleotides and polypeptides of the invention are useful as reagents for differential identification of the tissue(s) or cell type(s) present in a biological sample and for diagnosis of diseases and conditions which include, but are not limited to, cancers, particularly of the adrenal gland, and endocrine disorders. Similarly, polypeptides and antibodies directed to these polypeptides are useful in providing immunological probes for differential identification of the tissue(s) or cell type(s). For a number of disorders of the above tissues or cells, particularly of the adrenal gland, brain and gall bladder. expression of this gene at significantly higher or lower levels may be routinely detected in certain tissues or cell types (e.g., adrenal gland, brain and other tissue of the nervous system, pineal gland, and gall bladder, and cancerous and wounded tissues) or bodily fluids (e.g.lymph, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The tissue distribution and homology to CDC2 kinase indicates that the protein product of this clone is useful for treating cancers. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:12 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1572 of SEQ ID NO: 12, b is an integer of 15 to 1586, where both a and b correspond to the positions of nucleotide residues shown in SEQ ID NO:12, and where the b is greater than or equal to a+14.

Features of Protein Encoded by Gene No: 3

The gene encoding the disclosed cDNA is thought to reside on chromosome 11. Accordingly, polynucleotides related to this invention are useful as a marker in linkage analysis for chromosome 11.

This gene is expressed primarily in placenta, and to a lesser extent, in T-cells.

Therefore, polynucleotides and polypeptides of the invention are useful as reagents for differential identification of the tissue(s) or cell type(s) present in a biological sample and for diagnosis of diseases and conditions which include, but are not limited to, inflammation. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues and cell types (e.g.immune, hematopoietic, placenta, and T-cells, and cancerous and wounded tissues) or bodily fluids (e.g.lymph, amniotic fluid, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder. Preferred epitopes include those comprising a sequence shown in SEQ ID NO:54 as residues: Asn-60 to Phe-65.

The tissue distribution suggests that the protein product of this clone would be useful for the diagnosis and treatment of a variety of immune system disorders. Expression of this gene product in T-cells suggests a role in the regulation of the proliferation; survival; differentiation; and/or activation of potentially all hematopoietic cell lineages, including blood stem cells. This gene product may be involved in the regulation of cytokine production, antigen presentation, or other processes that may also suggest a usefulness in the treatment of cancer (e.g. by boosting immune responses). Since the gene is expressed in cells of lymphoid origin, the natural gene product may be involved in immune functions. Therefore it may be also used as an agent for immunological disorders including arthritis, asthma, immune deficiency diseases such as AIDS, leukemia, rheumatoid arthritis, inflammatory bowel disease, sepsis, acne, and psoriasis. In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:13 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 675 of SEQ ID NO:13, b is an integer of 15 to 689, where both a and b correspond to the positions of nucleotide residues shown in SEQ ID NO:13, and where the b is greater than or equal to a+14.

Features of Protein Encoded by Gene No: 4

The translation product of this gene shares sequence homology with mouse FGD-1, which is thought to be important in regulating the signal transduction response to small G proteins. See, for example, Genbank accession NO: gil722343.

This gene is expressed primarily in breast lymph nodes, and to a lesser extent in thymus.

Therefore, polynucleotides and polypeptides of the invention are useful as reagents for differential identification of the tissue(s) or cell type(s) present in a biological sample and for diagnosis of diseases and conditions which include, but are not limited to, immune response, particularly in breast cancer. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g.immune, mammary tissue, lymphoid tissue, and thymus, and cancerous and wounded tissues) or bodily fluids (e.g. lymph, breast milk, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder. Preferred epitopes include those comprising a sequence shown in SEQ ID NO:55 as residues: Lys-5 to Ser-10.

The tissue distribution and homology to FGD1 indicates that polynucleotides and polypeptides corresponding to the gene are useful for regulating signalling and growth of breast tumors and in inflammatory responses in the immune system. Expression of this gene product in lymph nodes suggests a role in the regulation of the proliferation; survival; differentiation; and/or activation of potentially all hematopoietic cell lineages, including blood stem cells. This gene product may be involved in the regulation of cytokine production, antigen presentation, or other processes that may also suggest a usefulness in the treatment of cancer (e.g. by boosting immune responses). Since the gene is expressed in cells of lymphoid origin, the natural gene product may be involved in immune functions. Therefore it may be also used as an agent for immunological disorders including arthritis, asthma, immune deficiency diseases such as AIDS, leukemia, rheumatoid arthritis, inflammatory bowel disease, sepsis, acne, and psoriasis. In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:14 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1334 of SEQ ID NO:14, b is an integer of 15 to 1348, where both a and b correspond to the positions of nucleotide residues shown in SEQ ID NO:14, and where the b is greater than or equal to a+14.

Features of Protein Encoded by Gene No: 5

The translation product of this gene shares sequence homology with a gene up-regulated by thyroid hormone in tadpoles and is expressed specifically in the tail and only at metamorphosis. (See Genbank accession NO: 1234787, see also, Brown, D. D., et al., Proc. Natl. Acad. Sci. U.S.A. 93:1924–1929 (1996). This protein is thought to be important in the tail resorption program of *Xenopus laevis*. Preferred polypeptide fragments comprise the amino acid sequence: FSVTNNTECGKLLEEIKCALCSPHSQS-LFHSPEREVLERDLVLPLLCKDYCK-EFFYTCRGHIPGFLQTTADEFCFY-YARKDGGLCFPDFPRKQVRGPASNYLDQMEEYDK EEISRKHKHNCFCIQEVVSGLRQPV-GALHSGDGSQRLFILEKEGYVILTPEGE-IFKEPYLDIHKLV (SEQ ID NO:93).

Also preferred are polynucleotide fragments encoding these polypeptide fragments.

This gene is expressed primarily in umbilical vein endothelial cells and, to a lesser extent, in primary dendritic cells.

Therefore, polynucleotides and polypeptides of the invention are useful as reagents for differential identification of the tissue(s) or cell type(s) present in a biological sample and for diagnosis of diseases and conditions which include, but are not limited to, vascular conditions, particularly where unwanted angiogenesis occurs such as retinopathy and in conditions such as restenosis and cancer, or immune disorders. Similarly, polypeptides and antibodies directed to these polypeptides are useful in providing immunological probes for differential identification of the tissue(s) or cell type(s). For a number of disorders of the above tissues or cells, particularly of the vascular system, expression of this gene at significantly higher or lower levels may be routinely detected in certain tissues and cell types (e.g.immune, vascular tissue, endothelial cells, and dendritic cells, and cancerous and wounded tissues) or bodily fluids (e.g.lymph, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder. Preferred epitopes include those comprising a sequence shown in SEQ ID NO:56 as residues: Lys-21 to Met-52, Asp-179 to Ala-189, Asp-194 to Val-202, Ile-205 to Asn-212, Asn-304 to Leu-309, Gly-311 to Ala-316.

The tissue distribution and homology to a conserved *Xenopus laevis* gene indicates that polynucleotides and polypeptides corresponding to the gene are useful for the treatment/diagnosis of problems involving the vascular system based upon its expression in endothelial cells. The secreted protein can also be used to determine biological activity, to raise antibodies, as tissue markers, to isolate cognate ligands or receptors, to identify agents that modulate their interactions and as nutritional supplements. It may also have a very wide range of biological activities. Typical of these are cytokine, cell proliferation/differentiation modulating activity or induction of other cytokines; immunostimulating/immunosuppressant activities (e.g. for treating human immunodeficiency virus infection, cancer, autoimmune diseases and allergy); regulation of hematopoiesis (e.g. for treating anaemia or as adjunct to chemotherapy); stimulation or growth of bone, cartilage, tendons, ligaments and/or nerves (e.g. for treating wounds, stimulation of follicle stimulating hormone for the control of fertility); chemotactic and chemokinetic activities (e.g. for treating infections, tumors); hemostatic or thrombolytic activity (e.g. for treating haemophilia, cardiac infarction etc.); anti-inflammatory activity (e.g. for treating septic shock, Crohn's disease); as antimicrobials; for treating psoriasis or other hyperproliferative diseases; for regulation of metabolism, and behaviour. Also contemplated is the use of the corresponding nucleic acid in gene therapy procedures. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:15 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1109 of SEQ ID NO:15, b is an integer of 15 to 1123, where both a and b correspond to the positions of nucleotide residues shown in SEQ ID NO:15, and where the b is greater than or equal to a+14.

Features of Protein Encoded by Gene No: 6

This gene is expressed primarily in an endometrial tumor and to a lesser extent in skin tumor.

Therefore, polynucleotides and polypeptides of the invention are useful as reagents for differential identification of the tissue(s) or cell type(s) present in a biological sample and for the diagnosis of diseases and conditions which include, but are not limited to, tumors, in particular, skin and endometrial tumors. Similarly, polypeptides and antibodies directed to these polypeptides are useful in providing immunological probes for differential identification of the tissue(s) or cell type(s). For a number of disorders of the above tissues or cells, particularly of the skin and reproductive system, expression of this gene at significantly higher or lower levels may be routinely detected in certain tissues or cell types (e.g.integumentary, endometrium, and epidermis, and cancerous and wounded tissues) or bodily fluids (e.g.lymph, serum, plasma, urine, synovial fluid or spinal fluid) or another tissue or cell sample taken from an individual having such a disorder, relative to the standard gene expression level, i.e., the expression level in.healthy tissue or bodily fluid from an individual not having the disorder.

The tissue distribution indicates that polynucleotides and polypeptides corresponding to the gene are useful for the treatment/diagnosis of endometrial and/or skin tumors, based on levels of expression in these tissues. Protein, as well as, antibodies directed against the protein may show utility as a tissue-specific marker and/or immunotherapy target for the above listed tissues.

Many polynucleotide sequences, such as EST sequences, are publicly available and accessible through sequence databases. Some of these sequences are related to SEQ ID NO:16 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 876 of SEQ ID NO:16, b is an integer of 15 to 890, where both a and b correspond to the positions of nucleotide residues shown in SEQ ID NO:16, and where the b is greater than or equal to a+14.

Features of Protein Encoded by Gene No: 7

This gene is expressed primarily in human neutrophils and to a lesser extent in fetal liver.

Therefore, polynucleotides and polypeptides of the invention are useful as reagents for differential identification of the tissue(s) or cell type(s) present in a biological sample and for the diagnosis of diseases and conditions which include, but are not limited to, cancers of the immune system and/or liver. Similarly, polypeptides and antibodies directed to these polypeptides are useful in providing immunological probes for differential identification of the tissue(s) or cell type(s). For a number of disorders of the above tissues or cells, particularly of the immune or hepatic systems, expression of this gene at significantly higher or lower levels may be routinely detected in certain tissues and cell types (e.g.immune, blood cells, and liver, and cancerous and wounded tissues) or bodily fluids (e.g.lymph, serum, bile, amniotic fluid, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The tissue distribution indicates that polynucleotides and polypeptides corresponding to the gene are useful for the regulation of cell division or the treatment of cancers, particularly of the immune and hepatic systems. Expression of this gene product in hematopoietic cells suggests a role in the regulation of the proliferation; survival; differentiation; and/or activation of potentially all hematopoietic cell lineages, including blood stem cells. This gene product may be involved in the regulation of cytokine production, antigen presentation, or other processes that may also suggest a usefulness in the treatment of cancer (e.g. by boosting immune responses). Since the gene is expressed in cells of lymphoid origin, the natural gene product may be involved in immune functions. Therefore it may be also used as an agent for immunological disorders including arthritis, asthma, immune deficiency diseases such as AIDS, leukemia, rheumatoid arthritis, inflammatory bowel disease, sepsis, acne, and psoriasis. In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:17 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 605 of SEQ ID NO:17, b is an integer of 15 to 619, where both a and b correspond to the positions of nucleotide residues shown in SEQ ID NO:17, and where the b is greater than or equal to a+14.

Features of Protein Encoded by Gene No: 8

This gene is expressed primarily in various regions of the brain including corpus callosum, hippocampus and amygdala, and to a lesser extent in multiple other tissues.

Therefore, polynucleotides and polypeptides of the invention are useful as reagents for differential identification of the tissue(s) or cell type(s) present in a biological sample and for diagnosis of diseases and conditions which include, but are not limited to, diseases of the central nervous system including ischemia, epilepsy, Parkinson's disease or any other neurodegenerative disorder. Similarly, polypeptides and antibodies directed to these polypeptides are useful in providing immunological probes for differential identification of the tissue(s) or cell type(s). For a number of disorders of the above tissues or cells, particularly of the central nervous system, expression of this gene at significantly higher or lower levels may be routinely detected in certain tissues and cell types (e.g., brain and other tissue of the nervous system, and amygdala, and cancerous and wounded tissues) or bodily fluids (e.g.lymph, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder. Preferred epitopes include those comprising a sequence shown in SEQ ID NO:59 as residues: Ser-11 to His-21.

The tissue distribution in brain suggests that the protein product of this clone would be useful for the detection/treatment of neurodegenerative disease states, behavioural disorders, or inflammatory conditions such as Alzheimers Disease, Parkinsons Disease, Huntingtons Disease, Tourette Syndrome, meningitis, encephalitis, demyelinating diseases, peripheral neuropathies, neoplasia, trauma, congenital malformations, spinal cord injuries, ischemia and infarction, aneurysms, hemorrhages, schizophrenia, mania, dementia, paranoia, obsessive compulsive disorder, panic disorder, learning disabilities, ALS, psychoses, autism, and altered bahaviors, including disorders in feeding, sleep patterns, balance, and preception. In addition, the gene or gene product may also play a role in the treatment and/or detection of developmental disorders associated with the developing embryo, sexually-linked disorders, or disorders of the cardiovascular system. Protein, as well as, antibodies directed against the protein may show utility as a tumor marker and/or immunotherapy targets for the abovelisted tissues.

Many polynucleotide sequences, such as EST sequences, are publicly available and accessible through sequence databases. Some of these sequences are related to SEQ ID NO:18 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1754 of SEQ ID NO:18, b is an integer of 15 to 1768, where both a and b correspond to the positions of nucleotide residues shown in SEQ ID NO:18, and where the b is greater than or equal to a+14.

Features of Protein Encoded by Gene No: 9

The translation product of this gene shares sequence homology with a thioredoxin homolog from C. elegans which possesses dithiol-disulfide oxidoreductase activity. Preferred polypeptide fragments comprise the amino acid sequence: DGNPCDFDWREVEILMFLSAIVMMKN-RRSITVEQHIGNIFMFSKVANTILF-FRLDIRMGLLYITLCIVILMTCKP-PLYMGPEYIKYFNDKTIDEELERDKRVTWIVEFFAN WSNDCQSFAPIYADLSLKYNCTGLNF-GKVDVGRYTDVSTRYKVSTSPLTKQLPT-LILFQGGKEAMRRPQIDKKGRAVSWTF-SEENVIREFNLNELYQRAKKLSKA (SEQ ID NO:94). Polynucleotides encoding these polypeptide fragments are also encompassed by the invention. The gene encoding the disclosed cDNA is thought to reside on chromosome 11. Accordingly, polynucleotides related to this invention are useful as a marker in linkage analysis for chromosome 11.

This gene is expressed primarily in fetal liver and to a lesser extent in other tissue.

Therefore, polynucleotides and polypeptides of the invention are useful as reagents for differential identification of the tissue(s) or cell type(s) present in a biological sample and for the diagnosis of diseases and conditions which include, but are not limited to, developmental diseases including problems with early hematapoiesis. Similarly, polypeptides and antibodies directed to these polypeptides are useful in providing immunological probes for differential identification of the tissue(s) or cell type(s). For a number of disorders of the above tissues or cells, particularly of the hematapoietic system, expression of this gene at significantly higher or lower levels may be routinely detected in certain tissues and cell types (e.g.developmental, liver, and cancerous and wounded tissues) or bodily fluids (e.g.lymph, amniotic fluid, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder. Preferred epitopes include those comprising a sequence shown in SEQ ID NO:60 as residues: Pro-50 to Phe-61, Phe-141 to Ile-146, Glu-148 to Arg-155, Trp-166 to Gln-171, Thr-200 to Ser-209, Arg-232 to Gly-239, Gln-262 to Ser-268, Ala-270 to Val-280.

The tissue distribution and homology to thioreductase suggests that polynucleotides and polypeptides corresponding to the gene are useful for the treatment of disorders involving protein folding abnormalities and diagnosis/treatment of developmental or hematapoietic disorders. Expression of this gene product in hematopoietic cells suggests a role in the regulation of the proliferation; survival; differentiation; and/or activation of potentially all hematopoietic cell lineages, including blood stem cells. This gene product may be involved in the regulation of cytokine production, antigen presentation, or other processes that may also suggest a usefulness in the treatment of cancer (e.g. by boosting immune responses). Since the gene is expressed in cells of lymphoid origin, the natural gene product may be involved in immune functions. Therefore it may be also used as an agent for immunological disorders including arthritis, asthma, immune deficiency diseases such as AIDS, leukemia, rheumatoid arthritis, inflammatory bowel disease, sepsis, acne, and psoriasis. In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:19 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1685 of SEQ ID NO:19, b is an integer of 15 to 1699, where both a and b correspond to the positions of nucleotide residues shown in SEQ ID NO:19, and where the b is greater than or equal to a+14.

Features of Protein Encoded by Gene No: 10

The gene encoding the disclosed cDNA is thought to reside on chromosome 14. Accordingly, polynucleotides related to this invention are useful as a marker in linkage analysis for chromosome 14.

This gene is expressed primarily in T-cells and to a lesser extent in smooth muscle.

Therefore, polynucleotides and polypeptides of the invention are useful as reagents for differential identification of the tissue(s) or cell type(s) present in a biological sample and for the diagnosis of diseases and conditions which include, but are not limited to, diseases of immune dysfunction such as inflammation and autoimmunity including rheumatoid arthritis and Lupus, in addition to vascular disorders. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues and cell types (e.g.immune, T-cells, and smooth muscle, and cancerous and wounded tissues) or bodily fluids (e.g.lymph, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder. Preferred epitopes include those comprising a sequence shown in SEQ ID NO:61 as residues: Ala-3 to Thr-9, Ser-40 to Asn-53, Ser-59 to Asp-85, Gly-89 to Thr-100.

The tissue distribution suggests that polynucleotides and polypeptides corresponding to the gene are useful for the treatment/diagnosis of immune and inflammatory diseases. Expression of this gene product in immune cells suggests a role in the regulation of the proliferation; survival; differentiation; and/or activation of potentially all hematopoietic cell lineages, including blood stem cells. This gene product may be involved in the regulation of cytokine production, antigen presentation, or other processes that may also suggest a usefulness in the treatment of cancer (e.g. by boosting immune responses). Since the gene is expressed in cells of lymphoid origin, the natural gene product may be involved in immune functions. Therefore it may be also used as an agent for immunological disorders including arthritis, asthma, immune deficiency diseases such as AIDS, leukemia, rheumatoid arthritis, inflammatory bowel disease, sepsis, acne, and psoriasis. In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:20 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 722 of SEQ ID NO:20, b is an integer of 15 to 736, where both a and b correspond to the positions of nucleotide residues shown in SEQ ID NO:20, and where the b is greater than or equal to a+14.

Features of Protein Encoded by Gene No: 11

The translation product of this gene shares sequence homology with a W04A4.5 protein found in the *Caenorhabditis elegans* genome (See Accession NO: 2414330). Preferred polypeptide fragments comprise the amino acid sequence: IHLALVELLKNLTKYPTDRDSIWKCLK-FLGSRHPTLVLPLVPELLSTHPFFD-TAEPDMDDPAYIAVLVLIFNAAKTCPTM-PALFSDHTFRHYAYLRDSLSHLVPALRLPGRKLVSS AVSPSIIPQEDPSQQFLQQSLERVYS-LQHLDPQGAQELLEFTIRDLQR-LGELQSELAGVADFSATYLRCQLL-LIKALQEKLWNVAAPLYLKQSDLASAAAKQIMEE TYKMEFMY SGVENKQVVIIHHMRLQAKALQLIV (SEQ ID NO:96); or QLIVTARTTRGLDPLFGMCEK-FLQEVDFFQRYFIADLPHLQDSFVD-KLLDLMPRLMTSKPAEVVKILQTML-RQSAFLHLPLPEQIHKASATIIEPAGEFRQPFAVYL WVGGCPGM LMQPWSMCRILRTLLRSRVLYPDGQXS-DDSPQACRLPESWPRAAPAHHSGLSL-PHRLDRGMPGGSEAAAGLQLQCSHSKMP (SEQ ID NO:95). Polynucleotides encoding this polypeptide are also encompassed by the invention. Based on the conserved homology between invertebrate and human, it is likely that this gene plays an essential role in the development or the functions of human and animal body. The gene encoding the disclosed cDNA is believed to reside on chromosome 11. Accordingly, polynucleotides related to this invention are useful as a marker in linkage analysis for chromosome 11.

This gene is expressed primarily in hypothalamus, and other brain tissues and to a lesser extent in human breast, colon carcinoma, and cells of T-cell origin including T-cell lymphoma.

Therefore, polynucleotides or polypeptides of the invention are useful as reagents for differential identification of the tissue(s) or cell type(s) present in a biological sample and for the diagnosis of diseases and conditions which include, but are not limited to, inflammatory and immune disorders, cancers involving cells of lymphoid origin, or other infected or neoplastic lesions with T-cell infiltration. Similarly, polypeptides and antibodies directed to these polypeptides are useful in providing immunological probes for differential identification of the tissue(s) or cell type(s). For a number of disorders of the above tissues or cells, particularly of the immune and central nervous system including autoimmune disorders, expression of this gene at significantly higher or lower levels may be routinely detected in certain tissues and cell types (e.g.immune, brain and other tissue of the nervous system, mammary tissue, colon, T-cells, lymphoid tissue, and cancerous and wounded tissues) or bodily fluids (e.g.lymph, amniotic fluid, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The tissue distribution in the hypothalamus indicates that the protein product of this clone is an endocrine or an extracellular protein regulatory factor in nature. The abundant presence in the brain tissues may indicate its involvement in neural development, such as neuronal survival and maintenance, neuronal connection and axonal guidance, in neural physiology, such as neural impulses transmission, short term and long term potentiation, or signal quenching. Furthermore, the gene product may have functions outside the nerve tissues as it is often found in tissues with T-cell enrichment. For example, in the lesions of colon carcinoma, breast cancer, bone marrow cells, T-cell lymphoma, activated T-cells, and tissues or cells of immune importance, the gene expression levels are significant, which indicates the immunological involvement, particularly cellular immunity processes, found in nature. Therefore polynucleotides and polypeptides corresponding to the gene are useful for treatment or diagnosis of disorders of the endocrine system, neural dysfunctions or neurodegeneration, immune or inflammatory diseases, or as a proliferative/differentiation agent for cells of lymphoid origin.

Many polynucleotide sequences, such as EST sequences, are publicly available and accessible through sequence databases. Some of these sequences are related to SEQ ID NO:21 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1674 of SEQ ID NO:21, b is an integer of 15 to 1688, where both a and b correspond to the positions of nucleotide residues shown in SEQ ID NO:21, and where the b is greater than or equal to a+14.

Features of Protein Encoded by Gene No: 12

The translation product of this gene shares sequence homology with a 27-kDa protein (mouse transporter protein (MTP)) with four predicted transmembrane-spanning domains, which is thought to be important in the transport of nucleosides and/or nucleoside derivatives between the cytosol and the lumen of an intracellular membrane-bound compartment. Preferred polypeptide fragments comprise the amino acid sequence: RFYSNSCCLCCHVRTGTILLGVWYLIINAVVLLILLSALADPDQYNFSS-SELGGDFEFMDDANMCIAIAISLLMILI-CAMATYGAYKQRAAGIIPFFCYQIFDFALNMLVAIT VLIYPNSIQEYIRQLPPNFPYRDD (SEQ ID NO:97); or FPTEMMSCAVNPTCLVLIILLFSISLT-FKGYLISCVWNCYRYINGRNSSDV-LVYVTSNDTTVLLPPYDDATVNGAAKEPPPPYVSA (SEQ ID NO: 98). Polynucleotides encoding these polypeptides are also encompassed by the invention. It is likely that a second signal sequence is located upstream from the predicted signal sequence. Moreover, it is likely that a frame shift exists, which can easily be clarified using known molecular biology techniques.

This gene is expressed primarily in an endometrial tumor and normal ovary and to a lesser extent in a stromal cell line, T-cells and other cancerous tissues including skin, testes chondrosarcoma, and synovial sarcoma.

Therefore, polynucleotides and polypeptides of the invention are useful as reagents for the differential identification of the tissue(s) or cell type(s) present in a biological sample and for the diagnosis of diseases and conditions which include, but are not limited to, cancer, particularly of the female reproductive organs, and inflammatory and immune disorders. Similarly, polypeptides and antibodies directed to these polypeptides are useful in providing immunological probes for differential identification of the tissue(s) or cell type(s). For a number of disorders of the above tissues or cells, particularly of the female reproductive and immune systems, expression of this gene at significantly higher or lower levels may be routinely detected in certain tissues and cell types (e.g.immune, hematopoietic, ovary and testes and other reproductive tissue, stromal cells, and T-cells, and cancerous and wounded tissues) or bodily fluids (e.g.lymph, seminal fluid, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The tissue distribution and homology to the MTP transporter gene suggests that polynucleotides and polypeptides corresponding to the gene are useful for the treatment/diagnosis of certain cancers by blocking the ability to utilize nucleotide and nucleoside derivatives, and may also be useful in the modulation of immune responses by regulating the transport of these molecules. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:22 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 2031 of SEQ ID NO:22, b is an integer of 15 to 2045, where both a and b correspond to the positions of nucleotide residues shown in SEQ ID NO:22, and where the b is greater than or equal to a+14.

Features of Protein Encoded by Gene No: 13

The translation product of this gene shares sequence homology with a mouse cysteine-rich glycoprotein/mouse monocyte surface antigen (MS2 precursor). (See Accession NO: 1709103.) Moreover, another group recently cloned this gene, calling it human MS2, a myelomonocytic cell surface protein. (See Accession NO: 1864005.) This transmembrane protein is a member of the hemorrhagic snake venom family. Thus, based on homology, it is likely that this gene has activity similar to the monocyte or myelomonocyte surface antigen M2S. Preferred polypeptide fragments comprise the amino acid sequence: IAPSRPWALMEQYEVV-LPWRLPGPRVRRALPSHLGLHPERVSYV-LGATGHNFTLHLRKNRDLLGSGYTETYTAANGS TEQPRGQDHCFYQGHLEG (SEQ ID NO:99); PDSAASLSTCAGLRGFFQVGS-DLHLIEPLDEGGEGGRHAVYQAE-HLLQTAGTCGVSDDSLGSLLGPRTAAV-FRPRPGDSLPSRETRYVELYVVVDNAEFQMLGSEA AVRHRVLEVVNHVDKLYQKLNFRVVLV-GLEIWNSQDRFHVSPDPSVTLEN-LLTWQARQRTRRHLHDNVQLITGVDFT-GTTVGFARVSAMCSHSSGAVNQDHSKNPVGVACT MAHEMGHNLGMDHDENVQGCRCQ (SEQ ID NO:100); and/or FEAGRCIMARPALAPSFPRMFSDC-SQAYLESFLERPQSVCLANAPDLSHLVG GPVCGNLFVERGEQCDCGPPEDCRNRC-
CNSTTCQLAEGAQCAHGTCCQECK
VKPAGELCRPKKDMC (SEQ ID NO:101). Polynucleotides encoding these polypeptides are also encompassed by the invention.

This gene is expressed primarily in human eosinophils and human tonsils.

Therefore, polynucleotides or polypeptides of the invention are useful as reagents for the differential identification of the tissue(s) or cell type(s) present in a biological sample and for the diagnosis of diseases and conditions which include, but are not limited to, disorders relating to eosinophilic leukocyte, and tonsillitis. Similarly, polypeptides and antibodies directed to these polypeptides are useful in providing immunological probes for differential identification of the tissue(s) or cell type(s). For a number of disorders of the above tissues or cells, particularly of the hematopoietic system and lymphoid system, expression of this gene at significantly higher or lower levels may be routinely detected in certain tissues and cell types (e.g.immune, hematopoietic, blood cells, and tonsils, and cancerous and wounded tissues) or bodily fluids (e.g. lymph, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The tissue distribution indicates that the protein product of this clone is useful for diagnosis and treatment of immune disorders. Expression of this gene product in tonsils suggests a role in the regulation of the proliferation; survival; differentiation; and/or activation of potentially all hematopoietic cell lineages, including blood stem cells. This gene product may be involved in the regulation of cytokine production, antigen presentation, or other processes that may also suggest a usefulness in the treatment of cancer (e.g. by boosting immune responses). Since the gene is expressed in cells of lymphoid origin, the natural gene product may be involved in immune functions. Therefore it may be also used as an agent for immunological disorders including arthritis, asthma, immune deficiency diseases such as AIDS, leukemia, rheumatoid arthritis, inflammatory bowel disease, sepsis, acne, and psoriasis. In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:23 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1087 of SEQ ID NO:23, b is an integer of 15 to 1101, where both a and b correspond to the positions of nucleotide residues shown in SEQ ID NO:23, and where the b is greater than or equal to a+14.

Features of Protein Encoded by Gene No: 14

A polypeptide sequence which overlaps with the translation product of this gene has recently been identified as g16 (see Genbank accession NO: gil2636658). These proteins are thought to be tumor suppressors. In specific embodiments, polypeptides of the invention comprise the following amino acid sequence: GSQEERFAPGWNRDYP-
PPPLKSHAQERHSGNFPGRDSLPFD-
FQGHSGPPFANVEEHSFSYGARDGPH-
GDYRGGEGPGHDFRGGDFSSSDFQSRDSSQLDFRG
RDIHSGDFRDREGPPMDYRGGDGTSM-
DYRGREAPHMNYRDRDAHAVDFR-
GRDAPPSDFRGRGTYDLDFRGRDGSHAD-
FRGRDLSDLDFRAREQSRSDFRNRDVSDLDFR
DKDGTQVDFRGRGSGTTDLDFRDRDT-
PHSDFRGRHRSRTDQDFRGREMGSC-
MEFKDREMPPVDPNILDYIQPSTQDREH-
SGMNVNRREESTHDHTIERPAFGIQKGEFEHSET
REGETQGVAFEHESPADFQN-
SQSPVQDQDKSQLSGREEQSSDAGLF-
KEEGGLDFLGRQDTDYRSMEYRDVDHR-
LPGSQMFGYGQSKSFPEGKTARDAQRDLQDQDY
RTGPSEEKPSRLIRLSGVPEDATKEE-
ILNAFRTPDGMPVKN (SEQ ID NO:102), or GLQD-
SARGGSQEERFAPGWNRDYPPPPLK-
SHAQERHSGNFPGRDSLPFDFQGHSGPPFANVEEH
FSYGARDGPHGDYRGGEGPGHDFRGGDF-
SSSDFQSRDS
LDFRGRDIHSGDFRDREGPP (SEQ ID NO:103). Polynucleotides encoding these polypeptides are also encompassed by the invention. The gene encoding the disclosed cDNA is believed to reside on chromosome 3. Accordingly, polynucleotides related to this invention are useful as a marker in linkage analysis for chromosome 3.

This gene is expressed primarily in immune system cells, e.g., eosinophils, activated T-cells, activated monocytes, activated neutrophils, dendritic cells, Hodgkin's lymphoma, and in vascularized tissues such as umbilical vein, microvascular endothelial cells and trachea.

Therefore, polynucleotides and polypeptides of the invention are useful as reagents for the differential identification of the tissue(s) or cell type(s) present in a biological sample and for the diagnosis of diseases and conditions which include, but are not limited to, immune system disorders such as cancer. Similarly, polypeptides and antibodies directed to these polypeptides are useful in providing immunological probes for differential identification of the tissue(s) or cell type(s). For a number of disorders of the above tissues or cells, particularly of the hematopoietic and immune systems, expression of this gene at significantly higher or lower levels may be routinely detected in certain tissues and cell types (e.g.immune, blood cells, dendritic cells, vascular tissue, and lymphoid tissue, and cancerous and wounded tissues) or bodily fluids (e.g.lymph, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder. Preferred epitopes include those comprising a sequence shown in SEQ ID NO:65 as residues: Met-1 to Arg-6.

The tissue distribution and similarity to g16 suggests that polynucleotides and polypeptides corresponding to the gene are useful for diagnosis and treatment of immune system disorders such as cancers. It is believed that tumor suppressor genes are often mutated in particular cancers. The secreted protein can also be used to determine biological activity, to raise antibodies, as tissue markers, to isolate cognate ligands or receptors, to identify agents that modu late their interactions and as nutritional supplements. It may also have a very wide range of biological acitivities. Typical of these are cytokine, cell proliferation/differentiation modulating activity or induction of other cytokines; immunostimulating/immunosuppressant activities (e.g. for treating human immunodeficiency virus infection, cancer, autoimmune diseases and allergy); regulation of hematopoiesis (e.g. for treating anaemia or as adjunct to chemotherapy); stimulation or growth of bone, cartilage, tendons, ligaments and/or nerves (e.g. for treating wounds, stimulation of follicle stimulating hormone (for control of fertility); chemotactic and chemokinetic activities (e.g. for treating infections, tumors); hemostatic or thrombolytic activity (e.g. for treating haemophilia, cardiac infarction etc.); anti-inflammatory activity (e.g. for treating septic shock, Crohn's disease); as antimicrobials; for treating psoriasis or other hyperproliferative diseases; for regulation of metabolism, and behaviour. Also contemplated is the use of the corresponding nucleic acid in gene therapy procedures. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:24 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1645 of SEQ ID NO:24, b is an integer of 15 to 1659, where both a and b correspond to the positions of nucleotide residues shown in SEQ ID NO:24, and where the b is greater than or equal to a+14.

Features of Protein Encoded by Gene No: 15

The translation product of this gene shares sequence homology with a frog thrombin receptor [Xenopus laevis]. Moreover, another group recently cloned this same gene, also recognizing the homology to thrombing receptors. (See Accession NO: 2347084.) Preferred polypeptide fragments comprise the amino acid sequence: MLPDWKXSLIL-MAYIIIFLTGLPANLLALRAFVGR-IRQPQPAPVHILLLSLTLADLLLLLLL-PFKIIEAASNFRWYLPKVVCALTSFGFYSSIYCS TWLLAGISIERYLGVAFPVQYKLSR-RPLYGVIAALVAWVMSFGHCTIVIIX-QYLNTTEQVRSGNEITCYENFTDNQLDV-VLPVRXELCLVLFFXPMAVTIFCYWRFVWIMLSQ PLVGAQRRRRAVGLAVVTLLNFLVCFG-PYNVSHLVGYHQRKSPWWRSIAVXFSSL-NASLDPLLFYFSSSVVRRAFGRGLQVL-RNQGSSLLGRRGKDTAEGTNEDRGVGQGEGMP SSDFTTE (SEQ ID NO:104); CSTWLLAGISIERYLGV (SEQ ID NO:105); or CTIVIIXQYLNTTEQVRSGNEIT-CYENFTDNQLDVVLPVRXELCLVLFFXP-MAVTIFCYWRFVWIMLSQPLVGAQR-RRRAVGLAVVTLLNFLVC (SEQ ID NO:106). Polynucleotides encoding these polypeptides are also encompassed by the invention. Also preferred are the polynucleotide fragments encoding these polypeptide fragments. This gene maps to chromosomal location 19q13.1, and therefore can be used as a marker in linkage analysis for chromosome 19.

This gene is expressed primarily in activated human neutrophil and IL5 induced eosinophil.

Therefore, polynucleotides and polypeptides of the invention are useful as reagents for differential identification of the tissue(s) or cell type(s) present in a biological sample and for diagnosis of diseases and conditions which include, but are not limited to, immune disorders, particularly neutropenia, neutrophilia, and eosinophilic leukocyte related disorders. Similarly, polypeptides and antibodies directed to these polypeptides are useful in providing immunological probes for differential identification of the tissue(s) or cell type(s). For a number of disorders of the above tissues or cells, particularly of the hematopoietic system and hemopoietic system, expression of this gene at significantly higher or lower levels may be routinely detected in certain tissues and cell types (e.g., immune, bone marrow, blood cells, and cancerous and wounded tissues) or bodily fluids (e.g., lymph, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder. Preferred epitopes include those comprising a sequence shown in SEQ ID NO:66 as residues: Tyr-41 to Trp-48.

The tissue distribution a suggests that polynucleotides and polypeptides corresponding to the gene are useful for diagnosis and treatment of immune disorders. Expression of this gene product in immune cells suggests a role in the regulation of the proliferation; survival; differentiation; and/or activation of potentially all hematopoietic cell lineages, including blood stem cells. This gene product may be involved in the regulation of cytokine production, antigen presentation, or other processes that may also suggest a usefulness in the treatment of cancer (e.g. by boosting immune responses). Since the gene is expressed in cells of lymphoid origin, the natural gene product may be involved in immune functions. Therefore it may be also used as an agent for immunological disorders including arthritis, asthma, immune deficiency diseases such as AIDS, leukemia, rheumatoid arthritis, inflammatory bowel disease, sepsis, acne, and psoriasis. In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:25 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1315 of SEQ ID NO:25, b is an integer of 15 to 1329, where both a and b correspond to the positions of nucleotide residues shown in SEQ ID NO:25, and where the b is greater than or equal to a+14.

Features of Protein Encoded by Gene No: 16

This gene is homologous to the mouse NP15.6 gene, a novel neuronal protein whose expression is developmentally regulated. (See Accession NO: 1771306.) Therefore, based on homology, it is likely that this gene would have activity similar to NP15.6. Preferred polypeptide fragments comprise the amino acid sequence: GLPAARVRWESSFSRTV-VAPSAVAXKRPPEPTTPWQEDPEPEDEN-LYEKNPDSHGYDKDPVLDVWNMRLVFFFGVS IILVLGSTFVAYLPDYRCTGCPRAWDG-MKEWSRREAERLVKYRE-ANGLPIMESNCFDPSKIQLPEDE (SEQ ID NO:107). Polynucleotides encoding these polypeptides are also encompassed by the invention. This gene maps to the X chromosome, and therefore polynucleotides of the present invention can be used in linkage analysis as a marker for the X chromosome.

This gene is expressed primarily in hematopoietic cells.

Therefore, polynucleotides and polypeptides of the invention are useful as reagents for differential identification of the tissue(s) or cell type(s) present in a biological sample and for diagnosis of diseases and conditions which include, but are not limited to, immune disorders. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues and cell types (e.g., hematopoietic cells, immune, and tissue of the nervous system, and cancerous and wounded tissues) or bodily fluids (e.g. lymph, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder. Preferred epitopes include those comprising a sequence shown in SEQ ID NO:67 as residues: Pro-24 to Gly-30, Gly-37 to Ala-46, Gln-72 to Glu-77.

The tissue distribution indicates that the protein product of this clone is useful for diagnosis and treatment of immune and endocrine disorders and neoplasias. Expression of this gene product in hematopoietic cells suggests a role in the regulation of the proliferation; survival; differentiation; and/or activation of potentially all hematopoietic cell lineages, including blood stem cells. This gene product may be involved in the regulation of cytokine production, antigen presentation, or other processes that may also suggest a usefulness in the treatment of cancer (e.g. by boosting immune responses). Since the gene is expressed in cells of lymphoid origin, the natural gene product may be involved in immune functions. Therefore it may be also used as an agent for immunological disorders including arthritis, asthma, immune deficiency diseases such as AIDS, leukemia, rheumatoid arthritis, inflammatory bowel disease, sepsis, acne, and psoriasis. In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:26 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 686 of SEQ ID NO:26, b is an integer of 15 to 700, where both a and b correspond to the positions of nucleotide residues shown in SEQ ID NO:26, and where the b is greater than or equal to a+14.

Features of Protein Encoded by Gene No: 17

The translation product of this gene shares sequence homology with Preprotachykinin B which is thought to be important in the signal transduction and information processing in the nervous system. (See Accession NO:163590; see also Kotani, H., et al., Proc. Natl. Acad. Sci. U.S.A. 83:7074–7078 (1986).) The tachykinin group of neuropeptides exists in four different forms which are derived from one gene in the rat. Alternative splicing accounts for the alpha, beta, gamma, and delta forms. The most famous of these neuropeptides is substance P which appears to mediate the pain sensation and wheal formation in certain in vivo models. It thus may be a key player in the inflammatory response. The tachykinins also have smooth muscle contraction (i.e. bronchoconstriction) and vasodilator effects. Additionally, neovascularization and various cell-type specific proliferation effects have been seen. The fact that this clone was isolated from placenta RNA may make this an interesting gene to characterize. The known neurokinins are expressed in either the central nervous system or peripheral neurons. It may be that this new neurokinin modulates smooth muscle or vascularization associated with reproduction. Therefore, based on the homology it is likely that the polypeptides of the invention are active in the signal transduction and information processing in the nervous system. Preferred polypeptide fragments comprise the amino acid sequence: PEKRDMHDFFVGLMGKRSVQPDSPTD-VNQE NVPSFG (SEQ ID NO:108); KRDMHD-FFVGLMGKR (SEQ ID NO:109); and/or DMHDFFVGLM (SEQ ID NO:110). Polynucleotides encoding these polypeptides are also encompassed by the invention. This maps to chromosome 12 and therefore can be used in linkage analysis as a marker for chromosome 12.

This gene is expressed primarily in human placenta and to a lesser extent in soares placenta.

Therefore, polynucleotides and polypeptides of the invention are useful as reagents for differential identification of the tissue(s) or cell type(s) present in a biological sample and for diagnosis of diseases and conditions which include, but are not limited to, embryonic and reproductive disorders. Similarly, polypeptides and antibodies directed to these polypeptides are useful in providing immunological probes for differential identification of the tissue(s) or cell type(s). For a number of disorders of the above tissues or cells, particularly of the reproductive and embryonic systems, expression of this gene at significantly higher or lower levels may be routinely detected in certain tissues or cell types (e.g., placenta, and tissue of the nervous system, and cancerous and wounded tissues) or bodily fluids (e.g., amniotic fluid, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder. Preferred epitopes include those comprising a sequence shown in SEQ ID NO:68 as residues: Gly-34 to Asp-42, Ala-67 to Asp-81, Arg-93 to Asn-107, Tyr-116 to Glu-121.

The tissue distribution and homology to preprotachykinin B suggests that polynucleotides and polypeptides corresponding to the gene are useful for the diagnosis and treatment of reproductive and embryonic disorders, and cancer. These polypeptides and polynucleotides of the invention can also be used to treat Alzheimer's disease by inhibition of neurotoxicity due to the beta-amyloid peptide and long-lasting analgesic and anti-inflammatory activities by neurokinin B analogs. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:27 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 818 of SEQ ID NO:27, b is an integer of 15 to 832, where both a and b correspond to the positions of nucleotide residues shown in SEQ ID NO:27, and where the b is greater than or equal to a+14.

Features of Protein Encoded by Gene No: 18

The translation product of this gene shares sequence homology with ftp-3, an hnRNP protein which is thought to be important in RNA splicing and packaging. In preferred embodiments, the polypeptides of the invention comprise the sequence: EWEATEEMEWIIREAM (SEQ ID NO:111); WEWGTITVEDMVLLMVWVVMAV-VVEAVEVTMGKAA (SEQ ID NO:112); GMGGYGRDG-MDNQGGYGS (SEQ ID NO:113); GMGNNYSGGYGT-PDGLGGYGRGGGGSGGYYGQGGMSGGGWRGM (SEQ ID NO:114), GMGNNYSGGYGTPDGLG-GYGRGGGGSGGYYGQGGMSGGGWRGM (SEQ ID NO:115), and/or WDSTTSWTTIWLQQRGNSSV-LSRVGNRANGITLTMDYQGRSTGEAFVQ-FASKEIAENALGKHKERIGHRYIE-IFRSSRSEIKGFYDPPRRLLGQRPGPYDRPIGGRGG YYGAGRGSMYDRMRRGGDGYDGGYGGFD-DYGGYNNYGYGNDGFDDRMRDGRGMGGH-GYGGAGDASSGFHGGHFVHMRGLPFRA-TENDIANFFSPLNPIRVHIDIGADGRAQEKQM (SEQ ID NO:116). Polynucleotides encoding these polypeptides are also encompassed by the invention. The gene encoding the disclosed cDNA is believed to reside on chromosome 10. Accordingly, polynucleotides related to this invention are useful as a marker in linkage analysis for chromosome 10.

This gene is expressed primarily in frontal cortex and amygdala of human brain and to a lesser extent in human smooth muscle.

Therefore, polynucleotides and polypeptides of the invention are useful as reagents for differential identification of the tissue(s) or cell type(s) present in a biological sample and for diagnosis of diseases and conditions which include, but are not limited to, human brain diseases. Similarly, polypeptides and antibodies directed to these polypeptides are useful in providing immunological probes for differential identification of the tissue(s) or cell type(s). For a number of disorders of the above tissues or cells, particularly of the nervous system, expression of this gene at significantly higher or lower levels may be routinely detected in certain tissues and cell types (e.g., brain and other tissue of the nervous system, and smooth muscle, and cancerous and wounded tissues) or bodily fluids (e.g., lymph, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The tissue distribution and homology to ftp-3 indicates that the protein product of this clone is useful for the diagnosis and treatment of human brain diseases and disorders involving improper RNA splicing such as thalessemia. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:28 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 2347 of SEQ ID NO:28, b is an integer of 15 to 2361, where both a and b correspond to the positions of nucleotide residues shown in SEQ ID NO:28, and where the b is greater than or equal to a+14

Features of Protein Encoded by Gene No: 19

The translation product of this gene shares sequence homology with immunoglobulin lambda light chain which is thought to be important in immune functions. The gene encoding the disclosed cDNA is believed to reside on chromosome 22. Accordingly, polynucleotides related to this invention are useful as a marker in linkage analysis for chromosome 22.

This gene is expressed primarily in human thymus and to a lesser extent in human colon, soares breast, bone marrow and breast lymph node.

Therefore, polynucleotides and polypeptides of the invention are useful as reagents for differential identification of the tissue(s) or cell type(s) present in a biological sample and for diagnosis of diseases and conditions which include, but are not limited to, immune or hematopoietic disorders. Similarly, polypeptides and antibodies directed to these polypeptides are useful in providing immunological probes for differential identification of the tissue(s) or cell type(s). For a number of disorders of the above tissues or cells, particularly of the immune system expression of this gene at significantly higher or lower levels may be routinely detected in certain tissues and cell types (e.g., thymus, colon, mammary tissue, bone marrow, and lymphoid tissue, and wounded tissues) or bodily fluids (e.g., lymph, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder. Preferred epitopes include those comprising a sequence shown in SEQ ID NO:70 as residues: Gly-43 to Asp-50, Gln-57 to Lys-65, Arg-70 to Gly-77, Pro-143 to Leu-148, Thr-185 to Tyr-195, Pro-205 to Ser-215.

The tissue distribution and homology with immunoglobulin lambda light chain indicates that polynucleotides and polypeptides corresponding to the gene are useful for the diagnosis and/or treatment of immunal diseases. This gene product may be involved in antigen presentation, or other processes that may also suggest a usefulness in the treatment of cancer (e.g. by boosting immune responses to tumor antigens). Since the gene is expressed in cells of lymphoid origin, the natural gene product may be involved in immune functions. Therefore it may be also used as an agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren's disease, scleroderma and tissues. In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:29 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 865 of SEQ ID NO:29, b is an integer of 15 to 879, where both a and b correspond to the positions of nucleotide residues shown in SEQ ID NO:29, and where the b is greater than or equal to a+14.

Features of Protein Encoded by Gene No: 20

The translation product of this gene shares sequence homology with Xenopus chordin (Accession NO:L35764) which is thought to be important in dorsal-ventral patterning and is activated by organizer-specific homeobox genes. See, e.g., Sasai, Y., et al., Cell 79:779–790 (1994).) This gene has also been determined to be a powerful morphogen.

This gene is expressed primarily in early stage human tissues, prostate, and adipose tissues and to a lesser extent, in other tissues.

Therefore, polynucleotides and polypeptides of the invention are useful as reagents for differential identification of the tissue(s) or cell type(s) present in a biological sample and for diagnosis of diseases and conditions which include, but are not limited to, developmental disorders. Similarly, polypeptides and antibodies directed to these polypeptides are useful in providing immunological probes for differential identification of the tissue(s) or cell type(s). For a number of disorders of the above tissues or cells, particularly of the embryo and fetal tissues, expression of this gene at significantly higher or lower levels may be routinely detected in certain tissues or cell types (e.g., embryonic and fetal tissue, prostate, and adipose tissue, and cancerous and wounded tissues) or bodily fluids (e.g., amniotic fluid, seminal fluid, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder. Preferred epitopes include those comprising a sequence shown in SEQ ID NO:71 as residues: Met-1 to Ala-6, Asn-28 to Trp-38, Val-57 to Lys-64, His-66 to Lys-82, Glu-90 to Gly-100, Asp-118 to Arg-123, Glu-210 to Cys-217.

Chordin plays important role dorsal-ventral patterning in Xenopus. The tissue distribution and homology to chordin suggests that polynucleotides and polypeptides corresponding to the gene are useful for diagnosis and treatment of wounds and developmental disorders, such as cancer. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:30 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1718 of SEQ ID NO:30, b is an integer of 15 to 1732, where both a and b correspond to the positions of nucleotide residues shown in SEQ ID NO:30, and where the b is greater than or equal to a+14.

Features of Protein Encoded by Gene No: 22

In one embodiment of the invention, the polypeptides of the invention comprise the sequence FTHSFILEHAFSL-LITLPVSSWAANN (SEQ ID NO:117).

This gene is expressed primarily in chronic synovitis and to a lesser extent in other tissues.

Therefore, polynucleotides and polypeptides of the invention are useful as reagents for differential identification of the tissue(s) or cell type(s) present in a biological sample and for diagnosis of chronic synovitis. Similarly, polypeptides and antibodies directed to these polypeptides are useful in providing immunological probes for differential identification of the tissue(s) or cell type(s). For a number of disorders of the synovium, expression of this gene at significantly higher or lower levels may be routinely detected in certain tissues or cell types (e.g., synovial tissue and cancerous and wounded tissues) or bodily fluids (e.g., lymph, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The tissue distribution suggests that polynucleotides and polypeptides corresponding to the gene are useful for diagnosis and treatment of chronic synovitis. In addition, the expression of this gene product in synovium would suggest a role in the detection and treatment of disorders and conditions affecting the skeletal system, in particular osteoporosis as well as disorders afflicting connective tissues (e.g. arthritis, trauma, tendonitis, chrondomalacia and inflammation), such as in the diagnosis or treatment of various autoimmune disorders such as rheumatoid arthritis, lupus, scleroderma, and dermatomyositis as well as dwarfism, spinal deformation, and specific joint abnormalities as well as chondrodysplasias (ie. spondyloepiphyseal dysplasia congenita, familial osteoarthritis, Atelosteogenesis type II, or metaphyseal chondrodysplasia.). Protein, as well as, anitbodies directed against the protein may show utility as a tumor marker and/or immunotherapy targets for the above listed tissues.

Features of Protein Encoded by Gene No: 23

This gene is expressed primarily in testes and to a lesser extent in other tissues.

Therefore, polynucleotides and polypeptides of the invention are useful as reagents for differential identification of the tissue(s) or cell type(s) present in a biological sample and for diagnosis of diseases and conditions which include, but are not limited to, testes related diseases such as infertility and endocrine disorders. Similarly, polypeptides and antibodies directed to these polypeptides are useful in providing immunological probes for differential identification of the tissue(s) or cell type(s). For a number of disorders of the above tissues or cells, particularly of the testes, expression of this gene at significantly higher or lower levels may be routinely detected in certain tissues or cell types (e.g., testes and other reproductive tissue, and cancerous and wounded tissues) or bodily fluids (e.g., seminal fluid, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The tissue distribution indicates that the protein product of this clone is useful for the treatment and diagnosis of conditions concerning proper testicular function (e.g. endocrine function, sperm maturation). Therefore, this gene product is useful in the treatment of male infertility and/or impotence. This gene product is also useful in assays designed to identify binding agents as such agents (antagonists) that are useful as male contraceptive agents. Similarly, the protein is believed to by useful in the treatment and/or diagnosis of testicular cancer. The testes are also a site of active gene expression of transcripts that may be expressed, particularly at low levels, in other tissues of the body. Therefore, this gene product may be expressed in other specific tissues or organs where it may play related functional roles in other processes, such as hematopoiesis, inflammation, bone formation, and kidney function, to name a few possible target indications. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:32 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 440 of SEQ ID NO:32, b is an integer of 15 to 454, where both a and b correspond to the positions of nucleotide residues shown in SEQ ID NO:32, and where the b is greater than or equal to a+14.

Features of Protein Encoded by Gene No: 24

The translation product of this gene shares sequence homology with the nucleotide sequence of a new HLA-DRB1(*)11 allele (DRB1(*)1124), which is thought to be important in organ transplantation and immune disorders. The translation product of this gene also shares homology with protease inhibitors such as aprotinin and others with Kunitz-type domains. Kunitz-type domains are known in the art to possess protease inhibiting activity. A Kunitz-type domain is contained within the translation product of this gene and has the amino acid sequence: CEMPKETGP-CLAYFLHWWYDKKDNTCSMFVYGGC-QGNNNNFQSKANCLNTC (SEQ ID NO:118). Thus, preferred polypeptides of the invention comprise the amino acid sequence of the Kunitz-type domain shown immediately above.

It has been discovered by analyzing hundreds of thousands of ESTs that this gene is expressed primarily in the testes and epididymus. Northern blot analysis has confirmed expression primarily in the testes.

Therefore, polynucleotides and polypeptides of the invention are useful as reagents for differential identification of the tissue(s) or cell type(s) present in a biological sample and for diagnosis of diseases and conditions which include, but are not limited to, diseases related to the testes and epididymus. Similarly, polypeptides and antibodies directed to these polypeptides are useful in providing immunological probes for differential identification of the tissue(s) or cell type(s). For a number of disorders of the above tissues or cells, particularly of the diseases related to the testes and epididymus, and organ transplantation. expression of this gene at significantly higher or lower levels may be routinely detected in certain tissues (e.g., testes and other reproductive tissue, and tissue and cells of the immune system, and cancerous and wounded tissues) or bodily fluids (e.g., seminal fluid, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder. Preferred epitopes include those comprising a sequence shown in SEQ ID NO:75 as residues: Pro-30 to Arg-37, Val-47 to Lys-59, Trp-94 to Thr-101, Cys-110 to Cys-123, Thr-126 to Pro-133.

The tissue distribution and homology to protease inhibitors indicates that polynucleotides and polypeptides corresponding to the gene are useful for diagnosis and treatment of diseases related to the testes, epididymus, and organ transplantation. More specifically, these polypeptides are particularly useful in the treatment of hyperfilbronolytic hemorrhage and traumatic hemorrhagic shock as well as in diseases connected with excessive release of pancreatic elastase (pancreatitis), serum elastase (artherosclerosis), leukocyte elastase in acute and chronic inflammation with damage to connective tissue, in damage to vessel walls, in necrotic diseases, and degeneration of lung tissue. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:33 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 216 of SEQ ID NO:33, b is an integer of 15 to 230, where both a and b correspond to the positions of nucleotide residues shown in SEQ ID NO:33, and where the b is greater than or equal to a+14.

Features of Protein Encoded by Gene No: 25

The translation product of this gene shares sequence homology with CpG islands genes which are short stretches of DNA containing a high density of non-methylated CpG dinucleotides, predominantly associated with coding regions. As CpG islands overlap with approximately 60% of human genes, the CpG island library can be used to isolate full-length cDNAs and to place genes on genomic maps. The translation product also shares distant homology with the A33 protein, which is a transmembrane protein and a member of the immunoglobulin superfamily.

This gene is expressed primarily in the testes and to a lesser extent in the lung, tonsils, placenta, and rhabdomyosarcoma.

Therefore, polynucleotides and polypeptides of the invention are useful as reagents for differential identification of the tissue(s) or cell type(s) present in a biological sample and for diagnosis of diseases and conditions which include, but are not limited to, diseases related to the testes, lung, tonsils, placenta, and tumors. Similarly, polypeptides and antibodies directed to these polypeptides are useful in providing immunological probes for differential identification of the tissue(s) or cell type(s). For a number of disorders of the above tissues or cells, particularly of the diseases related to the testes, lung, tonsils, placenta, and tumors, expression of this gene at significantly higher or lower levels may be routinely detected in certain tissues or cell types (e.g., testes and other reproductive tissue, lung, tonsils, placenta, and striated muscle, and cancerous and wounded tissues) or bodily fluids (e.g., seminal fluid, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder. Preferred epitopes include those comprising a sequence shown in SEQ ID NO:76 as residues: Met-1 to His-7,Preferred epitopes include those comprising a sequence shown in SEQ ID NO:76 as residues: Met-1 to His-7.

The tissue distribution indicates that polynucleotides and polypeptides corresponding to the gene are useful for diagnosis and treatment of diseases related to the testes, lung, tonsils, placenta, and tumors. More specifically, the tissue distribution indicates that the protein product of this clone is useful for the treatment and diagnosis of conditions concerning proper testicular function (e.g. endocrine function, sperm maturation). Therefore, this gene product is useful in the treatment of male infertility and/or impotence. This gene product is also useful in assays designed to identify binding agents as such agents (antagonists) are useful as male contraceptive agents. Similarly, the protein is believed to by useful in the treatment and/or diagnosis of testicular cancer. The testes are also a site of active gene expression of transcripts that may be expressed, particularly at low levels, in other tissues of the body. Therefore, this gene product may be expressed in other specific tissues or organs where it may play related functional roles in other processes, such as hematopoiesis, inflammation, bone formation, and kidney function, to name a few possible target indications. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:35 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1008 of SEQ ID NO:35, b is an integer of 15 to 1022, where both a and b correspond to the positions of nucleotide residues shown in SEQ ID NO:35, and where the b is greater than or equal to a+14.

Features of Protein Encoded by Gene No: 26

The translation product of this gene shares sequence homology with the sequence of human villin: a large duplicted domain homologue with other actin severing proteins and a unique small carboxy terminal domain related to villin specificity which is thought to be important in actin capping and processing. This gene has now been published. See DNA Res. (1997) 28:4(1):35–43. It has been shown that this gene is homozygously deleted in a lung carcinoma cell line suggesting a possible role for the translation product of this gene in suppressing tumors. In any case, a suppressor gene is likely located close to this gene and accordingly, this gene can be used as a cancer marker. Preferred polypeptides of this invention comprise the following amino acid sequence: MMIQWNGPKTSISEKARGLXLTYSLR-DRERGGGRAQIGVVDDEAKAPDLMQI-MEVLGRRVGXLRXATPSKDINQLQKAN-VRLYHVYEKGKDLVVLELATPPLTQDLLQEEDF YILDQGGFKIYVWQGRMSSLQERKAAFS-RAVGFIQAKGYPTYTNVEVVNDGAE-SAAFKQLFRTWSEKRRRNQKXGGRDKSI-HVKLDVGKLHTQPKLAAQLRMVDDGSGKVEVW CIQDLHRQPVDPKRHGQLCAGNCYLVLY-TYQRLGRVQYILYLWQGHQATA-DEIEALNSNAEELDVMYGGVLVQEHVT-MGSEPPHFLAIFQGQLVIFQERAGHHGKGQSASTT RLFQVQGTDSHNTRTMEVPARASSLNSS-DIFLLVTASVCYLWFGKG (SEQ ID NO:119).

It has been discovered by analyzing EST sequences that this gene is expressed primarily in a healing wound 7.5 hours after incision, pancreas tumor, CD34+ cell, human osteoclastoma, stromal cells, human thymus and to a lesser extent in pancreas tumor, spleen, and apoptotic T cell. Northern blots were carried out and showed that this gene was expressed in all tissues tested: spleen, thymus, prostate, testis, ovary, small intestine, colon, and peripheral blood leukocytes. The most intense band (expression) was seen in the colon, with the least intense band seen in peripheral blood leukocytes.

Therefore, polynucleotides and polypeptides of the invention are useful as reagents for differential identification of the tissue(s) or cell type(s) present in a biological sample and for diagnosis of diseases and conditions which include, but are not limited to, cancers including, lung carcinoma, osteoclastoma, pancreas tumor, immune disorders, and infectious diseases. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues and cell types (e.g., bone, stromal cells, thymus, pancreas, lung, spleen, and blood cells, and cancerous and wounded tissues) or bodily fluids (e.g., lymph, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The tissue distribution and homology to the Villin family of actin severing proteins suggests that polynucleotides and polypeptides corresponding to the gene are useful for diagnosis and treatment of cancers, particularly osteoclastoma, pancreas tumor, lung carcinoma, other immune disorders, and infectious diseases. It has recently been shown that sputum samples from cystic fibrosis patients contain actin filaments and that plasma gelsolin can reduce the viscosity of these samples. Accordingly, the translation product of this gene is useful in the treatment of cystic fibrosis. This gene has been mapped to 3p22-p21.3. Accordingly, polynucleotides related to this invention are useful as a marker in linkage analysis for chromosome 3.

Many polynucleotide sequences, such as EST sequences, are publicly available and accessible through sequence databases. Some of these sequences are related to SEQ ID NO:36 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 3030 of SEQ ID NO:36, b is an integer of 15 to 3044, where both a and b correspond to the positions of nucleotide residues shown in SEQ ID NO:36, and where the b is greater than or equal to a+14.

Features of Protein Encoded by Gene No: 27

This gene is expressed primarily in a human HCC cell line, mouse liver metastasis and muscle tissue from a human patient with multiple sclerosis.

Therefore, polynucleotides and polypeptides of the invention are useful as reagents for differential identification of the tissue(s) or cell type(s) present in a biological sample and for diagnosis of diseases and conditions which include, but are not limited to, tumor metastasis and multiple sclerosis. Similarly, polypeptides and antibodies directed to these polypeptides are useful in providing immunological probes for differential identification of the tissue(s) or cell type(s). For a number of disorders of the above tissues or cells, particularly of the immune system expression of this gene at significantly higher or lower levels may be routinely detected in certain tissues or cell types (e.g., liver, and muscle, and cancerous and wounded tissues) or bodily fluids (e.g., bile, lymph, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder. Preferred epitopes include those comprising a sequence shown in SEQ ID NO:78 as residues: Ser-21 to Asp-32.

The tissue distribution indicates that polynucleotides and polypeptides corresponding to the gene are useful for diagnosis and treatment of multiple sclerosis and tumor metastasis. The nucleotide sequence 3' of the poly A tail, as shown in the sequence listing is vector sequence as would be readily appreciated by those of skill in the art. Polypeptides of the invention preferrably do not contain such vector sequences or sequences which hybridize to such vector sequences.

Many polynucleotide sequences, such as EST sequences, are publicly available and accessible through sequence databases. Some of these sequences are related to SEQ ID NO:37 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 527 of SEQ ID NO:37, b is an integer of 15 to 541, where both a and b correspond to the positions of nucleotide residues shown in SEQ ID NO:37, and where the b is greater than or equal to a+14.

Features of Protein Encoded by Gene No: 28

The translation product of this gene shares sequence homology with the sequence CEESL52F (Genbank accession NO: U80441); coded for by *C. elegans* cDNA yk5 which is thought to be important in embryonic development. The translation product of this gene has recently been described elsewhere (See Proc. Natl. Acad. Sci. U S A (1997) 8:94(14):7481–7486, incorporated herein by reference in its entirety), as hCTR2: a human gene for copper uptake. The gene encoding the disclosed cDNA is thought to reside on chromosome 9. Accordingly, polynucleotides related to this invention are useful as a marker in linkage analysis for chromosome 9.

This gene is expressed primarily in placenta and human amygdala, and to a lesser extent in adult brain, primary dendritic cells, keratinocytes, activated monocytes, human cerebellum, and activated T-cells.

Therefore, polynucleotides and polypeptides of the invention are useful as reagents for differential identification of the tissue(s) or cell type(s) present in a biological sample and for diagnosis of diseases and conditions which include, but are not limited to, embryonic development, neuronal cell differentiation, disorders associated with copper metabolism and immune responses. Similarly, polypeptides and antibodies directed to these polypeptides are useful in providing immunological probes for differential identification of the tissue(s) or cell type(s). For a number of disorders of the above tissues or cells, particularly of the abnormal embryonic development, neuronal cell disorders, disorders involving abnormal copper metabolism and immune system disorders, expression of this gene at significantly higher or lower levels may be routinely detected in certain tissues or cell types (e.g., placenta, amygdala, brain and other tissue of the nervous system, dendritic cells, blood cells, keratinocytes, and cancerous and wounded tissues) or bodily fluids (e.g., lymph, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder. Preferred epitopes include those comprising a sequence shown in SEQ ID NO:79 as residues: Ser-24 to Trp-30.

The tissue distribution and similarity to hCTR1 and hCTR2 indicates that polynucleotides and polypeptides corresponding to the gene are useful for diagnosis and treatment of abnormal embryonic development, neuronal cell disorders, disorders involving copper metabolism and immune system disorders. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:38 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1738 of SEQ ID NO:38, b is an integer of 15 to 1752, where both a and b correspond to the positions of nucleotide residues shown in SEQ ID NO:38, and where the b is greater than or equal to a+14.

FIGS. 1A–G summarize the information corresponding to each "Gene No." described above. The nucleotide sequence identified as "NT SEQ ID NO:X" was assembled from partially homologous ("overlapping") sequences obtained from the "cDNA clone ID" identified in FIGS. 1A–G and, in some cases, from additional related DNA clones. The overlapping sequences were assembled into a single contiguous sequence of high redundancy (usually three to five overlapping sequences at each nucleotide position), resulting in a final sequence identified as SEQ ID NO:X.

The cDNA Clone ID was deposited on the date and given the corresponding deposit number listed in "ATCC Deposit No:Z and Date." Some of the deposits contain multiple different clones corresponding to the same gene. "Vector" refers to the type of vector contained in the cDNA Clone ID.

"Total NT Seq." refers to the total number of nucleotides in the contig identified by "Gene No." The deposited clone may contain all or most of these sequences, reflected by the nucleotide position indicated as "5' NT of Clone Seq." and the "3' NT of Clone Seq." of SEQ ID NO:X. The nucleotide position of SEQ ID NO:X of the putative start codon (methionine) is identified as "5' NT of Start Codon." Similarly, the nucleotide position of SEQ ID NO:X of the predicted signal sequence is identified as "5' NT of First AA of Signal Pep."

The translated amino acid sequence, beginning with the methionine, is identified as "AA SEQ ID NO:Y," although other reading frames can also be easily translated using known molecular biology techniques. The polypeptides produced by these alternative open reading frames are specifically contemplated by the present invention.

The first and last amino acid position of SEQ ID NO:Y of the predicted signal peptide is identified as "First AA of Sig Pep" and "Last AA of Sig Pep." The predicted first amino acid position of SEQ ID NO:Y of the secreted portion is identified as "Predicted First AA of Secreted Portion." Finally, the amino acid position of SEQ ID NO:Y of the last amino acid in the open reading frame is identified as "Last AA of ORF."

SEQ ID NO:X and the translated SEQ ID NO:Y are sufficiently accurate and otherwise suitable for a variety of uses well known in the art and described further below. For instance, SEQ ID NO:X is useful for designing nucleic acid hybridization probes that will detect nucleic acid sequences contained in SEQ ID NO:X or the cDNA contained in the deposited clone. These probes will also hybridize to nucleic acid molecules in biological samples, thereby enabling a variety of forensic and diagnostic methods of the invention. Similarly, polypeptides identified from SEQ ID NO:Y may be used to generate antibodies which bind specifically to the secreted proteins encoded by the cDNA clones identified in FIGS. 1A–G.

Nevertheless, DNA sequences generated by sequencing reactions can contain sequencing errors. The errors exist as misidentified nucleotides, or as insertions or deletions of nucleotides in the generated DNA sequence. The erroneously inserted or deleted nucleotides cause frame shifts in the reading frames of the predicted amino acid sequence. In these cases, the predicted amino acid sequence diverges from the actual amino acid sequence, even though the generated DNA sequence may be greater than 99.9% identical to the actual DNA sequence (for example, one base insertion or deletion in an open reading frame of over 1000 bases).

Accordingly, for those applications requiring precision in the nucleotide sequence or the amino acid sequence, the present invention provides not only the generated nucleotide sequence identified as SEQ ID NO:X and the predicted translated amino acid sequence identified as SEQ ID NO:Y, but also a sample of plasmid DNA containing a human cDNA of the invention deposited with the ATCC, as set forth in FIGS. 1A–G. The nucleotide sequence of each deposited clone can readily be determined by sequencing the deposited clone in accordance with known methods. The predicted amino acid sequence can then be verified from such deposits. Moreover, the amino acid sequence of the protein encoded by a particular clone can also be directly determined by peptide sequencing or by expressing the protein in a suitable host cell containing the deposited human cDNA, collecting the protein, and determining its sequence.

The present invention also relates to the genes corresponding to SEQ ID NO:X, SEQ ID NO:Y, or the deposited clone. The corresponding gene can be isolated in accordance with known methods using the sequence information disclosed herein. Such methods include preparing probes or primers from the disclosed sequence and identifying or amplifying the corresponding gene from appropriate sources of genomic material.

Also provided in the present invention are species homologs. Species homologs may be isolated and identified by making suitable probes or primers from the sequences provided herein and screening a suitable nucleic acid source for the desired homologue.

The polypeptides of the invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

The polypeptides may be in the form of the secreted protein, including the mature form, or may be a part of a larger protein, such as a fusion protein (see below). It is often advantageous to include an additional amino acid sequence which contains secretory or leader sequences, prosequences, sequences which aid in purification, such as multiple histidine residues, or an additional sequence for stability during recombinant production.

The polypeptides of the present invention are preferably provided in an isolated form, and preferably are substantially purified. A recombinantly produced version of a polypeptide, including the secreted polypeptide, can be substantially purified by the one-step method described in Smith and Johnson, Gene 67:31–40 (1988). Polypeptides of the invention also can be purified from natural or recombinant sources using antibodies of the invention raised against the secreted protein in methods which are well known in the art.

Signal Sequences

Methods for predicting whether a protein has a signal sequence, as well as the cleavage point for that sequence, are available. For instance, the method of McGeoch, Virus Res. 3:271–286 (1985), uses the information from a short N-terminal charged region and a subsequent uncharged region of the complete (uncleaved) protein. The method of von Heinje, Nucleic Acids Res. 14:4683–4690 (1986) uses the information from the residues surrounding the cleavage site, typically residues −13 to +2, where +1 indicates the amino terminus of the secreted protein. The accuracy of predicting the cleavage points of known mammalian secretory proteins for each of these methods is in the range of 75–80%. (von Heinje, supra.) However, the two methods do not always produce the same predicted cleavage point(s) for a given protein.

In the present case, the deduced amino acid sequence of the secreted polypeptide was analyzed by a computer program called SignalP (Henrik Nielsen et al., Protein Engineering 10:1–6 (1997)), which predicts the cellular location of a protein based on the amino acid sequence. As part of this computational prediction of localization, the methods of McGeoch and von Heinje are incorporated. The analysis of the amino acid sequences of the secreted proteins described herein by this program provided the results shown in FIGS. 1A–G.

As one of ordinary skill would appreciate, however, cleavage sites sometimes vary from organism to organism and cannot be predicted with absolute certainty. Accordingly, the present invention provides secreted polypeptides having a sequence shown in SEQ ID NO:Y which have an N-terminus beginning within 5 residues (i.e., + or −5 residues) of the predicted cleavage point. Similarly, it is also recognized that in some cases, cleavage of the signal sequence from a secreted protein is not entirely uniform, resulting in more than one secreted species. These polypeptides, and the polynucleotides encoding such polypeptides, are contemplated by the present invention.

Moreover, the signal sequence identified by the above analysis may not necessarily predict the naturally occurring signal sequence. For example, the naturally occurring signal sequence may be further upstream from the predicted signal sequence. However, it is likely that the predicted signal sequence will be capable of directing the secreted protein to the ER. These polypeptides, and the polynucleotides encoding such polypeptides, are contemplated by the present invention.

Polynucleotide and Polypeptide Variants

"Variant" refers to a polynucleotide or polypeptide differing from the polynucleotide or polypeptide of the present invention, but retaining essential properties thereof. Generally, variants are overall closely similar, and, in many regions, identical to the polynucleotide or polypeptide of the present invention.

By a polynucleotide having a nucleotide sequence at least, for example, 95% "identical" to a reference nucleotide sequence of the present invention, it is intended that the nucleotide sequence of the polynucleotide is identical to the reference sequence except that the polynucleotide sequence may include up to five point mutations per each 100 nucleotides of the reference nucleotide sequence encoding the polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. The query sequence may be an entire sequence shown in FIGS. 1A–G, the ORF (open reading frame), or any fragment specified as described herein.

As a practical matter, whether any particular nucleic acid molecule or polypeptide is at least 90%, 95%, 96%, 97%, 98% or 99% identical to a nucleotide sequence of the presence invention can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al. (Comp. App. Biosci. (1990) 6:237–245). In a sequence alignment the query and subject sequences are both DNA sequences. An RNA sequence can be compared by converting U's to T's. The result of said global sequence alignment is in percent identity. Preferred parameters used in a FASTDB alignment of DNA sequences to calculate percent identity are: Matrix=Unitary, k-tuple=4, Mismatch Penalty=1, Joining Penalty=30, Randomization Group Length=0, Cutoff Score=1, Gap Penalty=5, Gap Size Penalty 0.05, Window Size=500 or the length of the subject nucleotide sequence, whichever is shorter.

If the subject sequence is shorter than the query sequence because of 5' or 3' deletions, not because of internal deletions, a manual correction must be made to the results. This is because the FASTDB program does not account for 5' and 3' truncations of the subject sequence when calculating percent identity. For subject sequences truncated at the 5' or 3' ends, relative to the the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of the present invention. Only bases outside the 5' and 3' bases of the subject sequence, as displayed by the FASTDB alignment, which are not matched/aligned with the query sequence, are calculated for the purposes of manually adjusting the percent identity score.

For example, a 90 base subject sequence is aligned to a 100 base query sequence to determine percent identity. The deletions occur at the 5' end of the subject sequence and therefore, the FASTDB alignment does not show a matched/alignment of the first 10 bases at 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are to made for the purposes of the present invention.

By a polypeptide having an amino acid sequence at least, for example, 95% "identical" to a query amino acid sequence of the present invention, it is intended that the amino acid sequence of the subject polypeptide is identical to the query sequence except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence may be inserted, deleted, (indels) or substituted with another amino acid. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 90%, 95%, 96%, 97%, 98% or 99% identical to, for instance, the amino acid sequences shown in FIGS. 1A–G or to the amino acid sequence encoded by deposited DNA clone can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al. (Comp. App. Biosci. (1990) 6:237–245). In a sequence alignment the query and subject sequences are either both nucleotide sequences or both amino acid sequences. The result of said global sequence alignment is in percent identity. Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter.

If the subject sequence is shorter than the query sequence due to N- or C-terminal deletions, not because of internal deletions, a manual correction must be made to the results. This is because the FASTDB program does not account for N- and C-terminal truncations of the subject sequence when calculating global percent identity. For subject sequences truncated at the N- and C-termini, relative to the the query sequence, the percent identity is corrected by calculating the number of residues of the query sequence that are N- and C-terminal of the subject sequence, which are not matched/aligned with a corresponding subject residue, as a percent of the total bases of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present invention. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence.

For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected for. No other manual corrections are to made for the purposes of the present invention.

The variants may contain alterations in the coding regions, non-coding regions, or both. Especially preferred are polynucleotide variants containing alterations which produce silent substitutions, additions, or deletions, but do not alter the properties or activities of the encoded polypeptide. Nucleotide variants produced by silent substitutions due to the degeneracy of the genetic code are preferred. Moreover, variants in which 5–10, 1–5, or 1–2 amino acids are substituted, deleted, or added in any combination are also preferred. Polynucleotide variants can be produced for a variety of reasons, e.g., to optimize codon expression for a particular host (change codons in the human mRNA to those preferred by a bacterial host such as E. coli).

Naturally occurring variants are called "allelic variants," and refer to one of several alternate forms of a gene occupying a given locus on a chromosome of an organism. (Genes II, Lewin, B., ed., John Wiley & Sons, New York (1985).) These allelic variants can vary at either the polynucleotide and/or polypeptide level. Alternatively, non-naturally occurring variants may be produced by mutagenesis techniques or by direct synthesis.

Using known methods of protein engineering and recombinant DNA technology, variants may be generated to improve or alter the characteristics of the polypeptides of the present invention. For instance, one or more amino acids can be deleted from the N-terminus or C-terminus of the secreted protein without substantial loss of biological function. The authors of Ron et al., J. Biol. Chem. 268: 2984–2988 (1993), reported variant KGF proteins having heparin binding activity even after deleting 3, 8, or 27 amino-terminal amino acid residues. Similarly, Interferon gamma exhibited up to ten times higher activity after deleting 8–10 amino acid residues from the carboxy terminus of this protein. (Dobeli et al., J. Biotechnology 7:199–216 (1988).)

Moreover, ample evidence demonstrates that variants often retain a biological activity similar to that of the naturally occurring protein. For example, Gayle and coworkers (J. Biol. Chem 268:22105–22111 (1993)) conducted extensive mutational analysis of human cytokine IL-1a. They used random mutagenesis to generate over 3,500 individual IL-1a mutants that averaged 2.5 amino acid changes per variant over the entire length of the molecule. Multiple mutations were examined at every possible amino acid position. The investigators found that "[m]ost of the molecule could be altered with little effect on either [binding or biological activity]." (See, Abstract.) In fact, only 23 unique amino acid sequences, out of more than 3,500 nucleotide sequences examined, produced a protein that significantly differed in activity from wild-type.

Furthermore, even if deleting one or more amino acids from the N-terminus or C-terminus of a polypeptide results in modification or loss of one or more biological functions, other biological activities may still be retained. For example, the ability of a deletion variant to induce and/or to bind antibodies which recognize the secreted form will likely be retained when less than the majority of the residues of the secreted form are removed from the N-terminus or C-terminus. Whether a particular polypeptide lacking N- or C-terminal residues of a protein retains such immunogenic activities can readily be determined by routine methods described herein and otherwise known in the art.

Thus, the invention further includes polypeptide variants which show substantial biological activity. Such variants include deletions, insertions, inversions, repeats, and substitutions selected according to general rules known in the art so as have little effect on activity. For example, guidance concerning how to make phenotypically silent amino acid substitutions is provided in Bowie, J. U. et al., Science 247:1306–1310 (1990), wherein the authors indicate that there are two main strategies for studying the tolerance of an amino acid sequence to change.

The first strategy exploits the tolerance of amino acid substitutions by natural selection during the process of evolution. By comparing amino acid sequences in different species, conserved amino acids can be identified. These conserved amino acids are likely important for protein function. In contrast, the amino acid positions where substitutions have been tolerated by natural selection indicates that these positions are not critical for protein function. Thus, positions tolerating amino acid substitution could be modified while still maintaining biological activity of the protein.

The second strategy uses genetic engineering to introduce amino acid changes at specific positions of a cloned gene to identify regions critical for protein function. For example, site directed mutagenesis or alanine-scanning mutagenesis (introduction of single alanine mutations at every residue in the molecule) can be used. (Cunningham and Wells, Science 244:1081–1085 (1989).) The resulting mutant molecules can then be tested for biological activity.

As the authors state, these two strategies have revealed that proteins are surprisingly tolerant of amino acid substitutions. The authors further indicate which amino acid changes are likely to be permissive at certain amino acid positions in the protein. For example, most buried (within the tertiary structure of the protein) amino acid residues require nonpolar side chains, whereas few features of surface side chains are generally conserved. Moreover, tolerated conservative amino acid substitutions involve replacement of the aliphatic or hydrophobic amino acids Ala, Val, Leu and Ile; replacement of the hydroxyl residues Ser and Thr; replacement of the acidic residues Asp and Glu; replacement of the amide residues Asn and Gln, replacement of the basic residues Lys, Arg, and His; replacement of the aromatic residues Phe, Tyr, and Trp, and replacement of the small-sized amino acids Ala, Ser, Thr, Met, and Gly.

Besides conservative amino acid substitution, variants of the present invention include (i) substitutions with one or more of the non-conserved amino acid residues, where the substituted amino acid residues may or may not be one encoded by the genetic code, or (ii) substitution with one or more of amino acid residues having a substituent group, or (iii) fusion of the mature polypeptide with another compound, such as a compound to increase the stability and/or solubility of the polypeptide (for example, polyethylene glycol), or (iv) fusion of the polypeptide with additional amino acids, such as an IgG Fc fusion region peptide, or leader or secretory sequence, or a sequence facilitating purification. Such variant polypeptides are deemed to be within the scope of those skilled in the art from the teachings herein.

For example, polypeptide variants containing amino acid substitutions of charged amino acids with other charged or neutral amino acids may produce proteins with improved characteristics, such as less aggregation. Aggregation of pharmaceutical formulations both reduces activity and increases clearance due to the aggregate's immunogenic activity. (Pinckard et al., Clin. Exp. Immunol. 2:331–340 (1967); Robbins et al., Diabetes 36:838–845 (1987); Cleland et al., Crit. Rev. Therapeutic Drug Carrier Systems 10:307–377 (1993).)

Polynucleotide and Polypeptide Fragments

In the present invention, a "polynucleotide fragment" refers to a short polynucleotide having a nucleic acid sequence contained in the deposited clone or shown in SEQ ID NO:X. The short nucleotide fragments are preferably at least about 15 nt, and more preferably at least about 20 nt, still more preferably at least about 30 nt, and even more preferably, at least about 40 nt in length. A fragment "at least 20 nt in length," for example, is intended to include 20 or more contiguous bases from the cDNA sequence contained in the deposited clone or the nucleotide sequence shown in SEQ ID NO:X. These nucleotide fragments are useful as diagnostic probes and primers as discussed herein. Of course, larger fragments (e.g., 50, 150, 500, 600, 2000 nucleotides) are preferred.

Moreover, representative examples of polynucleotide fragments of the invention, include, for example, fragments having a sequence from about nucleotide number 1–50, 51–100, 101–150, 151–200, 201–250, 251–300, 301–350, 351–400, 401–450, 451–500, 501–550, 551–600, 651–700, 701–750, 751–800, 800–850, 851–900, 901–950, 951–1000, 1001–1050, 1051–1100, 1101–1150, 1151–1200, 1201–1250, 1251–1300, 1301–1350, 1351–1400, 1401–1450, 1451–1500, 1501–1550, 1551–1600, 1601–1650, 1651–1700, 1701–1750, 1751–1800, 1801–1850, 1851–1900, 1901–1950, 1951–2000, or 2001 to the end of SEQ ID NO:X or the cDNA contained in the deposited clone. In this context "about" includes the particularly recited ranges, larger or smaller by several (5, 4, 3, 2, or 1) nucleotides, at either terminus or at both termini. Preferably, these fragments encode a polypeptide which has biological activity. More preferably, these polynucleotides can be used as probes or primers as discussed herein.

In the present invention, a "polypeptide fragment" refers to a short amino acid sequence contained in SEQ ID NO:Y or encoded by the cDNA contained in the deposited clone. Protein fragments may be "free-standing," or comprised within a larger polypeptide of which the fragment forms a part or region, most preferably as a single continuous region. Representative examples of polypeptide fragments of the invention, include, for example, fragments from about amino acid number 1–20, 21–40, 41–60, 61–80, 81–100, 102–120, 121–140, 141–160, or 161 to the end of the coding region. Moreover, polypeptide fragments can be about 20, 30, 40, 50, 60, 70, 80, 90, 100, 110, 120, 130, 140, or 150 amino acids in length. In this context "about" includes the particularly recited ranges, larger or smaller by several (5, 4, 3, 2, or 1) amino acids, at either extreme or at both extremes.

Preferred polypeptide fragments include the secreted protein as well as the mature form. Further preferred polypeptide fragments include the secreted protein or the mature form having a continuous series of deleted residues from the amino or the carboxy terminus, or both. For example, any number of amino acids, ranging from 1– 60, can be deleted from the amino terminus of either the secreted polypeptide or the mature form. Similarly, any number of amino acids, ranging from 1–30, can be deleted from the carboxy terminus of the secreted protein or mature form. Furthermore, any combination of the above amino and carboxy terminus deletions are preferred. Similarly, polynucleotide fragments encoding these polypeptide fragments are also preferred.

Also preferred are polypeptide and polynucleotide fragments characterized by structural or functional domains, such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions. Polypeptide fragments of SEQ ID NO:Y falling within conserved domains are specifically contemplated by the present invention. Moreover, polynucleotide fragments encoding these domains are also contemplated.

Other preferred fragments are biologically active fragments. Biologically active fragments are those exhibiting activity similar, but not necessarily identical, to an activity of the polypeptide of the present invention. The biological activity of the fragments may include an improved desired activity, or a decreased undesirable activity.

Epitopes & Antibodies

In the present invention, "epitopes" refer to polypeptide fragments having antigenic or immunogenic activity in an animal, especially in a human. A preferred embodiment of the present invention relates to a polypeptide fragment comprising an epitope, as well as the polynucleotide encoding this fragment. A region of a protein molecule to which an antibody can bind is defined as an "antigenic epitope." In contrast, an "immunogenic epitope" is defined as a part of a protein that elicits an antibody response. (See, for instance, Geysen et al., Proc. Natl. Acad. Sci. USA 81:3998–4002 (1983).)

Fragments which function as epitopes may be produced by any conventional means. (See, e.g., Houghten, R. A., Proc. Natl. Acad. Sci. USA 82:5131–5135 (1985) further described in U.S. Pat. No. 4,631,211.)

In the present invention, antigenic epitopes preferably contain a sequence of at least seven, more preferably at least nine, and most preferably between about 15 to about 30 amino acids. Antigenic epitopes are useful to raise antibodies, including monoclonal antibodies, that specifically bind the epitope. (See, for instance, Wilson et al., Cell 37:767–778 (1984); Sutcliffe, J. G. et al., Science 219:660–666 (1983).)

Similarly, immunogenic epitopes can be used to induce antibodies according to methods well known in the art. (See, for instance, Sutcliffe et al., supra; Wilson et al., supra; Chow, M. et al., Proc. Natl. Acad. Sci. USA 82:910–914; and Bittle, F. J. et al., J. Gen. Virol. 66:2347–2354 (1985).) A preferred immunogenic epitope includes the secreted protein. The immunogenic epitopes may be presented together with a carrier protein, such as an albumin, to an animal system (such as rabbit or mouse) or, if it is long enough (at least about 25 amino acids), without a carrier. However, immunogenic epitopes comprising as few as 8 to 10 amino acids have been shown to be sufficient to raise antibodies capable of binding to, at the very least, linear epitopes in a denatured polypeptide (e.g., in Western blotting.)

As used herein, the term "antibody" (Ab) or "monoclonal antibody" (Mab) is meant to include intact molecules as well as antibody fragments (such as, for example, Fab and F(ab')2 fragments) which are capable of specifically binding to protein. Fab and F(ab')2 fragments lack the Fc fragment of intact antibody, clear more rapidly from the circulation, and may have less non-specific tissue binding than an intact antibody. (Wahl et al., J. Nucl. Med. 24:316–325 (1983).) Thus, these fragments are preferred, as well as the products of a FAB or other immunoglobulin expression library. Moreover, antibodies of the present invention include chimeric, single chain, and humanized antibodies.

Fusion Proteins

Any polypeptide of the present invention can be used to generate fusion proteins. For example, the polypeptide of the present invention, when fused to a second protein, can be used as an antigenic tag. Antibodies raised against the polypeptide of the present invention can be used to indirectly detect the second protein by binding to the polypeptide. Moreover, because secreted proteins target cellular locations based on trafficking signals, the polypeptides of the present invention can be used as targeting molecules once fused to other proteins.

Examples of domains that can be fused to polypeptides of the present invention include not only heterologous signal sequences, but also other heterologous functional regions. The fusion does not necessarily need to be direct, but may occur through linker sequences.

Moreover, fusion proteins may also be engineered to improve characteristics of the polypeptide of the present invention. For instance, a region of additional amino acids, particularly charged amino acids, may be added to the N-terminus of the polypeptide to improve stability and persistence during purification from the host cell or subsequent handling and storage. Also, peptide moieties may be added to the polypeptide to facilitate purification. Such regions may be removed prior to final preparation of the polypeptide. The addition of peptide moieties to facilitate handling of polypeptides are familiar and routine techniques in the art.

Moreover, polypeptides of the present invention, including fragments, and specifically epitopes, can be combined with parts of the constant domain of immunoglobulins (IgG), resulting in chimeric polypeptides. These fusion proteins facilitate purification and show an increased half-life in vivo. One reported example describes chimeric proteins consisting of the first two domains of the human CD4-polypeptide and various domains of the constant regions of the heavy or light chains of mammalian immunoglobulins. (EP A 394,827; Traunecker et al., Nature 331:84–86 (1988).) Fusion proteins having disulfide-linked dimeric structures (due to the IgG) can also be more efficient in binding and neutralizing other molecules, than the monomeric secreted protein or protein fragment alone. (Fountoulakis et al., J. Biochem. 270:3958–3964 (1995).)

Similarly, EP-A-O 464 533 (Canadian counterpart 2045869) discloses fusion proteins comprising various portions of constant region of immunoglobulin molecules together with another human protein or part thereof. In many cases, the Fc part in a fusion protein is beneficial in therapy and diagnosis, and thus can result in, for example, improved pharmacokinetic properties. (EP-A 0232 262.) Alternatively, deleting the Fc part after the fusion protein has been expressed, detected, and purified, would be desired. For example, the Fc portion may hinder therapy and diagnosis if the fusion protein is used as an antigen for immunizations. In drug discovery, for example, human proteins, such as hIL-5, have been fused with Fc portions for the purpose of high-throughput screening assays to identify antagonists of hIL-5. (See, D. Bennett et al., J. Molecular Recognition 8:52–58 (1995); K. Johanson et al., J. Biol. Chem. 270:9459–9471 (1995).)

Moreover, the polypeptides of the present invention can be fused to marker sequences, such as a peptide which facilitates purification of the fused polypeptide. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821–824 (1989), for instance, hexa-histidine provides for convenient purification of the fusion protein. Another peptide tag useful for purification, the "HA" tag, corresponds to an epitope derived from the influenza hemagglutinin protein. (Wilson et al., Cell 37:767 (1984).)

Thus, any of these above fusions can be engineered using the polynucleotides or the polypeptides of the present invention.

Vectors, Host Cells, and Protein Production

The present invention also relates to vectors containing the polynucleotide of the present invention, host cells, and the production of polypeptides by recombinant techniques. The vector may be, for example, a phage, plasmid, viral, or retroviral vector. Retroviral vectors may be replication competent or replication defective. In the latter case, viral propagation generally will occur only in complementing host cells.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

The polynucleotide insert should be operatively linked to an appropriate promoter, such as the phage lambda PL promoter, the E. coli lac, trp, phoA and tac promoters, the SV40 early and late promoters and promoters of retroviral LTRs, to name a few. Other suitable promoters will be known to the skilled artisan. The expression constructs will further contain sites for transcription initiation, termination, and, in the transcribed region, a ribosome binding site for translation. The coding portion of the transcripts expressed by the constructs will preferably include a translation initiating codon at the beginning and a termination codon (UAA, UGA or UAG) appropriately positioned at the end of the polypeptide to be translated.

As indicated, the expression vectors will preferably include at least one selectable marker. Such markers include dihydrofolate reductase, G418 or neomycin resistance for eukaryotic cell culture and tetracycline, kanamycin or ampicillin resistance genes for culturing in E. coli and other bacteria. Representative examples of appropriate hosts include, but are not limited to, bacterial cells, such as E. coli, Streptomyces and Salmonella typhimurium cells; fungal cells, such as yeast cells; insect cells such as Drosophila S2 and Spodoptera Sf9 cells; animal cells such as CHO, COS, 293, and Bowes melanoma cells; and plant cells. Appropriate culture mediums and conditions for the above-described host cells are known in the art.

Among vectors preferred for use in bacteria include pQE70, pQE60 and pQE-9, available from QIAGEN, Inc.; pBluescript vectors, Phagescript vectors, pNH8A, pNH16a, pNH18A, pNH46A, available from Stratagene Cloning Systems, Inc.; and ptrc99a, pKK223-3, pKK233-3, pDR540, pRIT5 available from Pharmacia Biotech, Inc. Among preferred eukaryotic vectors are pWLNEO, pSV2CAT, pOG44, pXT1 and pSG available from Stratagene; and pSVK3, pBPV, pMSG and pSVL available from Pharmacia. Other suitable vectors will be readily apparent to the skilled artisan.

Introduction of the construct into the host cell can be effected by calcium phosphate transfection, DEAE-dextran mediated transfection, cationic lipid-mediated transfection, electroporation, transduction, infection, or other methods. Such methods are described in many standard laboratory manuals, such as Davis et al., Basic Methods In Molecular Biology (1986). It is specifically contemplated that the polypeptides of the present invention may in fact be expressed by a host cell lacking a recombinant vector.

A polypeptide of this invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification.

Polypeptides of the present invention, and preferably the secreted form, can also be recovered from: products purified from natural sources, including bodily fluids, tissues and cells, whether directly isolated or cultured; products of chemical synthetic procedures; and products produced by recombinant techniques from a prokaryotic or eukaryotic host, including, for example, bacterial, yeast, higher plant, insect, and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes. Thus, it is well known in the art that the N-terminal methionine encoded by the translation initiation codon generally is removed with high efficiency from any protein after translation in all eukaryotic cells. While the N-terminal methionine on most proteins also is efficiently removed in most prokaryotes, for some proteins, this prokaryotic removal process is inefficient, depending on the nature of the amino acid to which the N-terminal methionine is covalently linked.

Uses of the Polynucleotides

Each of the polynucleotides identified herein can be used in numerous ways as reagents. The following description should be considered exemplary and utilizes known techniques.

The polynucleotides of the present invention are useful for chromosome identification. There exists an ongoing need to identify new chromosome markers, since few chromosome marking reagents, based on actual sequence data (repeat polymorphisms), are presently available. Each polynucleotide of the present invention can be used as a chromosome marker.

Briefly, sequences can be mapped to chromosomes by preparing PCR primers (preferably 15–25 bp) from the sequences shown in SEQ ID NO:X. Primers can be selected using computer analysis so that primers do not span more than one predicted exon in the genomic DNA. These primers are then used for PCR screening of somatic cell hybrids containing individual human chromosomes. Only those hybrids containing the human gene corresponding to the SEQ ID NO:X will yield an amplified fragment.

Similarly, somatic hybrids provide a rapid method of PCR mapping the polynucleotides to particular chromosomes. Three or more clones can be assigned per day using a single thermal cycler. Moreover, sublocalization of the polynucleotides can be achieved with panels of specific chromosome fragments. Other gene mapping strategies that can be used include in situ hybridization, prescreening with labeled flow-sorted chromosomes, and preselection by hybridization to construct chromosome specific-cDNA libraries.

Precise chromosomal location of the polynucleotides can also be achieved using fluorescence in situ hybridization (FISH) of a metaphase chromosomal spread. This technique uses polynucleotides as short as 500 or 600 bases; however, polynucleotides 2,000–4,000 bp are preferred. For a review of this technique, see Verma et al., "Human Chromosomes: a Manual of Basic Techniques," Pergamon Press, New York (1988).

For chromosome mapping, the polynucleotides can be used individually (to mark a single chromosome or a single site on that chromosome) or in panels (for marking multiple sites and/or multiple chromosomes). Preferred polynucleotides correspond to the noncoding regions of the cDNAs because the coding sequences are more likely conserved within gene families, thus increasing the chance of cross hybridization during chromosomal mapping.

Once a polynucleotide has been mapped to a precise chromosomal location, the physical position of the polynucleotide can be used in linkage analysis. Linkage analysis establishes coinheritance between a chromosomal location and presentation of a particular disease. (Disease mapping data are found, for example, in V. McKusick, Mendelian Inheritance in Man (available on line through Johns Hopkins University Welch Medical Library).) Assuming 1 megabase mapping resolution and one gene per 20 kb, a cDNA precisely localized to a chromosomal region associated with the disease could be one of 50–500 potential causative genes.

Thus, once coinheritance is established, differences in the polynucleotide and the corresponding gene between affected and unaffected individuals can be examined. First, visible structural alterations in the chromosomes, such as deletions or translocations, are examined in chromosome spreads or by PCR. If no structural alterations exist, the presence of point mutations are ascertained. Mutations observed in some or all affected individuals, but not in normal individuals, indicates that the mutation may cause the disease. However, complete sequencing of the polypeptide and the corresponding gene from several normal individuals is required to distinguish the mutation from a polymorphism. If a new polymorphism is identified, this polymorphic polypeptide can be used for further linkage analysis.

Furthermore, increased or decreased expression of the gene in affected individuals as compared to unaffected individuals can be assessed using polynucleotides of the present invention. Any of these alterations (altered expression, chromosomal rearrangement, or mutation) can be used as a diagnostic or prognostic marker.

In addition to the foregoing, a polynucleotide can be used to control gene expression through triple helix formation or antisense DNA or RNA. Both methods rely on binding of the polynucleotide to DNA or RNA. For these techniques, preferred polynucleotides are usually 20 to 40 bases in length and complementary to either the region of the gene involved in transcription (triple helix—see Lee et al., Nucl. Acids Res. 6:3073 (1979); Cooney et al., Science 241:456 (1988); and Dervan et al., Science 251:1360 (1991) ) or to the mRNA itself (antisense—Okano, J. Neurochem. 56:560 (1991); Oligodeoxy-nucleotides as Antisense Inhibitors of Gene Expression, CRC Press, Boca Raton, Fla. (1988).) Triple helix formation optimally results in a shut-off of RNA transcription from DNA, while antisense RNA hybridization blocks translation of an mRNA molecule into polypeptide. Both techniques are effective in model systems, and the information disclosed herein can be used to design antisense or triple helix polynucleotides in an effort to treat disease.

Polynucleotides of the present invention are also useful in gene therapy. One goal of gene therapy is to insert a normal gene into an organism having a defective gene, in an effort to correct the genetic defect. The polynucleotides disclosed in the present invention offer a means of targeting such genetic defects in a highly accurate manner. Another goal is to insert a new gene that was not present in the host genome, thereby producing a new trait in the host cell.

The polynucleotides are also useful for identifying individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identifying personnel. This method does not suffer from the current limitations of "Dog Tags" which can be lost, switched, or stolen, making positive identification difficult. The polynucleotides of the present invention can be used as additional DNA markers for RFLP.

The polynucleotides of the present invention can also be used as an alternative to RFLP, by determining the actual base-by-base DNA sequence of selected portions of an individual's genome. These sequences can be used to prepare PCR primers for amplifying and isolating such selected DNA, which can then be sequenced. Using this technique, individuals can be identified because each individual will have a unique set of DNA sequences. Once an unique ID database is established for an individual, positive identification of that individual, living or dead, can be made from extremely small tissue samples.

Forensic biology also benefits from using DNA-based identification techniques as disclosed herein. DNA sequences taken from very small biological samples such as tissues, e.g., hair or skin, or body fluids, e.g., blood, saliva, semen, etc., can be amplified using PCR. In one prior art technique, gene sequences amplified from polymorphic loci, such as DQa class II HLA gene, are used in forensic biology to identify individuals. (Erlich, H., PCR Technology, Freeman and Co. (1992).) Once these specific polymorphic loci are amplified, they are digested with one or more restriction enzymes, yielding an identifying set of bands on a Southern blot probed with DNA corresponding to the DQa class II HLA gene. Similarly, polynucleotides of the present invention can be used as polymorphic markers for forensic purposes.

There is also a need for reagents capable of identifying the source of a particular tissue. Such need arises, for example, in forensics when presented with tissue of unknown origin. Appropriate reagents can comprise, for example, DNA probes or primers specific to particular tissue prepared from the sequences of the present invention. Panels of such reagents can identify tissue by species and/or by organ type. In a similar fashion, these reagents can be used to screen tissue cultures for contamination.

In the very least, the polynucleotides of the present invention can be used as molecular weight markers on Southern gels, as diagnostic probes for the presence of a specific mRNA in a particular cell type, as a probe to "subtract-out" known sequences in the process of discovering novel polynucleotides, for selecting and making oligomers for attachment to a "gene chip" or other support, to raise anti-DNA antibodies using DNA immunization techniques, and as an antigen to elicit an immune response.

Uses of the Polypeptides

Each of the polypeptides identified herein can be used in numerous ways. The following description should be considered exemplary and utilizes known techniques.

A polypeptide of the present invention can be used to assay protein levels in a biological sample using antibody-based techniques. For example, protein expression in tissues can be studied with classical immunohistological methods. (Jalkanen, M., et al., J. Cell. Biol. 101:976–985 (1985); Jalkanen, M., et al., J. Cell. Biol. 105:3087–3096 (1987).) Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase, and radioisotopes, such as iodine (125I, 121I), carbon (14C), sulfur (35S), tritium (3H), indium (112In), and technetium (99mTc), and fluorescent labels, such as fluorescein and rhodamine, and biotin.

In addition to assaying secreted protein levels in a biological sample, proteins can also be detected in vivo by imaging. Antibody labels or markers for in vivo imaging of protein include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which may be incorporated into the antibody by labeling of nutrients for the relevant hybridoma.

A protein-specific antibody or antibody fragment which has been labeled with an appropriate detectable imaging moiety, such as a radioisotope (for example, 131I, 112In, 99 mTc), a radio-opaque substance, or a material detectable by nuclear magnetic resonance, is introduced (for example, parenterally, subcutaneously, or intraperitoneally) into the mammal. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of 99 mTc. The labeled antibody or antibody fragment will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982).)

Thus, the invention provides a diagnostic method of a disorder, which involves (a) assaying the expression of a polypeptide of the present invention in cells or body fluid of an individual; (b) comparing the level of gene expression with a standard gene expression level, whereby an increase or decrease in the assayed polypeptide gene expression level compared to the standard expression level is indicative of a disorder.

Moreover, polypeptides of the present invention can be used to treat disease. For example, patients can be administered a polypeptide of the present invention in an effort to replace absent or decreased levels of the polypeptide (e.g., insulin), to supplement absent or decreased levels of a different polypeptide (e.g., hemoglobin S for hemoglobin B), to inhibit the activity of a polypeptide (e.g., an oncogene), to activate the activity of a polypeptide (e.g., by binding to a receptor), to reduce the activity of a membrane bound receptor by competing with it for free ligand (e.g., soluble TNF receptors used in reducing inflammation), or to bring about a desired response (e.g., blood vessel growth).

Similarly, antibodies directed to a polypeptide of the present invention can also be used to treat disease. For example, administration of an antibody directed to a polypeptide of the present invention can bind and reduce overproduction of the polypeptide. Similarly, administration of an antibody can activate the polypeptide, such as by binding to a polypeptide bound to a membrane (receptor).

At the very least, the polypeptides of the present invention can be used as molecular weight markers on SDS-PAGE gels or on molecular sieve gel filtration columns using methods well known to those of skill in the art. Polypeptides can also be used to raise antibodies, which in turn are used to measure protein expression from a recombinant cell, as a way of assessing transformation of the host cell. Moreover, the polypeptides of the present invention can be used to test the following biological activities.

Biological Activities

The polynucleotides and polypeptides of the present invention can be used in assays to test for one or more biological activities. If these polynucleotides and polypeptides do exhibit activity in a particular assay, it is likely that these molecules may be involved in the diseases associated with the biological activity. Thus, the polynucleotides and polypeptides could be used to treat the associated disease.

Immune Activity

A polypeptide or polynucleotide of the present invention may be useful in treating deficiencies or disorders of the immune system, by activating or inhibiting the proliferation, differentiation, or mobilization (chemotaxis) of immune cells. Immune cells develop through a process called hematopoiesis, producing myeloid (platelets, red blood cells, neutrophils, and macrophages) and lymphoid (B and T lymphocytes) cells from pluripotent stem cells. The etiology of these immune deficiencies or disorders may be genetic, somatic, such as cancer or some autoimmune disorders, acquired (e.g., by chemotherapy or toxins), or infectious. Moreover, a polynucleotide or polypeptide of the present invention can be used as a marker or detector of a particular immune system disease or disorder.

A polynucleotide or polypeptide of the present invention may be useful in treating or detecting deficiencies or disorders of hematopoietic cells. A polypeptide or polynucleotide of the present invention could be used to increase differentiation and proliferation of hematopoietic cells, including the pluripotent stem cells, in an effort to treat those disorders associated with a decrease in certain (or many) types hematopoietic cells. Examples of immunologic deficiency syndromes include, but are not limited to: blood protein disorders (e.g. agammaglobulinemia, dysgammaglobulinemia), ataxia telangiectasia, common variable immunodeficiency, Digeorge Syndrome, HIV infection, HTLV-BLV infection, leukocyte adhesion deficiency syndrome, lymphopenia, phagocyte bactericidal dysfunction, severe combined immunodeficiency (SCIDs), Wiskott-Aldrich Disorder, anemia, thrombocytopenia, or hemoglobinuria.

Moreover, a polypeptide or polynucleotide of the present invention could also be used to modulate hemostatic (the stopping of bleeding) or thrombolytic activity (clot formation). For example, by increasing hemostatic or thrombolytic activity, a polynucleotide or polypeptide of the present invention could be used to treat blood coagulation disorders (e.g., afibrinogenemia, factor deficiencies), blood platelet disorders (e.g. thrombocytopenia), or wounds resulting from trauma, surgery, or other causes. Alternatively, a polynucleotide or polypeptide of the present invention that can decrease hemostatic or thrombolytic activity could be used to inhibit or dissolve clotting. These molecules could be important in the treatment of heart attacks (infarction), strokes, or scarring.

A polynucleotide or polypeptide of the present invention may also be useful in treating or detecting autoimmune disorders. Many autoimmune disorders result from inappropriate recognition of self as foreign material by immune cells. This inappropriate recognition results in an immune response leading to the destruction of the host tissue. Therefore, the administration of a polypeptide or polynucleotide of the present invention that inhibits an immune response, particularly the proliferation, differentiation, or chemotaxis of T-cells, may be an effective therapy in preventing autoimmune disorders.

Examples of autoimmune disorders that can be treated or detected by the present invention include, but are not limited to: Addison's Disease, hemolytic anemia, antiphospholipid syndrome, rheumatoid arthritis, dermatitis, allergic encephalomyelitis, glomerulonephritis, Goodpasture's Syndrome, Graves' Disease, Multiple Sclerosis, Myasthenia Gravis, Neuritis, Ophthalmia, Bullous Pemphigoid, Pemphigus, Polyendocrinopathies, Purpura, Reiter's Disease, Stiff-Man Syndrome, Autoimmune Thyroiditis, Systemic Lupus Erythematosus, Autoimmune Pulmonary Inflammation, Guillain-Barre Syndrome, insulin dependent diabetes mellitis, and autoimmune inflammatory eye disease.

Similarly, allergic reactions and conditions, such as asthma (particularly allergic asthma) or other respiratory problems, may also be treated by a polypeptide or polynucleotide of the present invention. Moreover, these molecules can be used to treat anaphylaxis, hypersensitivity to an antigenic molecule, or blood group incompatibility.

A polynucleotide or polypeptide of the present invention may also be used to treat and/or prevent organ rejection or graft-versus-host disease (GVHD). Organ rejection occurs by host immune cell destruction of the transplanted tissue through an immune response. Similarly, an immune response is also involved in GVHD, but, in this case, the foreign transplanted immune cells destroy the host tissues. The administration of a polypeptide or polynucleotide of the present invention that inhibits an immune response, particularly the proliferation, differentiation, or chemotaxis of T-cells, may be an effective therapy in preventing organ rejection or GVHD.

Similarly, a polypeptide or polynucleotide of the present invention may also be used to modulate inflammation. For example, the polypeptide or polynucleotide may inhibit the proliferation and differentiation of cells involved in an inflammatory response. These molecules can be used to treat inflammatory conditions, both chronic and acute conditions, including inflammation associated with infection (e.g., septic shock, sepsis, or systemic inflammatory response syndrome (SIRS)), ischemia-reperfusion injury, endotoxin lethality, arthritis, complement-mediated hyperacute rejection, nephritis, cytokine or chemokine induced lung injury, inflammatory bowel disease, Crohn's disease, or resulting from over production of cytokines (e.g., TNF or IL-1.)

Hyperproliferative Disorders

A polypeptide or polynucleotide can be used to treat or detect hyperproliferative disorders, including neoplasms. A polypeptide or polynucleotide of the present invention may inhibit the proliferation of the disorder through direct or indirect interactions. Alternatively, a polypeptide or polynucleotide of the present invention may proliferate other cells which can inhibit the hyperproliferative disorder.

For example, by increasing an immune response, particularly increasing antigenic qualities of the hyperproliferative disorder or by proliferating, differentiating, or mobilizing T-cells, hyperproliferative disorders can be treated. This immune response may be increased by either enhancing an existing immune response, or by initiating a new immune response. Alternatively, decreasing an immune response may also be a method of treating hyperproliferative disorders, such as a chemotherapeutic agent.

Examples of hyperproliferative disorders that can be treated or detected by a polynucleotide or polypeptide of the present invention include, but are not limited to neoplasms located in the: abdomen, bone, breast, digestive system, liver, pancreas, peritoneum, endocrine glands (adrenal, parathyroid, pituitary, testicles, ovary, thymus, thyroid), eye, head and neck, nervous (central and peripheral), lymphatic system, pelvic, skin, soft tissue, spleen, thoracic, and urogenital.

Similarly, other hyperproliferative disorders can also be treated or detected by a polynucleotide or polypeptide of the present invention. Examples of such hyperproliferative disorders include, but are not limited to: hypergammaglobulinemia, lymphoproliferative disorders, paraproteinemias, purpura, sarcoidosis, Sezary Syndrome, Waldenstron's Macroglobulinemia, Gaucher's Disease, histiocytosis, and any other hyperproliferative disease, besides neoplasia, located in an organ system listed above.

Infectious Disease

A polypeptide or polynucleotide of the present invention can be used to treat or detect infectious agents. For example, by increasing the immune response, particularly increasing the proliferation and differentiation of B and/or T cells, infectious diseases may be treated. The immune response may be increased by either enhancing an existing immune response, or by initiating a new immune response. Alternatively, the polypeptide or polynucleotide of the present invention may also directly inhibit the infectious agent, without necessarily eliciting an immune response.

Viruses are one example of an infectious agent that can cause disease or symptoms that can be treated or detected by a polynucleotide or polypeptide of the present invention. Examples of viruses, include, but are not limited to the following DNA and RNA viral families: Arbovirus, Adenoviridae, Arenaviridae, Arterivirus, Birnaviridae, Bunyaviridae, Caliciviridae, Circoviridae, Coronaviridae, Flaviviridae, Hepadnaviridae (Hepatitis), Herpesviridae (such as, Cytomegalovirus, Herpes Simplex, Herpes Zoster), Mononegavirus (e.g., Paramyxoviridae, Morbillivirus, Rhabdoviridae), Orthomyxoviridae (e.g., Influenza), Papovaviridae, Parvoviridae, Picornaviridae, Poxviridae (such as Smallpox or Vaccinia), Reoviridae (e.g., Rotavirus), Retroviridae (HTLV-I, HTLV-II, Lentivirus), and Togaviridae (e.g., Rubivirus). Viruses falling within these families can cause a variety of diseases or symptoms, including, but not limited to: arthritis, bronchiollitis, encephalitis, eye infections (e.g., conjunctivitis, keratitis), chronic fatigue syndrome, hepatitis (A, B, C, E, Chronic Active, Delta), meningitis, opportunistic infections (e.g., AIDS), pneumonia, Burkitt's Lymphoma, chickenpox, hemorrhagic fever, Measles, Mumps, Parainfluenza, Rabies, the common cold, Polio, leukemia, Rubella, sexually transmitted diseases, skin diseases (e.g., Kaposi's, warts), and viremia. A polypeptide or polynucleotide of the present invention can be used to treat or detect any of these symptoms or diseases.

Similarly, bacterial or fungal agents that can cause disease or symptoms and that can be treated or detected by a polynucleotide or polypeptide of the present invention include, but not limited to, the following Gram-Negative and Gram-positive bacterial families and fungi: Actinomycetales (e.g., Corynebacterium, Mycobacterium, Norcardia), Aspergillosis, Bacillaceae (e.g., Anthrax, Clostridium), Bacteroidaceae, Blastomycosis, Bordetella, Borrelia, Brucellosis, Candidiasis, Campylobacter, Coccidioidomycosis, Cryptococcosis, Dermatocycoses, Enterobacteriaceae (Klebsiella, Salmonella, Serratia, Yersinia), Erysipelothrix, Helicobacter, Legionellosis, Leptospirosis, Listeria, Mycoplasmatales, Neisseriaceae (e.g., Acinetobacter, Gonorrhea, Menigococcal), Pasteurellacea Infections (e.g., Actinobacillus, Heamophilus, Pasteurella), Pseudomonas, Rickettsiaceae, Chlamydiaceae, Syphilis, and Staphylococcal. These bacterial or fungal families can cause the following diseases or symptoms, including, but not limited to: bacteremia, endocarditis, eye infections (conjunctivitis, tuberculosis, uveitis), gingivitis, opportunistic infections (e.g., AIDS related infections), paronychia, prosthesis-related infections, Reiter's Disease, respiratory tract infections, such as Whooping Cough or Empyema, sepsis, Lyme Disease, Cat-Scratch Disease, Dysentery, Paratyphoid Fever, food poisoning, Typhoid, pneumonia; Gonorrhea, meningitis, Chlamydia, Syphilis, Diphtheria, Leprosy, Paratuberculosis, Tuberculosis, Lupus, Botulism, gangrene, tetanus, impetigo, Rheumatic Fever, Scarlet Fever, sexually transmitted diseases, skin diseases (e.g., cellulitis, dermatocycoses), toxemia, urinary tract infections, wound infections. A polypeptide or polynucleotide of the present invention can be used to treat or detect any of these symptoms or diseases.

Moreover, parasitic agents causing disease or symptoms that can be treated or detected by a polynucleotide or polypeptide of the present invention include, but not limited to, the following families: Amebiasis, Babesiosis, Coccidiosis, Cryptosporidiosis, Dientamoebiasis, Dourine, Ectoparasitic, Giardiasis, Helminthiasis, Leishmaniasis, Theileriasis, Toxoplasmosis, Trypanosomiasis, and Trichomonas. These parasites can cause a variety of diseases or symptoms, including, but not limited to: Scabies, Trombiculiasis, eye infections, intestinal disease (e.g., dysentery, giardiasis), liver disease, lung disease, opportunistic infections (e.g., AIDS related), Malaria, pregnancy complications, and toxoplasmosis. A polypeptide or polynucleotide of the present invention can be used to treat or detect any of these symptoms or diseases.

Preferably, treatment using a polypeptide or polynucleotide of the present invention could either be by administering an effective amount of a polypeptide to the patient, or by removing cells from the patient, supplying the cells with a polynucleotide of the present invention, and returning the engineered cells to the patient (ex vivo therapy). Moreover, the polypeptide or polynucleotide of the present invention can be used as an antigen in a vaccine to raise an immune response against infectious disease.

Regeneration

A polynucleotide or polypeptide of the present invention can be used to differentiate, proliferate, and attract cells, leading to the regeneration of tissues. (See, Science 276:59–87 (1997).) The regeneration of tissues could be used to repair, replace, or protect tissue damaged by congenital defects, trauma (wounds, bums, incisions, or ulcers), age, disease (e.g. osteoporosis, osteocarthritis, periodontal disease, liver failure), surgery, including cosmetic plastic surgery, fibrosis, reperfusion injury, or systemic cytokine damage.

Tissues that could be regenerated using the present invention include organs (e.g., pancreas, liver, intestine, kidney, skin, endothelium), muscle (smooth, skeletal or cardiac), vascular (including vascular endothelium), nervous, hematopoietic, and skeletal (bone, cartilage, tendon, and ligament) tissue. Preferably, regeneration occurs without or decreased scarring. Regeneration also may include angiogenesis.

Moreover, a polynucleotide or polypeptide of the present invention may increase regeneration of tissues difficult to heal. For example, increased tendon/ligament regeneration would quicken recovery time after damage. A polynucleotide or polypeptide of the present invention could also be used prophylactically in an effort to avoid damage. Specific diseases that could be treated include of tendinitis, carpal tunnel syndrome, and other tendon or ligament defects. A further example of tissue regeneration of non-healing wounds includes pressure ulcers, ulcers associated with vascular insufficiency, surgical, and traumatic wounds.

Similarly, nerve and brain tissue could also be regenerated by using a polynucleotide or polypeptide of the present invention to proliferate and differentiate nerve cells. Diseases that could be treated using this method include central and peripheral nervous system diseases, neuropathies, or mechanical and traumatic disorders (e.g., spinal cord disorders, head trauma, cerebrovascular disease, and stoke). Specifically, diseases associated with peripheral nerve injuries, peripheral neuropathy (e.g., resulting from chemotherapy or other medical therapies), localized neuropathies, and central nervous system diseases (e.g., Alzheimer's disease, Parkinson's disease, Huntington's disease, amyotrophic lateral sclerosis, and Shy-Drager syndrome), could all be treated using the polynucleotide or polypeptide of the present invention.

Chemotaxis

A polynucleotide or polypeptide of the present invention may have chemotaxis activity. A chemotaxic molecule attracts or mobilizes cells (e.g., monocytes, fibroblasts, neutrophils, T-cells, mast cells, eosinophils, epithelial and/or endothelial cells) to a particular site in the body, such as inflammation, infection, or site of hyperproliferation. The mobilized cells can then fight off and/or heal the particular trauma or abnormality.

A polynucleotide or polypeptide of the present invention may increase chemotaxic activity of particular cells. These chemotactic molecules can then be used to treat inflammation, infection, hyperproliferative disorders, or any immune system disorder by increasing the number of cells targeted to a particular location in the body. For example, chemotaxic molecules can be used to treat wounds and other trauma to tissues by attracting immune cells to the injured location. Chemotactic molecules of the present invention can also attract fibroblasts, which can be used to treat wounds.

It is also contemplated that a polynucleotide or polypeptide of the present invention may inhibit chemotactic activity. These molecules could also be used to treat disorders. Thus, a polynucleotide or polypeptide of the present invention could be used as an inhibitor of chemotaxis.

Binding Activity

A polypeptide of the present invention may be used to screen for molecules that bind to the polypeptide or for molecules to which the polypeptide binds. The binding of the polypeptide and the molecule may activate (agonist), increase, inhibit (antagonist), or decrease activity of the polypeptide or the molecule bound. Examples of such molecules include antibodies, oligonucleotides, proteins (e.g., receptors), or small molecules.

Preferably, the molecule is closely related to the natural ligand of the polypeptide, e.g., a fragment of the ligand, or a natural substrate, a ligand, a structural or functional mimetic. (See, Coligan et al., Current Protocols in Immunology 1(2):Chapter 5 (1991).) Similarly, the molecule can be closely related to the natural receptor to which the polypeptide binds, or at least, a fragment of the receptor capable of being bound by the polypeptide (e.g., active site). In either case, the molecule can be rationally designed using known techniques.

Preferably, the screening for these molecules involves producing appropriate cells which express the polypeptide, either as a secreted protein or on the cell membrane. Preferred cells include cells from mammals, yeast, Drosophila, or E. coli. Cells expressing the polypeptide (or cell membrane containing the expressed polypeptide) are then preferably contacted with a test compound potentially containing the molecule to observe binding, stimulation, or inhibition of activity of either the polypeptide or the molecule.

The assay may simply test binding of a candidate compound to the polypeptide, wherein binding is detected by a label, or in an assay involving competition with a labeled competitor. Further, the assay may test whether the candidate compound results in a signal generated by binding to the polypeptide.

Alternatively, the assay can be carried out using cell-free preparations, polypeptide/molecule affixed to a solid support, chemical libraries, or natural product mixtures. The assay may also simply comprise the steps of mixing a candidate compound with a solution containing a polypeptide, measuring polypeptide/molecule activity or binding, and comparing the polypeptide/molecule activity or binding to a standard.

Preferably, an ELISA assay can measure polypeptide level or activity in a sample (e.g., biological sample) using a monoclonal or polyclonal antibody. The antibody can measure polypeptide level or activity by either binding, directly or indirectly, to the polypeptide or by competing with the polypeptide for a substrate.

All of these above assays can be used as diagnostic or prognostic markers. The molecules discovered using these assays can be used to treat disease or to bring about a particular result in a patient (e.g., blood vessel growth) by activating or inhibiting the polypeptide/molecule. Moreover, the assays can discover agents which may inhibit or enhance the production of the polypeptide from suitably manipulated cells or tissues.

Therefore, the invention includes a method of identifying compounds which bind to a polypeptide of the invention comprising the steps of: (a) incubating a candidate binding compound with a polypeptide of the invention; and (b) determining if binding has occurred. Moreover, the invention includes a method of identifying agonists/antagonists comprising the steps of: (a) incubating a candidate compound with a polypeptide of the invention, (b) assaying a biological activity, and (b) determining if a biological activity of the polypeptide has been altered.

Other Activities

A polypeptide or polynucleotide of the present invention may also increase or decrease the differentiation or proliferation of embryonic stem cells, besides, as discussed above, hematopoietic lineage.

A polypeptide or polynucleotide of the present invention may also be used to modulate mammalian characteristics, such as body height, weight, hair color, eye color, skin, percentage of adipose tissue, pigmentation, size, and shape (e.g., cosmetic surgery). Similarly, a polypeptide or polynucleotide of the present invention may be used to modulate mammalian metabolism affecting catabolism, anabolism, processing, utilization, and storage of energy.

A polypeptide or polynucleotide of the present invention may be used to change a mammal's mental state or physical state by influencing biorhythms, caricadic rhythms, depression (including depressive disorders), tendency for violence, tolerance for pain, reproductive capabilities (preferably by Activin or Inhibin-like activity), hormonal or endocrine levels, appetite, libido, memory, stress, or other cognitive qualities.

A polypeptide or polynucleotide of the present invention may also be used as a food additive or preservative, such as to increase or decrease storage capabilities, fat content, lipid, protein, carbohydrate, vitamins, minerals, cofactors or other nutritional components.

Other Preferred Embodiments

Other preferred embodiments of the claimed invention include an isolated nucleic acid molecule comprising a nucleotide sequence which is at least 95% identical to a sequence of at least about 50 contiguous nucleotides in the nucleotide sequence of SEQ ID NO:X wherein X is any integer as defined in FIGS. 1A–G.

Also preferred is a nucleic acid molecule wherein said sequence of contiguous nucleotides is included in the nucleotide sequence of SEQ ID NO:X in the range of positions beginning with the nucleotide at about the position of the 5' Nucleotide of the Clone Sequence and ending with the nucleotide at about the position of the 3' Nucleotide of the Clone Sequence as defined for SEQ ID NO:X in FIGS. 1A–G.

Also preferred is a nucleic acid molecule wherein said sequence of contiguous nucleotides is included in the nucleotide sequence of SEQ ID NO:X in the range of positions beginning with the nucleotide at about the position of the 5' Nucleotide of the Start Codon and ending with the nucleotide at about the position of the 3' Nucleotide of the Clone Sequence as defined for SEQ ID NO:X in FIGS. 1A–G.

Similarly preferred is a nucleic acid molecule wherein said sequence of contiguous nucleotides is included in the nucleotide sequence of SEQ ID NO:X in the range of positions beginning with the nucleotide at about the position of the 5' Nucleotide of the First Amino Acid of the Signal Peptide and ending with the nucleotide at about the position of the 3' Nucleotide of the Clone Sequence as defined for SEQ ID NO:X in FIGS. 1A–G.

Also preferred is an isolated nucleic acid molecule comprising a nucleotide sequence which is at least 95% identical to a sequence of at least about 150 contiguous nucleotides in the nucleotide sequence of SEQ ID NO:X.

Further preferred is an isolated nucleic acid molecule comprising a nucleotide sequence which is at least 95% identical to a sequence of at least about 500 contiguous nucleotides in the nucleotide sequence of SEQ ID NO:X.

A further preferred embodiment is a nucleic acid molecule comprising a nucleotide sequence which is at least 95% identical to the nucleotide sequence of SEQ ID NO:X beginning with the nucleotide at about the position of the 5' Nucleotide of the First Amino Acid of the Signal Peptide and ending with the nucleotide at about the position of the 3' Nucleotide of the Clone Sequence as defined for SEQ ID NO:X in FIGS. 1A–G.

A further preferred embodiment is an isolated nucleic acid molecule comprising a nucleotide sequence which is at least 95% identical to the complete nucleotide sequence of SEQ ID NO:X.

Also preferred is an isolated nucleic acid molecule which hybridizes under stringent hybridization conditions to a nucleic acid molecule, wherein said nucleic acid molecule which hybridizes does not hybridize under stringent hybridization conditions to a nucleic acid molecule having a nucleotide sequence consisting of only A residues or of only T residues.

Also preferred is a composition of matter comprising a DNA molecule which comprises a human cDNA clone identified by a cDNA Clone Identifier in FIGS. 1A–G, which DNA molecule is contained in the material deposited with the American Type Culture Collection and given the ATCC Deposit Number shown in FIGS. 1A–G for said cDNA Clone Identifier.

Also preferred is an isolated nucleic acid molecule comprising a nucleotide sequence which is at least 95% identical to a sequence of at least 50 contiguous nucleotides in the nucleotide sequence of a human cDNA clone identified by a cDNA Clone Identifier in FIGS. 1A–G, which DNA molecule is contained in the deposit given the ATCC Deposit Number shown in FIGS. 1A–G.

Also preferred is an isolated nucleic acid molecule, wherein said sequence of at least 50 contiguous nucleotides is included in the nucleotide sequence of the complete open reading frame sequence encoded by said human cDNA clone.

Also preferred is an isolated nucleic acid molecule comprising a nucleotide sequence which is at least 95% identical to sequence of at least 150 contiguous nucleotides in the nucleotide sequence encoded by said human cDNA clone.

A further preferred embodiment is an isolated nucleic acid molecule comprising a nucleotide sequence which is at least 95% identical to sequence of at least 500 contiguous nucleotides in the nucleotide sequence encoded by said human cDNA clone.

A further preferred embodiment is an isolated nucleic acid molecule comprising a nucleotide sequence which is at least 95% identical to the complete nucleotide sequence encoded by said human cDNA clone.

A further preferred embodiment is a method for detecting in a biological sample a nucleic acid molecule comprising a nucleotide sequence which is at least 95% identical to a sequence of at least 50 contiguous nucleotides in a sequence selected from the group consisting of: a nucleotide sequence of SEQ ID NO:X wherein X is any integer as defined in FIGS. 1A–G; and a nucleotide sequence encoded by a human cDNA clone identified by a cDNA Clone Identifier in FIGS. 1A–G and contained in the deposit with the ATCC Deposit Number shown for said cDNA clone in FIGS. 1A–G; which method comprises a step of comparing a nucleotide sequence of at least one nucleic acid molecule in said sample with a sequence selected from said group and determining whether the sequence of said nucleic acid molecule in said sample is at least 95% identical to said selected sequence.

Also preferred is the above method wherein said step of comparing sequences comprises determining the extent of nucleic acid hybridization between nucleic acid molecules in said sample and a nucleic acid molecule comprising said sequence selected from said group. Similarly, also preferred is the above method wherein said step of comparing sequences is performed by comparing the nucleotide sequence determined from a nucleic acid molecule in said sample with said sequence selected from said group. The nucleic acid molecules can comprise DNA molecules or RNA molecules.

A further preferred embodiment is a method for identifying the species, tissue or cell type of a biological sample which method comprises a step of detecting nucleic acid molecules in said sample, if any, comprising a nucleotide sequence that is at least 95% identical to a sequence of at least 50 contiguous nucleotides in a sequence selected from the group consisting of: a nucleotide sequence of SEQ ID NO:X wherein X is any integer as defined in FIGS. 1A–G; and a nucleotide sequence encoded by a human cDNA clone identified by a cDNA Clone Identifier in FIGS. 1A–G and contained in the deposit with the ATCC Deposit Number shown for said cDNA clone in FIGS. 1A–G.

The method for identifying the species, tissue or cell type of a biological sample can comprise a step of detecting nucleic acid molecules comprising a nucleotide sequence in a panel of at least two nucleotide sequences, wherein at least one sequence in said panel is at least 95% identical to a sequence of at least 50 contiguous nucleotides in a sequence selected from said group.

Also preferred is a method for diagnosing in a subject a pathological condition associated with abnormal structure or expression of a gene encoding a secreted protein identified in FIGS. 1A–G, which method comprises a step of detecting in a biological sample obtained from said subject nucleic acid molecules, if any, comprising a nucleotide sequence that is at least 95% identical to a sequence of at least 50 contiguous nucleotides in a sequence selected from the group consisting of: a nucleotide sequence of SEQ ID NO:X wherein X is any integer as defined in FIGS. 1A–G; and a nucleotide sequence encoded by a human cDNA clone identified by a cDNA Clone Identifier in FIGS. 1A–G and contained in the deposit with the ATCC Deposit Number shown for said cDNA clone in FIGS. 1A–G.

The method for diagnosing a pathological condition can comprise a step of detecting nucleic acid molecules comprising a nucleotide sequence in a panel of at least two nucleotide sequences, wherein at least one sequence in said panel is at least 95% identical to a sequence of at least 50 contiguous nucleotides in a sequence selected from said group.

Also preferred is a composition of matter comprising isolated nucleic acid molecules wherein the nucleotide sequences of said nucleic acid molecules comprise a panel of at least two nucleotide sequences, wherein at least one sequence in said panel is at least 95% identical to a sequence of at least 50 contiguous nucleotides in a sequence selected from the group consisting of: a nucleotide sequence of SEQ ID NO:X wherein X is any integer as defined in FIGS. 1A–G; and a nucleotide sequence encoded by a human cDNA clone identified by a cDNA Clone Identifier in FIGS. 1A–G and contained in the deposit with the ATCC Deposit Number shown for said cDNA clone in FIGS. 1A–G. The nucleic acid molecules can comprise DNA molecules or RNA molecules.

Also preferred is an isolated polypeptide comprising an amino acid sequence at least 90% identical to a sequence of at least about 10 contiguous amino acids in the amino acid sequence of SEQ ID NO:Y wherein Y is any integer as defined in FIGS. 1A–G.

Also preferred is a polypeptide, wherein said sequence of continguous amino acids is included in the amino acid sequence of SEQ ID NO:Y in the range of positions beginning with the residue at about the position of the First Amino Acid of the Secreted Portion and ending with the residue at about the Last Amino Acid of the Open Reading Frame as set forth for SEQ ID NO:Y in FIGS. 1A–G.

Also preferred is an isolated polypeptide comprising an amino acid sequence at least 95% identical to a sequence of at least about 30 contiguous amino acids in the amino acid sequence of SEQ ID NO:Y.

Further preferred is an isolated polypeptide comprising an amino acid sequence at least 95% identical to a sequence of at least about 100 contiguous amino acids in the amino acid sequence of SEQ ID NO:Y.

Further preferred is an isolated polypeptide comprising an amino acid sequence at least 95% identical to the complete amino acid sequence of SEQ ID NO:Y.

Further preferred is an isolated polypeptide comprising an amino acid sequence at least 90% identical to a sequence of at least about 10 contiguous amino acids in the complete amino acid sequence of a secreted protein encoded by a human cDNA clone identified by a cDNA Clone Identifier in FIGS. 1A–G and contained in the deposit with the ATCC Deposit Number shown for said cDNA clone in FIGS. 1A–G.

Also preferred is a polypeptide wherein said sequence of contiguous amino acids is included in the amino acid sequence of a secreted portion of the secreted protein encoded by a human cDNA clone identified by a cDNA Clone Identifier in FIGS. 1A–G and contained in the deposit with the ATCC Deposit Number shown for said cDNA clone in FIGS. 1A–G.

Also preferred is an isolated polypeptide comprising an amino acid sequence at least 95% identical to a sequence of at least about 30 contiguous amino acids in the amino acid sequence of the secreted portion of the protein encoded by a human cDNA clone identified by a cDNA Clone Identifier in FIGS. 1A–G and contained in the deposit with the ATCC Deposit Number shown for said cDNA clone in FIGS. 1A–G.

Also preferred is an isolated polypeptide comprising an amino acid sequence at least 95% identical to the amino acid sequence of the secreted portion of the protein encoded by a human cDNA clone identified by a cDNA Clone Identifier in FIGS. 1A–G and contained in the deposit with the ATCC Deposit Number shown for said cDNA clone in FIGS. 1A–G.

Further preferred is an isolated antibody which binds specifically to a polypeptide comprising an amino acid sequence that is at least 90% identical to a sequence of at least 10 contiguous amino acids in a sequence selected from the group consisting of: an amino acid sequence of SEQ ID NO:Y wherein Y is any integer as defined in FIGS. 1A–G; and a complete amino acid sequence of a protein encoded by a human cDNA clone identified by a cDNA Clone Identifier in FIGS. 1A–G and contained in the deposit with the ATCC Deposit Number shown for said cDNA clone in FIGS. 1A–G.

Further preferred is a method for detecting in a biological sample a polypeptide comprising an amino acid sequence which is at least 90% identical to a sequence of at least 10 contiguous amino acids in a sequence selected from the group consisting of: an amino acid sequence of SEQ ID NO:Y wherein Y is any integer as defined in FIGS. 1A–G; and a complete amino acid sequence of a protein encoded by a human cDNA clone identified by a cDNA Clone Identifier in FIGS. 1A–G and contained in the deposit with the ATCC Deposit Number shown for said cDNA clone in FIGS. 1A–G; which method comprises a step of comparing an amino acid sequence of at least one polypeptide molecule in said sample with a sequence selected from said group and determining whether the sequence of said polypeptide molecule in said sample is at least 90% identical to said sequence of at least 10 contiguous amino acids.

Also preferred is the above method wherein said step of comparing an amino acid sequence of at least one polypeptide molecule in said sample with a sequence selected from said group comprises determining the extent of specific binding of polypeptides in said sample to an antibody which binds specifically to a polypeptide comprising an amino acid sequence that is at least 90% identical to a sequence of at least 10 contiguous amino acids in a sequence selected from the group consisting of: an amino acid sequence of SEQ ID NO:Y wherein Y is any integer as defined in FIGS. 1A–G; and a complete amino acid sequence of a protein encoded by a human cDNA clone identified by a cDNA Clone Identifier in FIGS. 1A–G and contained in the deposit with the ATCC Deposit Number shown for said cDNA clone in FIGS. 1A–G.

Also preferred is the above method wherein said step of comparing sequences is performed by comparing the amino acid sequence determined from a polypeptide molecule in said sample with said sequence selected from said group.

Also preferred is a method for identifying the species, tissue or cell type of a biological sample which method comprises a step of detecting polypeptide molecules in said sample, if any, comprising an amino acid sequence that is at least 90% identical to a sequence of at least 10 contiguous amino acids in a sequence selected from the group consisting of: an amino acid sequence of SEQ ID NO:Y wherein Y is any integer as defined in FIGS. 1A–G; and a complete amino acid sequence of a secreted protein encoded by a human cDNA clone identified by a cDNA Clone Identifier in FIGS. 1A–G and contained in the deposit with the ATCC Deposit Number shown for said cDNA clone in FIGS. 1A–G.

Also preferred is the above method for identifying the species, tissue or cell type of a biological sample, which method comprises a step of detecting polypeptide molecules comprising an amino acid sequence in a panel of at least two amino acid sequences, wherein at least one sequence in said panel is at least 90% identical to a sequence of at least 10 contiguous amino acids in a sequence selected from the above group.

Also preferred is a method for diagnosing in a subject a pathological condition associated with abnormal structure or expression of a gene encoding a secreted protein identified in FIGS. 1A–G, which method comprises a step of detecting in a biological sample obtained from said subject polypeptide molecules comprising an amino acid sequence in a panel of at least two amino acid sequences, wherein at least one sequence in said panel is at least 90% identical to a sequence of at least 10 contiguous amino acids in a sequence selected from the group consisting of: an amino acid sequence of SEQ ID NO:Y wherein Y is any integer as defined in FIGS. 1A–G; and a complete amino acid sequence of a secreted protein encoded by a human cDNA clone identified by a cDNA Clone Identifier in FIGS. 1A–G and contained in the deposit with the ATCC Deposit Number shown for said cDNA clone in FIGS. 1A–G.

In any of these methods, the step of detecting said polypeptide molecules includes using an antibody.

Also preferred is an isolated nucleic acid molecule comprising a nucleotide sequence which is at least 95% identical to a nucleotide sequence encoding a polypeptide wherein said polypeptide comprises an amino acid sequence that is at least 90% identical to a sequence of at least 10 contiguous amino acids in a sequence selected from the group consisting of: an amino acid sequence of SEQ ID NO:Y wherein Y is any integer as defined in FIGS. 1A–G; and a complete amino acid sequence of a secreted protein encoded by a human cDNA clone identified by a cDNA Clone Identifier in FIG. 1A–G and contained in the deposit with the ATCC Deposit Number shown for said cDNA clone in FIGS. 1A–G.

Also preferred is an isolated nucleic acid molecule, wherein said nucleotide sequence encoding a polypeptide has been optimized for expression of said polypeptide in a prokaryotic host.

Also preferred is an isolated nucleic acid molecule, wherein said polypeptide comprises an amino acid sequence selected from the group consisting of: an amino acid sequence of SEQ ID NO:Y wherein Y is any integer as defined in FIGS. 1A–G; and a complete amino acid sequence of a secreted protein encoded by a human cDNA clone identified by a cDNA Clone Identifier in FIGS. 1A–G and contained in the deposit with the ATCC Deposit Number shown for said cDNA clone in FIGS. 1A–G.

Further preferred is a method of making a recombinant vector comprising inserting any of the above isolated nucleic acid molecule into a vector. Also preferred is the recombinant vector produced by this method. Also preferred is a method of making a recombinant host cell comprising introducing the vector into a host cell, as well as the recombinant host cell produced by this method.

Also preferred is a method of making an isolated polypeptide comprising culturing this recombinant host cell under conditions such that said polypeptide is expressed and recovering said polypeptide. Also preferred is this method of making an isolated polypeptide, wherein said recombinant host cell is a eukaryotic cell and said polypeptide is a secreted portion of a human secreted protein comprising an amino acid sequence selected from the group consisting of: an amino acid sequence of SEQ ID NO:Y beginning with the residue at the position of the First Amino Acid of the Secreted Portion of SEQ ID NO:Y wherein Y is an integer set forth in FIGS. 1A–G and said position of the First Amino Acid of the Secreted Portion of SEQ ID NO:Y is defined in FIGS. 1A–G; and an amino acid sequence of a secreted portion of a protein encoded by a human cDNA clone identified by a cDNA Clone Identifier in FIGS. 1A–G and contained in the deposit with the ATCC Deposit Number shown for said cDNA clone in FIGS. 1A–G. The isolated polypeptide produced by this method is also preferred.

Also preferred is a method of treatment of an individual in need of an increased level of a secreted protein activity, which method comprises administering to such an individual a pharmaceutical composition comprising an amount of an isolated polypeptide, polynucleotide, or antibody of the claimed invention effective to increase the level of said protein activity in said individual.

Having generally described the invention, the same will be more readily understood by reference to the following examples, which are provided by way of illustration and are not intended as limiting.

EXAMPLES

Example 1

Isolation of a Selected cDNA Clone From the Deposited Sample

Each cDNA clone in a cited ATCC deposit is contained in a plasmid vector. Table 1 identifies the vectors used to construct the cDNA library from which each clone was isolated. In many cases, the vector used to construct the library is a phage vector from which a plasmid has been excised. The table immediately below correlates the related plasmid for each phage vector used in constructing the cDNA library. For example, where a particular clone is identified in Table 1 as being isolated in the vector "Lambda Zap," the corresponding deposited clone is in "pBluescript."

| Vector Used to Construct Library | Corresponding Deposited Plasmid |
| --- | --- |
| Lambda Zap | pBluescript (pBS) |
| Uni-Zap XR | pBluescript (pBS) |
| Zap Express | pBK |
| lafmid BA | plafmid BA |
| pSport1 | pSport1 |
| pCMVSport 2.0 | pCMVSport 2.0 |

-continued

| Vector Used to Construct Library | Corresponding Deposited Plasmid |
| --- | --- |
| pCMVSport 3.0 | pCMVSport 3.0 |
| pCR ®2.1 | pCR ®2.1 |

Vectors Lambda Zap (U.S. Pat. Nos. 5,128,256 and 5,286,636), Uni-Zap XR (U.S. Pat. Nos. 5,128,256 and 5,286,636), Zap Express (U.S. Pat. Nos. 5,128,256 and 5,286,636), pBluescript (pBS) (Short, J. M. et al., Nucleic Acids Res. 16:7583–7600 (1988); Alting-Mees, M. A. and Short, J. M., Nucleic Acids Res. 17:9494 (1989)) and pBK (Alting-Mees, M. A. et al., Strategies 5:58–61 (1992)) are commercially available from Stratagene Cloning Systems, Inc., 11011 N. Torrey Pines Road, La Jolla, Calif., 92037. pBS contains an ampicillin resistance gene and pBK contains a neomycin resistance gene. Both can be transformed into E. coli strain XL-1 Blue, also available from Stratagene. pBS comes in 4 forms SK+, SK–, KS+ and KS. The S and K refers to the orientation of the polylinker to the T7 and T3 primer sequences which flank the polylinker region ("S" is for SacI and "K" is for KpnI which are the first sites on each respective end of the linker). "+" or "−" refer to the orientation of the fI origin of replication ("ori"), such that in one orientation, single stranded rescue initiated from the fI ori generates sense strand DNA and in the other, antisense.

Vectors pSport1, pCMVSport 2.0 and pCMVSport 3.0, were obtained from Life Technologies, Inc., P. O. Box 6009, Gaithersburg, Md. 20897. All Sport vectors contain an ampicillin resistance gene and may be transformed into E. coli strain DH10B, also available from Life Technologies. (See, for instance, Gruber, C. E., et al., Focus 15:59 (1993).) Vector lafmid BA (Bento Soares, Columbia University, NY) contains an ampicillin resistance gene and can be transformed into E. coli strain XL-1 Blue. Vector pCR®2.1, which is available from Invitrogen, 1600 Faraday Avenue, Carlsbad, Calif. 92008, contains an ampicillin resistance gene and may be transformed into E. coli strain DH10B, available from Life Technologies. (See, for instance, Clark, J. M., Nuc. Acids Res. 16:9677–9686 (1988) and Mead, D. et al., Bio/Technology 9: (1991).) Preferably, a polynucleotide of the present invention does not comprise the phage vector sequences identified for the particular clone in Table 1, as well as the corresponding plasmid vector sequences designated above.

The deposited material in the sample assigned the ATCC Deposit Number cited in Table 1 for any given cDNA clone also may contain one or more additional plasmids, each comprising a cDNA clone different from that given clone. Thus, deposits sharing the same ATCC Deposit Number contain at least a plasmid for each cDNA clone identified in Table 1. Typically, each ATCC deposit sample cited in Table 1 comprises a mixture of approximately equal amounts (by weight) of about 50 plasmid DNAs, each containing a different cDNA clone; but such a deposit sample may include plasmids for more or less than 50 cDNA clones, up to about 500 cDNA clones.

Two approaches can be used to isolate a particular clone from the deposited sample of plasmid DNAs cited for that clone in Table 1. First, a plasmid is directly isolated by screening the clones using a polynucleotide probe corresponding to SEQ ID NO:X.

Particularly, a specific polynucleotide with 30–40 nucleotides is synthesized using an Applied Biosystems DNA synthesizer according to the sequence reported. The oligonucleotide is labeled, for instance, with $^{32}P$-γ-ATP using T4 polynucleotide kinase and purified according to routine methods. (E.g., Maniatis et al., Molecular Cloning: A Laboratory Manual, Cold Spring Harbor Press, Cold Spring, N.Y. (1982).) The plasmid mixture is transformed into a suitable host, as indicated above (such as XL-1 Blue (Stratagene)) using techniques known to those of skill in the art, such as those provided by the vector supplier or in related publications or patents cited above. The transformants are plated on 1.5% agar plates (containing the appropriate selection agent, e.g., ampicillin) to a density of about 150 transformants (colonies) per plate. These plates are screened using Nylon membranes according to routine methods for bacterial colony screening (e.g., Sambrook et al., Molecular Cloning: A Laboratory Manual, 2nd Edit., (1989), Cold Spring Harbor Laboratory Press, pages 1.93 to 1.104), or other techniques known to those of skill in the art.

Alternatively, two primers of 17–20 nucleotides derived from both ends of the SEQ ID NO:X (i.e., within the region of SEQ ID NO:X bounded by the 5' NT and the 3' NT of the clone defined in Table 1) are synthesized and used to amplify the desired cDNA using the deposited cDNA plasmid as a template. The polymerase chain reaction is carried out under routine conditions, for instance, in 25 $\mu$l of reaction mixture with 0.5 ug of the above cDNA template. A convenient reaction mixture is 1.5–5 mM $MgCl_2$, 0.01% (w/v) gelatin, 20 $\mu$M each of dATP, dCTP, dGTP, dTTP, 25 pmol of each primer and 0.25 Unit of Taq polymerase. Thirty five cycles of PCR (denaturation at 94° C. for 1 min; annealing at 55° C. for 1 min; elongation at 72° C. for 1 min) are performed with a Perkin-Elmer Cetus automated thermal cycler. The amplified product is analyzed by agarose gel electrophoresis and the DNA band with expected molecular weight is excised and purified. The PCR product is verified to be the selected sequence by subcloning and sequencing the DNA product.

Several methods are available for the identification of the 5' or 3' non-coding portions of a gene which may not be present in the deposited clone. These methods include but are not limited to, filter probing, clone enrichment using specific probes, and protocols similar or identical to 5' and 3' "RACE" protocols which are well known in the art. For instance, a method similar to 5' RACE is available for generating the missing 5' end of a desired full-length transcript. (Fromont-Racine et al., Nucleic Acids Res. 21(7):1683–1684 (1993).)

Briefly, a specific RNA oligonucleotide is ligated to the 5' ends of a population of RNA presumably containing full-length gene RNA transcripts. A primer set containing a primer specific to the ligated RNA oligonucleotide and a primer specific to a known sequence of the gene of interest is used to PCR amplify the 5' portion of the desired full-length gene. This amplified product may then be sequenced and used to generate the full length gene.

This above method starts with total RNA isolated from the desired source, although poly-A+ RNA can be used. The RNA preparation can then be treated with phosphatase if necessary to eliminate 5' phosphate groups on degraded or damaged RNA which may interfere with the later RNA ligase step. The phosphatase should then be inactivated and the RNA treated with tobacco acid pyrophosphatase in order to remove the cap structure present at the 5' ends of messenger RNAs. This reaction leaves a 5' phosphate group at the 5' end of the cap cleaved RNA which can then be ligated to an RNA oligonucleotide using T4 RNA ligase.

This modified RNA preparation is used as a template for first strand cDNA synthesis using a gene specific oligonucleotide. The first strand synthesis reaction is used as a template for PCR amplification of the desired 5' end using a primer specific to the ligated RNA oligonucleotide and a primer specific to the known sequence of the gene of interest. The resultant product is then sequenced and analyzed to confirm that the 5' end sequence belongs to the desired gene.

Example 2
Isolation of Genomic Clones Corresponding to a Polynucleotide

A human genomic P1 library (Genomic Systems, Inc.) is screened by PCR using primers selected for the cDNA sequence corresponding to SEQ ID NO:X., according to the method described in Example 1. (See also, Sambrook.)

Example 3
Tissue Distribution of Polypeptide

Tissue distribution of mRNA expression of polynucleotides of the present invention is determined using protocols for Northern blot analysis, described by, among others, Sambrook et al. For example, a cDNA probe produced by the method described in Example 1 is labeled with $p^{32}$ using the rediprime™ DNA labeling system (Amersham Life Science), according to manufacturer's instructions. After labeling, the probe is purified using CHROMA SPIN-100™ column (Clontech Laboratories, Inc.), according to manufacturer's protocol number PT1200-1. The purified labeled probe is then used to examine various human tissues for mRNA expression.

Multiple Tissue Northern (MTN) blots containing various human tissues (H) or human immune system tissues (IM) (Clontech) are examined with the labeled probe using ExpressHyb™ hybridization solution (Clontech) according to manufacturer's protocol number PT1190-1. Following hybridization and washing, the blots are mounted and exposed to film at −70° C. overnight, and the films developed according to standard procedures.

Example 4
Chromosomal Mapping of the Polynucleotides

An oligonucleotide primer set is designed according to the sequence at the 5' end of SEQ ID NO:X. This primer preferably spans about 100 nucleotides. This primer set is then used in a polymerase chain reaction under the following set of conditions : 30 seconds, 95° C.; 1 minute, 56° C.; 1 minute, 70° C. This cycle is repeated 32 times followed by one 5 minute cycle at 70° C. Human, mouse, and hamster DNA is used as template in addition to a somatic cell hybrid panel containing individual chromosomes or chromosome fragments (Bios, Inc). The reactions is analyzed on either 8% polyacrylamide gels or 3.5% agarose gels. Chromosome mapping is determined by the presence of an approximately 100 bp PCR fragment in the particular somatic cell hybrid.

Example 5
Bacterial Expression of a Polypeptide

A polynucleotide encoding a polypeptide of the present invention is amplified using PCR oligonucleotide primers corresponding to the 5' and 3' ends of the DNA sequence, as outlined in Example 1, to synthesize insertion fragments. The primers used to amplify the cDNA insert should preferably contain restriction sites, such as BamHI and XbaI, at the 5' end of the primers in order to clone the amplified product into the expression vector. For example, BamHI and XbaI correspond to the restriction enzyme sites on the bacterial expression vector pQE-9. (Qiagen, Inc., Chatsworth, Calif.). This plasmid vector encodes antibiotic resistance ($Amp^r$), a bacterial origin of replication (ori), an IPTG-regulatable promoter/operator (P/O), a ribosome binding site (RBS), a 6-histidine tag (6-His), and restriction enzyme cloning sites.

The pQE-9 vector is digested with BamHI and XbaI and the amplified fragment is ligated into the pQE-9 vector maintaining the reading frame initiated at the bacterial RBS. The ligation mixture is then used to transform the E. coli strain M15/rep4 (Qiagen, Inc.) which contains multiple copies of the plasmid pREP4, which expresses the lacI repressor and also confers kanamycin resistance (Kan'). Transformants are identified by their ability to grow on LB plates and ampicillin/kanamycin resistant colonies are selected. Plasmid DNA is isolated and confirmed by restriction analysis.

Clones containing the desired constructs are grown overnight (O/N) in liquid culture in LB media supplemented with both Amp (100 ug/ml) and Kan (25 ug/ml). The O/N culture is used to inoculate a large culture at a ratio of 1:100 to 1:250. The cells are grown to an optical density 600 (O.D.$^{600}$) of between 0.4 and 0.6. IPTG (Isopropyl-B-D-thiogalacto pyranoside) is then added to a final concentration of 1 mM. IPTG induces by inactivating the lacI repressor, clearing the P/O leading to increased gene expression.

Cells are grown for an extra 3 to 4 hours. Cells are then harvested by centrifugation (20 mins at 6000×g). The cell pellet is solubilized in the chaotropic agent 6 Molar Guanidine HCl by stirring for 3–4 hours at 4° C. The cell debris is removed by centrifugation, and the supernatant containing the polypeptide is loaded onto a nickel-nitrilo-tri-acetic acid ("Ni-NTA") affinity resin column (available from QIAGEN, Inc., supra). Proteins with a 6×His tag bind to the Ni-NTA resin with high affinity and can be purified in a simple one-step procedure (for details see: The QIAexpressionist (1995) QIAGEN, Inc., supra).

Briefly, the supernatant is loaded onto the column in 6 M guanidine-HCl, pH 8, the column is first washed with 10 volumes of 6 M guanidine-HCl, pH 8, then washed with 10 volumes of 6 M guanidine-HCl pH 6, and finally the polypeptide is eluted with 6 M guanidine-HCl, pH 5.

The purified protein is then renatured by dialyzing it against phosphate-buffered saline (PBS) or 50 mM Na-acetate, pH 6 buffer plus 200 mM NaCl. Alternatively, the protein can be successfully refolded while immobilized on the Ni-NTA column. The recommended conditions are as follows: renature using a linear 6M-1M urea gradient in 500 mM NaCl, 20% glycerol, 20 mM Tris/HCl pH 7.4, containing protease inhibitors. The renaturation should be performed over a period of 1.5 hours or more. After renaturation the proteins are eluted by the addition of 250 mM immidazole. Immidazole is removed by a final dialyzing step against PBS or 50 mM sodium acetate pH 6 buffer plus 200 mM NaCl. The purified protein is stored at 4° C. or frozen at −80° C.

In addition to the above expression vector, the present invention further includes an expression vector comprising phage operator and promoter elements operatively linked to a polynucleotide of the present invention, called pHE4a. (ATCC Accession Number 209645, deposited on Feb. 25, 1998.) This vector contains: 1) a neomycinphosphotransferase gene as a selection marker, 2) an E. coli origin of replication, 3) a T5 phage promoter sequence, 4) two lac operator sequences, 5) a Shine-Delgarno sequence, and 6) the lactose operon repressor gene (lacIq). The origin of replication (oriC) is derived from pUC19 (LTI, Gaithersburg, Md.). The promoter sequence and operator sequences are made synthetically.

DNA can be inserted into the pHEa by restricting the vector with NdeI and XbaI, BamHI, XhoI, or Asp718, running the restricted product on a gel, and isolating the larger fragment (the stuffer fragment should be about 310 base pairs). The DNA insert is generated according to the PCR protocol described in Example 1, using PCR primers having restriction sites for NdeI (5' primer) and XbaI, BamHI, XhoI, or Asp718 (3' primer). The PCR insert is gel purified and restricted with compatible enzymes. The insert and vector are ligated according to standard protocols.

The engineered vector could easily be substituted in the above protocol to express protein in a bacterial system.

Example 6

Purification of a Polypeptide from an Inclusion Body

The following alternative method can be used to purify a polypeptide expressed in E coli when it is present in the form of inclusion bodies. Unless otherwise specified, all of the following steps are conducted at 4–10° C.

Upon completion of the production phase of the E. coli fermentation, the cell culture is cooled to 4–10° C. and the cells harvested by continuous centrifugation at 15,000 rpm (Heraeus Sepatech). On the basis of the expected yield of protein per unit weight of cell paste and the amount of purified protein required, an appropriate amount of cell paste, by weight, is suspended in a buffer solution containing 100 mM Tris, 50 mM EDTA, pH 7.4. The cells are dispersed to a homogeneous suspension using a high shear mixer.

The cells are then lysed by passing the solution through a microfluidizer (Microfuidics, Corp. or APV Gaulin, Inc.) twice at 4000–6000 psi. The homogenate is then mixed with NaCl solution to a final concentration of 0.5 M NaCl, followed by centrifugation at 7000×g for 15 min. The resultant pellet is washed again using 0.5M NaCl, 100 mM Tris, 50 mM EDTA, pH 7.4.

The resulting washed inclusion bodies are solubilized with 1.5 M guanidine hydrochloride (GuHCl) for 2–4 hours. After 7000×g centrifugation for 15 min., the pellet is discarded and the polypeptide containing supernatant is incubated at 4° C. overnight to allow further GuHCl extraction.

Following high speed centrifugation (30,000×g) to remove insoluble particles, the GuHCl solubilized protein is refolded by quickly mixing the GuHCl extract with 20 volumes of buffer containing 50 mM sodium, pH 4.5, 150 mM NaCl, 2 mM EDTA by vigorous stirring. The refolded diluted protein solution is kept at 4° C. without mixing for 12 hours prior to further purification steps.

To clarify the refolded polypeptide solution, a previously prepared tangential filtration unit equipped with 0.16 μm membrane filter with appropriate surface area (e.g., Filtron), equilibrated with 40 mM sodium acetate, pH 6.0 is employed. The filtered sample is loaded onto a cation exchange resin (e.g., Poros HS-50, Perseptive Biosystems). The column is washed with 40 mM sodium acetate, pH 6.0 and eluted with 250 mM, 500 mM, 1000 mM, and 1500 mM NaCl in the same buffer, in a stepwise manner. The absorbance at 280 nm of the effluent is continuously monitored. Fractions are collected and further analyzed by SDS-PAGE.

Fractions containing the polypeptide are then pooled and mixed with 4 volumes of water. The diluted sample is then loaded onto a previously prepared set of tandem columns of strong anion (Poros HQ-50, Perseptive Biosystems) and weak anion (Poros CM-20, Perseptive Biosystems) exchange resins. The columns are equilibrated with 40 mM sodium acetate, pH 6.0. Both columns are washed with 40 mM sodium acetate, pH 6.0, 200 mM NaCl. The CM-20 column is then eluted using a 10 column volume linear gradient ranging from 0.2 M NaCl, 50 mM sodium acetate, pH 6.0 to 1.0 M NaCl, 50 mM sodium acetate, pH 6.5. Fractions are collected under constant $A_{280}$ monitoring of the effluent. Fractions containing the polypeptide (determined, for instance, by 16% SDS-PAGE) are then pooled.

The resultant polypeptide should exhibit greater than 95% purity after the above refolding and purification steps. No major contaminant bands should be observed from Commassie blue stained 16% SDS-PAGE gel when 5 µg of purified protein is loaded. The purified protein can also be tested for endotoxin/LPS contamination, and typically the LPS content is less than 0.1 ng/ml according to LAL assays.

Example 7
Cloning and Expression of a Polypeptide in a Baculovirus Expression System In this example, the plasmid shuttle vector pA2 is used to insert a polynucleotide into a baculovirus to express a polypeptide. This expression vector contains the strong polyhedrin promoter of the Autographa californica nuclear polyhedrosis virus (AcMNPV) followed by convenient restriction sites such as BamHI, Xba I and Asp718. The polyadenylation site of the simian virus 40 ("SV40") is used for efficient polyadenylation. For easy selection of recombinant virus, the plasmid contains the beta-galactosidase gene from E. coli under control of a weak Drosophila promoter in the same orientation, followed by the polyadenylation signal of the polyhedrin gene. The inserted genes are flanked on both sides by viral sequences for cell-mediated homologous recombination with wild-type viral DNA to generate a viable virus that express the cloned polynucleotide.

Many other baculovirus vectors can be used in place of the vector above, such as pAc373, pVL941, and pAcIM1, as one skilled in the art would readily appreciate, as long as the construct provides appropriately located signals for transcription, translation, secretion and the like, including a signal peptide and an in-frame AUG as required. Such vectors are described, for instance, in Luckow et al., Virology 170:31–39 (1989).

Specifically, the cDNA sequence contained in the deposited clone, including the AUG initiation codon and the naturally associated leader sequence identified in Table 1, is amplified using the PCR protocol described in Example 1. If the naturally occurring signal sequence is used to produce the secreted protein, the pA2 vector does not need a second signal peptide. Alternatively, the vector can be modified (pA2 GP) to include a baculovirus leader sequence, using the standard methods described in Summers et al., "A Manual of Methods for Baculovirus Vectors and Insect Cell Culture Procedures," Texas Agricultural Experimental Station Bulletin No. 1555 (1987).

The amplified fragment is isolated from a 1% agarose gel using a commercially available kit ("Geneclean," BIO 101 Inc., La Jolla, Calif.). The fragment then is digested with appropriate restriction enzymes and again purified on a 1% agarose gel.

The plasmid is digested with the corresponding restriction enzymes and optionally, can be dephosphorylated using calf intestinal phosphatase, using routine procedures known in the art. The DNA is then isolated from a 1% agarose gel using a commercially available kit ("Geneclean" BIO 101 Inc., La Jolla, Calif.).

The fragment and the dephosphorylated plasmid are ligated together with T4 DNA ligase. E. coli HB101 or other suitable E. coli hosts such as XL-1 Blue (Stratagene Cloning Systems, La Jolla, Calif.) cells are transformed with the ligation mixture and spread on culture plates. Bacteria containing the plasmid are identified by digesting DNA from individual colonies and analyzing the digestion product by gel electrophoresis. The sequence of the cloned fragment is confirmed by DNA sequencing.

Five µg of a plasmid containing the polynucleotide is co-transfected with 1.0 µg of a commercially available linearized baculovirus DNA ("BaculoGold™ baculovirus DNA", Pharmingen, San Diego, Calif.), using the lipofection method described by Felgner et al., Proc. Natl. Acad. Sci. USA 84:7413–7417 (1987). One µg of BaculoGold™ virus DNA and 5 µg of the plasmid are mixed in a sterile well of a microtiter plate containing 50 µl of serum-free Grace's medium (Life Technologies Inc., Gaithersburg, Md. ). Afterwards, 10 µl Lipofectin plus 90 µl Grace's medium are added, mixed and incubated for 15 minutes at room temperature. Then the transfection mixture is added drop-wise to Sf9 insect cells (ATCC CRL 1711) seeded in a 35 mm tissue culture plate with 1 ml Grace's medium without serum. The plate is then incubated for 5 hours at 27° C. The transfection solution is then removed from the plate and 1 ml of Grace's insect medium supplemented with 10% fetal calf serum is added. Cultivation is then continued at 27° C. for four days.

After four days the supernatant is collected and a plaque assay is performed, as described by Summers and Smith, supra. An agarose gel with "Blue Gal" (Life Technologies Inc., Gaithersburg) is used to allow easy identification and isolation of gal-expressing clones, which produce blue-stained plaques. (A detailed description of a "plaque assay" of this type can also be found in the user's guide for insect cell culture and baculovirology distributed by Life Technologies Inc., Gaithersburg, page 9–10.) After appropriate incubation, blue stained plaques are picked with the tip of a micropipettor (e.g., Eppendorf). The agar containing the recombinant viruses is then resuspended in a microcentrifuge tube containing 200 µl of Grace's medium and the suspension containing the recombinant baculovirus is used to infect Sf9 cells seeded in 35 mm dishes. Four days later the supernatants of these culture dishes are harvested and then they are stored at 4° C.

To verify the expression of the polypeptide, Sf9 cells are grown in Grace's medium supplemented with 10% heat-inactivated FBS. The cells are infected with the recombinant baculovirus containing the polynucleotide at a multiplicity of infection ("MOI") of about 2. If radiolabeled proteins are desired, 6 hours later the medium is removed and is replaced with SF900 II medium minus methionine and cysteine (available from Life Technologies Inc., Rockville, Md.). After 42 hours, 5 µCi of $^{53}$S-methionine and 5 µCi $^{35}$S-cysteine (available from Amersham) are added. The cells are further incubated for 16 hours and then are harvested by centrifugation. The proteins in the supernatant as well as the intracellular proteins are analyzed by SDS-PAGE followed by autoradiography (if radiolabeled).

Microsequencing of the amino acid sequence of the amino terminus of purified protein may be used to determine the amino terminal sequence of the produced protein.

Example 8
Expression of a Polypeptide in Mammalian Cells

The polypeptide of the present invention can be expressed in a mammalian cell. A typical mammalian expression vector contains a promoter element, which mediates the initiation of transcription of mRNA, a protein coding sequence, and signals required for the termination of transcription and polyadenylation of the transcript. Additional elements include enhancers, Kozak sequences and intervening sequences flanked by donor and acceptor sites for RNA splicing. Highly efficient transcription is achieved with the early and late promoters from SV40, the long terminal repeats (LTRs) from Retroviruses, e.g., RSV, HTLVI, HIVI and the early promoter of the cytomegalovirus (CMV). However, cellular elements can also be used (e.g., the human actin promoter).

Suitable expression vectors for use in practicing the present invention include, for example, vectors such as pSVL and pMSG (Pharmacia, Uppsala, Sweden), pRSVcat (ATCC 37152), pSV2dhfr (ATCC 37146), pBC12MI (ATCC 67109), pCMVSport 2.0, and pCMVSport 3.0. Mammalian host cells that could be used include, human Hela, 293, H9 and Jurkat cells, mouse NIH3T3 and C127 cells, Cos 1, Cos 7 and CV1, quail QC1-3 cells, mouse L cells and Chinese hamster ovary (CHO) cells.

Alternatively, the polypeptide can be expressed in stable cell lines containing the polynucleotide integrated into a chromosome. The co-transfection with a selectable marker such as dhfr, gpt, neomycin, hygromycin allows the identification and isolation of the transfected cells.

The transfected gene can also be amplified to express large amounts of the encoded protein. The DHFR (dihydrofolate reductase) marker is useful in developing cell lines that carry several hundred or even several thousand copies of the gene of interest. (See, e.g., Alt, F. W., et al., J. Biol. Chem. 253:1357–1370 (1978); Hamlin, J. L. and Ma, C., Biochem. et Biophys. Acta, 1097:107–143 (1990); Page, M. J. and Sydenham, M. A., Biotechnology 9:64–68 (1991).) Another useful selection marker is the enzyme glutamine synthase (GS) (Murphy et al., Biochem J. 227:277–279 (1991); Bebbington et al., Bio/Technology 10: 169–175 (1992). Using these markers, the mammalian cells are grown in selective medium and the cells with the highest resistance are selected. These cell lines contain the amplified gene(s) integrated into a chromosome. Chinese hamster ovary (CHO) and NSO cells are often used for the production of proteins.

Derivatives of the plasmid pSV2-dhfr (ATCC Accession No. 37146), the expression vectors pC4 (ATCC Accession No. 209646) and pC6 (ATCC Accession No.209647) contain the strong promoter (LTR) of the Rous Sarcoma Virus (Cullen et al., Molecular and Cellular Biology, 438–447 (March, 1985)) plus a fragment of the CMV-enhancer (Boshart et al., Cell 41:521–530 (1985).) Multiple cloning sites, e.g., with the restriction enzyme cleavage sites BamHI, XbaI and Asp718, facilitate the cloning of the gene of interest. The vectors also contain the 3' intron, the polyadenylation and termination signal of the rat preproinsulin gene, and the mouse DHFR gene under control of the SV40 early promoter.

Specifically, the plasmid pC6, for example, is digested with appropriate restriction enzymes and then dephosphorylated using calf intestinal phosphates by procedures known in the art. The vector is then isolated from a 1% agarose gel.

A polynucleotide of the present invention is amplified according to the protocol outlined in Example 1. If the naturally occurring signal sequence is used to produce the secreted protein, the vector does not need a second signal peptide. Alternatively, if the naturally occurring signal sequence is not used, the vector can be modified to include a heterologous signal sequence. (See, e.g., WO 96/34891.) The amplified fragment is isolated from a 1% agarose gel using a commercially available kit ("Geneclean," BIO 101 Inc., La Jolla, Calif.). The fragment then is digested with appropriate restriction enzymes and again purified on a 1% agarose gel.

The amplified fragment is then digested with the same restriction enzyme and purified on a 1% agarose gel. The isolated fragment and the dephosphorylated vector are then ligated with T4 DNA ligase. E. coli HB101 or XL-1 Blue cells are then transformed and bacteria are identified that contain the fragment inserted into plasmid pC6 using, for instance, restriction enzyme analysis.

Chinese hamster ovary cells lacking an active DHFR gene is used for transfection. Five $\mu$g of the expression plasmid pC6 is cotransfected with 0.5 $\mu$g of the plasmid pSVneo using lipofectin (Felgner et al., supra). The plasmid pSV2-neo contains a dominant selectable marker, the neo gene from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) in alpha minus MEM supplemented with 10, 25, or 50 ng/ml of metothrexate plus 1 mg/mil G418. After about 10–14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 $\mu$M, 2 $\mu$M, 5 $\mu$M, 10 mM, 20 mM). The same procedure is repeated until clones are obtained which grow at a concentration of 100–200 $\mu$M. Expression of the desired gene product is analyzed, for instance, by SDS-PAGE and Western blot or by reversed phase HPLC analysis.

Example 9

Protein Fusions

The polypeptides of the present invention are preferably fused to other proteins. These fusion proteins can be used for a variety of applications. For example, fusion of the present polypeptides to His-tag, HA-tag, protein A, IgG domains, and maltose binding protein facilitates purification. (See Example 5; see also EPA 394,827; Traunecker, et al., Nature 331:84–86 (1988).) Similarly, fusion to IgG-1, IgG-3, and albumin increases the halflife time in vivo. Nuclear localization signals fused to the polypeptides of the present invention can target the protein to a specific subcellular localization, while covalent heterodimer or homodimers can increase or decrease the activity of a fusion protein. Fusion proteins can also create chimeric molecules having more than one function. Finally, fusion proteins can increase solubility and/or stability of the fused protein compared to the non-fused protein. All of the types of fusion proteins described above can be made by modifying the following protocol, which outlines the fusion of a polypeptide to an IgG molecule, or the protocol described in Example 5.

Briefly, the human Fc portion of the IgG molecule can be PCR amplified, using primers that span the 5' and 3' ends of the sequence described below. These primers also should have convenient restriction enzyme sites that will facilitate cloning into an expression vector, preferably a mammalian expression vector.

For example, if pC4 (Accession No. 209646) is used, the human Fc portion can be ligated into the BamHI cloning site. Note that the 3' BamHI site should be destroyed. Next, the vector containing the human Fc portion is re-restricted with BamHI, linearizing the vector, and a polynucleotide of the present invention, isolated by the PCR protocol described in Example 1, is ligated into this BamHI site. Note that the polynucleotide is cloned without a stop codon, otherwise a fusion protein will not be produced.

If the naturally occurring signal sequence is used to produce the secreted protein, pC4 does not need a second signal peptide. Alternatively, if the naturally occurring signal sequence is not used, the vector can be modified to include a heterologous signal sequence. (See, e.g., WO 96/34891.) Human IgG Fc region:
G G G A T C C G G A G C C C A A A T C T T C T G A-
C A A A A C T C A C A C A T G C C C A C C G T G C-

CCAGCACCTGAATTCGAGGGTGCACCGT-
CAGTCTTCCTCTTCCCCCCAAAACCCAAGGACA
CCCTCATGATCTCCCGGACTCCTGAGGT-
CACATGCGTGGTGGTGGACGTAAGCCAC-
GAAGACCCTGAGGTCAAGTTCAACTGG-
TACGTGGACGGCGTGGAGGTGCATAATGCCA
GACAAAGCCGCGGGAGGAGCAGTACAA-
CAGCACGTACCGTGTGGTCAGCGTCCT-
CACCGTCCTGCACCAGGACTGGCT-
GAATGGCAAGGAGTACAAGTGCAAGGTCTCC
AACAAAGCCCTCCCAACCCCCATC-
GAGAAAACCATCTCCAAAGC-
CAAAGGGCAGCCCCGAGAACCACAGGTG-
TACACCCTGCCCCCATCCCGGGATGAGCTGAC
CAAGAACCAGGTCAGCCTGACCTGCCTG-
GTCAAAGGCTTCTATCCAAGCGA-
CATCGCCGTGGAGTGGGAGAG-
CAATGGGCAGCCGGAGAACAACTACAAGACCA
CGCCTCCCGTGCTGGACTCCGACGGCTC-
CTTCTTCCTCTACAGCAAGCTCACCGTG-
GACAAGAGCAGGTGGCAGCAGGG-
GAACGTCTTCTCATGCTCCGTGATGCATGAGG
CTCTGCACAACCACTACACGCAGAA-
GAGCCTCTCCCTGTCTCCGGGTAAAT-
GAGTGCGACGGCCGCGACTCTAGAGGAT (SEQ ID
NO:1)

Example 10
Production of an Antibody from a Polypeptide

The antibodies of the present invention can be prepared by a variety of methods. (See, Current Protocols, Chapter 2.) For example, cells expressing a polypeptide of the present invention is administered to an animal to induce the production of sera containing polyclonal antibodies. In a preferred method, a preparation of the secreted protein is prepared and purified to render it substantially free of natural contaminants. Such a preparation is then introduced into an animal in order to produce polyclonal antisera of greater specific activity.

In the most preferred method, the antibodies of the present invention are monoclonal antibodies (or protein binding fragments thereof). Such monoclonal antibodies can be prepared using hybridoma technology. (Köhler et al., Nature 256:495 (1975); Köhler et al., Eur. J. Immunol. 6:511 (1976); Köhler et al., Eur. J. Immunol. 6:292 (1976); Hammerling et al., in: Monoclonal Antibodies and T-Cell Hybridomas, Elsevier, N.Y., pp. 563–681 (1981).) In general, such procedures involve immunizing an animal (preferably a mouse) with polypeptide or, more preferably, with a secreted polypeptide-expressing cell. Such cells may be cultured in any suitable tissue culture medium; however, it is preferable to culture cells in Earle's modified Eagle's medium supplemented with 10% fetal bovine serum (inactivated at about 56° C.), and supplemented with about 10 g/l of nonessential amino acids, about 1,000 U/mi of penicillin, and about 100 μg/ml of streptomycin.

The splenocytes of such mice are extracted and fused with a suitable myeloma cell line. Any suitable myeloma cell line may be employed in accordance with the present invention; however, it is preferable to employ the parent myeloma cell line (SP2O), available from the ATCC. After fusion, the resulting hybridoma cells are selectively maintained in HAT medium, and then cloned by limiting dilution as described by Wands et al. (Gastroenterology 80:225–232 (1981).) The hybridoma cells obtained through such a selection are then assayed to identify clones which secrete antibodies capable of binding the polypeptide.

Alternatively, additional antibodies capable of binding to the polypeptide can be produced in a two-step procedure using anti-idiotypic antibodies. Such a method makes use of the fact that antibodies are themselves antigens, and therefore, it is possible to obtain an antibody which binds to a second antibody. In accordance with this method, protein specific antibodies are used to immunize an animal, preferably a mouse. The splenocytes of such an animal are then used to produce hybridoma cells, and the hybridoma cells are screened to identify clones which produce an antibody whose ability to bind to the protein-specific antibody can be blocked by the polypeptide. Such antibodies comprise anti-idiotypic antibodies to the protein-specific antibody and can be used to immunize an animal to induce formation of further protein-specific antibodies.

It will be appreciated that Fab and F(ab')2 and other fragments of the antibodies of the present invention may be used according to the methods disclosed herein. Such fragments are typically produced by proteolytic cleavage, using enzymes such as papain (to produce Fab fragments) or pepsin (to produce F(ab')2 fragments). Alternatively, secreted protein-binding fragments can be produced through the application of recombinant DNA technology or through synthetic chemistry.

For in vivo use of antibodies in humans, it may be preferable to use "humanized" chimeric monoclonal antibodies. Such antibodies can be produced using genetic constructs derived from hybridoma cells producing the monoclonal antibodies described above. Methods for producing chimeric antibodies are known in the art. (See, for review, Morrison, Science 229:1202 (1985); Oi et al., Bio-Techniques 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., Nature 312:643 (1984); Neuberger et al., Nature 314:268 (1985).)

Example 11
Production Of Secreted Protein For High-Throughput Screening Assays

The following protocol produces a supernatant containing a polypeptide to be tested. This supernatant can then be used in the Screening Assays described in Examples 13–20.

First, dilute Poly-D-Lysine (644 587 Boehringer-Mannheim) stock solution (1 mg/ml in PBS) 1:20 in PBS (w/o calcium or magnesium 17-516F Biowhittaker) for a working solution of 50 ug/ml. Add 200 ul of this solution to each well (24 well plates) and incubate at RT for 20 minutes. Be sure to distribute the solution over each well (note: a 12-channel pipetter may be used with tips on every other channel). Aspirate off the Poly-D-Lysine solution and rinse with 1 ml PBS (Phosphate Buffered Saline). The PBS should remain in the well until just prior to plating the cells and plates may be poly-lysine coated in advance for up to two weeks.

Plate 293T cells (do not carry cells past P+20) at $2\times10^5$ cells/well in 0.5 ml DMEM(Dulbecco's Modified Eagle Medium)(with 4.5 G/L glucose and L-glutamine (12-604F Biowhittaker))/10% heat inactivated FBS(14-503F Biowhittaker)/1×Penstrep(17-602E Biowhittaker). Let the cells grow overnight.

The next day, mix together in a sterile solution basin: 300 ul Lipofectamine (18324-012 Gibco/BRL) and 5 ml Opti-mem I (31985070 Gibco/BRL)/96-well plate. With a small volume multi-channel pipetter, aliquot approximately 2 ug of an expression vector containing a polynucleotide insert, produced by the methods described in Examples 8 or 9, into an appropriately labeled 96-well round bottom plate. With a multi-channel pipetter, add 50 ul of the Lipofectamine/ Optimem I mixture to each well. Pipette up and down gently to mix. Incubate at RT 15–45 minutes. After about 20 minutes, use a multi-channel pipetter to add 150 ul Optimem I to each well. As a control, one plate of vector DNA lacking an insert should be transfected with each set of transfections.

Preferably, the transfection should be performed by tag-teaming the following tasks. By tag-teaming, hands on time is cut in half, and the cells do not spend too much time on PBS. First, person A aspirates off the media from four 24-well plates of cells, and then person B rinses each well with 0.5–1 ml PBS. Person A then aspirates off PBS rinse, and person B, using a 12-channel pipetter with tips on every other channel, adds the 200 ul of DNA/Lipofectamine/ Optimem I complex to the odd wells first, then to the even wells, to each row on the 24-well plates. Incubate at 37° C. for 6 hours.

While cells are incubating, prepare appropriate media, either 1%BSA in DMEM with 1xpenstrep, or CHO-5 media (116.6 mg/L of CaCl2 (anhyd); 0.00130 mg/L $CuSO_4$-$5H_2O$; 0.050 mg/L of $Fe(NO_3)_3$-$9H_2O$; 0.417 mg/L of $FeSO_4$-$7H_2O$; 311.80 mg/L of Kcl; 28.64 mg/L of $MgCl_2$; 48.84 mg/L of $MgSO_4$; 6995.50 mg/L of NaCl; 2400.0 mg/L of $NaHCO_3$; 62.50 mg/L of $NaH_2PO_4$—$H_2O$; 71.02 mg/L of Na2HPO4; 0.4320 mg/L of $ZnSO_4$-$7H_2O$; 0.002 mg/L of Arachidonic Acid; 1.022 mg/L of Cholesterol; 0.070 mg/L of DL-alpha-Tocopherol-Acetate; 0.0520 mg/L of Linoleic Acid; 0.010 mg/L of Linolenic Acid; 0.010 mg/L of Myristic Acid; 0.010 mg/L of Oleic Acid; 0.010 mg/L of Palmitric Acid; 0.010 mg/L of Palmitic Acid; 100 mg/L of Pluronic F-68; 0.010 mg/L of Stearic Acid; 2.20 mg/L of Tween 80; 4551 mg/L of D-Glucose; 130.85 mg/ml of L- Alanine; 147.50 mg/ml of L-Arginine-HCL; 7.50 mg/ml of L-Asparagine-$H_2O$; 6.65 mg/ml of L-Aspartic Acid; 29.56 mg/ml of L-Cystine-2HCL—$H_2O$; 31.29 mg/ml of L-Cystine-2HCL; 7.35 mg/ml of L-Glutamic Acid; 365.0 mg/ml of L-Glutamine; 18.75 mg/ml of Glycine; 52.48 mg/ml of L-Histidine-HCL-$H_2O$; 106.97 mg/ml of L-Isoleucine; 111.45 mg/ml of L-Leucine; 163.75 mg/ml of L-Lysine HCL; 32.34 mg/ml of L-Methionine; 68.48 mg/ml of L-Phenylalainine; 40.0 mg/ml of L-Proline; 26.25 mg/ml of L-Serine; 101.05 mg/ml of L-Threonine; 19.22 mg/ml of L-Tryptophan; 91.79 mg/mil of L-Tryrosine-2Na-$2H_2O$; 99.65 mg/ml of L-Valine; 0.0035 mg/L of Biotin; 3.24 mg/L of D-Ca Pantothenate; 11.78 mg/L of Choline Chloride; 4.65 mg/L of Folic Acid; 15.60 mg/L of i-Inositol; 3.02 mg/L of Niacinamide; 3.00 mg/L of Pyridoxal HCL; 0.031 mg/L of Pyridoxine HCL; 0.319 mg/L of Riboflavin; 3.17 mg/L of Thiamine HCL; 0.365 mg/L of Thymidine; and 0.680 mg/L of Vitamin $B_{12}$; 25 mM of HEPES Buffer; 2.39 mg/L of Na Hypoxanthine; 0.105 mg/L of Lipoic Acid; 0.081 mg/L of Sodium Putrescine-2HCL; 55.0 mg/L of Sodium Pyruvate; 0.0067 mg/L of Sodium Selenite; 2 uM of Ethanolamine; 0.122 mg/L of Ferric Citrate; 41.70 mg/L of Methyl-B-Cyclodextrin complexed with Linoleic Acid; 33.33 mg/L of Methyl-B-Cyclodextrin complexed with Oleic Acid; and 10 mg/L of Methyl-B-Cyclodextrin complexed with Retinal) with 2 mm glutamine and 1xpenstrep. (BSA (81-068-3 Bayer) 100 gm dissolved in 1 L DMEM for a 10% BSA stock solution). Filter the media and collect 50 ul for endotoxin assay in 15 ml polystyrene conical.

The transfection reaction is terminated, preferably by tag-teaming, at the end of the incubation period. Person A aspirates off the transfection media, while person B adds 1.5 ml appropriate media to each well. Incubate at 37° C. for 45 or 72 hours depending on the media used: 1%BSA for 45 hours or CHO-5 for 72 hours.

On day four, using a 300 ul multichannel pipetter, aliquot 600 ul in one 1 ml deep well plate and the remaining supernatant into a 2 ml deep well. The supernatants from each well can then be used in the assays described in Examples 13–20.

It is specifically understood that when activity is obtained in any of the assays described below using a supernatant, the activity originates from either the polypeptide directly (e.g., as a secreted protein) or by the polypeptide inducing expression of other proteins, which are then secreted into the supernatant. Thus, the invention further provides a method of identifying the protein in the supernatant characterized by an activity in a particular assay.

Example 12

Construction of GAS Reporter Construct

One signal transduction pathway involved in the differentiation and proliferation of cells is called the Jaks-STATs pathway. Activated proteins in the Jaks-STATs pathway bind to gamma activation site "GAS" elements or interferon-sensitive responsive element ("ISRE"), located in the promoter of many genes. The binding of a protein to these elements alter the expression of the associated gene.

GAS and ISRE elements are recognized by a class of transcription factors called Signal Transducers and Activators of Transcription, or "STATs." There are six members of the STATs family. Stat1 and Stat3 are present in many cell types, as is Stat2 (as response to IFN-alpha is widespread). Stat4 is more restricted and is not in many cell types though it has been found in T helper class I, cells after treatment with IL-12. Stat5 was originally called mammary growth factor, but has been found at higher concentrations in other cells including myeloid cells. It can be activated in tissue culture cells by many cytokines.

The STATs are activated to translocate from the cytoplasm to the nucleus upon tyrosine phosphorylation by a set of kinases known as the Janus Kinase ("Jaks") family. Jaks represent a distinct family of soluble tyrosine kinases and include Tyk2, Jak1, Jak2, and Jak3. These kinases display significant sequence similarity and are generally catalytically inactive in resting cells.

The Jaks are activated by a wide range of receptors summarized in the Table below. (Adapted from review by Schidler and Darnell, Ann. Rev. Biochem. 64:621–51 (1995).) A cytokine receptor family, capable of activating Jaks, is divided into two groups: (a) Class 1 includes receptors for IL-2, IL-3, IL-4, IL-6, IL-7, IL-9, IL-11, IL-12, IL-15, Epo, PRL, GH, G-CSF, GM-CSF, LIF, CNTF, and thrombopoietin; and (b) Class 2 includes IFN-a, IFN-g, and IL-10. The Class 1 receptors share a conserved cysteine motif (a set of four conserved cysteines and one tryptophan) and a WSXWS motif (a membrane proxial region encoding Trp-Ser-Xxx-Trp-Ser (SEQ ID NO:2)).

Thus, on binding of a ligand to a receptor, Jaks are activated, which in turn activate STATs, which then translocate and bind to GAS elements. This entire process is encompassed in the Jaks-STATs signal transduction pathway.

Therefore, activation of the Jaks-STATs pathway, reflected by the binding of the GAS or the ISRE element, can be used to indicate proteins involved in the proliferation and differentiation of cells. For example, growth factors and cytokines are known to activate the Jaks-STATs pathway. (See Table below.) Thus, by using GAS elements linked to reporter molecules, activators of the Jaks-STATs pathway can be identified.

| Ligand | tyk2 | Jak1 | Jak2 | Jak3 | STATS | GAS(elements) or ISRE |
|---|---|---|---|---|---|---|
| IFN family | | | | | | |
| IFN-a/B | + | + | – | – | 1,2,3 | ISRE |
| IFN-g | | + | + | – | 1 | GAS (IRF1>Lys6>IFP) |
| Il-10 | + | ? | ? | – | 1,3 | |
| gp130 family | | | | | | |
| IL-6(Pleiotrohic) | + | + | + | ? | 1,3 | GAS (IRF1>Lys6>IFP) |
| Il-11(Pleiotrohic) | ? | + | ? | ? | 1,3 | |
| OnM(Pleiotrohic) | ? | + | + | ? | 1,3 | |
| LIF(Pleiotrohic) | ? | + | + | ? | 1,3 | |
| CNTF(Pleiotrohic) | –/+ | + | + | ? | 1,3 | |
| G-CSF(Pleiotrohic) | ? | + | ? | ? | 1,3 | |
| IL-12(Pleiotrohic) | + | – | + | + | 1,3 | |
| g-C family | | | | | | |
| IL-2 (lymphocytes) | – | + | – | + | 1,3,5 | GAS |
| IL-4 (lymph/myeloid) | – | + | – | + | 6 | GAS (IRF1 = IFP>>Ly6)(IgH) |
| IL-7 (lymphocytes) | – | + | – | + | 5 | GAS |
| IL-9 (lymphocytes) | – | + | – | + | 5 | GAS |
| IL-13 (lymphocyte) | – | + | ? | ? | 6 | GAS |
| IL-15 | ? | + | ? | + | 5 | GAS |
| gp140 family | | | | | | |
| IL-3 (myeloid) | – | – | + | – | 5 | GAS (IRF1>IFP>>Ly6) |
| IL-5 (myeloid) | – | – | + | – | 5 | GAS |
| GM-CSF (myeloid) | – | – | + | – | 5 | GAS |
| Growth hormone family | | | | | | |
| GH | ? | – | + | – | 5 | |
| PRL | ? | +/– | + | – | 1,3,5 | |
| EPO | ? | – | + | – | 5 | GAS(B-CAS>IRF1 = IFP>>Ly6) |
| Receptor Tyrosine Kinases | | | | | | |
| EGF | ? | + | + | – | 1,3 | GAS(IRF1) |
| PDGF | ? | + | + | – | 1,3 | |
| CSF-1 | ? | + | + | – | 1,3 | GAS(not IRF1) |

To construct a synthetic GAS containing promoter element, which is used in the Biological Assays described in Examples 13–14, a PCR based strategy is employed to generate a GAS-SV40 promoter sequence. The 5' primer contains four tandem copies of the GAS binding site found in the IRF1 promoter and previously demonstrated to bind STATs upon induction with a range of cytokines (Rothman et al., Immunity 1:457–468 (1994).), although other GAS or ISRE elements can be used instead. The 5' primer also contains 18 bp of sequence complementary to the SV40 early promoter sequence and is flanked with an XhoI site. The sequence of the 5' primer is: 5':GCGCCTC-GAGATTTCCCCGAAATCTAGATTTC-CCCGAAATGATTTCCCCGAAATGATTTC-CCCGAAATATCTGCCATCTCAATTAG:3' (SEQ ID NO:3)

The downstream primer is complementary to the SV40 promoter and is flanked with a Hind III site: 5':GCG-GCAAGCTTTTGCAAAGCCTAGGC:3' (SEQ ID NO:4)

PCR amplification is performed using the SV40 promoter template present in the B-gal:promoter plasmid obtained from Clontech. The resulting PCR fragment is digested with XhoI/Hind III and subcloned into BLSK2-. (Stratagene.) Sequencing with forward and reverse primers confirms that the insert contains the following sequence: 5': CTCGAGATTTCCCCGAAATCTAGATTCCCCGAA ATGATTTCCCCGAAATGATTTC-CCCGAAATATCTGCCATCTCAATTAGT-CAGCAACCATAGTCCCGCCCCTAACTC-CGCCCATCCCGCCCCTAACTCCGCCCAGTTCCGC CCATTCTCCGCCCCATGGCTGAC-TAATTTTFTTTTTATTTATGCAGAGGC-CGAGGCCGCCTCGGCCTCTGAGCTATTC-CAGAAGTAGTGAGGAGGCTTTGGAGGCCTAGG CTTTTGCAAAAAGCTT:3' (SEQ ID NO:5)

With this GAS promoter element linked to the SV40 promoter, a GAS:SEAP2 reporter construct is next engineered. Here, the reporter molecule is a secreted alkaline phosphatase, or "SEAP." Clearly, however, any reporter molecule can be instead of SEAP, in this or in any of the other Examples. Well known reporter molecules that can be used instead of SEAP include chloramphenicol acetyltransferase (CAT), luciferase, alkaline phosphatase, B-galactosidase, green fluorescent protein (GFP), or any protein detectable by an antibody.

The above sequence confirmed synthetic GAS-SV40 promoter element is subcloned into the pSEAP-Promoter vector obtained from Clontech using HindIII and XhoI, effectively replacing the SV40 promoter with the amplified GAS:SV40 promoter element, to create the GAS-SEAP vector. However, this vector does not contain a neomycin resistance gene, and therefore, is not preferred for mammalian expression systems.

Thus, in order to generate mammalian stable cell lines expressing the GAS-SEAP reporter, the GAS-SEAP cassette is removed from the GAS-SEAP vector using SalI and NotI, and inserted into a backbone vector containing the neomycin resistance gene, such as pGFP-1 (Clontech), using these restriction sites in the multiple cloning site, to create the GAS-SEAP/Neo vector. Once this vector is transfected into mammalian cells, this vector can then be used as a reporter molecule for GAS binding as described in Examples 13–14.

Other constructs can be made using the above description and replacing GAS with a different promoter sequence. For example, construction of reporter molecules containing NFK-B and EGR promoter sequences are described in Examples 15 and 16. However, many other promoters can be substituted using the protocols described in these Examples. For instance, SRE, IL-2, NFAT, or Osteocalcin promoters can be substituted, alone or in combination (e.g., GAS/NF-KB/IEGR, GAS/NF-KB, Il-2/NFAT, or NF-KB/GAS). Similarly, other cell lines can be used to test reporter construct activity, such as HELA (epithelial), HUVEC (endothelial), Reh (B-cell), Saos-2 (osteoblast), HUVAC (aortic), or Cardiomyocyte.

Example 13
High-Throughput Screening Assay for T-cell Activity

The following protocol is used to assess T-cell activity by identifying factors, such as growth factors and cytokines, that may proliferate or differentiate T-cells. T-cell activity is assessed using the GAS/SEAP/Neo construct produced in Example 12. Thus, factors that increase SEAP activity indicate the ability to activate the Jaks-STATS signal transduction pathway. The T-cell used in this assay is Jurkat T-cells (ATCC Accession No. TIB-152), although Molt-3 cells (ATCC Accession No. CRL-1552) and Molt-4 cells (ATCC Accession No. CRL-1582) cells can also be used.

Jurkat T-cells are lymphoblastic CD4+Th1 helper cells. In order to generate stable cell lines, approximately 2 million Jurkat cells are transfected with the GAS-SEAP/neo vector using DMRIE-C (Life Technologies)(transfection procedure described below). The transfected cells are seeded to a density of approximately 20,000 cells per well and transfectants resistant to 1 mg/ml genticin selected. Resistant colonies are expanded and then tested for their response to increasing concentrations of interferon gamma. The dose response of a selected clone is demonstrated.

Specifically, the following protocol will yield sufficient cells for 75 wells containing 200 ul of cells. Thus, it is either scaled up, or performed in multiple to generate sufficient cells for multiple 96 well plates. Jurkat cells are maintained in RPMI+10% serum with 1%Pen-Strep. Combine 2.5 mls of OPTI-MEM (Life Technologies) with 10 ug of plasmid DNA in a T25 flask. Add 2.5 ml OPTI-MEM containing 50 ul of DMRIE-C and incubate at room temperature for 15–45 mins.

During the incubation period, count cell concentration, spin down the required number of cells ($10^7$ per transfection), and resuspend in OPTI-MEM to a final concentration of $10^7$ cells/ml. Then add 1 ml of $1 \times 10^7$ cells in OPTI-MEM to T25 flask and incubate at 37° C. for 6 hrs. After the incubation, add 10 ml of RPMI+15% serum.

The Jurkat:GAS-SEAP stable reporter lines are maintained in RPMI+10% serum, 1 mg/ml Genticin, and 1% Pen-Strep. These cells are treated with supernatants containing a polypeptide as produced by the protocol described in Example 11.

On the day of treatment with the supernatant, the cells should be washed and resuspended in fresh RPMI+10% serum to a density of 500,000 cells per ml. The exact number of cells required will depend on the number of supernatants being screened. For one 96 well plate, approximately 10 million cells (for 10 plates, 100 million cells) are required.

Transfer the cells to a triangular reservoir boat, in order to dispense the cells into a 96 well dish, using a 12 channel pipette. Using a 12 channel pipette, transfer 200 ul of cells into each well (therefore adding 100, 000 cells per well).

After all the plates have been seeded, 50 ul of the supernatants are transferred directly from the 96 well plate containing the supernatants into each well using a 12 channel pipette. In addition, a dose of exogenous interferon gamma (0.1, 1.0, 10 ng) is added to wells H9, H10, and H11 to serve as additional positive controls for the assay.

The 96 well dishes containing Jurkat cells treated with supernatants are placed in an incubator for 48 hrs (note: this time is variable between 48–72 hrs). 35 ul samples from each well are then transferred to an opaque 96 well plate using a 12 channel pipette. The opaque plates should be covered (using sellophene covers) and stored at −20° C. until SEAP assays are performed according to Example 17. The plates containing the remaining treated cells are placed at 4° C. and serve as a source of material for repeating the assay on a specific well if desired.

As a positive control, 100 Unit/ml interferon gamma can be used which is known to activate Jurkat T cells. Over 30 fold induction is typically observed in the positive control wells. Example 14

High-Throughput Screening Assay Identifying Myeloid Activity

The following protocol is used to assess myeloid activity by identifying factors, such as growth factors and cytokines, that may proliferate or differentiate myeloid cells. Myeloid cell activity is assessed using the GAS/SEAP/Neo construct produced in Example 12. Thus, factors that increase SEAP activity indicate the ability to activate the Jaks-STATS signal transduction pathway. The myeloid cell used in this assay is U937, a pre-monocyte cell line, although TF-1, HL60, or KG1 can be used.

To transiently transfect U937 cells with the GAS/SEAP/Neo construct produced in Example 12, a DEAE-Dextran method (Kharbanda et. al., 1994, Cell Growth & Differentiation, 5:259–265) is used. First, harvest $2 \times 10e^7$ U937 cells and wash with PBS. The U937 cells are usually grown in RPMI 1640 medium containing 10% heat-inactivated fetal bovine serum (FBS) supplemented with 100 units/ml penicillin and 100 mg/ml streptomycin.

Next, suspend the cells in 1 ml of 20 mM Tris-HCl (pH 7.4) buffer containing 0.5 mg/ml DEAE-Dextran, 8 ug GAS-SEAP2 plasmid DNA, 140 mM NaCl, 5 mM KCl, 375 uM $Na_2HPO_4.7H_2O$, 1 mM $MgCl_2$, and 675 uM $CaCl_2$. Incubate at 37° C. for 45 min.

Wash the cells with RPMI 1640 medium containing 10% FBS and then resuspend in 10 ml complete medium and incubate at 37° C. for 36 hr.

The GAS-SEAP/U937 stable cells are obtained by growing the cells in 400 ug/ml G418. The G418-free medium is used for routine growth but every one to two months, the cells should be re-grown in 400 ug/ml G418 for couple of passages.

These cells are tested by harvesting $1 \times 10^8$ cells (this is enough for ten 96-well plates assay) and wash with PBS. Suspend the cells in 200 ml above described growth medium, with a final density of $5 \times 10^5$ cells/ml. Plate 200 ul cells per well in the 96-well plate (or $1 \times 10^5$ cells/well).

Add 50 ul of the supernatant prepared by the protocol described in Example 11. Incubate at 37° C. for 48 to 72 hr. As a positive control, 100 Unit/ml interferon gamma can be used which is known to activate U937 cells. Over 30 fold induction is typically observed in the positive control wells. SEAP assay the supernatant according to the protocol described in Example 17.

Example 15
High-Throughput Screening Assay Identifying Neuronal Activity When cells undergo differentiation and proliferation, a group of genes are activated through many different signal transduction pathways. One of these genes, EGR1 (early growth response gene 1), is induced in various tissues and cell types upon activation. The promoter of EGRI is responsible for such induction. Using the EGR1 promoter linked to reporter molecules, activation of cells can be assessed.

Particularly, the following protocol is used to assess neuronal activity in PC12 cell lines. PC12 cells (rat phenochromocytoma cells) are known to proliferate and/or differentiate by activation with a number of mitogens, such as TPA (tetradecanoyl phorbol acetate), NGF (nerve growth factor), and EGF (epidermal growth factor). The EGR1 gene expression is activated during this treatment. Thus, by stably transfecting PC12 cells with a construct containing an EGR promoter linked to SEAP reporter, activation of PC12 cells can be assessed.

The EGR/SEAP reporter construct can be assembled by the following protocol. The EGR-1 promoter sequence (−633 to +1)(Sakamoto K et al., Oncogene 6:867–871 (1991)) can be PCR amplified from human genomic DNA using the following primers:

5'
GCGCTCGAGGGATGACAGCGATAGAACCCCGG-3' (SEQ ID NO:6)
5' GCGAAGCTTCGCGACTCCCCGGATCCGCCTC-3' (SEQ ID NO:7)

Using the GAS:SEAP/Neo vector produced in Example 12, EGR1amplified product can then be inserted into this vector. Linearize the GAS:SEAP/Neo vector using restriction enzymes XhoI/HindIII, removing the GAS/SV40 stuffer. Restrict the EGR1 amplified product with these same enzymes. Ligate the vector and the EGR1 promoter.

To prepare 96 well-plates for cell culture, two mls of a coating solution (1:30 dilution of collagen type I (Upstate Biotech Inc. Cat#08-115) in 30% ethanol (filter sterilized)) is added per one 10 cm plate or 50 ml per well of the 96-well plate, and allowed to air dry for 2 hr.

PC12 cells are routinely grown in RPMI-1640 medium (Bio Whittaker) containing 10% horse serum (JRH BIOSCIENCES, Cat. #12449–78P), 5% heat-inactivated fetal bovine serum (FBS) supplemented with 100 units/ml penicillin and 100 ug/ml streptomycin on a precoated 10 cm tissue culture dish. One to four split is done every three to four days. Cells are removed from the plates by scraping and resuspended with pipetting up and down for more than 15 times.

Transfect the EGR/SEAP/Neo construct into PC12 using the Lipofectamine protocol described in Example 11. EGR-SEAP/PC12 stable cells are obtained by growing the cells in 300 ug/ml G418. The G418-free medium is used for routine growth but every one to two months, the cells should be re-grown in 300 ug/ml G418 for couple of passages.

To assay for neuronal activity, a 10 cm plate with cells around 70 to 80% confluent is screened by removing the old medium. Wash the cells once with PBS (Phosphate buffered saline). Then starve the cells in low serum medium (RPMI-1640 containing 1% horse serum and 0.5% FBS with antibiotics) overnight.

The next morning, remove the medium and wash the cells with PBS. Scrape off the cells from the plate, suspend the cells well in 2 ml low serum medium. Count the cell number and add more low serum medium to reach final cell density as $5\times10^5$ cells/ml.

Add 200 ul of the cell suspension to each well of 96-well plate (equivalent to $1\times10^5$ cells/well). Add 50 ul supernatant produced by Example 11, 37° C. for 48 to 72 hr. As a positive control, a growth factor known to activate PC12 cells through EGR can be used, such as 50 ng/ul of Neuronal Growth Factor (NGF). Over fifty-fold induction of SEAP is typically seen in the positive control wells. SEAP assay the supernatant according to Example 17.

Example 16
High-Throughput Screening Assay for T-cell Activity

NF-κB (Nuclear Factor κB) is a transcription factor activated by a wide variety of agents including the inflammatory cytokines IL-1 and TNF, CD30 and CD40, lymphotoxin-alpha and lymphotoxin-beta, by exposure to LPS or thrombin, and by expression of certain viral gene products. As a transcription factor, NF-κB regulates the expression of genes involved in immune cell activation, control of apoptosis (NF-κB appears to shield cells from apoptosis), B and T-cell development, anti-viral and antimicrobial responses, and multiple stress responses.

In non-stimulated conditions, NF-κB is retained in the cytoplasm with I-κB (Inhibitor κB). However, upon stimulation, I-κB is phosphorylated and degraded, causing NF-κB to shuttle to the nucleus, thereby activating transcription of target genes. Target genes activated by NF-κB include IL-2, IL-6, GM-CSF, ICAM-1 and class 1 MHC.

Due to its central role and ability to respond to a range of stimuli, reporter constructs utilizing the NF-κB promoter element are used to screen the supernatants produced in Example 11. Activators or inhibitors of NF-κB would be useful in treating diseases. For example, inhibitors of NF-κB could be used to treat those diseases related to the acute or chronic activation of NF-κB, such as rheumatoid arthritis.

To construct a vector containing the NF-κB promoter element, a PCR based strategy is employed. The upstream primer contains four tandem copies of the NF-κB binding site (GGGGACTTTCCC) (SEQ ID NO:8), 18 bp of sequence complementary to the 5' end of the SV40 early promoter sequence, and is flanked with an XhoI site:
5':GCGGCCTCGAGGGGACTTTCCCGGG-GACTTTCCGGGGACTTTCCGGGAC TTTCCATC-CTGCCATCTCAATTAG:3' (SEQ ID NO:9)

The downstream primer is complementary to the 3' end of the SV40 promoter and is flanked with a Hind III site:
5':GCGGCAAGCTTTTGCAAAGCCTAGGC:3' (SEQ ID NO:4)

PCR amplification is performed using the SV40 promoter template present in the pB-gal:promoter plasmid obtained from Clontech. The resulting PCR fragment is digested with XhoI and Hind III and subcloned into BLSK2-. (Stratagene) Sequencing with the T7 and T3 primers confirms the insert contains the following sequence:
5':CTCGAGGGGACTTTCCCGGGGACTTTC-CGGGGACTTTCCGGGACTTTCCATCTGC-CATCTCAATTAGTCAGCAACCATAGTC-CCGCCCCTAACTCCGCCCATCCCGCCCCTAACT CCGCCCAGTTCCGCCCATTCTCCGC-CCCATGGCTGACTAATTTTTTTATT-TATGCAGAGGCCGAGGCCGCCTCGGC-CTCTGAGCTATTC CAGAAGTAGTGAGGAGGCTTTTTTGGAG-GCCTAGGCTTTTGCAAAAAGCTT: 3' (SEQ ID NO:10)

Next, replace the SV40 minimal promoter element present in the pSEAP2-promoter plasmid (Clontech) with this NF-κB/SV40 fragment using XhoI and HindIII. However, this vector does not contain a neomycin resistance gene, and therefore, is not preferred for mammalian expression systems.

In order to generate stable mammalian cell lines, the NF-κB/SV40/SEAP cassette is removed from the above NF-κB/SEAP vector using restriction enzymes SalI and NotI, and inserted into a vector containing neomycin resistance. Particularly, the NF-κB/SV40/SEAP cassette was inserted into pGFP-1 (Clontech), replacing the GFP gene, after restricting pGFP-1 with SalI and NotI.

Once NF-κB/SV40/SEAP/Neo vector is created, stable Jurkat T-cells are created and maintained according to the protocol described in Example 13. Similarly, the method for assaying supernatants with these stable Jurkat T-cells is also described Example 13. As a positive control, exogenous TNF alpha (0.1,1, 10 ng) is added to 1s H9, H10, and H11, with a 5–10 fold activation typically observed.

Example 17

Assay for SEAP Activity

As a reporter molecule for the assays described in Examples 13–16, SEAP activity is assayed using the Tropix Phospho-light Kit (Cat. BP-400) according to the lowing general procedure. The Tropix Phospho-light Kit supplies the Dilution, Assay, and Reaction Buffers used below.

Prime a dispenser with the 2.5×Dilution Buffer and dispense 15 μl of 2.5×dilution buffer into Optiplates containing 35 μl of a supernatant. Seal the plates with a plastic sealer and incubate at 65° C. for 30 min. Separate the Optiplates to avoid uneven heating.

Cool the samples to room temperature for 15 minutes. Empty the dispenser and prime with the Assay Buffer. Add 50 μl Assay Buffer and incubate at room temperature 5 min. Empty the dispenser and prime with the Reaction Buffer (see the table below). Add 50 μl Reaction Buffer and incubate at room temperature for 20 minutes. Since the intensity of the chemiluminescent signal is time dependent, and it takes about 10 minutes to read 5 plates on luminometer, one should treat 5 plates at each time and start the second set 10 minutes later.

Read the relative light unit in the luminometer. Set H12 as blank, and print the results. An increase in chemiluminescence indicates reporter activity.

| Reaction Buffer Formulation: | | |
|---|---|---|
| # of plates | Rxn buffer diluent (ml) | CSPD (ml) |
| 10 | 60 | 3 |
| 11 | 65 | 3.25 |
| 12 | 70 | 3.5 |
| 13 | 75 | 3.75 |
| 14 | 80 | 4 |
| 15 | 85 | 4.25 |
| 16 | 90 | 4.5 |
| 17 | 95 | 4.75 |
| 18 | 100 | 5 |
| 19 | 105 | 5.25 |
| 20 | 110 | 5.5 |
| 21 | 115 | 5.75 |
| 22 | 120 | 6 |
| 23 | 125 | 6.25 |
| 24 | 130 | 6.5 |
| 25 | 135 | 6.75 |
| 26 | 140 | 7 |
| 27 | 145 | 7.25 |
| 28 | 150 | 7.5 |
| 29 | 155 | 7.75 |
| 30 | 160 | 8 |
| 31 | 165 | 8.25 |
| 32 | 170 | 8.5 |
| 33 | 175 | 8.75 |
| 34 | 180 | 9 |
| 35 | 185 | 9.25 |
| 36 | 190 | 9.5 |
| 37 | 195 | 9.75 |
| 38 | 200 | 10 |
| 39 | 205 | 10.25 |
| 40 | 210 | 10.5 |
| 41 | 215 | 10.75 |
| 42 | 220 | 11 |
| 43 | 225 | 11.25 |
| 44 | 230 | 11.5 |
| 45 | 235 | 11.75 |
| 46 | 240 | 12 |
| 47 | 245 | 12.25 |
| 48 | 250 | 12.5 |
| 49 | 255 | 12.75 |
| 50 | 260 | 13 |

Example 18

High-Throughput Screening Assay Identifying Changes in Small Molecule Concentration and Membrane Permeability Binding of a ligand to a receptor is known to alter intracellular levels of small molecules, such as calcium, potassium, sodium, and pH, as well as alter membrane potential. These alterations can be measured in an assay to identify supernatants which bind to receptors of a particular cell. Although the following protocol describes an assay for calcium, this protocol can easily be modified to detect changes in potassium, sodium, pH, membrane potential, or any other small molecule which is detectable by a fluorescent probe.

The following assay uses Fluorometric Imaging Plate Reader ("FLIPR") to measure changes in fluorescent molecules (Molecular Probes) that bind small molecules. Clearly, any fluorescent molecule detecting a small molecule can be used instead of the calcium fluorescent molecule, fluo-3, used here.

For adherent cells, seed the cells at 10,000–20,000 cells/well in a Co-star black 96-well plate with clear bottom. The plate is incubated in a $CO_2$ incubator for 20 hours. The adherent cells are washed two times in Biotek washer with 200 ul of HBSS (Hank's Balanced Salt Solution) leaving 100 ul of buffer after the final wash.

A stock solution of 1 mg/ml fluo-3 is made in 10% pluronic acid DMSO. To load the cells with fluo-3, 50 ul of 12 ug/ml fluo-3 is added to each well. The plate is incubated at 37° C. in a $CO_2$ incubator for 60 min. The plate is washed four times in the Biotek washer with HBSS leaving 100 ul of buffer.

For non-adherent cells, the cells are spun down from culture media. Cells are re-suspended to $2-5 \times 10^6$ cells/ml with HBSS in a 50-ml conical tube. 4 ul of 1 mg/ml fluo-3 solution in 10% pluronic acid DMSO is added to each ml of cell suspension. The tube is then placed in a 37° C. water bath for 30–60 min. The cells are washed twice with HBSS, resuspended to $1 \times 10^6$ cells/ml, and dispensed into a microplate, 100 ul/well. The plate is centrifuged at 1000 rpm for 5 min. The plate is then washed once in Denley CellWash with 200 ul, followed by an aspiration step to 100 ul final volume.

For a non-cell based assay, each well contains a fluorescent molecule, such as fluo-3. The supernatant is added to the well, and a change in fluorescence is detected.

To measure the fluorescence of intracellular calcium, the FLIPR is set for the following parameters: (1) System gain is 300–800 mW; (2) Exposure time is 0.4 second; (3)

Camera F/stop is F/2; (4) Excitation is 488 nm; (5) Emission is 530 nm; and (6) Sample addition is 50 ul. Increased emission at 530 nm indicates an extracellular signaling event which has resulted in an increase in the intracellular Ca++ concentration.

Example 19
High-Throughput Screening Assay Identifying Tyrosine Kinase Activity

The Protein Tyrosine Kinases (PTK) represent a diverse group of transmembrane and cytoplasmic kinases. Within the Receptor Protein Tyrosine Kinase RPTK) group are receptors for a range of mitogenic and metabolic growth factors including the PDGF, FGF, EGF, NGF, HGF and Insulin receptor subfamilies. In addition there are a large family of RPTKs for which the corresponding ligand is unknown. Ligands for RPTKs include mainly secreted small proteins, but also membrane-bound and extracellular matrix proteins.

Activation of RPTK by ligands involves ligand-mediated receptor dimerization, resulting in transphosphorylation of the receptor subunits and activation of the cytoplasmic tyrosine kinases. The cytoplasmic tyrosine kinases include receptor associated tyrosine kinases of the src-family (e.g., src, yes, Ick, lyn, fyn) and non-receptor linked and cytosolic protein tyrosine kinases, such as the Jak family, members of which mediate signal transduction triggered by the cytokine superfamily of receptors (e.g., the Interleukins, Interferons, GM-CSF, and Leptin).

Because of the wide range of known factors capable of stimulating tyrosine kinase activity, the identification of novel human secreted proteins capable of activating tyrosine kinase signal transduction pathways are of interest. Therefore, the following protocol is designed to identify those novel human secreted proteins capable of activating the tyrosine kinase signal transduction pathways.

Seed target cells (e.g., primary keratinocytes) at a density of approximately 25,000 cells per well in a 96 well Loprodyne Silent Screen Plates purchased from Nalge Nunc (Naperville, Ill.). The plates are sterilized with two 30 minute rinses with 100% ethanol, rinsed with water and dried overnight. Some plates are coated for 2 hr with 100 ml of cell culture grade type I collagen (50 mg/ml), gelatin (2%) or polylysine (50 mg/ml), all of which can be purchased from Sigma Chemicals (St. Louis, Mo.) or 10% Matrigel purchased from Becton Dickinson (Bedford,Mass.), or calf serum, rinsed with PBS and stored at 40° C. Cell growth on these plates is assayed by seeding 5,000 cells/well in growth medium and indirect quantitation of cell number through use of alamarBlue as described by the manufacturer Alamar Biosciences, Inc. (Sacramento, Calif.) after 48 hr. Falcon plate covers #3071 from Becton Dickinson (Bedford,Mass.) are used to cover the Loprodyne Silent Screen Plates. Falcon Microtest III cell culture plates can also be used in some proliferation experiments.

To prepare extracts, A431 cells are seeded onto the nylon membranes of Loprodyne plates (20,000/200 ml/well) and cultured overnight in complete medium. Cells are quiesced by incubation in serum-free basal medium for 24 hr. After 5–20 minutes treatment with EGF (60 ng/ml) or 50 ul of the supernatant produced in Example 11, the medium was removed and 100 ml of extraction buffer ((20 mM HEPES pH 7.5, 0.15 M NaCl, 1% Triton X-100, 0.1% SDS, 2 mM Na3VO4, 2 mM Na4P2O7 and a cocktail of protease inhibitors (#1836170) obtained from Boeheringer Mannheim (Indianapolis, Ind.) is added to each well and the plate is shaken on a rotating shaker for 5 minutes at 4° C. The plate is then placed in a vacuum transfer manifold and the extract filtered through the 0.45 mm membrane bottoms of each well using house vacuum. Extracts are collected in a 96-well catch/assay plate in the bottom of the vacuum manifold and immediately placed on ice. To obtain extracts clarified by centrifugation, the content of each well, after detergent solubilization for 5 minutes, is removed and centrifuged for 15 minutes at 4° C. at 16,000×g.

Test the filtered extracts for levels of tyrosine kinase activity. Although many methods of detecting tyrosine kinase activity are known, one method is described here.

Generally, the tyrosine kinase activity of a supernatant is evaluated by determining its ability to phosphorylate a tyrosine residue on a specific substrate (a biotinylated peptide). Biotinylated peptides that can be used for this purpose include PSK1 (corresponding to amino acids 6–20 of the cell division kinase cdc2-p34) and PSK2 (corresponding to amino acids 1–17 of gastrin). Both peptides are substrates for a range of tyrosine kinases and are available from Boehringer Mannheim.

The tyrosine kinase reaction is set up by adding the following components in order. First, add 10 ul of 5 uM Biotinylated Peptide, then 10 ul ATP/Mg$_{2+}$ (5 mM ATP/50 mM MgCl$_2$), then 10 ul of 5×Assay Buffer (40 mM imidazole hydrochloride, pH7.3, 40 mM beta-glycerophosphate, 1 mM EGTA, 100 mM MgCl$_2$, 5 mM MnCl$_2$, 0.5 mg/ml BSA), then 5 ul of Sodium Vanadate(1 mM), and then 5 ul of water. Mix the components gently and preincubate the reaction mix at 30° C. for 2 min. Initial the reaction by adding 10 ul of the control enzyme or the filtered supernatant.

The tyrosine kinase assay reaction is then terminated by adding 10 ul of 120 mm EDTA and place the reactions on ice.

Tyrosine kinase activity is determined by transferring 50 ul aliquot of reaction mixture to a microtiter plate (MTP) module and incubating at 37° C. for 20 min. This allows the streptavadin coated 96 well plate to associate with the biotinylated peptide. Wash the MTP module with 300 ul/well of PBS four times. Next add 75 ul of anti-phosphotyrosine antibody conjugated to horse radish peroxidase(anti-P-Tyr-POD(0.5 u/ml)) to each well and incubate at 37° C. for one hour. Wash the well as above.

Next add 100 ul of peroxidase substrate solution (Boehringer Mannheim) and incubate at room temperature for at least 5 mins (up to 30 min). Measure the absorbance of the sample at 405 nm by using ELISA reader. The level of bound peroxidase activity is quantitated using an ELISA reader and reflects the level of tyrosine kinase activity.

Example 20
High-Throughput Screening Assay Identifying Phosphorylation Activity

As a potential alternative and/or compliment to the assay of protein tyrosine kinase activity described in Example 19, an assay which detects activation (phosphorylation) of major intracellular signal transduction intermediates can also be used. For example, as described below one particular assay can detect tyrosine phosphorylation of the Erk-1 and Erk-2 kinases. However, phosphorylation of other molecules, such as Raf, JNK, p38 MAP, Map kinase kinase (MEK), MEK kinase, Src, Muscle specific kinase (MuSK), IRAK, Tec, and Janus, as well as any other phosphoserine, phosphotyrosine, or phosphothreonine molecule, can be detected by substituting these molecules for Erk-1 or Erk-2 in the following assay.

Specifically, assay plates are made by coating the wells of a 96-well ELISA plate with 0.1 ml of protein G (1 ug/ml) for 2 hr at room temp, (RT). The plates are then rinsed with PBS and blocked with 3% BSA/PBS for 1 hr at RT. The protein G plates are then treated with 2 commercial monoclonal antibodies (100 ng/well) against Erk-1 and Erk-2 (1 hr at RT) (Santa Cruz Biotechnology). (To detect other molecules, this step can easily be modified by substituting a monoclonal antibody detecting any of the above described molecules.) After 3–5 rinses with PBS, the plates are stored at 4° C. until use.

A431 cells are seeded at 20,000/well in a 96-well Loprodyne filterplate and cultured overnight in growth medium. The cells are then starved for 48 hr in basal medium (DMEM) and then treated with EGF (6 ng/well) or 50 ul of the supernatants obtained in Example 11 for 5–20 minutes. The cells are then solubilized and extracts filtered directly into the assay plate.

After incubation with the extract for 1 hr at RT, the wells are again rinsed. As a positive control, a commercial preparation of MAP kinase (10 ng/well) is used in place of A431 extract. Plates are then treated with a commercial polyclonal (rabbit) antibody (1 ug/ml) which specifically recognizes the phosphorylated epitope of the Erk-1 and Erk-2 kinases (1 hr at RT). This antibody is biotinylated by standard procedures. The bound polyclonal antibody is then quantitated by successive incubations with Europium-streptavidin and Europium fluorescence enhancing reagent in the Wallac DELFIA instrument (time-resolved fluorescence). An increased fluorescent signal over background indicates a phosphorylation.

Example 21
Method of Determining Alterations in a Gene Corresponding to a Polynucleotide RNA isolated from entire families or individual patients presenting with a phenotype of interest (such as a disease) is be isolated. cDNA is then generated from these RNA samples using protocols known in the art. (See, Sambrook.) The cDNA is then used as a template for PCR, employing primers surrounding regions of interest in SEQ ID NO:X. Suggested PCR conditions consist of 35 cycles at 95° C. for 30 seconds; 60–120 seconds at 52–58° C.; and 60–120 seconds at 70° C., using buffer solutions described in Sidransky, D., et al., Science 252:706 (1991).

PCR products are then sequenced using primers labeled at their 5' end with T4 polynucleotide kinase, employing SequiTherm Polymerase. (Epicentre Technologies). The intron-exon borders of selected exons is also determined and genomic PCR products analyzed to confirm the results. PCR products harboring suspected mutations is then cloned and sequenced to validate the results of the direct sequencing.

PCR products is cloned into T-tailed vectors as described in Holton, T. A. and Graham, M. W., Nucleic Acids Research, 19:1156 (1991) and sequenced with T7 polymerase (United States Biochemical). Affected individuals are identified by mutations not present in unaffected individuals.

Genomic rearrangements are also observed as a method of determining alterations in a gene corresponding to a polynucleotide. Genomic clones isolated according to Example 2 are nick-translated with digoxigenindeoxy-uridine 5'-triphosphate (Boehringer Manheim), and FISH performed as described in Johnson, Cg. et al., Methods Cell Biol. 35:73–99 (1991). Hybridization with the labeled probe is carried out using a vast excess of human cot-1 DNA for specific hybridization to the corresponding genomic locus.

Chromosomes are counterstained with 4,6-diamino-2-phenylidole and propidium iodide, producing a combination of C- and R-bands. Aligned images for precise mapping are obtained using a triple-band filter set (Chroma Technology, Brattleboro, Vt.) in combination with a cooled charge-coupled device camera (Photometrics, Tucson, Ariz.) and variable excitation wavelength filters. (Johnson, Cv. et al., Genet. Anal. Tech. Appl., 8:75 (1991).) Image collection, analysis and chromosomal fractional length measurements are performed using the ISee Graphical Program System. (Inovision Corporation, Durham, N.C.) Chromosome alterations of the genomic region hybridized by the probe are identified as insertions, deletions, and translocations. These alterations are used as a diagnostic marker for an associated disease.

Example 22
Method of Detecting Abnormal Levels of a Polypeptide in a Biological Sample A polypeptide of the present invention can be detected in a biological sample, and if an increased or decreased level of the polypeptide is detected, this polypeptide is a marker for a particular phenotype. Methods of detection are numerous, and thus, it is understood that one skilled in the art can modify the following assay to fit their particular needs.

For example, antibody-sandwich ELISAs are used to detect polypeptides in a sample, preferably a biological sample. Wells of a microtiter plate are coated with specific antibodies, at a final concentration of 0.2 to 10 ug/ml. The antibodies are either monoclonal or polyclonal and are produced by the method described in Example 10. The wells are blocked so that non-specific binding of the polypeptide to the well is reduced.

The coated wells are then incubated for >2 hours at RT with a sample containing the polypeptide. Preferably, serial dilutions of the sample should be used to validate results. The plates are then washed three times with deionized or distilled water to remove unbounded polypeptide.

Next, 50 ul of specific antibody-alkaline phosphatase conjugate, at a concentration of 25–400 ng, is added and incubated for 2 hours at room temperature. The plates are again washed three times with deionized or distilled water to remove unbounded conjugate.

Add 75 ul of 4-methylumbelliferyl phosphate (MUP) or p-nitrophenyl phosphate (NPP) substrate solution to each well and incubate 1 hour at room temperature. Measure the reaction by a microtiter plate reader. Prepare a standard curve, using serial dilutions of a control sample, and plot polypeptide concentration on the X-axis (log scale) and fluorescence or absorbance of the Y-axis (linear scale). Interpolate the concentration of the polypeptide in the sample using the standard curve.

Example 23
Formulating a Polypeptide

The secreted polypeptide composition will be formulated and dosed in a fashion consistent with good medical practice, taking into account the clinical condition of the individual patient (especially the side effects of treatment with the secreted polypeptide alone), the site of delivery, the method of administration, the scheduling of administration, and other factors known to practitioners. The "effective amount" for purposes herein is thus determined by such considerations.

As a general proposition, the total pharmaceutically effective amount of secreted polypeptide administered parenterally per dose will be in the range of about 1 µg/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, the secreted polypeptide is typically administered at a dose rate of about 1 μg/kg/hour to about 50 μg/kg/hour, either by 1–4 injections per day or by continuous subcutaneous infusions, for example, using a mini-pump. An intravenous bag solution may also be employed. The length of treatment needed to observe changes and the interval following treatment for responses to occur appears to vary depending on the desired effect.

Pharmaceutical compositions containing the secreted protein of the invention are administered orally, rectally, parenterally, intracistemally, intravaginally, intraperitoneally, topically (as by powders, ointments, gels, drops or transdermal patch), bucally, or as an oral or nasal spray. "Pharmaceutically acceptable carrier" refers to a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

The secreted polypeptide is also suitably administered by sustained-release systems. Suitable examples of sustained-release compositions include semi-permeable polymer matrices in the form of shaped articles, e.g., films, or mirocapsules. Sustained-release matrices include polylactides (U.S. Pat. No. 3,773,919, EP 58,481), copolymers of L-glutamic acid and gamma-ethyl-L-glutamate (Sidman, U. et al., Biopolymers 22:547–556 (1983)), poly (2-hydroxyethyl methacrylate) (R. Langer et al., J. Biomed. Mater. Res. 15:167–277 (1981), and R. Langer, Chem. Tech. 12:98–105 (1982)), ethylene vinyl acetate (R. Langer et al.) or poly-D-(-)-3-hydroxybutyric acid (EP 133,988). Sustained-release compositions also include liposomally entrapped polypeptides. Liposomes containing the secreted polypeptide are prepared by methods known per se: DE 3,218,121; Epstein et al., Proc. Natl. Acad. Sci. USA 82:3688–3692 (1985); Hwang et al., Proc. Natl. Acad. Sci. USA 77:4030–4034 (1980); EP 52,322; EP 36,676; EP 88,046; EP 143,949; EP 142,641; Japanese Pat. Appl. 83–118008; U.S. Pat. Nos. 4,485,045 and 4,544,545; and EP 102,324. Ordinarily, the liposomes are of the small (about 200–800 Angstroms) unilamellar type in which the lipid content is greater than about 30 mol. percent cholesterol, the selected proportion being adjusted for the optimal secreted polypeptide therapy.

For parenteral administration, in one embodiment, the secreted polypeptide is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides.

Generally, the formulations are prepared by contacting the polypeptide uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, manose, or dextrins; chelating agents such as EDTA; sugar alcohols such as mannitol or sorbitol; counterions such as sodium; and/or nonionic surfactants such as polysorbates, poloxamers, or PEG.

The secreted polypeptide is typically formulated in such vehicles at a concentration of about 0.1 mg/ml to 100 mg/ml, preferably 1–10 mg/ml, at a pH of about 3 to 8. It will be understood that the use of certain of the foregoing excipients, carriers, or stabilizers will result in the formation of polypeptide salts.

Any polypeptide to be used for therapeutic administration can be sterile. Sterility is readily accomplished by filtration through sterile filtration membranes (e.g., 0.2 micron membranes). Therapeutic polypeptide compositions generally are placed into a container having a sterile access port, for example, an intravenous solution bag or vial having a stopper pierceable by a hypodermic injection needle.

Polypeptides ordinarily will be stored in unit or multi-dose containers, for example, sealed ampoules or vials, as an aqueous solution or as a lyophilized formulation for reconstitution. As an example of a lyophilized formulation, 10-mil vials are filled with 5 ml of sterile-filtered 1% (w/v) aqueous polypeptide solution, and the resulting mixture is lyophilized. The infusion solution is prepared by reconstituting the lyophilized polypeptide using bacteriostatic Water-for-Injection.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptides of the present invention may be employed in conjunction with other therapeutic compounds.

Example 24

Method of Treating Decreased Levels of the Polypeptide

It will be appreciated that conditions caused by a decrease in the standard or normal expression level of a secreted protein in an individual can be treated by administering the polypeptide of the present invention, preferably in the secreted form. Thus, the invention also provides a method of treatment of an individual in need of an increased level of the polypeptide comprising administering to such an individual a pharmaceutical composition comprising an amount of the polypeptide to increase the activity level of the polypeptide in such an individual.

For example, a patient with decreased levels of a polypeptide receives a daily dose 0.1–100 ug/kg of the polypeptide for six consecutive days. Preferably, the polypeptide is in the secreted form. The exact details of the dosing scheme, based on administration and formulation, are provided in Example 23.

Example 25
Method of Treating Increased Levels of the Polypeptide

Antisense technology is used to inhibit production of a polypeptide of the present invention. This technology is one example of a method of decreasing levels of a polypeptide, preferably a secreted form, due to a variety of etiologies, such as cancer.

For example, a patient diagnosed with abnormally increased levels of a polypeptide is administered intravenously antisense polynucleotides at 0.5, 1.0, 1.5, 2.0 and 3.0 mg/kg day for 21 days. This treatment is repeated after a 7-day rest period if the treatment was well tolerated. The formulation of the antisense polynucleotide is provided in Example 23.

Example 26
Method of Treatment Using Gene Therapy

One method of gene therapy transplants fibroblasts, which are capable of expressing a polypeptide, onto a patient. Generally, fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin) is added. The flasks are then incubated at 37° C. for approximately one week.

At this time, fresh media is added and subsequently changed every several days. After an additional two weeks in culture, a monolayer of fibroblasts emerge. The monolayer is trypsinized and scaled into larger flasks.

pMV-7 (Kirschmeier, P.T. et al., DNA, 7:219–25 (1988)), flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding a polypeptide of the present invention can be amplified using PCR primers which correspond to the 5' and 3' end sequences respectively as set forth in Example 1. Preferably, the 5' primer contains an EcoRI site and the 3' primer includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is then used to transform bacteria HB101, which are then plated onto agar containing kanamycin for the purpose of confirming that the vector has the gene of interest properly inserted.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his. Once the fibroblasts have been efficiently infected, the fibroblasts are analyzed to determine whether protein is produced.

The engineered fibroblasts are then transplanted onto the host, either alone or after having been grown to confluence on cytodex 3 microcarrier beads.

It will be clear that the invention may be practiced otherwise than as particularly described in the foregoing description and examples. Numerous modifications and variations of the present invention are possible in light of the above teachings and, therefore, are within the scope of the appended claims.

The entire disclosure of each document cited (including patents, patent applications, journal articles, abstracts, laboratory manuals, books, or other disclosures) in the Background of the Invention, Detailed Description, and Examples is hereby incorporated herein by reference. Further, the hard copy of the sequence listing submitted herewith and the corresponding computer readable form are both incorporated herein by reference in their entireties.

What is claimed is:

1. An isolated protein comprising amino acid residues 22 to 133 of SEQ ID NO:75.

2. The isolated protein of claim 1 which comprises amino acid residues 2 to 133 of SEQ ID NO:75.

3. The isolated protein of claim 1 which comprises amino acid residues 1 to 133 of SEQ ID NO:75.

4. The protein of claim 1 which comprises a heterologous polypeptide sequence.

5. A composition comprising the protein of claim 1 and a pharmaceutically acceptable carrier.

6. An isolated protein produced by the method comprising:

(a) expressing the protein of claim 1 by a cell; and (b) recovering said protein.

7. An isolated protein comprising the amino acid sequence of the secreted portion of the polypeptide encoded by the HTEBY11 cDNA contained in ATCC Deposit No. 97922.

8. The isolated protein of claim 7 which comprises the amino acid sequence of the complete polypeptide encoded by the HTEBY11 cDNA contained in ATCC Deposit No. 97922.

9. The isolated protein of claim 7 which comprises the amino acid sequence of the complete polypeptide encoded by the HTEBY11 cDNA contained in ATCC Deposit No. 97922.

10. The protein of claim 7 which comprises a heterologous polypeptide sequence.

11. A composition comprising the protein of claim 7 and a pharmaceutically acceptable carrier.

12. An isolated protein produced by the method comprising:

(a) expressing the protein of claim 7 by a cell; and (b) recovering said protein.

13. An isolated protein comprising a polypeptide sequence which is at least 90% identical to amino acid residues 22 to 133 of SEQ ID NO:75.

14. The isolated protein of claim 13 wherein said polypeptide sequence is at least 90% identical to amino acid residues 1 to 133 of SEQ ID NO:75.

15. The isolated protein of claim 13 wherein said polypeptide sequence is at least 95% identical to amino acid residues 22 to 133 of SEQ ID NO:75.

16. The isolated protein of claim 13 wherein said polypeptide sequence is at least 95% identical to amino acid residues 1 to 133 of SEQ ID NO:75.

17. The protein of claim 13 which comprises a heterologous polypeptide sequence.

18. A composition comprising the protein of claim 13 and a pharmaceutically acceptable carrier.

19. An isolated protein produced by the method comprising:

(a) expressing the protein of claim 13 by a cell; and (b) recovering said protein.

20. An isolated protein comprising a polypeptide sequence which is at least 90% identical to the secreted portion of the polypeptide encoded by the HTEBY11 cDNA contained in ATCC Deposit No. 97922.

21. The isolated protein of claim 20 wherein said polypeptide sequence is at least 90% identical to the complete polypeptide encoded by the HTEBY11 cDNA contained in ATCC Deposit No. 97922.

22. The isolated protein of claim 20 wherein said polypeptide sequence is at least 95% identical to the secreted portion of the polypeptide encoded by the HTEBY11 cDNA contained in ATCC Deposit No. 97922.

23. The isolated protein of claim 20 wherein said polypeptide sequence is at least 95% identical to the complete polypeptide encoded by the HTEBY11 cDNA contained in ATCC Deposit No. 97922.

24. The protein of claim 20 which comprises a heterologous polypeptide sequence.

25. A composition comprising the protein of claim 20 and a pharmaceutically acceptable carrier.

26. An isolated protein produced by the method comprising:

(a) expressing the protein of claim 20 by a cell; and (b) recovering said protein.

27. An isolated protein which comprises at least 50 contiguous amino acid residues of amino acid residues 22 to 133 of SEQ ID NO:75.

28. The protein of claim 27 which comprises a heterologous polypeptide sequence.

29. A composition comprising the protein of claim 27 and a pharmaceutically acceptable carrier.

30. An isolated protein produced by the method comprising:

(a) expressing the protein of claim 27 by a cell; and (b) recovering said protein.

31. An isolated protein comprising at least 30 contiguous amino acid residues of the secreted portion of the polypeptide encoded by the HTEBY11 cDNA contained in ATCC Deposit No. 97922.

32. The isolated protein of claim 31 which comprises at least 50 contiguous amino acid residues of the secreted portion of the polypeptide encoded by the HTEBY11 cDNA contained in ATCC Deposit No. 97922.

33. The protein of claim 31 which comprises a heterologous polypeptide sequence.

34. A composition comprising the protein of claim 31 and pharmaceutically acceptable carrier.

35. An isolated protein produced by the method comprising:
   (a) expressing the protein of claim 31 by a cell; and
   (b) recovering said protein.

36. An isolated protein comprising at least 30 contiguous amino acid residues of the complete polypeptide encoded by the HTEBY11 cDNA contained in ATCC Deposit No. 97922.

37. The isolated protein of claim 36 which comprises at least 50 contiguous amino acid residues of the complete polypeptide encoded by the HTEBY11 cDNA contained in ATCC Deposit No. 97922.

38. The protein of claim 36 which comprises a heterologous polypeptide sequence.

39. A composition comprising the protein of claim 36 and pharmaceutically acceptable carrier.

40. An isolated protein produced by the method comprising:
   (a) expressing the protein of claim 36 by a cell; and
   (b) recovering said protein.

\* \* \* \* \*

UNITED STATES PATENT AND TRADEMARK OFFICE
CERTIFICATE OF CORRECTION

PATENT NO. : 6,448,230 B1
DATED : September 10, 2002
INVENTOR(S) : Li et al.

It is certified that error appears in the above-identified patent and that said Letters Patent is hereby corrected as shown below:

Column 221,
Lines 36-39, claim 8 should read:

8. The isolated protein of claim 7 which comprises the amino acid sequence of the complete polypeptide encoded by the HTEBY11 cDNA contained in ATCC Deposit No. 97922, excepting the N-terminal methionine.

Signed and Sealed this

First Day of April, 2003

JAMES E. ROGAN
*Director of the United States Patent and Trademark Office*